United States Patent
Criscione et al.

(10) Patent No.: US 11,345,723 B2
(45) Date of Patent: May 31, 2022

(54) PROCESS TECHNOLOGY FOR BIOLOGICAL PRODUCT MANUFACTURING AND DOWNSTREAM PURIFICATION

(71) Applicant: Mobius Biomedical, Inc., Lowell, MA (US)

(72) Inventors: Jason M. Criscione, Chelmsford, MA (US); Ali Ersen, Chestnut Hill, MA (US); John R. Linton, Concord, MA (US); Sammy S. Datwani, Pleasanton, CA (US)

(73) Assignee: Mobius Biomedical, Inc., Lowell, MA (US)

( * ) Notice: Subject to any disclaimer, the term of this patent is extended or adjusted under 35 U.S.C. 154(b) by 0 days.

(21) Appl. No.: 17/474,232

(22) Filed: Sep. 14, 2021

(65) Prior Publication Data

US 2022/0081469 A1     Mar. 17, 2022

Related U.S. Application Data

(60) Provisional application No. 63/154,108, filed on Feb. 26, 2021, provisional application No. 63/154,109, filed on Feb. 26, 2021, provisional application No. 63/077,766, filed on Sep. 14, 2020.

(51) Int. Cl.

| | |
|---|---|
| C07K 1/22 | (2006.01) |
| C07K 1/26 | (2006.01) |
| B01D 69/10 | (2006.01) |
| B01D 15/38 | (2006.01) |
| B01D 57/02 | (2006.01) |
| B01D 15/20 | (2006.01) |
| B01D 15/18 | (2006.01) |
| B01D 71/68 | (2006.01) |
| B01D 63/10 | (2006.01) |
| B01D 69/02 | (2006.01) |
| B01D 69/14 | (2006.01) |
| C07K 16/00 | (2006.01) |
| C07K 1/36 | (2006.01) |
| C07K 1/34 | (2006.01) |

(52) U.S. Cl.
CPC ............ *C07K 1/36* (2013.01); *B01D 15/1892* (2013.01); *B01D 15/203* (2013.01); *B01D 15/3809* (2013.01); *B01D 57/02* (2013.01); *B01D 63/10* (2013.01); *B01D 69/02* (2013.01); *B01D 69/10* (2013.01); *B01D 69/14* (2013.01); *B01D 71/68* (2013.01); *C07K 1/22* (2013.01); *C07K 1/26* (2013.01); *C07K 1/34* (2013.01); *C07K 16/00* (2013.01); *B01D 2313/24* (2013.01); *B01D 2325/02* (2013.01); *C07K 2319/30* (2013.01)

(58) Field of Classification Search
CPC ... C07K 1/36; C07K 1/22; C07K 1/26; C07K 1/34; C07K 16/00; C07K 2319/30; B01D 15/1892; B01D 15/203; B01D 15/3809; B01D 57/02; B01D 63/10; B01D 60/02; B01D 69/10; B01D 69/14; B01D 71/68; B01D 2313/24; B01D 2325/02
See application file for complete search history.

(56) References Cited

U.S. PATENT DOCUMENTS

| | | |
|---|---|---|
| 4,698,142 A | 10/1987 | Muroi et al. |
| 7,357,852 B2 | 4/2008 | Woudenberg et al. |
| 8,999,129 B2 | 4/2015 | Jung et al. |
| 2016/0109405 A1 | 4/2016 | Cao et al. |
| 2019/0337979 A1 | 11/2019 | Bransby |

FOREIGN PATENT DOCUMENTS

| | | |
|---|---|---|
| EP | 0171676 B1 | 11/1990 |
| GB | 2578680 A | 5/2020 |
| WO | 2008025806 A1 | 3/2008 |

OTHER PUBLICATIONS (Oct. 2015) Continuous Chromatography in Downstream Processing of a Monoclonal Antibody, GE Healthcare, 8 pages.
Filliation Processes Applied in Therapeutic Monoclonal Antibody Production, Bioprocess, Biologicals & Pharmaceutical, 8 pages.
Integrated Semi-Continuous Process for mAb Production, gelifesciences. com, 4 pages.
Agostino et al. (2015) "Advances in Steady-state Continuous-flow Purification by Small-scale Free-flow Electrophoresis", Trends in Analytical Chemistry, 72:68-79.
Agostino et al. (2013) "Steady-State Continuous-Flow Purification by Electrophoresis", Angewandte Chemie International Edition, 52:7256-7260.
Albrecht et al. (Dec. 15, 2007) "Cascaded Free-Flow Isoelectric Focusing for Improved Focusing Speed and Resolution", Analytical Chemistry, 79(24):9364-9371.
Bisschops et al. (2013) "The Impact of Continuous Multicolumn Chromatography on Biomanufacturing Efficiency", Pharmaceutical Bioprocessing, 1(4):361-372.
Brechmann et al. (2019) "Pilot-scale Process For Magnetic Bead Purification of Antibodies Directly From Non-clarified Cho Cell Culture", Biotechnology Progress, 35(3):1-10.
Chen et al. (2009) "Microfluidic Cell Sorter With Integrated Piezoelectric Actuator", Biomedical Microdevices, 11:1223-1231.
Chiu et al. (2016) "Enhancement of Microfluidic Particle Separation Using Cross-flow Filters With Hydrodynamic Focusing", Biomicrofluidics, 10(1):13 pages.

(Continued)

*Primary Examiner* — Dirk R Bass
(74) *Attorney, Agent, or Firm* — Mintz Levin Cohn Ferris Glovsky and Popeo, P.C.

(57) ABSTRACT

Provided herein are, inter alia, biological manufacturing and downstream purification processes.

15 Claims, 66 Drawing Sheets
(66 of 66 Drawing Sheet(s) Filed in Color)

(56) References Cited

OTHER PUBLICATIONS

Courtney et al. (2020) "Counterflow Gradient Focusing in Free-Flow Electrophoresis for Protein Fractionation", Analytical Chemistry, 92:7317-7324.
Dutta Debashis. (2018) "Joule Heating Induced Stream Broadening in Free-flow Zone Electrophoresis", Electrophoresis, 39:760-769(11 pages).
Dutta et al. (Nov. 10, 2015) "Purification of Monoclonal Antibodies From Clarified Cell Culture Fluid Using Protein a Capture Continuous Countercurrent Tangential Chromatography", Journal of Biotechnology, 213:54-64(33 pages).
Fu et al. (2017) "Advances in Piezoelectric Thin Films For Acoustic Biosensors, Acoustofluidics and Lab-on-chip Applications", Progress in Materials Science, 89:31-91.
Gomis-Fons et al. (2020) "Optimization Study on Periodic Countercurrent Chromatography Integrated in a Monoclonal Antibody Downstream Process", Journal of Chromatography A, 1621:13 pages.
Gottschlich et al. (1997) "Purification of Monoclonal Antibodies by Simulated Moving-bed Chromatography", Journal of Chromatography A, 765:201-206.
Gronemeyer et al. (2014) "Trends in Upstream and Downstream Process Development for Antibody Manufacturing", Bioengineering, 1:188-212.
Herzog et al. (2015) "Gas Removal in Free-flow Electrophoresis Using an Integrated Nanoporous Membrane", Microchim Acta, 182:887-892.
Hosken et al. (2016) "Isolation and Characterization of Monoclonal Antibody Charge Variants by Free Flow Isoelectric Focusing", Analytical Chemistry, 88:5662-5669.
Hsu et al. (Jan. 13, 2019) "Acoustophoretic Control of Microparticle Transport Using Dual-Wavelength Surface Acoustic Wave Devices", Micromachines, 10(1):19 pages.
Ichihara et al. (2019) "Polishing Approach With Fully Connected Flow-through Purification For Therapeutic Monoclonal Antibody", Engineering in Life Sciences, 19:31-36.
Inglis et al. (2006) "Microfluidic High Gradient Magnetic Cell Separation", Journal of Applied Physics, 99:3 pages.
Juodenas et al. (2013) "Piezoelectric Actuation For Microfluidic Cell Sorting", Journal of Measurements in Engineering, Dec. 1(4):228-232.
Khashan et al. (2017) "Microdevice For Continuous Flow Magnetic Separation For Bioengineering Applications", Journal of Micromechanics and Microengineering, 27:11 pages.
Kohlheyer et al. (2006) "Free-flow Zone Electrophoresis and Isoelectric Focusing Using a Microfabricated Glass Device With Ion Permeable Membranes", Lab Chip, 6:374-380.
Kohlheyer et al. (2008) "Miniaturizing Free-flow Electrophoresis—a Critical Review", Electrophoresis, 29:977-993.
Kye et al. (Jul. 1, 2019) "Dual-neodymium Magnet-based Microfluidic Separation Device", Scientific Reports, 10 pages.
Mihlbachler DR. K. (Apr. 16, 2015) "Integrated Continuous Downstream Processing—an Enabling Approach", LEWA Process Technologies, 22 pages.
Morrison et al. (Nov. 1984) "Chimeric Human Antibody Molecules: Mouse Antigen-Binding Domains with Human Constant Region Domains", Proceedings of the National Academy of Sciences, 81:6851-6855.
Novo et al. (2016) "Free Flow Electrophoresis Separation of Proteins and DNA Using Microfluidics and Polycarbonate Membranes", Procedia Engineering, 168:1382-1385.
Pedersen et al., "Dynabeads Magnetic Beads—the Key to Successful Immunoprecipitation", Thermo Fisher Scientific, 5 pages.
Petersson et al. (Jun. 15, 2007) "Free Flow Acoustophoresis: Microfluidic-Based Mode of Particle and Cell Separation", Analytical Chemistry, 79(14):5117-5123.
Reis et al. (2007) "Bioprocess Membrane Technology", Journal of Membrane Science, 297:16-50.
Schwaminger et al. (Sep. 2019) "Magnetic Separation in Bioprocessing Beyond the Analytical Scale: From Biotechnology to the Food Industry", Frontiers in Bioengineering and Biotechnology, 7(233):12 pages.
Shukla et al. (2017) "Evolving Trends in Mab Production Processes", Bioengineering & Translational Medicine, 2 (1):58-69.
Sivaramakrishnan et al. (Mar. 2020) "Active Microfluidic Systems For Cell Sorting and Separation", Current Opinion in Biomedical Engineering, 13:60-68.
Slais et al. (2014) "Electrolyte System For Fast Preparative Focusing in Wide pH Range Based on Bidirectional Isotachophoresis", Electrophoresis, 35:2438-2445.
Soltani et al. (2017) "Integrated Continuous and Single-use (ICS) bio-production platform Linking continuous berfusion bioreactor with Continuous Countercurrent Tangential Chromatography", Bioprocess International, 4 pages.
Stastna et al. (Oct. 2015) "Continuous Fast Focusing in a Trapezoidal Void Channel Based On Bidirectional Isotachophoresis in a Wide PH Range", Electrophoresis, 36(20):2579-2586.
Stastna Miroslava (2020) "Continuous Flow Electrophoretic Separation—recent Developments and Applications to Biological Sample Analysis", Electrophoresis, 41:36-55.
Wang et al. (Sep. 2019) "Carrier Ampholyte-free Free-flow Isoelectric Focusing For Separation of Protein", Electrophoresis, 40(18-19):2610-2617.
Warikoo et al. (Dec. 2012) "Integrated Continuous Production of Recombinant Therapeutic Proteins", Biotechnology and Bioengineering, 109(12):3018-3029.
Weber et al. (2008) "Free-Flow Electrophoresis System for Proteomics Applications", Methods in Molecular Biology, 384:703-716.
Weber, et al. (Dec. 2004) "A Versatile Free-Flow Electrophoresis System for Proteomics Applications" American Biotechnology Laboratory, 2 pages.
Wu et al. (Jun. 3, 2019) "Acoustofluidic Separation of Cells and Particles", Microsystems & Nanoengineering, 5:32 (18 pages).
Yan et al. (Oct. 2016) "Hybrid Microfluidics Combined With Active and Passive Approaches For Continuous Cell Separation", Electrophoresis, 13 pages.
Yin et al. (2019) "Multi-Stage Particle Separation based on Microstructure Filtration and Dielectrophoresis", Micromachines, 10(103):11 pages.
Yoon et al. (May 20, 2016) "Clogging-free Microfluidics For Continuous Size-based Separation of Microparticles", Scientific Reports, 6(26531):8 pages.
Zhang et al. (Mar. 19, 2020) "A Concise Review of Microfluidic Particle Manipulation Methods", Microfluidics and Nanofluidics, 24:24(20 pages).
Zhang et al. (2019) "DEP-on-a-Chip: Dielectrophoresis Applied to Microfluidic Platforms", Micromachines, 10(6):22 pages.
Zhang et al. (Apr. 2018) "Tunable Particle Separation in a Hybrid Dielectrophoresis (DEP)—Inertial Microfluidic Device", Sensors and Actuators B: Chemical, 31 pages.
Zhou et al. (2019) "Hybrid Microfluidic Sorting of Rare Cells Based on High Throughput Inertial Focusing and High Accuracy Acoustic Manipulation†", RSC Advances, 9:31186-31195.

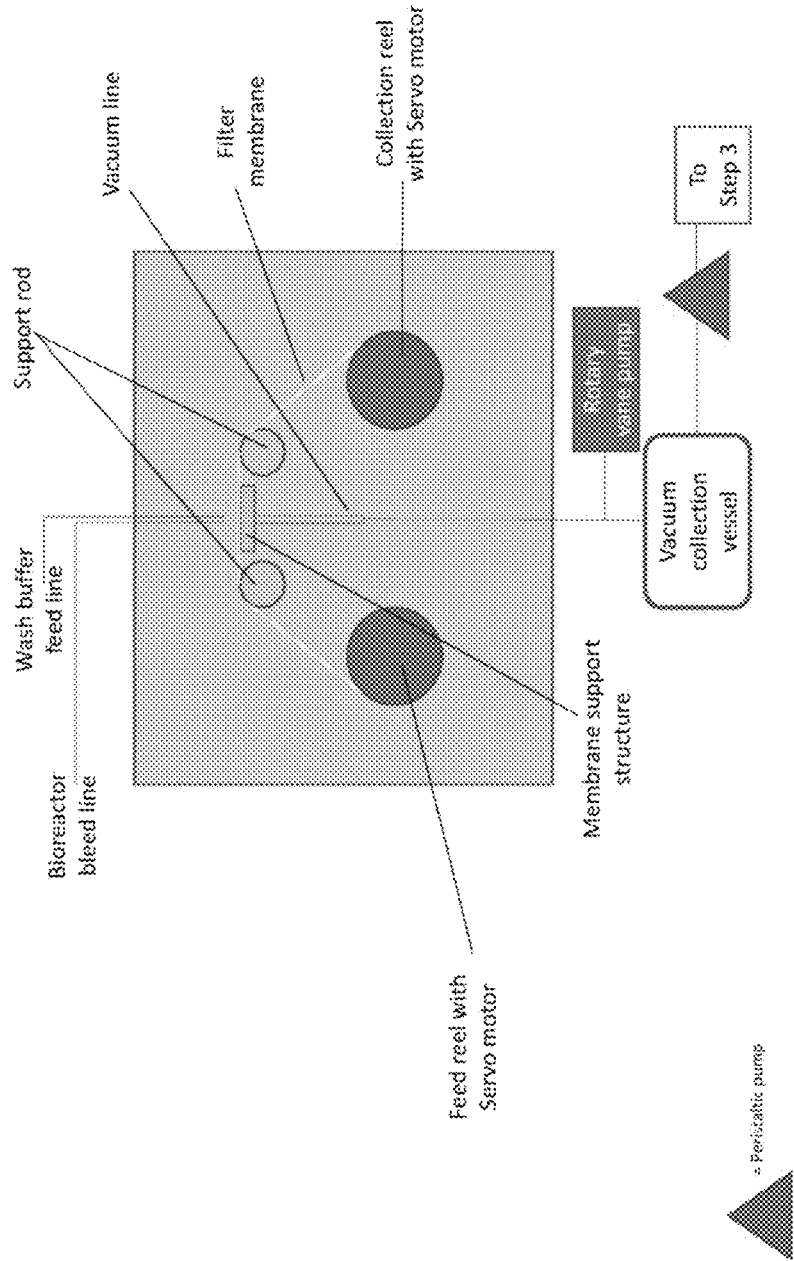

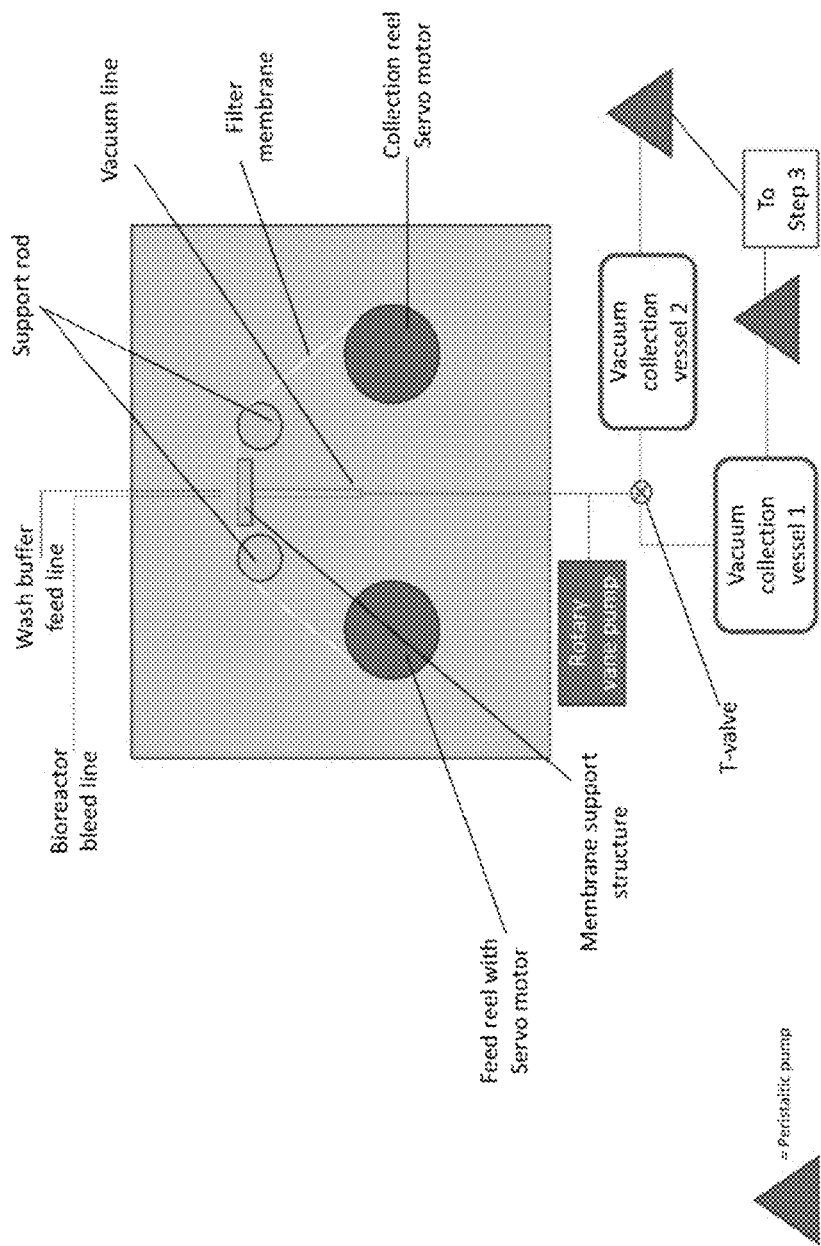

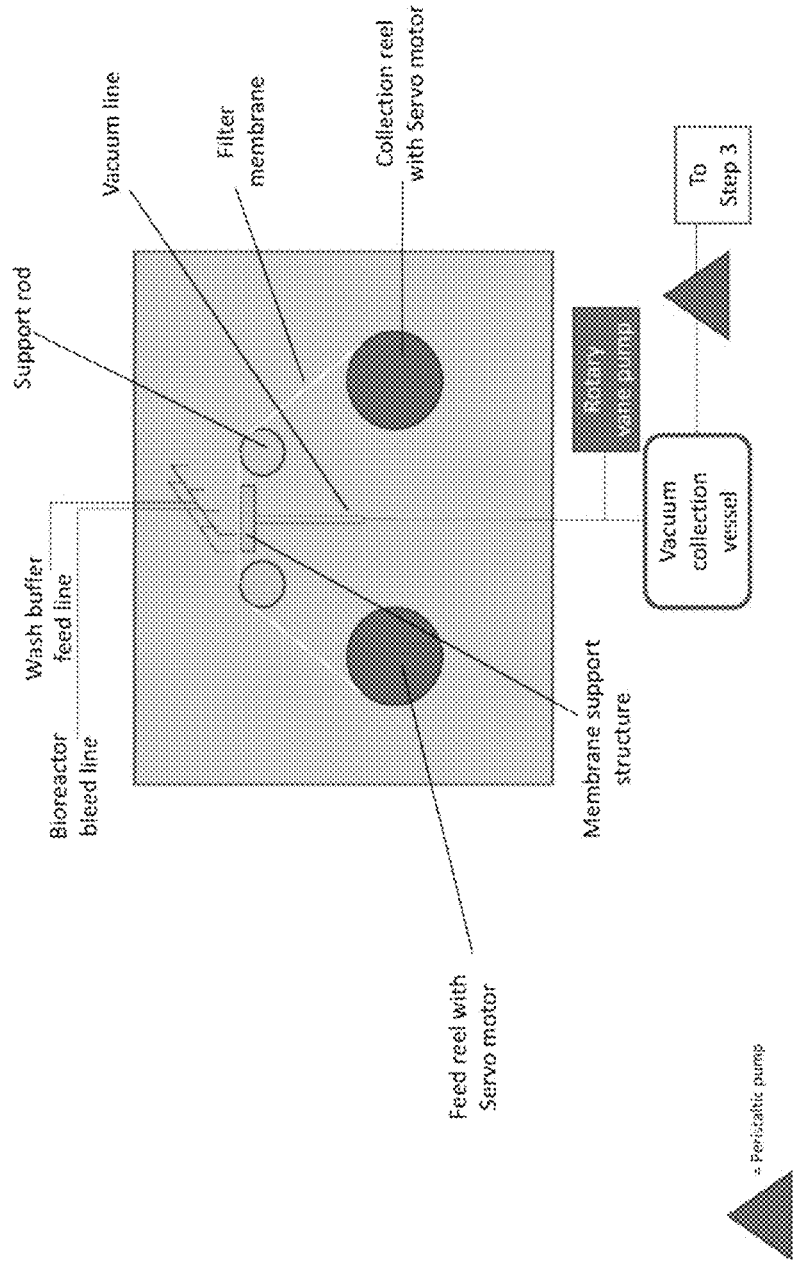

FIG. 8
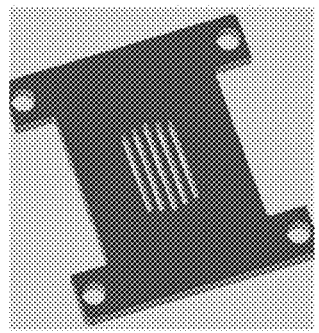
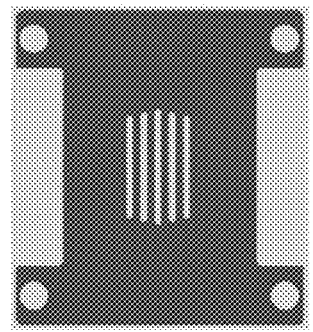

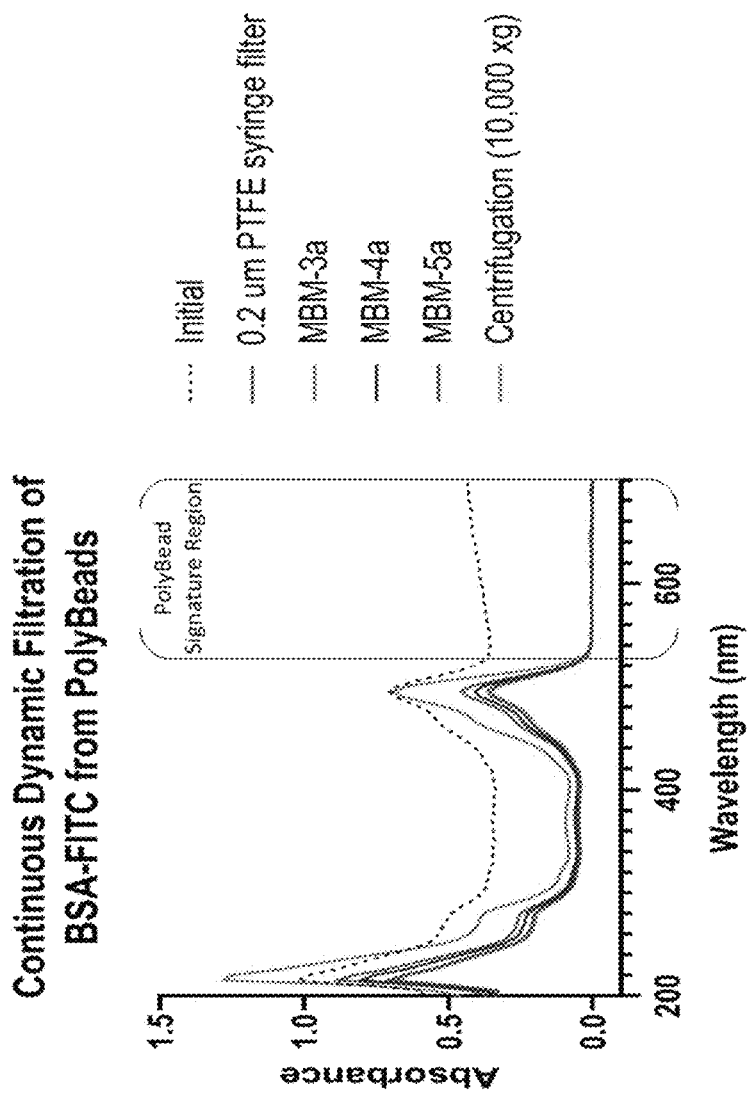

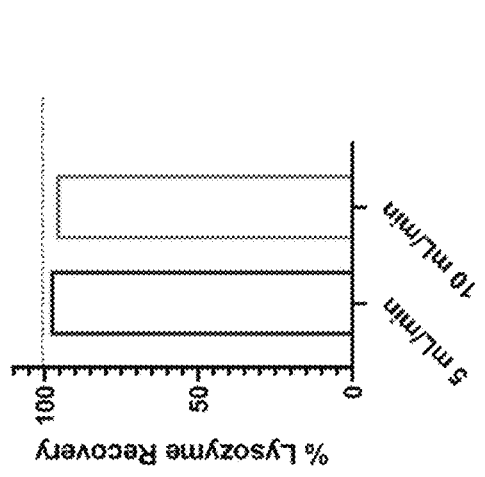
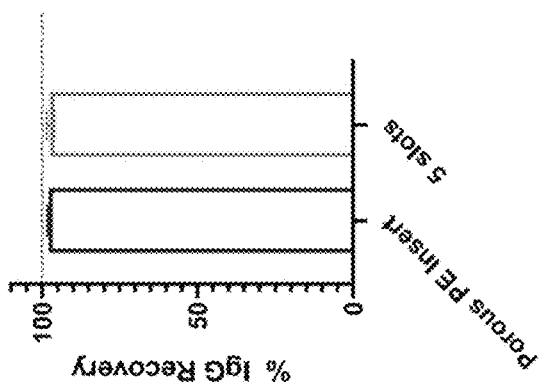
FIG. 12

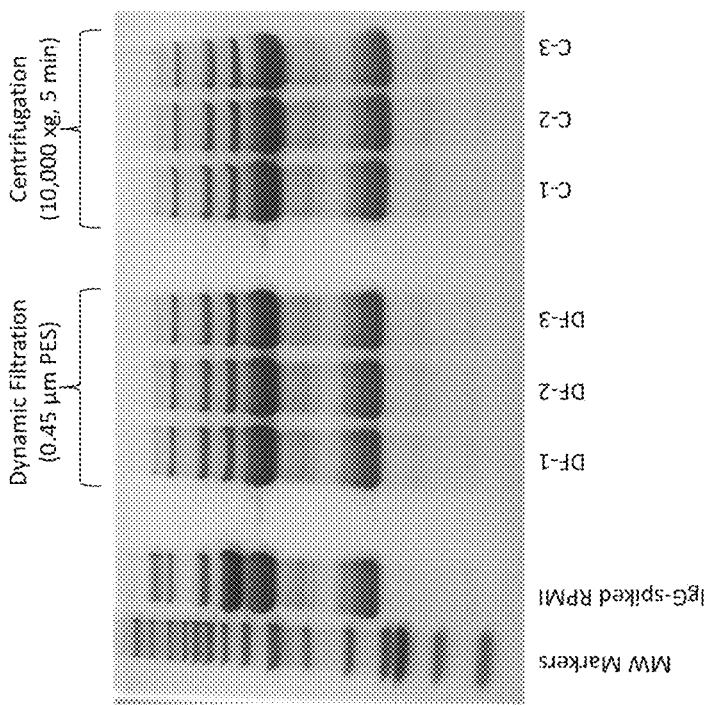
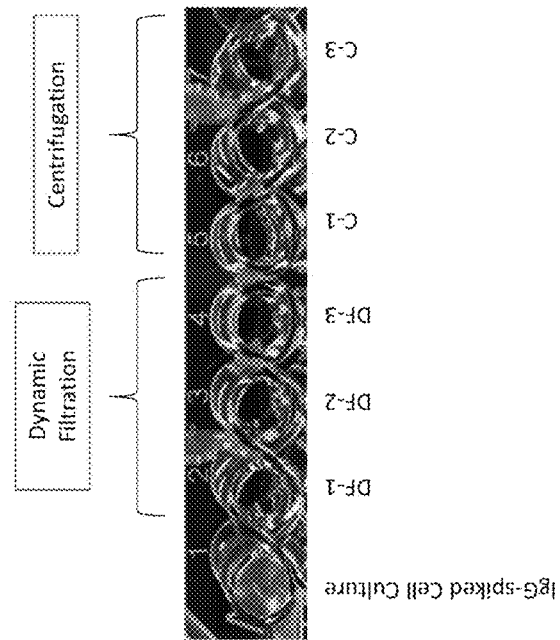
FIG. 13

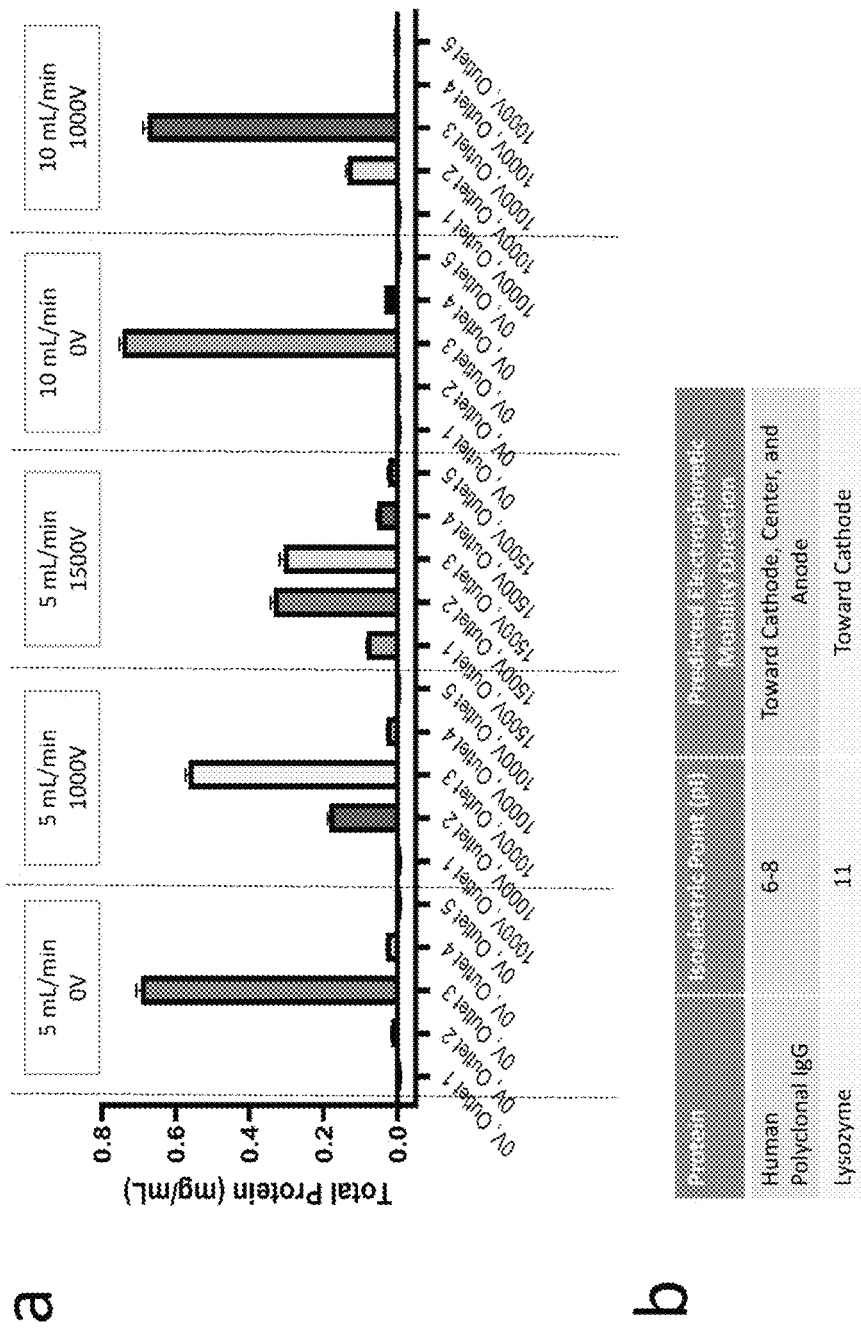

PROCESS TECHNOLOGY FOR BIOLOGICAL PRODUCT MANUFACTURING AND DOWNSTREAM PURIFICATION

RELATED APPLICATIONS

This application claims the benefit of priority under 35 U.S.C. § 119(e) to U.S. Provisional Application No. 63/077,766, filed on Sep. 14, 2020, Provisional Application No. 63/154,108, filed on Feb. 26, 2021, and Provisional Application No. 63/154,109, filed on Feb. 26, 2021, the entire contents of each of which is incorporated herein by reference in their entireties.

FIELD OF INVENTION

New processes and methods for manufacturing and downstream purification of biological products are provided.

BRIEF SUMMARY

Provided herein, inter alia, are processes and apparatuses for purifying a biological product. In aspects, provided herein is a process for purifying a biological product, where the process includes receiving, via an input line, a heterogeneous mixture containing the biological product, removing impurities from the heterogeneous mixture by filtration in a dynamic filtration module. Impurities are removed from the heterogeneous mixture by feeding the biological product from at least one output head in fluid communication with the input line to the dynamic filtration module under negative pressure, thereby producing a filtrate comprising the biological product.

The dynamic filtration module includes a dynamic filtration apparatus, a target region that is configured to receive the heterogeneous mixture from at least one output head, and a membrane support member with a substantially smooth contact surface that is in communication with a vacuum collection system that is positioned between the feed reel and the collection reel. Additionally dynamic filtration apparatus includes a filter membrane extending between a feed reel and a collection reel with at least one support member having a substantially smooth contact surface. Purifying the biological product further includes transferring the filtrate to a first module capable of separating the solution into two or more fractions, where at least one fraction contains the biological product; the first module includes an affinity-based purification apparatus. The affinity-based purification apparatus has at least one first inlet and at least one first outlet configured to permit fluid flow between the at least one first inlet and the at least one first outlet via a mechanical rotary system. The mechanical rotary system includes a vessel carousel containing at least one discrete vessel comprising a suspension of beads. As described herein, the process further includes transferring the fraction containing the biological product from the at least one outlet of the first module to a second module having at least one inlet for receiving flow from the at least one first outlet of the first module. The second module includes at least one free-flow electrophoresis apparatus, and the second module has at least one second inlet and at least one second outlet and is configured to permit continuous fluid flow between the second inlet and the second outlet; and thereby recovering the biological product.

In embodiments, the affinity-based purification apparatus further includes a lid system and a collection vessel system in fluid communication with the at least one discrete vessel. For example, the lid system has at least one lid having a gasket, at least two buffer inlets, a filling inlet, a gas inlet, and a venting valve. Moreover, the lid system is capable of motion along the z-axis. The vessel carousel of the affinity-based purification apparatus is capable of rotational motion in a plane transverse to the z-axis, and the collection vessel is capable of motion along the z-axis.

As described herein, the vessel carousel of the affinity-based purification method includes at least one position to bind the biological product, at least one position to wash to remove unbound products, at least one position to elute and collect the biological product, and at least one regeneration position to enable recycling of the beads.

In examples, the surface of the beads of the affinity-based purification is coupled to Protein A, Protein G, Protein L, an antigenic protein, a protein, a receptor, an antibody, or an aptamer configured to selectively bind said biological product. The initial concentration of the beads (e.g., in the discrete vessel at the position to bind the biological product) is in a concentration range from about 0.01% to about 25% by weight. Alternatively, the initial concentration of beads is in the range from about 0.01% to about 20%, or from about 0.01% to about 10%, or from about 0.01% to about 5%, or from about 1% to about 20%, or from about 5% to about 10% by weight). In examples, the beads have a diameter ranging from about 0.2 µm to about 200 µm. In other examples, the beads have a diameter from about 0.2 µm to about 100 µM, or from about 1 µm to about 200 µm, or from about 10 µm to about 200 µm, or from about 20 µm to about 200 µm, or from about 30 µm to about 200 µm, or from about 50 to about 200 µm, or from about 150 to about 200 µm. Alternatively, the beads have a diameter from about 1 µm to about 100 µm, or from about 50 µm to about 100 µm.

In embodiments, the beads (e.g., of the affinity-based purification) remain mobile during the process to maintain an increased surface area available for binding. For example, the beads remain separated (circulating or dispersed) in solution during the process (e.g., they are discrete beads). Moreover, the mobile beads may also mean that the beads do not aggregate together, e.g., at least two or more beads aggregated or grouped together. Additionally, the mobile beads may also mean that the beads may form small aggregates that remain dispersed and free to move within a solution. Conversely the beads used herein are not packed, but remain mobile, and free to move within a solution.

In embodiments, the free-flow electrophoresis apparatus includes electrode channels, including an anodic electrode channel and a cathodic electrode channel, having liquid contact with a main separation channel via a wall gap.

The free-flow electrophoresis apparatus has at least one electrode channel de-bubbler including at least one gas permeable and hydrophobic membrane configured to remove bubbles by a vacuum system creating a bubble-free main separation channel, and at least one liquid circuit breaker. In embodiments, the at least one de-bubbler of the free-flow electrophoresis apparatus is configured to continuously remove $O_2$ and $H_2$ gas bubbles that evolve in the electrode channels under applied voltage. In some embodiments, removal of electrolysis bubbles from the electrode channels is essential to enable continuous operation for substantially long periods of time. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar. Contrary to current methods, the process described herein removes gas bubbles prior to entering the main separation channel.

In embodiments, the liquid circuit breaker of the free-flow electrophoresis apparatus includes a pressurized vessel configured to maintain flow rate and creates droplets that break the circuit from the solution connected to voltage.

In embodiments, the purification process maintains approximately a constant flow rate in the dynamic filtration module, the first module, and the second module. For example, the flow rate ranges from about 0.1 mL/minute to about 50 mL/minute, or from about 5 mL/minute to about 10 mL/minute.

In embodiments, the process for purifying a biological product is performed at a temperature in the range of about 4° C. to about 37° C.

In further embodiments, the processes may include at least two dynamic filtration modules, where each dynamic filtration module has a filter membrane includes the same or different pore sizes (e.g., wherein the heterogeneous mixture contacts a larger pore size filter membrane first (e.g., 0.45 µm), followed by contact with a smaller pore size filter membrane next (e.g., 0.2 µm).

In embodiments, the process includes at least two free-flow electrophoresis modules configured to operate in an isoelectric focusing mode, a zone electrophoresis mode, an isotachophoresis mode, or combinations thereof. The processes described herein further includes at least two dynamic filtration modules, at least two affinity-based purification modules, or at least two free-flow electrophoresis modules operated in parallel.

In aspects, provided herein is a dynamic filtration apparatus for removing impurities from a biological product in a heterogeneous mixture. The apparatus includes a filter membrane extending between a feed reel and a collection reel, the filter membrane having a target region that is configured to receive the heterogeneous mixture from at least one output head configured to dispense the heterogeneous mixture onto the target region. The membrane support structure of the apparatus has a substantially smooth contact surface to structurally support a portion of the filter membrane that is positioned between the feed reel and the collection reel to create the target region. Moreover, the dynamic filtration apparatus has at least one support member with a substantially smooth contact surface to stabilize the transport of the filter membrane across the membrane support structure. The dynamic filtration apparatus has a system configured to control the transport velocity of the filter membrane. The dynamic filtration apparatus has a vacuum system having at least one vacuum line in communication with the membrane support structure and configured to apply negative gauge pressure across the dynamic filter membrane, where the negative pressure enables collection of the filtrate containing the biological product. In other examples, the dynamic filtration apparatus includes a wash buffer line.

In embodiments, the dynamic filtration apparatus has a filter membrane which may include polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), hydrophilic PTFE, or any combination thereof. The pore size of the filter membrane is in the range from about 0.1 µm to about 1 µm. In other examples, the pore size is in the range from about 0.1 to about 0.9 µm, or from about 0.1 µm to about 0.8 µm, or from about 0.1 µm to about 0.7 µm, or from about 0.1 µm to about 0.6 µm, or from about 0.1 µm to about 0.5 µm, or from about 0.1 µm to about 0.4 µm, or from about 0.1 µm to about 0.3 µm, or from about 0.1 µm to about 0.2 µm. As described herein, if two or more dynamic filtration apparatuses are used, they may include filter membranes of similar or different sizes.

The dynamic filtration apparatus described herein includes a membrane support structure that has a series of parallel slots, e.g., from about 1 to about 10 parallel slots. In specific examples, the membrane support structure has 5 parallel slots.

The dynamic filtration apparatus described herein includes a membrane support structure with a substantially smooth contact surface, where the contact surface is a measure of its static coefficient of friction, e.g., from about 0.01 to about 0.1, or from about 0.01 to about 0.05, or from about 0.05 to about 0.1. In specific examples, the static coefficient of friction is 0.04.

In embodiments, the vacuum system of the dynamic filtration module is configured to apply negative gauge pressure, e.g., in the range from about t−0.05 bar to about −0.98 bar.

In aspects, provided herein is a free-flow electrophoresis apparatus for separating a mixture into two or more fractions, at least one fraction containing a biological product. The free-flow electrophoresis apparatus includes at least one inlet and at least one outlet configured to permit continuous fluid flow between the at least one inlet and the at least one outlet; at least one fluidic channel created between two parallel plates and configured to create an electric field gradient orthogonal to the direction of fluid flow; electrode channels comprising an anodic electrode channel and a cathodic electrode channel, wherein the electrode channels are configured to be connected to the main separation channel by liquid contact through a wall gap positioned between the electrode channels and the main separation channel; at least one electrode channel de-bubbler comprising at least one gas permeable and hydrophobic membrane or porous material configured to remove electrolysis bubbles near the point of generation by a vacuum system to create a bubble-free main separation channel; at least one liquid circuit breaker configured to disconnect the solution connected to voltage prior to interacting with at least one sensor or detector; an active cooling system; and at least one collection vessel.

The free-flow electrophoresis apparatus described herein provides for an electrode channel having a de-bubbler wherein the top portion of the electrode channels are sealed with at least one gas permeable and hydrophobic membrane in communication with a vacuum system to remove bubbles, and wherein the electrode channels are open at the bottom of the channels and configured to enable liquid contact of electrode solution with the main separation channel solution through a wall gap.

The free-flow electrophoresis apparatus has at least one electrode channel de-bubbler including at least one gas permeable and hydrophobic membrane configured to remove bubbles by a vacuum system creating a bubble-free main separation channel, and at least one liquid circuit breaker.

In embodiments, the free-flow electrophoresis apparatus further comprises at least one de-bubbler system to continuously remove $O_2$ and $H_2$ gas bubbles that evolve in the electrode channels under applied voltage. In some embodiments, removal of electrolysis bubbles is essential to enable continuous operation for substantially long periods of time. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar. Contrary to current methods, the process described herein removes gas bubbles prior to entering the main separation channel.

In embodiments, the wall gap (e.g., the space where the electrode channels are open at the bottom of the channels and are configured to enable liquid contact of electrode solution with the main separation channel solution) is about 0.01 mm to about 0.25 mm. In examples, the wall gap is from about 0.01 mm to about 0.2 mm, or from about 0.01 mm to about 0.015 mm, or from about 0.01 mm to about 0.01 mm.

In other embodiments, the liquid circuit breaker of the free-flow electrophoresis apparatus includes a pressurized vessel configured to maintain flow rate and creates droplets that break the circuit from the solution connected to voltage.

In embodiments, the free-flow electrophoresis apparatus further includes an in-line sensor. In examples, the in-line sensor may include a flow sensor, a pH sensor, a conductivity sensor, or any combination thereof.

In embodiments, the free-flow electrophoresis apparatus described herein can include at least two free-flow electrophoresis apparatuses connected in series and operated in an isoelectric focusing mode, a zone electrophoresis mode, an isotachophoresis mode, or combinations thereof, to enable a staged purification.

Also provided herein, is the use of the free-flow electrophoresis apparatus to purify a biological product from a mixture. The disclosure further provides use of the dynamic filtration apparatus to purify a biological product from a heterogeneous mixture.

In aspects, provided herein is a process for purifying a biological product. The process comprises receiving, via an input line, a heterogeneous mixture containing the biological product. In embodiments, the process comprises continuously receiving, via an input line, a heterogeneous mixture containing the biological product. In embodiments, the biological product includes a protein or fragment thereof (a polypeptide), an antibody or fragment thereof, a cytokine, a chemokine, a growth factor, an enzyme, an oligonucleotide, a virus, an adenovirus, an adeno-associated virus (AAV), or a lentivirus.

In embodiments, the process includes removing impurities (e.g., large impurities such as cells, cell debris, and aggregates) from the heterogeneous mixture by dynamic filtration.

In some embodiments, the dynamic filtration process may be a continuous process for removing large impurities from a heterogeneous mixture. Said dynamic filtration process includes at least one dynamic filtration module that continuously feeds the heterogeneous mixture containing the biological product from at least one output head in fluid communication with the input line to the dynamic filtration module under negative pressure, thereby producing a filtrate comprising the biological product.

In embodiments, the process includes transferring the filtrate to a first module capable of separating the solution into two or more fractions, wherein at least one fraction contains the biological product. In other embodiments, the process includes continuously transferring the filtrate to a first module capable of separating the solution into two or more fractions, wherein at least one fraction contains the biological product. For example, separating the solution into two or more fractions, may include one fraction containing the biological product, and the at least one other fraction containing small impurities (e.g., host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

In embodiments, the first module comprises an affinity-based, magnetic purification apparatus. In examples, the first module has at least one first inlet and at least one first outlet and is configured to permit continuous fluid flow between the first inlet and the first outlet via a loop conveyor system. In other examples, the first module has at least one first inlet and at least one first outlet and is configured to permit continuous fluid flow between the first inlet and the first outlet via a pick and place robotics system.

In embodiments, the process includes transferring the fraction containing the biological product from the at least one first outlet of the first module to a second module having at least one inlet for receiving flow from the at least one first outlet of the first module, and the second module comprises a charge-based, magnetic purification apparatus or an isoelectric point-based, fluidic purification apparatus (also referred to herein as a free-flow electrophoresis apparatus). In other embodiments, the process includes continuously transferring the fraction containing the biological product from the at least one first outlet of the first module to a second module having at least one inlet for receiving flow from the at least one first outlet of the first module, and the second module comprises a charge-based, magnetic purification apparatus or an isoelectric point-based, fluidic purification apparatus, also referred to herein as a free-flow electrophoresis apparatus. In examples, the second module comprises a charge-based, magnetic purification apparatus having at least one second inlet and at least one second outlet and is configured to permit continuous fluid flow between the second inlet and the second outlet via a loop conveyor system. In some examples, the second module comprises a charge-based, magnetic purification apparatus having at least one second inlet and at least one second outlet and is configured to permit continuous fluid flow between the second inlet and the second outlet via a pick and place robotics system. In other examples, the second module comprises a free-flow electrophoresis apparatus having at least one second inlet and at least one second outlet and is configured to permit continuous fluid flow between the second inlet and the second outlet. In embodiments, the process described herein thereby purifies the biological product.

In embodiments, also provided herein is a process for purifying a biological product including continuously receiving, via an input line, a heterogeneous mixture containing the biological product, and removing large impurities from the heterogeneous mixture by dynamic filtration. In some embodiments, the dynamic filtration process may be a continuous process for removing large impurities from a heterogeneous mixture. Said dynamic filtration process includes a dynamic filtration module that continuously feeds the biological product from at least one output head in fluid communication with the input line to the dynamic filtration module under negative pressure, thereby producing a filtrate comprising the biological product.

In embodiments, the process includes transferring the filtrate to a first module capable of separating the solution into two or more, wherein at least one fraction contains the biological product. In other embodiments, the process includes continuously transferring the filtrate to a first module capable of separating the solution into two or more fractions, wherein at least one fraction contains the biological product. In examples, the first module includes an affinity-based purification apparatus. In examples, the first module has at least one first inlet and at least one first outlet and is configured to permit continuous fluid flow between the first inlet and the first outlet via a mechanical rotary system. In other examples, the first module has at least one first inlet and at least one first outlet and is configured to permit continuous fluid flow between the first inlet and the first outlet via a staged linear system.

In embodiments, the process includes transferring the fraction containing the biological product from the at least one first outlet of the first module to a second module having at least one inlet for receiving flow from the at least one first outlet of the first module, and the second module includes a charge-based purification apparatus or an isoelectric point-based, fluidic purification apparatus, also referred to herein as a free-flow electrophoresis apparatus. In other embodiments, the process includes continuously transferring the fraction containing the biological product from the at least one first outlet of the first module to a second module having at least one inlet for receiving flow from the at least one first outlet of the first module, and the second module includes a charge-based purification apparatus or an isoelectric point-based, fluidic purification apparatus, also referred to herein as a free-flow electrophoresis apparatus. In examples, the second module comprises a charge-based purification apparatus having at least one second inlet and at least one second outlet and is configured to permit continuous fluid flow between the second inlet and the second outlet via a mechanical rotary system. In some examples, the second module has at least one second inlet and at least one second outlet and is configured to permit continuous fluid flow between the second inlet and the second outlet via a staged linear system. In other examples, the second module comprises a free-flow electrophoresis apparatus having at least one second inlet and at least one second outlet and is configured to permit continuous fluid flow between the second inlet and the second outlet. In embodiments, the process described herein thereby purifies the biological product.

In embodiments, also provided herein is a process for purifying a biological product including continuously receiving, via an input line, a heterogeneous mixture containing the biological product, and removing large impurities from the heterogeneous mixture by dynamic filtration. In some embodiments, the dynamic filtration process may be a continuous process for removing large impurities from a heterogeneous mixture. Said dynamic filtration process includes a dynamic filtration module that continuously feeds the biological product from at least one output head in fluid communication with the input line to the dynamic filtration module under negative pressure, thereby producing a filtrate comprising the biological product.

In embodiments, the process includes transferring the filtrate to a first module capable of separating the solution into two or more fractions wherein at least one fraction contains the biological product. In other embodiments, the process includes continuously transferring the filtrate to a first module capable of separating the solution into two or more fractions, wherein at least one fraction contains the biological product. In embodiments, the first module includes an affinity-based, fluidic purification apparatus. In examples, the first module has at least one first inlet and at least one first outlet and is configured to permit continuous fluid flow between the first inlet and the first outlet.

In embodiments, the process includes transferring the fraction containing the biological product from the at least one first outlet of the first module to a second module having at least one inlet for receiving flow from the at least one first outlet of the first module, and the second module includes a charge-based, fluidic purification apparatus or an isoelectric point-based, fluidic purification apparatus, also referred to herein as a free-flow electrophoresis apparatus. In embodiments, the process includes continuously transferring the fraction containing the biological product from the at least one first outlet of the first module to a second module having at least one inlet for receiving flow from the at least one first outlet of the first module, and the second module includes a charge-based, fluidic purification apparatus or an isoelectric point-based, fluidic purification apparatus, also referred to herein as a free-flow electrophoresis apparatus. In examples, the second module comprises a charge-based, fluidic purification apparatus having at least one second inlet and at least one second outlet and is configured to permit continuous fluid flow between the second inlet and the second outlet. In other examples, the second module comprises a free-flow electrophoresis apparatus having at least one second inlet and at least one second outlet and is configured to permit continuous fluid flow between the second inlet and the second outlet. In embodiments, the process described herein thereby purifies the biological product.

In embodiments, the process includes transferring the filtrate to a first module capable of separating the solution into two or more fractions, wherein at least one fraction contains the biological product. In other embodiments, the process includes continuously transferring the filtrate to a first module capable of separating the solution into two or more fractions, wherein at least one fraction contains the biological product. In embodiments, the first module comprises an affinity-based tangential flow filtration (TFF) purification apparatus. In examples, the first module has at least one first inlet and at least one first outlet and is configured to permit continuous fluid flow between the first inlet and the first outlet.

In embodiments, the process includes transferring the fraction containing the biological product from the at least one first outlet of the first module to a second module having at least one inlet for receiving flow from the at least one first outlet of the first module, and the second module comprises a charge-based TFF purification apparatus or an isoelectric point-based, fluidic purification apparatus, also referred to herein as a free-flow electrophoresis apparatus. In other embodiments, the process includes continuously transferring the fraction containing the biological product from the at least one first outlet of the first module to a second module having at least one inlet for receiving flow from the at least one first outlet of the first module, and the second module comprises a charge-based TFF purification apparatus or an isoelectric point-based, fluidic purification apparatus, also referred to herein as a free-flow electrophoresis apparatus. In examples, the second module comprises a charge-based TFF purification apparatus having at least one second inlet and at least one second outlet and is configured to permit continuous fluid flow between the second inlet and the second outlet. In other examples, the second module comprises a free-flow electrophoresis apparatus having at least one second inlet and at least one second outlet and is configured to permit continuous fluid flow between the second inlet and the second outlet. In embodiments, the process described herein thereby purifies the biological product.

As described herein, the process of removing large impurities from the heterogeneous mixture does not include centrifugation, disk-stack centrifugation, depth filtration, static filtration, tangential flow filtration, or any combination thereof. Alternatively, the process described herein may receive a heterogeneous mixture containing a biological product via an input line derived from any large impurity removal input, for example, without intent to be limiting, a centrifuge and depth filtration process.

As described herein, the process of continuously removing large impurities from the heterogeneous mixture does not include centrifugation, disk-stack centrifugation, depth filtration, static filtration, tangential flow filtration, a hydrocyclone or any combination thereof. Alternatively, the process described herein may continuously receive a heterogeneous mixture containing a biological product via an input line derived from any continuous large impurity removal input, for example, without intent to be limiting, a continuous, disk-stack centrifuge and depth filtration process or a hydrocyclone process.

In embodiments, the process described herein includes purifying a biological product (e.g. a monoclonal antibody) that is produced in a bioreactor. In some embodiments, the process described herein includes purifying a biological product that is continuously produced in a bioreactor. For example, the bioreactor includes a bioreactor feed line and an output bleed line to enable steady-state cell culture growth conditions, and the output bleed line functions as the input line to permit continuous fluid flow from the bioreactor to the dynamic filtration module. In examples, the bioreactor type includes, but is not limited to, a fed-batch bioreactor, a perfusion bioreactor, a chemostat bioreactor, or a multi-compartment bioreactor. For example, the flow from the bioreactor bleed line is always feeding the downstream purification system. Alternatively, the process described herein includes purifying a biological product (e.g. mRNA) that is not produced in a bioreactor.

In embodiments, provided herein is a process for purifying a biological product, the method including receiving, via an input line, a heterogeneous mixture containing the biological product, removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based, magnetic purification apparatus, and wherein the first module has at least one first inlet and at least one first outlet and is configured to permit fluid flow between the first inlet and the first outlet via a loop conveyor system or a pick and place robotics system; transferring the fraction containing the biological product from the at least one first outlet of the first module to a second module having at least one inlet for receiving flow from the at least one first outlet of the first module, wherein the second module comprises a charge-based, magnetic purification apparatus, and wherein the second module has at least one second inlet and the at least one second outlet and is configured to permit continuous fluid flow between the second inlet and the second outlet via a loop conveyor system or a pick and place robotics system; and thereby purifying the biological product.

In other embodiments, a process for purifying a biological product is provided. The method includes, receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based, magnetic purification apparatus, and wherein the first module has at least one first inlet and at least one first outlet and is configured to permit fluid flow between the first inlet and the first outlet via a loop conveyor system or a pick and place robotics system; transferring the fraction containing the biological product from the at least one first outlet of the first module to a second module having at least one inlet for receiving flow from the at least one first outlet of the first module, wherein the second module comprises an isoelectric point-based fluidic purification apparatus, also referred to herein as a free-flow electrophoresis apparatus, and wherein the second module has at least one second inlet and at least one second outlet and is configured to permit continuous fluid flow between the second inlet and the second outlet; and thereby purifying the biological product.

In embodiments, a process for purifying a biological product is included, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based purification apparatus, and wherein the first module has at least one first inlet and at least one first outlet and is configured to permit fluid flow between the first inlet and the first outlet via a mechanical rotary system; transferring the fraction containing the biological product from the at least one first outlet of the first module to a second module having at least one inlet for receiving flow from the at least one first outlet of the first module, wherein the second module comprises a charge-based purification apparatus, and wherein the second module has at least one second inlet and at least one second outlet and is configured to permit fluid flow between the second inlet and the second outlet via a mechanical rotary system; and thereby purifying the biological product.

In other embodiments, a process for purifying a biological product, is provided, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based purification apparatus, and wherein the first module has at least one first inlet and at least one first outlet and is configured to permit fluid flow between the first inlet and the first outlet via a mechanical rotary system; transferring the fraction containing the biological product from the at least one first outlet of the first module to a second module having at least one inlet for receiving flow from the at least one first outlet of the first module, wherein the second module comprises an isoelectric point-based fluidic purification apparatus, also referred to herein as a free-flow electrophoresis apparatus, and wherein the second module has at least one second inlet and at least one second outlet and is configured to permit continuous fluid flow between the second inlet and the second outlet; and thereby purifying the biological product.

In embodiments, a process for purifying a biological product is included, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based purification apparatus, and wherein the first module has at least one first inlet and at least one first outlet and is configured to permit fluid flow between the first inlet and the first outlet via a staged linear system; transferring the fraction containing the biological product from the at least one first outlet of the first module to a second module having at least one inlet for receiving flow from the at least one first outlet of the first module, wherein the second module comprises a charge-based purification apparatus, and wherein the second module has at least one second inlet and at least one second outlet and is configured to permit fluid flow between the second inlet and the second outlet via a staged linear system; and thereby purifying the biological product.

In other embodiments, a process for purifying a biological product, is provided, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based purification apparatus, and wherein the first module has at least one first inlet and at least one first outlet and is configured to permit fluid flow between the first inlet and the first outlet via a staged linear system; transferring the fraction containing the biological product from the at least one first outlet of the first module to a second module having at least one inlet for receiving flow from the at least one first outlet of the first module, wherein the second module comprises an isoelectric point-based fluidic purification apparatus, also referred to herein as a free-flow electrophoresis apparatus, and wherein the second module has at least one second inlet and at least one second outlet and is configured to permit continuous fluid flow between the second inlet and the second outlet; and thereby purifying the biological product.

In embodiments, a process for purifying a biological product is included, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based, fluidic purification apparatus, and wherein the first module has at least one first inlet and at least one first outlet and is configured to permit fluid flow between the first inlet and the first outlet; transferring the fraction containing the biological product from the at least one first outlet of the first module to a second module having at least one inlet for receiving flow from the at least one first outlet of the first module, wherein the second module comprises a charge-based, fluidic purification apparatus, and wherein the second module has at least one second inlet and at least one second outlet and is configured to permit fluid flow between the second inlet and the second outlet; and thereby purifying the biological product.

In other embodiments, a process for purifying a biological product, is provided, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based, fluidic purification apparatus, and wherein the first module has at least one first inlet and at least one first outlet and is configured to permit fluid flow between the first inlet and the first outlet; transferring the fraction containing the biological product from the at least one first outlet of the first module to a second module having at least one inlet for receiving flow from the at least one first outlet of the first module, wherein the second module comprises an isoelectric point-based fluidic purification apparatus, also referred to herein as a free-flow electrophoresis apparatus, and wherein the second module has at least one second inlet and at least one second outlet and is configured to permit continuous fluid flow between the second inlet and the second outlet; and thereby purifying the biological product.

In embodiments, a process for purifying a biological product is included, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based TFF purification apparatus, and wherein the first module has at least one first inlet and at least one first outlet and is configured to permit fluid flow between the first inlet and the first outlet; transferring the fraction containing the biological product from the at least one first outlet of the first module to a second module having at least one inlet for receiving flow from the at least one first outlet of the first module, wherein the second module comprises a charge-based TFF purification apparatus, and wherein the second module has at least one second inlet and at least one second outlet and is configured to permit fluid flow between the second inlet and the second outlet; and thereby purifying the biological product.

In other embodiments, a process for purifying a biological product, is provided, the method including receiving, via an input line, a heterogeneous mixture containing the biological product; removing impurities from the heterogeneous mixture by dynamic filtration in a dynamic filtration module by feeding the biological product from at least one output head in fluid communication with the input line to the dynamic filtration module under negative pressure, thereby producing a filtrate comprising the biological product; transferring the filtrate to a first module capable of separating the solution into two or more fractions comprising at least one fraction containing the biological product, wherein the first module comprises an affinity-based TFF purification apparatus, and wherein the first module has at least one first inlet and at least one first outlet and is configured to permit fluid flow between the first inlet and the first outlet; transferring the fraction containing the biological product from the at least one first outlet of the first module to a second module having at least one inlet for receiving flow from the at least one first outlet of the first module, wherein the second module comprises an isoelectric point-based fluidic purification apparatus, also referred to herein as a free-flow electrophoresis apparatus, and wherein the second module has at least one second inlet and at least one second outlet and is configured to permit continuous fluid flow between the second inlet and the second outlet; and thereby purifying the biological product.

Advantages of the process and methods described herein include the ability to remove large impurities (e.g., cells, cell debris, and aggregates) without membrane fouling or occlusion. For example, it is known in the art that clarification of cells, cell debris and aggregates from cell culture media with traditional filtration or tangential flow filtration systems typically leads to fouling or occlusion of the filter membrane, thus rendering these methodologies unsuitable as a means to continuously remove large impurities from a heterogeneous mixture containing a biological product over long-term continuous processing. In contrast, the dynamic filtration apparatus described herein enables continuous removal of large impurities from a heterogeneous mixture containing a biological product without membrane fouling, as the active target region of the filter membrane is constantly being refreshed.

Additionally, because the entire process of producing and purifying the biological product may be continuous and can maintain a flow rate that ranges from about 0.1 mL/minute to about 50 mL/minute across the entirety of the process, the process equipment and overall process footprint is able to have a significantly smaller footprint than current standard processes, without sacrificing product throughput or yield on a kilogram/year basis. For example, the process for producing and purifying a monoclonal antibody as described herein is operated with a footprint that occupies up to about 30,000 square feet. In contrast, current mononclonal antibody production and downsteam processes require at least 200,000 square feet. In examples, the process of purifying the biological product has a flow rate that ranges from about 1 mL/minute to about 10 mL/minute. In some examples, the flow rate of the step of continuously removing large impurities from the heterogeneous mixture ranges from about 0.1 mL/minute to about 50 mL/minute. In other examples, the flow rate of the step of continuously removing large impurities from the heterogeneous mixture is equivalent to the flow rate from the bioreactor bleed line. In other examples, the process provides that the flow rate of the step of continuously transferring the filtrate to a first module ranges from about 0.1 mL/minute to about 50 mL/minute. In yet other examples, the process provides that the flow rate of the step of continuously transferring the fraction containing the biological product from the first outlet to a second module ranges from about 0.1 mL/minute to about 50 mL/minute.

An important advantage of the process and methods utilizing magnetic resin beads (e.g. magnetic agarose) or traditional resin beads (e.g. agarose) described herein includes that these systems do not require traditional stationary phase or packed resin columns (e.g., for standard chromatographies) to be sanitized, recycled and/or regenerated. For example, these systems provide for recycling and/or regeneration of the resin beads (e.g., magnetic or non-magnetic resin beads) to create a limitless surface area of the resin beads during operation, and in turn provides a continuous and cost-effective method.

Put in another way, the modules described herein do not have a fixed binding or association capacity. In specific examples, the resin beads used during purification of the biological product, as described herein, are constantly being recycled and regenerated, and therefore able to accept flow from the previous step, either a dynamic filtration module or a purification module, without interruption of the flow from the bioreactor bleed line. Put another way, the modules described in the present invention do not have to be left idle in order to be sanitized, regenerated and/or recycled after running, as they are continuously undergoing these steps. The method differs from current continuous chromatographic methods, in that current methods have defined column capacity limitations due to resin packing constraints and thus require column switching of multiple packed columns to accept continuous input flow and enable regeneration and/or recycling of the columns that have reached full capacity.

Another advantage of the methods described herein includes that the resin beads are not packed into a stationary phase, rather the resin beads have mobility. This mobility of the beads increases their surface area that is available for binding or association, as substantially more of the resin bead surface is exposed and free to bind, e.g., more biological product can bind to the beads. Additionally, the resin beads in a traditionally packed column (e.g., where the beads lack mobility, have decreased surface area) and are exposed to a high pressure differential in order to generate flow through the column. This high pressure differential damages the integrity of the beads, thereby decreasing the column lifetime. The mobile resin beads in the presently described invention are subjected to substantially lower pressures which is much gentler on the fragile beads, resulting in longer lifetimes. Additionally, this mobility makes the beads more likely to be regenerated (e.g., fully regenerated) and returned to their initial condition. This further adds to the cost-effectiveness of the methods described herein, e.g., as the resin is utilized more efficiently.

As described herein, the resin beads of the claimed methods and apparatuses are mobile throughout the process. Traditional chromatographic purification methods require column packing, e.g., where beads are sufficiently packed together resulting in a stationary phase and high density. For example, the beads remain separated (circulating or dispersed) in solution during the process (e.g., they are discrete beads). Moreover, the mobile beads may also mean that the beads do not aggregate together, e.g., at least two or more beads aggregated or grouped together. Additionally, the mobile beads may also mean that the beads may form small aggregates that remain dispersed and free to move within a solution. Conversely the beads used herein are not packed, but remain mobile, and free to move within a solution.

An important advantage of the process and methods utilizing free-flow electrophoresis described herein includes that this system represents a "no product loss" process, in that, there is no need for the product to interact with a resin or other purifying moieties, as the separation occurs in aqueous solution according to the physicochemical properties of the target biological product via interaction with an electric field. Another advantage is observed in the resolving power (e.g., the ability purify products having a high degree of physicochemical similarity) of this approach, as a higher purity product is achievable when compared to traditional ion-exchange chromatographies. For example, using the free-flow electrophoresis module and method herein may achieve purities of at least about 90%, 91%, 92%, 93%, 94%, 95%, 96%, 97%, 98%, 99% or greater of the biological product. Moreover, the methods and apparatuses described herein can result in an increased purity (of the biological product), relative to traditional purification and chromatographic methods. For example, the term "increased" with respect to a level refers to any % increase above a control level (e.g., a level of purity resulting from purification using traditional methods). In various embodiments, the increased level may be at least or about a 1%, 2%, 3%, 4%, or 5% increase in purity, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to traditional purification methods. In other examples of the disclosure, the purity of the biological product resulting from the methods and apparatuses described herein is increased by about 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, or 3.0×, compared to the purity of a biological product using standard commercial or chromatographic techniques.

Additionally, the separation based on intrinsic physicochemical properties of the biological product (e.g., isoelectric point, surface charge, net charge, zeta potential, electrophoretic mobility, electrostatic interactions, etc. . . . ) extends the utility of this approach for the purification a plethora of biological products, including, but not limited to, a protein or fragment thereof (a polypeptide), an antibody or fragment thereof, a cytokine, a chemokine, a growth factor, an enzyme, an oligonucleotide, a virus, an adenovirus, an adeno-associated virus (AAV), or a lentivirus.

Further, the modular approach affords flexibility in process design to accommodate a diverse range of biological products.

In embodiments, in the process described herein, during the purification by dynamic filtration, filtrate comprising the biological product is created and fed under negative pressure into a vacuum collection vessel capable of collecting from about 50 mL to about 100 L. In examples, the vacuum collection vessel capable of collecting the filtrate is from about 1 L to about 10 L. In other examples, the vacuum collection vessel capable of collecting the filtrate is from about 1 L to about 50 L.

In embodiments, the dynamic filtration module includes at least one output head for modulating flow of the heterogeneous mixture and dispensing the heterogeneous mixture onto the active target region of the filter membrane. In examples, the at least one output head is a tube or a slot die.

In embodiments, the at least one dynamic filtration module may further include at least one additional input line to supply a wash buffer via a coaxial output head, a separate monoaxial output head, a separate slot die output head, a slot die output head with multiple openings, or any combination thereof.

In some embodiments, the dynamic filtration module includes elements known to those skilled in the art, for example, without intent to be limiting, active or passive edge guides, tension control (e.g. a dancer), break and tension detectors, or any combination thereof.

In embodiments, the process herein includes that the at least one output head (in fluid communication with the input line to the dynamic filtration module) is capable of xy rastering or rθ rastering. In examples, the at least one output head is capable of xy rastering. In some examples, the at least one output head is capable of rθ rastering. In other examples, the at least one output head is capable of motion along the z-axis. In yet other examples, the at least one output head is capable of xy rastering and motion along the z-axis.

In embodiments, the dynamic filtration module includes a filter membrane roll, a membrane support structure, at least one support rod or roller, at least one vacuum line, a vacuum system, and at least one vacuum collection vessel.

In embodiments, the filter membrane roll includes a rolled filter membrane, wherein the filter membrane includes, but is not limited to, polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), hydrophilic PTFE, or any combination thereof.

In embodiments, the pore size of the rolled filter membrane depends on the biological product being purified. In examples, the rolled filter membrane has a pore size in the range from 0.1 µm to 1 µm. Alternatively, the pore size is in the range from about 0.2 µm to about 0.45 µm, or the pore size is less than about 0.45 µm. In other examples, when purifying an antibody, the pore size of the rolled filter membrane is in the range of 0.2 µm to about 0.45 µm.

In embodiments, the filter membrane roll has a width from about 10 mm to about 600 mm. The width of the filter membrane roll, for example, may depend on the size of the dynamic filtration system, the size of the at least one output head, or the membrane support structure.

In embodiments, the filter membrane roll further functions as a feed reel that communicates with a collection reel, meaning the filter membrane originates from the pre-fabricated roll and spans to an initially empty collecting roll, thus creating a reel-to-reel system.

In embodiments, the membrane support structure of the dynamic filtration module includes a mechanically smooth contact surface derived from a material having a low static coefficient of friction (e.g. polytetrafluoroethylene (PTFE)) and an opening that has continuity with the vacuum line. For example, the static coefficient of friction ranges from about 0.01 to about 0.1, or from about 0.01 to about 0.05, or from about 0.05 to about 0.1. In examples, the membrane support structure of the dynamic filtration module includes an opening. The opening, for example, may include a mesh, at least one slot, at least one hole, a frit, a porous material, or any combination thereof.

In embodiments, the membrane support structure of the dynamic filtration module includes a temperature control mechanism. The temperature control mechanism maintains a temperature from 4° C. to 37° C. For example, during purification of an antibody, the temperature control mechanism maintains a temperature from 15° C. to 37° C. Exemplary temperature control mechanisms include, but are not limited to, single loop controllers, multi-loop controllers, closed loop controllers, proportional-integral-derivative (PID) controllers, Peltier devices, resistive heating elements, and/or thermal chucks with circulating water/propylene glycol jackets.

In embodiments, the at least one support rod or roller of the dynamic filtration module has a mechanically smooth contact surface derived from a material having a low static coefficient of friction (e.g. PTFE, perfluoroalkoxy alkane (PFA)). For example, the static coefficient of friction ranges from about 0.01 to about 0.1, or from about 0.01 to about 0.05, or from about 0.05 to about 0.1. In examples, the support rod or roller may be stationary or may rotate. In some examples, the support rod may further include a bearing, for example, a sleeve bearing.

In embodiments, the vacuum system of the dynamic filtration module maintains a gauge pressure of about −0.05 bar to about −0.98 bar.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 µm) in fluid communication with at least one second dynamic filtration apparatus having a rolled filter membrane with a small pore size (e.g., 0.2 µm), thereby producing a filtrate comprising the biological product. Alternatively, a similar result could be achieved by a single dynamic filtration apparatus having at least two rolled filter membranes being fed by separate feed reels, resulting in a layered set of filter membranes across the target region (e.g., active target region), wherein the heterogeneous mixture contacts a larger pore size filter membrane first (e.g., 0.45 µm), followed by contact with a smaller pore size filter membrane next (e.g., 0.2 µm).

In embodiments, the process described herein includes continuously transferring the filtrate to a first module capable of separating the solution into two or more fractions comprising at least one fraction containing the biological product, and the first module includes an affinity-based, magnetic purification apparatus. For example, the affinity-based, magnetic purification apparatus further includes a suspension of magnetic resin beads. The surface of the magnetic resin beads, for example, without intent to be limiting, is coupled with Protein A, Protein G, Protein L, an antigenic protein, a protein, a receptor, an antibody, or an aptamer. In examples, the magnetic resin beads may be paramagnetic or superparamagnetic.

In examples, the magnetic resin beads of the affinity-based, magnetic purification apparatus have a diameter of about 0.2 micron to about 200 micron. In other examples, the beads have a diameter from about 0.2 µm to about 100 µM, or from about 1 µm to about 200 µm, or from about 10 µm to about 200 µm, or from about 20 µm to about 200 µm, or from about 30 µm to about 200 µm, or from about 50 to about 200 µm, or from about 150 to about 200 µm. Alternatively, the beads have a diameter from about 1 µm to about 100 µm, or from about 50 µm to about 100 µm. The diameter of the magnetic resin beads may depend on the biological product being purified and the overall flow rate of the process. For example, purification of a monoclonal antibody may include magnetic resin beads that are about 40 to about 90 microns in size. Moreover, the magnetic resin beads may have a concentration ranging from about 0.01% to about 25% by weight. For example, the concentration of the magnetic resin beads may be about 1% by weight. In some examples, purification of a monoclonal antibody may include magnetic resin beads that have a concentration of about 1% to about 10% by weight. In other examples, the binding capacity of the magnetic resin beads is a function of the bead concentration, surface area-to-volume ratio, affinity ligand density, or any combination thereof. In yet other examples, the magnetic resin beads may be solid, porous, nanoporous, microporous, or any combination thereof.

In embodiments, the process described herein includes continuously transferring the fraction containing the biological product from the at least one first outlet of the first module to a second module, and where the second module includes a charge-based, magnetic purification apparatus (e.g., a positive and/or negative charge-based, magnetic purification apparatus), the charge-based, magnetic purification apparatus further comprising magnetic resin beads. For example, the surface of the magnetic resin beads may have cationic functionality, derived from the coupling of positively charged functional groups, to enable purification based on charge or electrostatic interactions. For example, the positively charged functional groups include amines, cationic polymers, net positively charged peptides, net positively charged proteins, or any combination thereof. Alternatively, the surface of the magnetic resin beads may have anionic functionality, derived from the coupling of negatively charged functional groups, to enable purification based on charge or electrostatic interactions. For example, the negatively charged functional groups include carboxyls, anionic polymers, net negatively charged peptides, net negatively charged proteins, oligonucleotides, or any combination thereof. In examples, the magnetic resin beads may be paramagnetic or superparamagnetic.

In embodiments, the magnetic resin beads of the charged-based, magnetic purification apparatus have a diameter of about 0.2 micron to about 200 micron. The diameter of the magnetic resin beads may depend on the biological product being purified and the overall flow rate of the process. For example, purification of a monoclonal antibody may include magnetic resin beads that are about 40 to about 90 microns in size. Moreover, the magnetic resin beads may have a concentration ranging from about 0.01% to about 25% by weight. For example, the concentration of the magnetic resin beads may be about 1% by weight. In some examples, purification of a monoclonal antibody may include magnetic resin beads that have a concentration of about 1% to about 10% by weight. In other examples, the charge or electrostatic association capacity of the magnetic resin beads is a function of the bead concentration, surface area-to-volume ratio, surface charge density, net charge, or any combination thereof. In yet other examples, the magnetic resin beads may be solid, porous, nanoporous, microporous, or any combination thereof.

In embodiments, as described herein, one or both of the first (affinity-based, magnetic purification) and/or second (charged-based, magnetic purification, including a positive and/or negative charged-based, magnetic purification apparatus) module(s) may also include at least one external magnetic field. For example, the at least one external magnetic field includes a permanent magnet or an electromagnet.

The at least one external magnetic field includes a magnetic field strength of about 0.01 Tesla to about 1 Tesla (e.g., up to 1 Tesla). Alternatively, the at least one external magnetic field is shielded.

In embodiments, the loop conveyor system has at least two transport vessels charged with magnetic resin beads that are configured to continuously receive a mixture containing a biological product and subsequently transport the resulting heterogeneous mixture containing a biological product, magnetic resin beads, a buffer, or any combination thereof. For example, at least one of the at least two transport vessels is positioned in or within close proximity of an external magnetic field to attract the magnetic resin beads.

In embodiments, the pick and place robotics system has at least two transport vessels charged with magnetic resin beads that are configured to continuously receive a mixture containing a biological product and subsequently transport the resulting heterogeneous mixture containing a biological product, magnetic resin beads, a buffer, or any combination thereof. For example, at least one of the at least two transport vessels is placed in or within close proximity of an external magnetic field to attract the magnetic resin beads.

In embodiments, the first (affinity-based, magnetic purification) and/or the second (charge-based, magnetic purification, including a positive and/or negative charged-based, magnetic purification apparatus) module further includes at least one tangential flow filtration system operated in fed-batch or perfusion mode. In examples, the tangential flow filtration system may be used to concentrate and buffer exchange the fraction containing the biological product.

In embodiments, the process described herein includes continuously transferring the filtrate to a first module capable of separating the solution into two or more fractions comprising at least one fraction containing the biological product, and the first module includes an affinity-based purification apparatus. For example, the affinity-based purification apparatus further includes a suspension of resin beads. The surface of the resin beads, for example, without intent to be limiting, is coupled with Protein A, Protein G, Protein L, an antigenic protein, a protein, a receptor, an antibody, or an aptamer.

In examples, the resin beads of the affinity-based purification apparatus have a diameter of about 0.2 micron to about 200 micron. The diameter of the resin beads may depend on the biological product being purified and the overall flow rate of the process. For example, purification of a monoclonal antibody may include resin beads that are about 90 microns in size. Moreover, the resin beads may have a concentration ranging from about 0.01% to about 25% by weight. For example, the concentration of the resin beads may be about 1% by weight. In some examples, purification of a monoclonal antibody may include resin beads that have a concentration of about 1% to about 10% by weight. In other examples, the binding capacity of the resin beads is a function of the bead concentration, surface area-to-volume ratio, affinity ligand density, or any combination thereof.

In yet other examples, the resin beads may be solid, porous, nanoporous, microporous, or any combination thereof.

In embodiments, the process described herein includes continuously transferring the fraction containing the biological product from the at least one first outlet of the first module to a second module, and where the second module includes a charge-based purification apparatus (e.g., a positive and/or negative charged-based purification apparatus), the charge-based purification apparatus further comprising resin beads. For example, the surface of the resin beads may have cationic functionality, derived from the coupling of positively charged functional groups, to enable purification based on charge or electrostatic interactions. For example, the positively charged functional groups include amines, cationic polymers, net positively charged peptides, net positively charged proteins, or any combination thereof. Alternatively, the surface of the resin beads may have anionic functionality, derived from the coupling of negatively charged functional groups, to enable purification based on charge or electrostatic interactions. For example, the negatively charged functional groups include, carboxyls, anionic polymers, net negatively charged peptides, net negatively charged proteins, oligonucleotides, or any combination thereof.

In embodiments, the resin beads of the charged-based purification apparatus have a diameter of about 0.2 micron to about 200 micron. The diameter of the resin beads may depend on the biological product being purified and the overall flow rate of the process. For example, purification of a monoclonal antibody may include resin beads that are about 90 microns in size. Moreover, the resin beads may have a concentration ranging from about 0.01% to about 25% by weight. For example, the concentration of the resin beads may be about 1% by weight. In some examples, purification of a monoclonal antibody may include resin beads that have a concentration of about 1% to about 10% by weight. In other examples, the charge or electrostatic association capacity of the resin beads is a function of the bead concentration, surface area-to-volume ratio, surface charge density, net charge, or any combination thereof. In yet other examples, the resin beads may be solid, porous, nanoporous, microporous, or any combination thereof.

In embodiments, the mechanical rotary system (e.g., which permits continuous fluid flow between a first and/or second inlet and the first and/or second outlet) has at least two vessels including mobile resin beads (e.g., charged with mobile resin beads) that are configured to receive a mixture (e.g., continuously receive) containing a biological product and subsequently transport the resulting heterogeneous mixture containing a biological product, resin beads, a buffer, or any combination thereof, to a designated purification position.

In other embodiments, the system (e.g., a staged linear system which permits continuous fluid flow between a first and/or second inlet and the first and/or second outlet) has at least two vessels with mobile resin beads (e.g., charged with mobile resin beads) that are configured to receive a mixture (e.g., continuously receive) containing a biological product and subsequently process the resulting mixture containing a biological product, resin beads, a buffer, or any combination thereof.

In embodiments, the first (affinity-based purification) and/or the second (charge-based purification, including a positive and/or negative charged-based purification apparatus) module further includes at least one tangential flow filtration system operated in fed-batch or perfusion mode to concentrate and buffer exchange the fraction containing the biological product.

In embodiments, the process described herein includes continuously transferring the filtrate to a first module capable of separating the solution into two or more fractions including at least one fraction containing the biological product, wherein the first module is an affinity-based, fluidic purification apparatus having at least one hybrid fluidic device or chip. In embodiments, the at least one hybrid fluidic device or chip has a cross-flow channel, at least one magnetic field, and at least one mechanical force generator. Moreover, the at least one mechanical force generator can include an ultrasonic transducer or a piezoelectric component capable of generating a defined, unidirectional force. In other examples, the at least one external magnetic field comprises a permanent magnet, an electromagnet, a patterned magnet, or combinations thereof. For example, the at least one external magnetic field may have a magnetic field strength of about 0.01 Tesla (T) to about 1 Tesla (e.g., up to 1 Tesla). In other examples, the magnetic field strength is about 0.01 T, about 0.1 T, or about 1 T. In other embodiments, the at least one hybrid fluidic device or chip has a cross-flow channel, at least one magnetic field, and at least one dielectrophoretic electrode. The at least one dielectrophoretic electrode is capable of inducing a defined, unidirectional force. Moreover, the at least one external magnetic field comprises a permanent magnet, an electromagnet, a patterned magnet, or combinations thereof. For example, the at least one external magnetic field may have a magnetic field strength of about 0.01 Tesla about 1 Tesla (e.g., up to about 1 Tesla).

In embodiments, the affinity-based, fluidic purification apparatus that further comprises magnetic resin beads. The surface of the magnetic resin bead for example, without intent to be limiting, is coupled with Protein A, Protein G, Protein L, an antigenic protein, a protein, a receptor, an antibody, or an aptamer. In examples, the magnetic resin beads may be paramagnetic or superparamagnetic.

In embodiments, the magnetic resin beads of affinity-based, fluidic purification apparatus have a diameter of about 0.2 micron to about 200 micron. For example, purification of a monoclonal antibody may include magnetic resin beads that are about 40 microns in size. Moreover, the magnetic resin beads may have a concentration ranging from about 0.01% to about 25% by weight. For example, the initial concentration of the magnetic resin beads may be about 1% by weight. In some examples, purification of a monoclonal antibody may include magnetic resin beads that have a concentration of about 1% to about 10% by weight. In other examples, the binding capacity of the magnetic resin beads is a function of the bead concentration, surface area-to-volume ratio, affinity ligand density, or any combination thereof. In yet other examples, the magnetic resin beads may be solid, porous, nanoporous, microporous, or any combination thereof.

In embodiments, the process described herein includes continuously transferring the fraction containing the biological product from the at least one first outlet of the first module to a second module, wherein the second module includes a charge-based, fluidic purification apparatus. For example, the charge-based, fluidic purification apparatus has at least one hybrid fluidic device or chip. The at least one hybrid fluidic device or chip may have a cross-flow channel, at least one magnetic field, and at least one mechanical force generator. Moreover, the at least one mechanical force generator comprises an ultrasonic transducer or a piezoelectric component capable of generating a defined, unidirectional force. In other examples, the at least one external magnetic field comprises a permanent magnet, an electromagnet, a patterned magnet, or combinations thereof. For example, the at least one external magnetic field may have a magnetic field strength of about 0.01 Tesla (T) to about 1 Tesla (e.g., up to about 1 Tesla). In other examples, the magnetic field strength is about 0.01 T, about 0.1 T, or about 1 T. In other embodiments, the hybrid fluidic device or chip may have a cross-flow channel, at least one magnetic field, and at least one dielectrophoretic electrode, wherein the at least one dielectrophoretic electrode is capable of inducing a defined, unidirectional force. Moreover, the at least one external magnetic field comprises a permanent magnet or an electromagnet. In examples, the at least one external magnetic field comprises a magnetic field strength from about 0.01 Tesla to about 1 Tesla (e.g., up to about 1 Tesla).

In embodiments, the charge-based, fluidic purification apparatus (e.g., a positive and/or negative charged-based, fluidic purification apparatus) further includes a suspension of magnetic resin beads. The surface of the magnetic resin beads have cationic functionality, derived from the coupling of positively charged functional groups, to enable purification based on charge or electrostatic interactions. The positively charged functional groups include amines, cationic polymers, net positively charged peptides, net positively charged proteins, or any combination thereof. Alternatively, the magnetic resin bead surface may include anionic functionality, derived from the coupling of negatively charged functional groups, to enable purification based on charge or electrostatic interactions. The negatively charged functional groups include carboxyls, anionic polymers, net negatively charged peptides, net negatively charged proteins, oligonucleotides, or any combination thereof. In examples, the magnetic resin beads may be paramagnetic or superparamagnetic.

In examples, the magnetic resin beads of the charge-based, fluidic purification apparatus have a diameter of about 0.2 micron to about 200 micron. The diameter of the magnetic resin beads may depend on the biological product being purified and the flow rate of the process. For example, purification of a monoclonal antibody may include magnetic resin beads that are about 40 microns in size. Moreover, the magnetic resin beads may have a concentration ranging from about 0.01% to about 25% by weight. For example, the concentration of the magnetic resin beads may be about 1% by weight. In some examples, purification of a monoclonal antibody may include magnetic resin beads that have a concentration of about 1% to about 10% by weight. In other examples, the charge or electrostatic association capacity of the magnetic resin beads is a function of the bead concentration, surface area-to-volume ratio, surface charge density, net charge, or any combination thereof. In yet other examples, the magnetic resin beads may be solid, porous, nanoporous, microporous, or any combination thereof.

In embodiments, the first (affinity-based, fluidic purification) module further has at least one equilibration vessel to allow for binding of the biological product to the magnetic resin bead surface, and at least one low pH equilibration vessel to allow for de-binding interactions of the biological product from the magnetic resin bead surface.

In embodiments, the second (charge-based, fluidic purification, including a positive and/or negative charged-based, fluidic purification apparatus) module further has at least one association equilibration vessel to allow for association, based on charge or electrostatic interactions, of the biological product with the magnetic resin bead surface, and at least one dissociation equilibration vessel to allow for dissociation of the biological product from the magnetic resin bead surface. In examples, multiple dissociation equilibration vessels are utilized with multiple charge-based, fluidic purification apparatuses to achieve a gradient dissociation, for example, a pH gradient or an ionic strength gradient.

In embodiments, the magnetic resin beads as described herein are recycled, and re-used. For example, the beads may be re-used at least 2, 3, 4, or more times for purifying a biological product. To enable recycling and reuse of the magnetic resin beads, the at least one regeneration equilibration vessel may be utilized in combination with a tangential flow filtration system to concentrate and buffer exchange the magnetic resin beads to return the magnetic resin beads to their initial condition.

As described herein, the first (affinity-based, fluidic purification) and/or the second (charge-based, fluidic purification, including a positive and/or negative charged-based, fluidic purification apparatus) module includes a hybrid microfluidic, mesofluidic, millifluidic, macrofluidic device or chip, or any combination thereof, to purify a biological product, for example, a hybrid microfluidic device comprising at least one magnetic field and at least one of a piezoelectric component or a dielectrophoretic electrode.

In embodiments, the first (affinity-based, fluidic purification) and/or the second (charge-based, fluidic purification, including a positive and/or negative charged-based, fluidic purification apparatus) module further includes at least one tangential flow filtration system operated in fed-batch or perfusion mode to concentrate and buffer exchange the fraction containing the biological product.

In embodiments, the process described herein includes continuously transferring the filtrate to a first module capable of separating the solution into two or more fractions comprising at least one fraction containing the biological product, and the first module includes an affinity-based TFF purification apparatus. For example, the affinity-based TFF purification apparatus has at least three tangential flow filtration systems in fluid communication.

In embodiments, the affinity-based TFF purification apparatus further includes a suspension of resin beads. The surface of the resin beads, for example, without intent to be limiting, is coupled with Protein A, Protein G, Protein L, an antigenic protein, a protein, a receptor, an antibody, or an aptamer.

In embodiments, the resin beads of the affinity-based TFF purification apparatus have a diameter of about 10 micron to about 200 micron. The diameter of the resin beads may depend on the biological product being purified and the overall flow rate of the process. For example, purification of a monoclonal antibody may include resin beads that are about 90 microns in size. Moreover, the resin beads may have a concentration ranging from about 0.01% to about 25% by weight. For example, the concentration of the resin beads may be about 1% to about 20% by weight. In other examples, the binding capacity of the resin beads is a function of the bead concentration, surface area-to-volume ratio, affinity ligand density, or any combination thereof. In yet other examples, the resin beads may be solid, porous, nanoporous, microporous, or any combination thereof.

In embodiments, the process described herein includes continuously transferring the fraction containing the biological product from the at least one first outlet of the first module to a second module, and wherein the second module includes a charge-based TFF purification apparatus (e.g., a positive and/or negative charged-based TFF purification apparatus). For example, the charge-based TFF purification apparatus has at least three tangential flow filtration systems in fluid communication.

In embodiments, the charge-based TFF purification apparatus further includes a suspension of resin beads. For example, the surface of the resin beads may have cationic functionality, derived from the coupling of positively charged functional groups, to enable purification based on charge or electrostatic interactions. For example, the positively charged functional groups include amines, cationic polymers, net positively charged peptides, net positively charged proteins, or any combination thereof. Alternatively, the surface of the resin bead may have anionic functionality, derived from the coupling of negatively charged functional groups, to enable purification based on charge or electrostatic interactions. For example, the negatively charged functional groups include, carboxyls, anionic polymers, net negatively charged peptides, net negatively charged proteins, oligonucleotides, or any combination thereof.

In embodiments, the resin beads of the charged-based TFF purification apparatus have a diameter of about 0.2 micron to about 200 micron. The diameter of the resin beads may depend on the biological product being purified and the overall flow rate of the process. For example, purification of a monoclonal antibody may include resin beads that are about 90 microns in size. Moreover, the resin beads may have a concentration ranging from about 0.01% to about 25% by weight. For example, the concentration of the resin beads may be about 1% to about 20% by weight. In other examples, the charge or electrostatic association capacity of the resin beads is a function of the bead concentration, surface area-to-volume ratio, surface charge density, net charge, or any combination thereof. In yet other examples, the resin beads may be solid, porous, nanoporous, microporous, or any combination thereof.

In embodiments, the first (affinity-based TFF purification) module further has at least one equilibration vessel to allow for binding of the biological product to the resin bead surface, and at least one low pH equilibration vessel to allow for de-binding interactions of the biological product from the resin bead surface.

In embodiments, the second (charge-based TFF purification, including a positive and/or negative charged-based TFF purification apparatus) module further has at least one association equilibration vessel to allow for association, based on charge or electrostatic interactions, of the biological product with the resin bead surface, and at least one dissociation equilibration vessel to allow for dissociation of the biological product from the resin bead surface. In examples, multiple dissociation equilibration vessels are utilized with multiple charge-based, fluidic purification apparatuses to achieve a gradient dissociation, for example, a pH gradient or an ionic strength gradient.

In embodiments, the resin beads as described herein are recycled, and re-used. For example, the beads may be re-used at least 2, 3, 4, or more times for purifying a biological product. To enable recycling and reuse of the resin beads, the at least one regeneration equilibration vessel may be utilized in combination with a tangential flow filtration system to concentrate and buffer exchange the resin beads to return the resin beads to their initial condition.

In embodiments, the first (affinity-based TFF purification) and/or the second (charge-based TFF purification, including a positive and/or negative charged-based TFF purification apparatus) module further includes at least one tangential flow filtration system to concentrate and buffer exchange the fraction containing the biological product.

In other embodiments, the process described herein includes continuously transferring the fraction containing the biological product from the at least one first outlet of the first module to a second module, wherein the second module includes an isoelectric point-based, fluidic purification apparatus, also referred to herein as a free-flow electrophoresis apparatus. For example, the free-flow electrophoresis apparatus has at least one fluidic device comprising a fluidic channel created between two parallel plates, an electric field or electric field gradient orthogonal to the fluid flow direction, and a pH gradient to operate in an isoelectric focusing mode of operation. In other examples, the isoelectric point-based, fluidic purification module includes at least one first fluidic device comprising a fluidic channel created between two parallel plates, an electric field or electric field gradient orthogonal to the fluid flow direction, and a coarse pH gradient across the main separation channel (e.g., a pH range from about 2 to about 10); and at least one second fluidic device comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6). Alternatively, the free-flow electrophoresis apparatus has at least one fluidic device comprising a fluidic channel created between two parallel plates, an electric field or electric field gradient orthogonal to the fluid flow direction, and no pH gradient to operate in a zone electrophoresis or charge separating mode of operation.

In other examples, the isoelectric point-based, fluidic purification module includes at least one first fluidic device comprising a fluidic channel created between two parallel plates, an electric field or electric field gradient orthogonal to the fluid flow direction, and constant basic pH (e.g., a pH of greater than 7); and at least one second fluidic device comprising a fluidic channel created between two parallel plates, an electric field or electric field gradient orthogonal to the fluid flow direction, and a constant acidic pH (e.g., a pH of less than 7). Furthermore, the free-flow electrophoresis apparatus has at least one fluidic device comprising a fluidic channel created between two parallel plates, an electric field or electric field gradient orthogonal to the fluid flow direction, and both an acidic pH gradient and a basic pH gradient separated by a spacer solution (e.g. a NaCl solution) to operate in an isotachophoresis mode of operation.

In some embodiments, the isoelectric point-based, fluidic purification module includes at least one first fluidic device comprising a fluidic channel created between two parallel plates and an electric field or electric field gradient orthogonal to the fluid flow direction, and at least one second fluidic device comprising a fluidic channel created between two parallel plates and an electric field or electric field gradient orthogonal to the fluid flow direction, wherein each device connected in series is capable of operating in an independent mode of operation to enable purification. For example, the at least one first free-flow electrophoresis apparatus may operate in an isoelectric focusing mode and the at least one second free-flow electrophoresis apparatus may operate in an isotachophoresis mode are operated sequentially through connection in series to increase separation resolution.

In other embodiments, without intent to be limiting, the isoelectric point-based, fluidic purification module includes at least one first fluidic device comprising fluidic channel having at least one dielectrophoretic electrode capable of inducing a defined, unidirectional force; at least one second fluidic device comprising a fluidic channel created between two parallel plates, an electric field or electric field gradient orthogonal to the fluid flow direction, and a coarse pH gradient across the main separation channel (e.g., a pH range from about 2 to about 10); and at least one third fluidic device comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In yet other embodiments, the isoelectric point-based fluidic purification apparatus further comprises an active cooling system (e.g., a Peltier device, a thermal chuck with a circulating water/propylene glycol jacket) to enable temperature control and Joule heat dissipation. For example, the active cooling system may control cooling and/or Joule heat dissipation to enable operation in the range from about 4° C. to about 50° C., preferably from about 4° C. to about 37° C. For example, when isolating a biological product (e.g., a monoclonal antibody), the temperature is maintained from about 4° C. to about 37° C.

In further embodiments, the process for purifying a biological product may also include viral inactivation, viral filtration, tangential flow filtration (TFF), high performance tangential flow filtration (HP-TFF), ultrafiltration/diafiltration (UF/DF), filter sterilization, fill-finish, lyophilization, or any combination thereof, performed semi-continuously and downstream of the second module.

In examples, the entire process described herein (the process for purifying a biological product) is performed at a temperature in the range of about 4° C. to about 50° C., preferably from about 4° C. to about 37° C. Moreover, the commercial production-scale process for purifying a biological product is conducted in a system with a footprint that occupies significantly less square footage than current techniques, without sacrificing product throughput or yield on a kilograms/year basis. For example, the process for producing, purifying a monoclonal antibody as described herein is operated with a footprint that occupies up to about 30,000 square feet. In contrast, current mononclonal antibody production and downsteam processes require at least 200,000 square feet.

The process described herein is used to purify a biological product, and the biological product includes, but is not limited to, a protein or fragment thereof (a polypeptide), an antibody or fragment thereof, a cytokine, a chemokine, an enzyme, a growth factor, an oligonucleotide, a virus, an adenovirus, an adeno-associated virus, or a lentivirus.

Dynamic Filtration Module

In aspects, provided herein is a dynamic filtration module for removing large impurities from a biological product in a heterogeneous mixture. The dynamic filtration module continuously feeds the biological product from at least one output head in fluid communication with the input line to the dynamic filtration module under negative pressure.

In embodiments, the dynamic filtration module includes a filter membrane roll, a membrane support structure, at least one support rod or roller, at least one vacuum line, a vacuum system, and at least one vacuum collection vessel.

The dynamic filtration module includes a rolled filter membrane extending between a feed reel and a collection reel, the filter membrane having a target region (e.g., an active target region) that is configured to receive the heterogeneous mixture. For example, the filter membrane of the filter membrane roll is made of a suitable material, including, but not limited to, polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), or hydrophilic PTFE.

In embodiments, the pore size of the rolled filter membrane depends on the biological product being purified. In examples, the rolled filter membrane has a pore size in the range from 0.1 µm to 1 µm. Alternatively, the pore size is in the range from about 0.2 µm to about 0.45 µm, or the pore size is less than about 0.45 µm. In other examples, when purifying an antibody, the pore size of the rolled filter membrane is in the range of 0.2 µm to about 0.45 µm.

In embodiments, the filter membrane roll has a width from about 10 mm to about 600 mm. The width of the filter membrane roll, for example, may depend on factors such as the size of the dynamic filtration system and the size of the membrane support structure.

In embodiments, the filter membrane roll further functions as a feed reel that communicates with a collection reel, thus creating a reel-to-reel system. In operation, the heterogeneous mixture is applied to a fresh, unused target region of the filter membrane, herein also referred to as the "target region" (or "active target region"), wherein the filter membrane is continuously moved at an appropriate transport velocity across the membrane support structure as a result of the collection reel collecting the filter membrane portion that has been used. In examples, the feed reel motion is governed by a Servo motor coupled with a gear box to limit rotations per minute (RPM) by a ratio of 200:1 to enable low membrane transport velocities with high torque. The collection reel motion is governed by a Servo motor coupled with a gear box to limit RPM by a ratio of 200:1 to enable low membrane transport velocities with high torque. Further, the feed reel motor and the collection reel motor are controlled by a closed-loop controller that operates a feedback mechanism to ensure consistent membrane transport velocity with the constantly changing diameters of the filter membrane roll on both the feed reel and the collection reel during operation.

For example, ensuring consistent membrane transport velocity may be accomplished using a thickness monitoring system or a rotary encoder. In examples, the feed reel and the collection reel operate in the same direction with equivalent velocities. In other examples, the feed reel and the collection reel operate in the same direction with different velocities. Other methods of filter membrane transport from the feed reel to the collection reel can be contemplated by those of skill in the art of the coating and converting industry. In other examples, two dynamic filtration systems are run in parallel. For example, the two parallel dynamic filtration systems may allow for continuous flow through the system during the replacement of the spent filter membrane roll. Furthermore, the two parallel dynamic filtration systems may allow for equilibration of a full vacuum collection vessel to atmospheric pressure to enable fluid flow to the first purification module without interruption of the process of continuously receiving the heterogeneous mixture from the bioreactor bleed line.

Additionally, the dynamic filtration module includes a membrane support structure to support the target region (e.g., an active target region) of the filter membrane as it experiences negative pressure. The membrane support structure is positioned between the feed reel and the collection reel, has a mechanically smooth contact surface derived from a material having a low static coefficient of friction (e.g. PTFE), and has an opening that has continuity with the vacuum line. In examples, the opening may include a mesh, at least one slot, at least one hole, a frit, a porous material, or any combination thereof.

In embodiments, the at least one support rod or roller of the dynamic filtration module has a mechanically smooth contact surface derived from a material having a low static coefficient of friction (e.g. PTFE, PFA). In examples, the dynamic filtration module includes at least one support rod or roller with a mechanically smooth contact surface to stabilize the motion of the filter membrane across the membrane support structure.

In embodiments, the membrane support structure of the dynamic filtration module includes a temperature control mechanism to maintain desired temperature in the presence of evaporative cooling. The temperature control mechanism maintains a temperature from about 4° C. to about 37° C. For example, during purification of an antibody, the temperature control mechanism maintains a temperature in a range from about 15° C. to about 37° C.

In embodiments, the dynamic filtration module includes at least one output head for modulating flow of the heterogeneous mixture and dispensing the heterogeneous mixture onto the target region (e.g., an active target region) of the filter membrane. In examples, the at least one output head is a tube or a slot die.

In some embodiments, the dynamic filtration module further includes at least one additional input line to supply a wash buffer via a coaxial output head, a separate monoaxial output head, a separate slot die output head, or a slot die output head with multiple openings.

In some embodiments, the dynamic filtration module includes elements known in the coating and converting industry, for example, without intent to be limiting, active or passive edge guides, tension control (e.g. a dancer), break and tension detectors, or any combination thereof.

In embodiments, the dynamic filtration module includes a vacuum system having continuity with the membrane support structure to apply negative pressure across the target region (e.g., an active target region) of the filter membrane, where the negative pressure allows for target region (e.g., an active target region) f the filter membrane across the membrane support structure and enables collection of the filtrate containing the biological product. In examples, the vacuum system of the dynamic filtration module maintains a gauge pressure of about −0.05 bar to about −0.98 bar for continuous filtration.

In embodiments, the dynamic filtration module further includes at least one vacuum collection vessel configured to collect the filtrate, and at least one sensor or detector. In examples, two parallel dynamic filtration systems are run staggered in time to allow for continuous flow through the system following the complete filling and equilibration to atmospheric pressure of the first vacuum collection vessel.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 µm) in fluid communication with at least one second dynamic filtration apparatus having a rolled filter membrane with a small pore size (e.g., 0.2 µm), thereby producing a filtrate comprising the biological product. Alternatively, a similar result could be achieved by a single dynamic filtration apparatus having at least two rolled filter membranes being fed by separate feed reels, resulting in a layered set of filter membranes across the active target region, wherein the heterogeneous mixture contacts a larger pore size filter membrane first (e.g., 0.45 µm), followed by contact with a smaller pore size filter membrane next (e.g., 0.2 µm).

Affinity-Based, Magnetic Purification Module

In aspects, provided herein is an affinity-based, magnetic purification module for separating a mixture into two or more fractions, where at least one fraction contains the biological product. The affinity-based, magnetic purification module includes at least one inlet and at least one outlet configured to permit continuous fluid flow between the at least one inlet and the at least one outlet and wherein the flow rate may be, for example, consistent and constant during steady-state operation.

In embodiments, the affinity-based, magnetic purification module includes a suspension of magnetic resin beads, wherein the magnetic resin bead surface, without intent to be limiting, is coupled to Protein A, Protein G, Protein L, an antigenic protein, a protein, a receptor, an antibody, or an aptamer configured to selectively bind said biological product. In examples, the magnetic resin beads are mobile.

Moreover, the affinity-based, magnetic purification module includes a loop conveyor system including at least two transport vessels charged with magnetic resin beads that are configured to continuously receive a mixture containing a biological product and subsequently transport the resulting heterogeneous mixture containing a biological product, magnetic resin beads, a buffer, or any combination thereof.

Alternatively, the affinity-based, magnetic purification module includes a pick and place robotics system including at least two transport vessels charged with magnetic resin beads that are configured to continuously receive a mixture containing a biological product and subsequently transport the resulting heterogeneous mixture containing a biological product, magnetic resin beads, a buffer, or any combination thereof.

In embodiments, the affinity-based, magnetic purification module includes at least one external magnetic field that may be used to attract, and thus separate, said magnetic resin beads from the heterogeneous mixture to enable washing. Further, the at least one external magnetic field may be used to attract, and thus separate, said magnetic resin beads from the heterogeneous mixture to enable elution of said biological product. Alternatively, the at least one external magnetic field may be used to enable recycling of said magnetic resin beads. In examples, mixing of the magnetic resin beads may be accomplished by placing the at least one transport vessel between two separate and opposing magnetic fields that toggle between states of on and off.

In embodiments, the affinity-based, magnetic purification module includes at least one binding/wash buffer system.

In embodiments, the affinity-based, magnetic purification module includes at least one elution buffer system.

In embodiments, the affinity-based, magnetic purification module includes at least one magnetic resin bead regeneration buffer system.

In embodiments, the affinity-based, magnetic purification module includes at least one aspirator system to remove waste solution from the at least two transport vessels.

In embodiments, the affinity-based, magnetic purification module includes at least one sensor or detector.

In embodiments, the affinity-based, magnetic purification module includes at least one fluid handling pump.

Positive Charge-Based, Magnetic Purification Module

In aspects, provided herein is a positive charge-based, magnetic purification module for separating a mixture into two or more fractions, where at least one fraction contains a biological product. The positive charge-based, magnetic purification module includes at least one inlet and at least one outlet configured to permit continuous fluid flow between the at least one inlet and the at least one outlet and wherein the flow rate may be, for example, consistent and constant during steady-state operation.

In embodiments, the positive charge-based, magnetic purification module includes a suspension of magnetic resin beads, wherein the magnetic resin bead surface comprises cationic functionality configured to selectively associate with said biological product at a specific pH and ionic strength. In examples, the magnetic resin beads are mobile.

Moreover, the positive charge-based, magnetic purification module includes a loop conveyor system comprising at least two transport vessels charged with magnetic resin beads that are configured to continuously receive a mixture containing a biological product and subsequently transport the resulting heterogeneous mixture containing a biological product, magnetic resin beads, a buffer, or any combination thereof.

Alternatively, the positive charge-based, magnetic purification module includes a pick and place robotics system comprising at least two transport vessels charged with magnetic resin beads that are configured to continuously receive a mixture containing a biological product and subsequently transport the resulting heterogeneous mixture containing a biological product, magnetic resin beads, a buffer, or any combination thereof.

In embodiments, the positive charge-based, magnetic purification module includes at least one external magnetic field that may be used to attract, and thus separate, said magnetic resin beads from the heterogeneous mixture to enable washing. Further, the at least one external magnetic field may be used to attract, and thus separate, said magnetic resin beads from the heterogeneous mixture to enable dissociation and purification of said biological product. Alternatively, the at least one external magnetic field may be used to enable recycling of said magnetic resin beads. In examples, mixing of the magnetic resin beads may be accomplished by placing the at least one transport vessel between two separate and opposing magnetic fields that toggle between states of on and off.

In embodiments, the positive charge-based, magnetic purification module includes at least one association/wash buffer system.

In embodiments, the positive charge-based, magnetic purification module includes at least one dissociation buffer system. In examples, multiple dissociation buffers varying pH, ionic strength, or any combination thereof, are utilized sequentially to create a gradient dissociation effect.

In embodiments, the positive charge-based, magnetic purification module includes at least one magnetic resin bead regeneration buffer system.

In embodiments, the positive charge-based, magnetic purification module includes at least one aspirator system to remove waste solution from the at least two transport vessels.

In embodiments, the positive charge-based, magnetic purification module includes at least one sensor or detector.

In embodiments, the positive charge-based, magnetic purification module includes and at least one fluid handling pump.

Negative Charge-Based, Magnetic Purification Module

In aspects, provided herein is a negative charge-based, magnetic purification module for separating a mixture into two or more fractions, at least one fraction containing a biological product. The negative charge-based, magnetic purification module includes at least one inlet and at least one outlet configured to permit continuous fluid flow between the at least one inlet and the at least one outlet and wherein the flow rate may be, for example, consistent and constant during steady-state operation.

In embodiments, the negative charge-based, magnetic purification module includes a suspension of magnetic resin beads, wherein the magnetic resin bead surface comprises anionic functionality configured to selectively associate with said biological product at a specific pH and ionic strength. In examples, the magnetic resin beads are mobile.

Moreover, the negative charge-based, magnetic purification module includes a loop conveyor system comprising at least two transport vessels charged with magnetic resin beads that are configured to continuously receive a mixture containing a biological product and subsequently transport the resulting heterogeneous mixture containing a biological product, magnetic resin beads, a buffer, or any combination thereof.

Alternatively, the negative charge-based, magnetic purification module includes a pick and place robotics system comprising at least two transport vessels charged with magnetic resin beads that are configured to continuously receive a mixture containing a biological product and subsequently transport the resulting heterogeneous mixture containing a biological product, magnetic resin beads, a buffer, or any combination thereof.

In embodiments, the negative charge-based, magnetic purification module includes at least one external magnetic field that may be used to attract, and thus separate, said magnetic resin beads from the heterogeneous mixture to enable washing. Further, the at least one external magnetic field may be used to attract, and thus separate, said magnetic resin beads from the heterogeneous mixture to enable dissociation and purification of said biological product. Alternatively, the at least one external magnetic field may be used to enable recycling of said magnetic resin beads. In examples, mixing of the magnetic resin beads may be accomplished by placing the at least one transport vessel between two separate and opposing magnetic fields that toggle between states of on and off.

In embodiments, the negative charge-based, magnetic purification module includes at least one association/wash buffer system.

In embodiments, the negative charge-based, magnetic purification module includes at least one dissociation buffer system. In examples, multiple dissociation buffers varying pH, ionic strength, or any combination thereof, are utilized sequentially to create a gradient dissociation effect.

In embodiments, the negative charge-based, magnetic purification module includes at least one magnetic resin bead regeneration buffer system.

In embodiments, the negative charge-based, magnetic purification module includes at least one aspirator system to remove waste solution from the at least two transport vessels.

In embodiments, the negative charge-based, magnetic purification module includes at least one sensor or detector.

In embodiments, the negative charge-based, magnetic purification module includes at least one fluid handling pump.

Affinity-Based Purification Module

In aspects, provided herein is an affinity-based purification module for separating a mixture into two or more fractions, where at least one fraction contains the biological product. The affinity-based purification module includes at least one inlet and at least one outlet configured to permit continuous fluid flow between the at least one inlet and the at least one outlet and wherein the flow rate may be, for example, consistent and constant during steady-state operation.

In embodiments, the affinity-based purification module includes a suspension of resin beads, wherein the resin bead surface, without intent to be limiting, is coupled to Protein A, Protein G, Protein L, an antigenic protein, a protein, a receptor, an antibody, or an aptamer, which is configured to selectively bind said biological product. In examples, the resin beads are mobile.

In embodiments, the affinity-based purification module includes a lid system having at least one gasketed lid, where the at least one gasketed lid has at least one inlet to introduce a gas to enable control of positive head pressure. Furthermore, the lid system has at least one vent port to enable equilibration to atmospheric pressure, at least one inlet to introduce a suspension of resin beads, at least one inlet to receive the filtrate containing a biological product, and/or at least two inlets to introduce a buffer system to disperse the resin beads to enable washing of, elution from, or regeneration of said resin beads. In some embodiments, the at least one gasketed lid also includes a port to accept an overhead stirring impeller to enable dispersion of the resin beads. In examples, the lid system has control of motion along the z-axis.

In embodiments, the affinity-based purification module includes a mechanical rotary system, for example, a carousel comprising at least two vessels charged with resin beads that are configured to continuously receive a mixture containing a biological product and subsequently transport the resulting heterogeneous mixture containing a biological product, resin beads, a buffer, or any combination thereof. In examples, the carousel is a rotating structure that holds and transports at least two vessels to different process positions. In some examples, the mechanical rotary system is configured to mate with the lid system to enable pressurization and liquid handling. In other examples, the mechanical rotary system has control of motion or rotation in the xy-plane.

In embodiments, the at least two vessels of the affinity-based purification module each have a supported, basement filter or filter membrane. In examples, the basement filter (or filter membrane) enables enable retention of the resin beads during process steps of binding, de-binding, washing, elution, and/or regeneration. In examples, the at least two vessels may further include a valve to control liquid flow.

In other embodiments, the affinity-based purification module includes a staged linear system, for example, at least two vessels charged with resin beads that are configured to continuously receive a mixture containing a biological product and subsequently process the resulting heterogeneous mixture containing a biological product, resin beads, a buffer, or any combination thereof. In examples, the at least two vessels are configured to mate with the lid system to enable pressurization and liquid handling.

In embodiments, the affinity-based purification module includes a collection system that interfaces with at least one of the at least two vessels of the mechanical rotary system to enable collection of waste, the fraction containing the biological product, or any combination thereof. In examples, the collection system has control of motion along the z-axis.

In other embodiments, the affinity-based purification module includes a collection system that interfaces with at least one of the at least two vessels of the staged linear system to enable collection of waste, the fraction containing the biological product, or any combination thereof. In examples, the collection system is connected to the at least one of the at least two vessels.

In embodiments, the affinity-based purification module includes at least one gas. In some embodiments, without intent to be limiting the gas comprises filtered nitrogen or compressed dry air. In examples, the gas creates a pressure head of about 0.1 to about 30 psi.

In embodiments, the affinity-based purification module includes at least one binding/wash buffer system.

In embodiments, the affinity-based purification module includes at least one low pH elution buffer system.

In embodiments, the affinity-based purification module includes at least one resin bead regeneration buffer system.

In embodiments, the affinity-based purification module includes at least one collection vessel.

In embodiments, the affinity-based purification module includes at least one sensor or detector.

In embodiments, the affinity-based purification module includes at least one fluid handling pump.

Positive Charge-Based Purification Module

Also provided herein is a positive charge-based purification module for separating a mixture into two or more fractions, where at least one fraction contains a biological product. The positive charge-based purification module includes at least one inlet and at least one outlet configured to permit continuous fluid flow between the at least one inlet and the at least one outlet and wherein the flow rate may be, for example, consistent and constant during steady-state operation.

In embodiments, the positive charge-based purification module includes a suspension of resin beads, wherein the resin bead surface comprises cationic functionality configured to selectively associate with said biological product at a specific pH and ionic strength. In examples, the resin beads are mobile.

In embodiments, the positive charge-based purification module includes lid system having at least one gasketed lid, the at least one gasketed lid comprising at least one inlet to introduce a gas to enable control of positive head pressure; at least one inlet to introduce a suspension of resin beads; at least one vent port to enable equilibration to atmospheric pressure; at least one inlet to receive the filtrate containing a biological product; at least two inlets to introduce a buffer system to disperse the resin beads to enable washing of, dissociation from, or regeneration of said resin beads. In some embodiments, the at least one gasketed lid further comprises a port to accept an overhead stirring impeller to enable dispersion of the resin beads. In examples, the lid system has control of motion along the z-axis.

In embodiments, the positive charge-based purification module includes a mechanical rotary system, for example, a carousel comprising at least two vessels charged with resin beads that are configured to continuously receive a mixture containing a biological product and subsequently transport the resulting heterogeneous mixture containing a biological product, resin beads, a buffer, or any combination thereof. In examples, the carousel is a rotating structure that holds and transports at least two vessels to different process positions. In some examples, the mechanical rotary system is configured to mate with the lid system to enable pressurization. In other examples, the mechanical rotary system has control of motion or rotation in the xy-plane.

In embodiments, the at least two vessels of the positive charge-based purification module each have a supported, basement filter or filter membrane. In examples, the basement filter (or filter membrane) enables enable retention of the resin beads during process steps of association, washing, dissociation, and/or regeneration. In examples, the at least two vessels may further include a valve to control liquid flow.

In other embodiments, the positive charge-based purification module includes a staged linear system, for example, at least two vessels charged with resin beads that are configured to continuously receive a mixture containing a biological product and subsequently process the resulting heterogeneous mixture containing a biological product, resin beads, a buffer, or any combination thereof. In examples, the at least two vessels are configured to mate with the lid system to enable pressurization and liquid handling.

In embodiments, the positive charge-based purification module includes a collection system that interfaces with at least one of the at least two vessels of the mechanical rotary system to enable collection of waste, the fraction containing the biological product, or any combination thereof. In examples, the collection system has control of motion along the z-axis.

In other embodiments, the positive charge-based purification module includes a collection system that interfaces with at least one of the at least two vessels of the staged linear system to enable collection of waste, the fraction containing the biological product, or any combination thereof. In examples, the collection system is connected to the at least one of the at least two vessels.

In embodiments, the affinity-based purification module includes at least one gas. In some embodiments, without intent to be limiting the gas comprises filtered nitrogen or compressed dry air. In examples, the gas creates a pressure head of about 0.1 to about 30 psi.

In embodiments, the positive charge-based purification module includes at least one association/wash buffer system.

In embodiments, the positive charge-based purification module includes at least one dissociation buffer system. In examples, multiple dissociation buffers varying pH, ionic strength, or any combination thereof, are utilized continuously or sequentially to create a gradient dissociation effect.

In embodiments, the positive charge-based purification module includes at least one resin bead regeneration buffer system.

In embodiments, the positive charge-based purification module includes at least one collection vessel.

In embodiments, the positive charge-based purification module includes at least one sensor or detector.

In embodiments, the positive charge-based purification module includes at least one fluid handling pump.

Negative Charge-Based Purification Module

In aspects, provided herein is a negative charge-based purification module for separating a mixture into two or more fractions, where at least one fraction contains a biological product. The negative charge-based purification module includes at least one inlet and at least one outlet configured to permit continuous fluid flow between the at least one inlet and the at least one outlet and wherein the flow rate may be, for example, consistent and constant during steady-state operation.

In embodiments, the negative charge-based purification module includes a suspension of resin beads, wherein the resin bead surface comprises cationic functionality configured to selectively associate with said biological product at a specific pH and ionic strength.

In embodiments, the negative charge-based purification module includes lid system having at least one gasketed lid, the at least one gasketed lid comprising at least one inlet to introduce a gas to enable control of positive head pressure; at least one vent port to enable equilibration to atmospheric pressure; at least one inlet to introduce a suspension of resin beads; at least one inlet to receive the filtrate containing a biological product; at least two inlets to introduce a buffer system to disperse the resin beads to enable washing of, dissociation from, or regeneration of said resin beads. In some embodiments, the at least one gasketed lid further comprises a port to accept an overhead stirring impeller to enable dispersion of the resin beads. In examples, the lid system has control of motion along the z-axis.

In embodiments, the negative charge-based purification module includes a mechanical rotary system, for example, a carousel comprising at least two vessels charged with resin beads that are configured to continuously receive a mixture containing a biological product and subsequently transport the resulting heterogeneous mixture containing a biological product, resin beads, a buffer, or any combination thereof. In examples, the carousel is a rotating structure that holds and transports at least two vessels to different process positions. In some examples, the mechanical rotary system is configured to mate with the lid system to enable pressurization. In other examples, the mechanical rotary system has control of motion or rotation in the xy-plane.

In embodiments, the at least two vessels of the positive charge-based purification module each have a supported, basement filter or filter membrane. In examples, the basement filter (or filter membrane) enables enable retention of the resin beads during process steps of association, washing, dissociation, and/or regeneration. In examples, the at least two vessels may further include a valve to control liquid flow.

In other embodiments, the positive charge-based purification module includes a staged linear system, for example, at least two vessels charged with resin beads that are configured to continuously receive a mixture containing a biological product and subsequently process the resulting heterogeneous mixture containing a biological product, resin beads, a buffer, or any combination thereof. In examples, the at least two vessels are configured to mate with the lid system to enable pressurization and liquid handling.

In embodiments, the positive charge-based purification module includes a collection system that interfaces with at least one of the at least two vessels of the mechanical rotary system to enable collection of waste, the fraction containing the biological product, or any combination thereof. In examples, the collection system has control of motion along the z-axis.

In other embodiments, the positive charge-based purification module includes a collection system that interfaces with at least one of the at least two vessels of the staged linear system to enable collection of waste, the fraction containing the biological product, or any combination thereof. In examples, the collection system is connected to the at least one of the at least two vessels.

In embodiments, the affinity-based purification module includes at least one gas. In some embodiments, without intent to be limiting the gas comprises filtered nitrogen or compressed dry air. In examples, the gas creates a pressure head of about 0.1 to about 30 psi.

In embodiments, the negative charge-based purification module includes at least one association/wash buffer system.

In embodiments, the negative charge-based purification module includes at least one dissociation buffer system. In examples, multiple dissociation buffers varying pH, ionic strength, or any combination thereof, are utilized continuously or sequentially to create a gradient dissociation effect.

In embodiments, the negative charge-based purification module includes at least one resin bead regeneration buffer system.

In embodiments, the negative charge-based purification module includes at least one collection vessel.

In embodiments, the negative charge-based purification module includes at least one sensor or detector.

In embodiments, the negative charge-based purification module includes at least one fluid handling pump.

Affinity-Based, Fluidic Purification Module

In aspects, provided herein is an affinity-based, fluidic purification module for separating a mixture into two or more fractions, at least one fraction containing a biological product. The affinity-based, fluidic purification module includes at least one inlet and at least one outlet configured to permit continuous fluid flow between the at least one inlet and the at least one outlet and wherein the flow rate may be, for example, consistent and constant during steady-state operation.

In embodiments, the affinity-based, fluidic purification module includes a suspension of magnetic resin beads, wherein the magnetic resin bead surface, without intent to be limiting, is coupled to Protein A, Protein G, Protein L, an antigenic protein, a protein, a receptor, an antibody, or an aptamer configured to selectively bind said biological product. In examples, the magnetic resin beads are mobile.

In embodiments, the affinity-based, fluidic purification module includes at least one equilibration vessel to allow for binding of the biological product to the magnetic resin bead surface; and, at least one first hybrid cross-flow fluidic device comprising a cross-flow channel, at least one magnetic field, and at least one of a piezoelectric component or a dielectrophoretic electrode configured to generate or induce a unidirectional force to separate said biological product bound magnetic resin beads from said heterogeneous mixture.

In embodiments, the affinity-based, fluidic purification module further includes at least one low pH equilibration vessel to allow for de-binding of the biological product from the magnetic resin bead surface; and, at least one second hybrid cross-flow fluidic device comprising a cross-flow channel, at least one magnetic field, and at least one of a piezoelectric component or a dielectrophoretic electrode configured to generate or induce a unidirectional force to separate said magnetic resin beads from said unbound biological product and complete its elution.

In embodiments, the affinity-based, fluidic purification module further includes at least one tangential flow filtration system operated in fed-batch or perfusion mode to concentrate and buffer exchange the fraction containing the biological product.

In embodiments, the affinity-based, fluidic purification module includes at least two buffer systems.

In embodiments, the affinity-based, fluidic purification module includes at least one magnetic resin bead regeneration buffer system.

In embodiments, the affinity-based, fluidic purification module includes at least one equilibration vessel configured to enable recycling of said magnetic resin beads.

In embodiments, the affinity-based, fluidic purification module includes at least one sensor or detector.

In embodiments, the affinity-based, fluidic purification module includes at least one fluid handling pump.

Positive Charge-Based, Fluidic Purification Module

In aspects, provided herein is a positive charge-based, fluidic purification module for separating a mixture into two or more fractions, at least one fraction containing a biological product. The positive charge-based, fluidic purification module includes at least one inlet and at least one outlet configured to permit continuous fluid flow between the at least one inlet and the at least one outlet and wherein the flow rate may be, for example, consistent and constant during steady-state operation.

In embodiments, the positive charge-based, fluidic purification module includes a suspension of magnetic resin beads, wherein the magnetic resin bead surface comprises cationic functionality configured to selectively associate with said biological product at a specific pH and ionic strength. In examples, the magnetic resin beads are mobile.

In embodiments, the positive charge-based, fluidic purification module includes at least one association equilibration vessel to allow for association of the biological product with the magnetic resin bead surface; and, at least one first hybrid cross-flow fluidic device comprising a cross-flow channel, at least one magnetic field, and at least one of a piezoelectric component or a dielectrophoretic electrode configured to generate or induce a unidirectional force to separate said biological product associated magnetic resin beads from said heterogeneous mixture.

In embodiments, the positive charge-based, fluidic purification module includes at least one dissociation equilibration vessel to allow for dissociation of the biological product from the magnetic resin bead surface; and, at least one second hybrid cross-flow fluidic device comprising a cross-flow channel, at least one magnetic field, and at least one of a piezoelectric component or a dielectrophoretic electrode configured to generate or induce a unidirectional force to separate said magnetic resin beads from said dissociated biological product and complete its purification. In examples, multiple dissociation equilibration vessels comprising discrete buffers varying pH, ionic strength, or any combination thereof, are utilized sequentially to create a gradient dissociation effect.

In embodiments, the positive charge-based, fluidic purification module further includes at least one tangential flow filtration system operated in fed-batch or perfusion mode to concentrate and buffer exchange the fraction containing the biological product.

In embodiments, the positive charge-based, fluidic purification module includes at least two buffer systems.

In embodiments, the positive charge-based, fluidic purification module includes at least one magnetic resin bead regeneration buffer system.

In embodiments, the positive charge-based, fluidic purification module includes at least one equilibration vessel configured to enable recycling of said magnetic resin beads.

In embodiments, the positive charge-based, fluidic purification module includes at least one sensor or detector.

In embodiments, the positive charge-based, fluidic purification module includes at least one fluid handling pump.

Negative Charge-Based, Fluidic Purification Module

In aspects, provided herein is a negative charge-based, fluidic purification module for separating a mixture into two or more fractions, at least one fraction containing a biological product. The negative charge-based, fluidic purification module includes at least one inlet and at least one outlet configured to permit continuous fluid flow between the at least one inlet and the at least one outlet and wherein the flow rate may be, for example, consistent and constant during steady-state operation.

In embodiments, the negative charge-based, fluidic purification module includes a suspension of magnetic resin beads, wherein the magnetic resin bead surface comprises anionic functionality configured to selectively associate with said biological product at a specific pH and ionic strength. In examples, the magnetic resin beads are mobile.

In embodiments, the negative charge-based, fluidic purification module includes at least one association equilibration vessel to allow for association of the biological product with the magnetic resin bead surface; and, at least one first hybrid cross-flow fluidic device comprising a cross-flow channel, at least one magnetic field, and at least one of a piezoelectric component or a dielectrophoretic electrode configured to generate or induce a unidirectional force to separate said biological product associated magnetic resin beads from said heterogeneous mixture.

In embodiments, the negative charge-based, fluidic purification module includes at least one dissociation equilibration vessel to allow for dissociation of the biological product from the magnetic resin bead surface; and, at least one second hybrid cross-flow fluidic device comprising a cross-flow channel, at least one magnetic field, and at least one of a piezoelectric component or a dielectrophoretic electrode configured to generate or induce a unidirectional force to separate said magnetic resin beads from said dissociated biological product and complete its purification. In examples, multiple dissociation equilibration vessels comprising discrete buffers varying pH, ionic strength, or any combination thereof, are utilized sequentially to create a gradient dissociation effect.

In embodiments, the negative charge-based, fluidic purification module further includes at least one tangential flow filtration system operated in fed-batch or perfusion mode to concentrate and buffer exchange the fraction containing the biological product.

In embodiments, the negative charge-based, fluidic purification module includes at least two buffer systems.

In embodiments, the negative charge-based, fluidic purification module includes at least one magnetic resin bead regeneration buffer system.

In embodiments, the negative charge-based, fluidic purification module includes at least one equilibration vessel configured to enable recycling of said magnetic resin beads.

In embodiments, the negative charge-based, fluidic purification module includes at least one sensor or detector.

In embodiments, the negative charge-based, fluidic purification module includes at least one fluid handling pump.

Affinity-Based TFF Purification Module

In aspects, provided herein is an affinity-based TFF purification module for separating a mixture into two or more fractions, at least one fraction containing a biological product. The affinity-based TFF purification module includes at least one inlet and at least one outlet configured to permit continuous fluid flow between the at least one inlet and the at least one outlet and wherein the flow rate is consistent and constant during steady-state operation.

In embodiments, the affinity-based TFF purification module includes a suspension of resin beads, wherein the resin bead surface, without intent to be limiting, is coupled to Protein A, Protein G, Protein L, an antigenic protein, a protein, a receptor, an antibody, or an aptamer configured to selectively bind said biological product. In examples, the magnetic resin beads are mobile.

In embodiments, the affinity-based TFF purification module includes at least one equilibration vessel to allow for binding of the biological product to the resin bead surface; and, at least one first tangential flow filtration system to separate said biological product bound resin beads from said heterogeneous mixture.

In embodiments, the affinity-based TFF purification module further includes at least one low pH equilibration vessel to allow for de-binding of the biological product from the resin bead surface; and, at least one second tangential flow filtration system to separate said resin beads from said unbound biological product and complete its elution.

In embodiments, the affinity-based TFF purification module includes at least one regeneration equilibration vessel; and at least one third tangential flow filtration system to allow for concentration and buffer exchange of the resin beads to return the resin beads to their initial condition, thus enabling recycling and reuse of the resin beads.

In embodiments, the affinity-based TFF purification module includes at least one collection vessel; and at least one fourth tangential flow filtration system to allow for concentration and buffer exchange of the biological product, thus purifying the biological product.

In embodiments, the at least one equilibration vessel, the at least one low pH equilibration vessel, and the at least one regeneration equilibration vessel of the affinity-based TFF purification module may comprise a single vessel that is transitioned between the corresponding tangential flow filtration systems to enable purification and regeneration of the resin beads with appropriate buffers, while maintaining continuous flow of the filtrate via at least one additional vessel on a parallel flow path.

In embodiments, the regeneration of the resin beads may be accomplished with the at least one low pH equilibration vessel and the at least one second tangential flow filtration system of the affinity-based TFF purification module configured to comprise both the low pH elution buffer and the regeneration buffer to enable purification, concentration and buffer exchange, thus regenerating the resin beads without necessitating a separate regeneration equilibration vessel and corresponding tangential flow filtration system.

In embodiments, the affinity-based TFF purification module includes at least two buffer systems.

In embodiments, the affinity-based TFF purification module includes at least one resin bead regeneration buffer system.

In embodiments, the affinity-based TFF purification module includes at least one hollow fiber membrane filter.

In embodiments, the affinity-based TFF purification module includes at least one sensor or detector.

In embodiments, the affinity-based TFF purification module includes at least one fluid handling pump.

Positive Charge-Based TFF Purification Module

In aspects, provided herein is a positive charge-based TFF purification module for separating a mixture into two or more fractions, at least one fraction containing a biological product. The positive charge-based TFF purification module includes at least one inlet and at least one outlet configured to permit continuous fluid flow between the at least one inlet and the at least one outlet and wherein the flow rate is consistent and constant during steady-state operation.

In embodiments, the positive charge-based TFF purification module includes a suspension of resin beads, wherein the resin bead surface comprises cationic functionality configured to selectively associate with said biological product at a specific pH and ionic strength. In examples, the magnetic resin beads are mobile.

In embodiments, the positive charge-based TFF purification module includes at least one association equilibration vessel to allow for association of the biological product with the resin bead surface; and, at least one first tangential flow filtration system to separate said biological product associated resin beads from said heterogeneous mixture.

In embodiments, the positive charge-based TFF purification module includes at least one dissociation equilibration vessel to allow for dissociation of the biological product from the resin bead surface; and, at least one second tangential flow filtration system to separate said resin beads from said dissociated biological product and complete its purification. In some aspects, multiple dissociation equilibration vessels are utilized with multiple tangential flow filtration systems to achieve a gradient dissociation, for example, a pH gradient or an ionic strength gradient.

In embodiments, the positive charge-based TFF purification module includes at least one regeneration equilibration vessel; and at least one third tangential flow filtration system to allow for concentration and buffer exchange of the resin beads to return the resin beads to their initial condition, thus enabling recycling and reuse of the resin beads.

In embodiments, the positive charge-based TFF purification module includes at least one collection vessel; and at least one fourth tangential flow filtration system to allow for concentration and buffer exchange of the biological product, thus purifying the biological product.

In embodiments, the at least one association equilibration vessel, the at least one dissociation vessel, and the at least one regeneration equilibration vessel of the positive charge-based TFF purification module may comprise a single vessel that is transitioned between the corresponding tangential flow filtration systems to enable purification and regeneration of the resin beads with appropriate buffers, while maintaining continuous flow of the filtrate via at least one additional vessel on a parallel flow path.

In embodiments, the regeneration of the resin beads may be accomplished with the at least one dissociation vessel and the at least one second tangential flow filtration system of the positive charge-based TFF purification module configured to comprise both the dissociation buffer and the regeneration buffer to enable purification, concentration and buffer exchange, thus regenerating the resin beads without necessitating a separate regeneration equilibration vessel and corresponding tangential flow filtration system.

In embodiments, the positive charge-based TFF purification module includes at least two buffer systems.

In embodiments, the positive charge-based TFF purification module includes at least one resin bead regeneration buffer system.

In embodiments, the positive charge-based TFF purification module includes at least one hollow fiber membrane filter.

In embodiments, the positive charge-based TFF purification module includes at least one sensor or detector.

In embodiments, the positive charge-based TFF purification module includes at least one fluid handling pump.

Negative Charge-Based TFF Purification Module

In aspects, provided herein is a negative charge-based TFF purification module for separating a mixture into two or more fractions, at least one fraction containing a biological product. The negative charge-based TFF purification module includes at least one inlet and at least one outlet configured to permit continuous fluid flow between the at least one inlet and the at least one outlet and wherein the flow rate is consistent and constant during steady-state operation.

In embodiments, the negative charge-based TFF purification module includes a suspension of resin beads, wherein the resin bead surface comprises anionic functionality configured to selectively associate with said biological product at a specific pH and ionic strength.

In embodiments, the negative charge-based TFF purification module includes at least one association equilibration vessel to allow for association of the biological product with the resin bead surface; and, at least one first tangential flow filtration system to separate said biological product associated resin beads from said heterogeneous mixture.

In embodiments, the negative charge-based TFF purification module includes at least one dissociation equilibration vessel to allow for dissociation of the biological product from the resin bead surface; and, at least one second tangential flow filtration system to separate said resin beads from said dissociated biological product and complete its purification. In some aspects, multiple dissociation equilibration vessels are utilized with multiple tangential flow filtration systems to achieve a gradient dissociation, for example, a pH gradient or an ionic strength gradient.

In embodiments, the negative charge-based TFF purification module includes at least one regeneration equilibration vessel; and at least one third tangential flow filtration system to allow for concentration and buffer exchange of the resin beads to return the resin beads to their initial condition, thus, enabling recycling and reuse of the resin beads.

In embodiments, the negative charge-based TFF purification module includes at least one collection vessel; and at least one fourth tangential flow filtration system to allow for concentration and buffer exchange of the biological product, thus purifying the biological product.

In embodiments, the at least one association equilibration vessel, the at least one dissociation vessel, and the at least one regeneration equilibration vessel of the negative charge-based TFF purification module may comprise a single vessel that is transitioned between the corresponding tangential flow filtration systems to enable purification and regeneration of the resin beads with appropriate buffers, while maintaining continuous flow of the filtrate via at least one additional vessel on a parallel flow path.

In embodiments, the regeneration of the resin beads may be accomplished with the at least one dissociation vessel and the at least one second tangential flow filtration system of the negative charge-based TFF purification module configured to comprise both the dissociation buffer and the regeneration buffer to enable purification, concentration and buffer exchange, thus regenerating the resin beads without necessitating a separate regeneration equilibration vessel and corresponding tangential flow filtration system.

In embodiments, the negative charge-based TFF purification module includes at least two buffer systems.

In embodiments, the negative charge-based TFF purification module includes at least one resin bead regeneration buffer system.

In embodiments, the negative charge-based TFF purification module includes at least one hollow fiber membrane filter.

In embodiments, the negative charge-based TFF purification module includes at least one sensor or detector.

In embodiments, the negative charge-based TFF purification module includes at least one fluid handling pump.

Isoelectric Point-Based, Fluidic Purification Module

In aspects, provided herein is an isoelectric point-based, fluidic purification module for separating a mixture into two or more fractions, at least one fraction containing a biological product. The isoelectric point-based fluidic purification module includes at least one inlet and at least one outlet configured to permit continuous fluid flow between the at least one inlet and the at least one outlet and wherein the flow rate may be, for example, consistent and constant during steady-state operation.

In embodiments, the process described herein of continuously transferring the fraction containing the biological product from the at least one first outlet of the first module to a second module, wherein the second module includes free-flow electrophoresis apparatus. For example, the free-flow electrophoresis apparatus has at least one fluidic device comprising a fluidic channel created between two parallel plates, an electric field or electric field gradient orthogonal to the fluid flow direction, and an aqueous solution (e.g., an ionic solution, or a solution providing a buffer or ampholyte). In examples, the solution contacting surfaces of the two parallel plates comprise glass, ceramic, plastic, or any combination thereof. In some examples, the aqueous ionic solution may give rise to a pH gradient. In other examples, the aqueous ionic solution may confer constant pH.

In embodiments, the free-flow electrophoresis apparatus has at least one fluidic device comprising a fluidic channel created between two parallel plates, an electric field or electric field gradient orthogonal to the fluid flow direction, and a pH gradient. In examples, the isoelectric point-based, fluidic purification module includes at least one first fluidic device comprising a fluidic channel created between two parallel plates, an electric field or electric field gradient orthogonal to the fluid flow direction, and a coarse pH gradient across the main separation channel (in examples, a coarse pH gradient may be a pH range from about 2 to about 10); and at least one second fluidic device comprising a fluidic channel created between two parallel plates, an electric field or electric field gradient orthogonal to the fluid flow direction, and a fine pH gradient across the main separation channel (in examples, a fine pH gradient may be a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In other embodiments, the free-flow electrophoresis apparatus has at least one fluidic device comprising a fluidic channel created between two parallel plates, an electric field or electric field gradient orthogonal to the fluid flow direction, and no pH gradient to operate in a zone electrophoresis or charge separating mode of operation. In examples, the isoelectric point-based, fluidic purification module includes at least one first fluidic device comprising a fluidic channel created between two parallel plates, an electric field or electric field gradient orthogonal to the fluid flow direction, and constant basic pH (e.g., a pH of greater than 7); and at least one second fluidic device comprising a fluidic channel created between two parallel plates, an electric field or electric field gradient orthogonal to the fluid flow direction, and a constant acidic pH (e.g., a pH of less than 7).

In other embodiments, the free-flow electrophoresis apparatus has at least one fluidic device comprising a fluidic channel created between two parallel plates, an electric field or electric field gradient orthogonal to the fluid flow direction, and both an acidic pH gradient and a basic pH gradient separated by a spacer solution (e.g. NaCl solution) to operate in an isotachophoresis mode of operation.

In other embodiments, the isoelectric point-based, fluidic purification module includes at least one first free-flow electrophoresis apparatus comprising a fluidic channel created between two parallel plates and an electric field or electric field gradient orthogonal to the fluid flow direction, and at least one second free-flow electrophoresis apparatus comprising a fluidic channel created between two parallel plates and an electric field or electric field gradient orthogonal to the fluid flow direction, wherein each device connected in series and is capable of operating in an independent mode of operation to enable purification. For example, the at least one first free-flow electrophoresis apparatus may operate in an isoelectric focusing mode and the at least one second free-flow electrophoresis apparatus may operate in an isotachophoresis mode to increase separation resolution.

In other embodiments, the isoelectric point-based, fluidic purification module includes at least one first fluidic device comprising fluidic channel having at least one dielectrophoretic electrode capable of inducing a defined, unidirectional force; at least one second free-flow electrophoresis apparatus comprising a fluidic channel created between two parallel plates, an electric field or electric field gradient orthogonal to the fluid flow direction, and a coarse pH gradient across the main separation channel (e.g., a pH range from about 2 to about 10); and at least one third free-flow electrophoresis apparatus comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In embodiments, the isoelectric point-based fluidic purification apparatus further comprises at least two electrodes (e.g. platinum wire electrodes) to function as an anode or a cathode.

In embodiments, the backpressure within the isoelectric point-based fluidic purification apparatus is dependent on the channel geometry and dimensions, the inlet and outlet opening and/or tubing diameters, and the input flow rate. In examples, the backpressure ranges from about 0.5 psi to about 10 psi. In some examples, the backpressure is controlled by, for example, without intent to be limiting, a needle valve.

In embodiments, the isoelectric point-based fluidic purification apparatus further comprises at least one de-bubbler system to continuously remove $O_2$ and $H_2$ gas bubbles that evolve in the electrode channels under applied voltage. In some embodiments, removal of electrolysis bubbles is essential to enable continuous operation for substantially long periods of time. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar.

In embodiments, the isoelectric point-based fluidic purification apparatus further comprises an active cooling system or heat sink to enable temperature control and Joule heat dissipation. In examples, the active cooling system comprises an aluminum thermal chuck containing a chilled, circulating water/propylene glycol jacket.

In embodiments, the isoelectric point-based, fluidic purification module includes at least one buffer or ampholyte system.

In embodiments, the isoelectric point-based, fluidic purification module includes at least one electrode solution. In some embodiments, the at least one electrode solution comprises an electrolyte solution configured to contact and enable the appropriate function of an anode or a cathode, for example, phosphoric acid and sodium hydroxide, respectively. In other embodiments, the at least one electrode solution comprises at least one ampholyte solution configured to contact and enable the appropriate function of an anode or a cathode, for example, Tris buffered saline flowing through the main separation channel, the anode channel, and the cathode channel.

In embodiments, the isoelectric point-based, fluidic purification module includes at least one sensor or detector. In examples, the at least one sensor or detector is positioned in-line. In some examples, the at least one sensor or detector includes, but is not limited to, a flow sensor, a temperature sensor, a conductivity sensor, a pH sensor, a refractive index detector, a UV detector, or a backpressure sensor.

In embodiments, the isoelectric point-based, fluidic purification module includes at least one liquid circuit breaker or disconnect downstream of the device and upstream of the at least one in-line sensor or detector to ensure the ability to perform sensing or detection in a voltage-free solution.

In embodiments, the isoelectric point-based, fluidic purification module includes at least one fluid handling pump.

In embodiments, the isoelectric point-based, fluidic purification module includes at least one collection vessel.

Methods

Provided herein are methods of purifying a biological product from a heterogeneous mixture derived from a bioreactor producing said biological product comprising the processes described herein. In examples, the bioreactor type includes, but is not limited to, a batch bioreactor, a fed-batch bioreactor, a perfusion bioreactor, a chemostat bioreactor, or a multi-compartment bioreactor. In some examples, the bioreactor produce said biological product at steady-state.

In embodiments, provided herein is a method of purifying a biological product from a heterogeneous mixture derived from a bioreactor producing said biological product comprising utilizing at least one of the modules described herein, for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module.

In some embodiments, provided herein is a method of continuously purifying a biological product from a heterogeneous mixture derived from a bioreactor producing said biological product at steady-state comprising utilizing at least one of the modules described herein, for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module.

In other embodiments, provided herein is a method of purifying a biological product from a heterogeneous mixture not derived from a bioreactor producing said biological product at steady-state comprising utilizing at least one of the modules described herein, for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module.

Other aspects of the invention are disclosed infra.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows an exemplary continuous process flow wherein Step 1 comprises a bioreactor producing a biological product at steady-state, Step 2 comprises a continuous dynamic filtration module, Step 3 comprises an affinity-based, magnetic purification module, Step 4 comprises at least one charge-based, magnetic purification module, Step 5 comprises a standard industry viral inactivation and filtration process, for example, performed in fed-batch or perfusion mode, and Step 6 comprises high performance tangential flow filtration with a charged membrane, for example, performed in fed-batch or perfusion mode to prepare for the standard industry fill-finish process in Step 7. FIG. 1B shows an exemplary continuous process flow wherein Step 1 comprises a bioreactor producing a biological product at steady-state, Step 2 comprises a continuous dynamic filtration module, Step 3 comprises an affinity-based, magnetic purification module, Step 4 comprises a positive charge-based, magnetic purification module, Step 5 comprises a negative charge-based, magnetic purification module, and Step 6 comprises high performance tangential flow filtration with a charged membrane, for example, performed in fed-batch or perfusion mode to prepare for the standard industry fill-finish process in Step 7. FIG. 1C shows an exemplary continuous process flow wherein Step 1 comprises a bioreactor producing a biological product at steady-state, Step 2 comprises a continuous dynamic filtration module, Step 3 comprises an affinity-based, magnetic purification module, Step 4 comprises an isoelectric point-based, fluidic purification module, Step 5 comprises a standard industry viral inactivation and filtration process, for example, performed in fed-batch or perfusion mode, and Step 6 comprises high performance tangential flow filtration with a charged membrane performed in fed-batch or perfusion mode to prepare for the standard industry fill-finish process in Step 7. FIG. 1D shows an exemplary continuous process flow wherein Step 1 comprises a bioreactor producing a biological product at steady-state, Step 2 comprises a continuous dynamic filtration module, Step 3 comprises an affinity-based, magnetic purification module, Step 4 comprises an isoelectric point-based, fluidic purification module, Step 5 comprises high performance tangential flow filtration with a charged membrane performed in fed-batch or perfusion mode to prepare for the standard industry fill-finish process in Step 6.

FIG. 2A shows an exemplary continuous process flow wherein Step 1 comprises a bioreactor producing a biological product at steady-state, Step 2 comprises a continuous dynamic filtration module, Step 3 comprises an affinity-based purification module, Step 4 comprises at least one charge-based purification module, Step 5 comprises a standard industry viral inactivation and filtration process, for example, performed in fed-batch or perfusion mode, and Step 6 comprises high performance tangential flow filtration with a charged membrane, for example, performed in fed-batch or perfusion mode to prepare for the standard industry fill-finish process in Step 7. FIG. 2B shows an exemplary continuous process flow wherein Step 1 comprises a bioreactor producing a biological product at steady-state, Step 2 comprises a continuous dynamic filtration module, Step 3 comprises an affinity-based purification module, Step 4 comprises a positive charge-based purification module, Step 5 comprises a negative charge-based purification module, and Step 6 comprises high performance tangential flow filtration with a charged membrane, for example, performed in fed-batch or perfusion mode to prepare for the standard industry fill-finish process in Step 7. FIG. 2C shows an exemplary continuous process flow wherein Step 1 comprises a bioreactor producing a biological product at steady-state, Step 2 comprises a continuous dynamic filtration module, Step 3 comprises an affinity-based purification module, Step 4 comprises an isoelectric point-based, fluidic purification module, Step 5 comprises a standard industry viral inactivation and filtration process, for example, performed in fed-batch or perfusion mode, and Step 6 comprises high performance tangential flow filtration with a charged membrane performed in fed-batch or perfusion mode to prepare for the standard industry fill-finish process in Step 7. FIG. 2D shows an exemplary continuous process flow wherein Step 1 comprises a bioreactor producing a biological product at steady-state, Step 2 comprises a continuous dynamic filtration module, Step 3 comprises an affinity-based purification module, Step 4 comprises an isoelectric point-based, fluidic purification module, Step 5 comprises high performance tangential flow filtration with a charged membrane performed in fed-batch or perfusion mode to prepare for the standard industry fill-finish process in Step 6.

FIG. 3A shows an exemplary continuous process flow wherein Step 1 comprises a bioreactor producing a biological product at steady-state, Step 2 comprises a continuous dynamic filtration module, Step 3 comprises an affinity-based, fluidic purification module, Step 4 comprises at least one charge-based, fluidic purification module, Step 5 comprises a standard industry viral inactivation and filtration process, for example, performed in fed-batch or perfusion mode, and Step 6 comprises high performance tangential flow filtration with a charged membrane, for example, performed in fed-batch or perfusion mode to prepare for the standard industry fill-finish process in Step 7. FIG. 3B shows an exemplary continuous process flow wherein Step 1 comprises a bioreactor producing a biological product at steady-state, Step 2 comprises a continuous dynamic filtration module, Step 3 comprises an affinity-based, fluidic purification module, Step 4 comprises a positive charge-based, fluidic purification module, Step 5 comprises a negative charge-based, fluidic purification module, and Step 6 comprises high performance tangential flow filtration with a charged membrane, for example, performed in fed-batch or perfusion mode to prepare for the standard industry fill-finish process in Step 7. FIG. 3C shows an exemplary continuous process flow wherein Step 1 comprises a bioreactor producing a biological product at steady-state, Step 2 comprises a continuous dynamic filtration module, Step 3 comprises an affinity-based, fluidic purification module, Step 4 comprises an isoelectric point-based, fluidic purification module, Step 5 comprises a standard industry viral inactivation and filtration process, for example, performed in fed-batch or perfusion mode, and Step 6 comprises high performance tangential flow filtration with a charged membrane performed in fed-batch or perfusion mode to prepare for the standard industry fill-finish process in Step 7. FIG. 3D shows an exemplary continuous process flow wherein Step 1 comprises a bioreactor producing a biological product at steady-state, Step 2 comprises a continuous dynamic filtration module, Step 3 comprises an affinity-based, fluidic purification module, Step 4 comprises an isoelectric point-based, fluidic purification module, Step 5 comprises high performance tangential flow filtration with a charged membrane performed in fed-batch or perfusion mode to prepare for the standard industry fill-finish process in Step 6.

FIG. 4A shows an exemplary continuous process flow wherein Step 1 comprises a bioreactor producing a biological product at steady-state, Step 2 comprises a continuous dynamic filtration module, Step 3 comprises an affinity-based TFF purification module, Step 4 comprises at least one charge-based TFF purification module, Step 5 comprises a standard industry viral inactivation and filtration process, for example, performed in fed-batch or perfusion mode, and Step 6 comprises high performance tangential flow filtration with a charged membrane, for example, performed in fed-batch or perfusion mode to prepare for the standard industry fill-finish process in Step 7. FIG. 4B shows an exemplary continuous process flow wherein Step 1 comprises a bioreactor producing a biological product at steady-state, Step 2 comprises a continuous dynamic filtration module, Step 3 comprises an affinity-based TFF purification module, Step 4 comprises a positive charge-based TFF purification module, Step 5 comprises a negative charge-based TFF purification module, and Step 6 comprises high performance tangential flow filtration with a charged membrane, for example, performed in fed-batch or perfusion mode to prepare for the standard industry fill-finish process in Step 7. FIG. 4C shows an exemplary continuous process flow wherein Step 1 comprises a bioreactor producing a biological product at steady-state, Step 2 comprises a continuous dynamic filtration module, Step 3 comprises an affinity-based TFF purification module, Step 4 comprises an isoelectric point-based, fluidic purification module, Step 5 comprises a standard industry viral inactivation and filtration process, for example, performed in fed-batch or perfusion mode, and Step 6 comprises high performance tangential flow filtration with a charged membrane performed in fed-batch or perfusion mode to prepare for the standard industry fill-finish process in Step 7. FIG. 4D shows an exemplary continuous process flow wherein Step 1 comprises a bioreactor producing a biological product at steady-state, Step 2 comprises a continuous dynamic filtration module, Step 3 comprises an affinity-based TFF purification module, Step 4 comprises an isoelectric point-based, fluidic purification module, Step 5 comprises high performance tangential flow filtration with a charged membrane performed in fed-batch or perfusion mode to prepare for the standard industry fill-finish process in Step 6.

FIGS. 6A and 6B show a series of exemplary designs of the dynamic filtration apparatus comprising a single output head to continuously transfer a heterogeneous mixture containing a biological product from a steady-state bioreactor bleed output line and a separate output head to supply a wash buffer. FIG. 6A is a schematic of a dynamic filtration apparatus design comprising a single output head to continuously transfer a heterogeneous mixture containing a biological product from a steady-state bioreactor bleed output line, a separate output head to supply a wash buffer, a rolled filter membrane functioning as a supply reel, a collection reel, two Servo motors to control the feed reel-to-collection reel system, two support rods having a mechanically smooth contact surface, a membrane support structure having a mechanically smooth contact surface and an opening having continuity with the vacuum line, a vacuum collection vessel, a diaphragm pump, and a peristaltic pump. FIG. 6B is a schematic of a dynamic filtration apparatus design comprising a single output head to continuously transfer a heterogeneous mixture containing a biological product from a steady-state bioreactor bleed output line, a separate output head to supply a wash buffer, a rolled filter membrane functioning as a feed reel, a collection reel, two Servo motors to control the feed reel-to-collection reel system, two support rods having a mechanically smooth contact surface, a membrane support structure having a mechanically smooth contact surface and an opening having continuity with the vacuum line, a controllable T-valve, two vacuum collection vessels, a diaphragm pump, and two peristaltic pumps.

FIGS. 7A and 7B show two exemplary designs of the dynamic filtration apparatus comprising multiple output heads to continuously transfer a heterogeneous mixture containing a biological product from a steady-state bioreactor bleed output line and multiple separate output heads to supply a wash buffer. FIG. 7A depicts a schematic of a dynamic filtration apparatus design comprising multiple output heads to transfer a heterogeneous mixture containing a biological product from a steady-state bioreactor bleed output line, multiple separate output heads to supply a wash buffer, a rolled filter membrane functioning as a feed reel, a collection reel, two Servo motors to control the feed reel-to-collection reel system, two support rods having a mechanically smooth contact surface, a membrane support structure having a mechanically smooth contact surface and an opening having continuity with the vacuum line, a vacuum collection vessel, a diaphragm pump, and a peristaltic pump. FIG. 7B depicts a schematic of a dynamic filtration apparatus design comprising a multiple output heads to continuously transfer a heterogeneous mixture containing a biological product from a steady-state bioreactor bleed output line, multiple separate output heads to supply a wash buffer, a rolled filter membrane functioning as a feed reel, a collection reel, two Servo motors to control the feed reel-to-collection reel system, two support rods having a mechanically smooth contact surface, a membrane support structure having a mechanically smooth contact surface and an opening having continuity with the vacuum line, a controllable T-valve, two vacuum collection vessels, a diaphragm pump, and two peristaltic pumps.

FIG. 8 depict images of an exemplary membrane support structure having an opening with five parallel slots.

FIG. 9A is an image depicting the visual comparison (left-to-right) of the initial heterogeneous mixture of PolyBeads (0.05% solids; 2 µm, 6 µm, and 10 µm diameter) in 1×PBS, the filtrate resulting from purification of the heterogeneous mixture with a 0.2 µm PTFE syringe filter, the filtrate resulting from purification of the heterogeneous mixture with an exemplary dynamic filtration apparatus (MBM-3 represents a sample with a dynamic filtration with a 0.45 µm PVDF filter membrane and a flow rate of 0.25 mL/min), and the filtrate resulting from purification of the heterogeneous mixture with an exemplary dynamic filtration apparatus (MBM-4 represents a sample with a dynamic filtration with a 0.45 µm PES filter membrane and flow rates of 0.25, 0.5, 1.0, 2.0, and 5.0 mL/min). FIG. 9B is a bar graph showing the UV-Vis spectrophotometric comparison of the initial heterogeneous mixture of PolyBeads (0.05% solids; 2 µm, 6 µm, and 10 µm diameter) in 1×PBS, the filtrate resulting from purification of the heterogeneous mixture with a 0.2 µm PTFE syringe filter, the filtrate resulting from purification of the heterogeneous mixture with an exemplary dynamic filtration apparatus having a 0.45 µm PVDF filter membrane and a flow rate of 0.25 mL/min (MBM-3), and the filtrate resulting from purification of the heterogeneous mixture with an exemplary dynamic filtration apparatus having a 0.45 µm PES filter membrane and flow rates of 0.25, 0.5, 1.0, 2.0, and 5.0 mL/min (MBM-4), thus demonstrating successful removal of the PolyBeads from the heterogeneous mixture with the exemplary dynamic filtration apparatus.

FIGS. 10A-10D are a series of data showing the removal of PolyBeads (0.05% solids; 2 µm (red), 6 µm (red), and 10 µm (blue) diameter) from a heterogeneous mixture of Poly-Beads suspended in a 0.5 mg/mL solution of BSA-FITC in 1×PBS. FIG. 10A is a graph showing UV-Vis spectrophotometric traces of a serially diluted heterogeneous mixture of PolyBeads (0.05% solids; 2 µm, 6 µm, and 10 µm diameter) suspended in a 0.5 mg/mL solution of BSA-FITC in 1×PBS showing the PolyBead signature region and indicating the presence of PolyBeads. FIG. 10B is a graph showing UV-Vis spectrophotometric traces of a serially diluted 0.5 mg/mL solution of BSA-FITC in 1×PBS showing the PolyBead signature region and indicating the absence of PolyBeads. FIG. 10C depicts an image of a visual comparison (left-to-right) of the initial heterogeneous mixture of PolyBeads (0.05% solids; 2 µm, 6 µm, and 10 µm diameter) suspended in a 0.5 mg/mL solution of BSA-FITC in 1×PBS, the filtrate resulting from purification of the heterogeneous mixture with a 0.2 µm PTFE syringe filter, the filtrate resulting from purification of the heterogeneous mixture with an exemplary dynamic filtration apparatus (MBM-3a represents a sample with a dynamic filtration with a 0.45 µm PVDF filter membrane and a flow rate of 0.25 mL/min), the filtrate resulting from purification of the heterogeneous mixture with an exemplary dynamic filtration apparatus (MBM-4a represents a sample with dynamic filtration with a 0.45 µm PES filter membrane and a flow rate of 0.5 mL/min), the filtrate resulting from purification of the heterogeneous mixture with an exemplary dynamic filtration apparatus (MBM-5a represents a sample with dynamic filtration with a 0.45 µm PES filter membrane and a flow rate of 2.0 mL/min), and the supernatant collected from purification of the heterogeneous mixture by centrifugation (5 min at 10,000×g). FIG. 10D is a graph showing the UV-Vis spectrophotometric comparison of the initial heterogeneous mixture of PolyBeads (0.05% solids; 2 µm, 6 µm, and 10 µm diameter) suspended in a 0.5 mg/mL solution of BSA-FITC in 1×PBS, the filtrate resulting from purification of the heterogeneous mixture with a 0.2 µm PTFE syringe filter, the filtrate resulting from purification of the heterogeneous mixture with an exemplary dynamic filtration apparatus (MBM-3a), the filtrate resulting from purification of the heterogeneous mixture with an exemplary dynamic filtration apparatus (MBM-4a), the filtrate resulting from purification of the heterogeneous mixture with an exemplary dynamic filtration apparatus (MBM-5a), and the supernatant collected from purification by centrifugation (5 min at 10,000×g), thus demonstrating successful purification of BSA-FITC by removal of the PolyBeads, as indicated by the absence of PolyBeads in the PolyBead signature region, with the exemplary dynamic filtration apparatus.

FIG. 12A shows the dynamic filtration via a slot die output head. FIG. 11A depicts an image of a visual comparison (left-to-right) of the initial heterogeneous mixture of PolyBeads (2 µm, 6 µm, and 10 µm diameter at $1.1 \times 10^8$, $4.2 \times 10^6$, and $1.0 \times 10^6$ particles/mL, respectively) suspended in a 0.5 mg/mL solution of hIgG in 1×PBS, the filtrate resulting from purification of the heterogeneous mixture with an exemplary dynamic filtration apparatus having a 0.45 µm PES filter membrane and a flow rate of 10 mL/min, and the supernatant collected from purification of the heterogeneous mixture by centrifugation (5 min at 10,000×g). FIG. 11D is a graph showing the spectrophotometric comparison of the total protein concentration as determined by BCA assay of the filtrates obtained by dynamic filtration and the supernatant collected by centrifugation.

FIGS. 12A-12D show the protein recovery of dynamic filtration across different proteins, protein concentrations, filter membrane materials and pore sizes, and membrane support structures and during continuous operation at different input flow rates. FIG. 12A shows the recovery of proteins of different size and charge (bovine serum albumin (BSA), Lysozyme, and hIgG at 0.5-10 mg/mL, 5 mg/mL, and 0.5 mg/mL, respectively) by BCA assay of the filtrates obtained by dynamic filtration with a 0.45 µm PES filter membrane having a 0.5 mm/sec transport velocity and an input flow rate of 10 mL/min. FIG. 12B shows the recovery of hIgG at 0.5 mg/mL by BCA assay of the filtrates obtained by dynamic filtration with filter membranes of different materials and pore sizes (0.45 µm PES, 0.45 µm hydrophilic PVDF, 0.22 µm PES) having a 0.5 mm/sec transport velocity and an input flow rate of 10 mL/min. FIG. 12C shows the recovery of hIgG at 0.5 mg/mL by BCA assay of the filtrates obtained by dynamic filtration with different membrane support structures (a PTFE membrane support structure with 5 parallel slots and a PTFE membrane support structure with a porous hydrophilic polyethylene (PE) insert) and a 0.45 µm PES filter membrane having a 0.5 mm/sec transport velocity and an input flow rate of 10 mL/min. FIG. 12D shows the recovery of Lysozyme at 0.5 mg/mL by BCA assay of the filtrates obtained by dynamic filtration at different flow rates (5 and 10 mL/min) during long-term, continuous operation with a 0.45 µm PES filter membrane having a 0.5 mm/sec transport velocity.

FIG. 13A shows optical imaging (left-to-right) of the initial hIgG-spiked, murine myeloma suspension cell culture in RPMI media (1 g/L hIgG in $2\times10^6$ cells/mL), filtrates (DF-1, DF-2, DF-3) obtained by dynamic filtration at an input flow rate of 2 mL/min with a 0.45 µm PES filter membrane having a transport velocity of 0.5 mm/sec, and supernatants (C-1, C-2, C-3) collected from centrifugation for 5 minutes at 10,000×g. FIG. 13B shows SDS-PAGE analysis (left-to-right) of the initial hIgG-spiked, murine myeloma suspension cell culture in RPMI media (1 g/L hIgG in $2\times10^6$ cells/mL), filtrates (DF-1, DF-2, DF-3) derived from dynamic filtration at an input flow rate of 2 mL/min with a 0.45 µm PES filter membrane having a transport velocity of 0.5 mm/sec, and supernatants (C-1, C-2, C-3) derived from centrifugation for 5 minutes at 10,000×g. FIG. 13C shows the comparison of the recovery of hIgG from the heterogeneous mixture (suspension cell culture in RPMI media spiked with 1 g/L hIgG) by BCA assay of the filtrates obtained by dynamic filtration at an input flow rate of 2 mL/min with a 0.45 µm PES filter membrane having a transport velocity of 0.5 mm/sec (blue outlined bar) and the supernatants collected from centrifugation for 5 minutes at 10,000×g.

FIG. 20A shows total protein analysis by BCA assay across fractions collected from 3 sequential cycles of magnetic affinity bead use and recycling demonstrating the ability to reproducibly recycle and reuse the magnetic affinity beads without compromising binding capacity and performance. FIG. 20B shows SDS-PAGE analysis across fractions collected from 3 sequential cycles of magnetic affinity bead use and recycling demonstrating the ability to reproducibly recycle and reuse the magnetic affinity beads without compromising binding capacity and performance.

FIG. 21A is a schematic of a lid system. FIG. 21B is a schematic of a vessel carousel. FIG. 21C is a schematic of a collection system. FIG. 21D depicts the manner to which the lid system and collection system interface with the vessel carousel.

FIG. 22A is a schematic of a lid system. FIG. 22B is a schematic of a vessel carousel. FIG. 22C is a schematic of a collection system. FIG. 22D depicts the manner to which the lid system and collection system interface with the vessel carousel.

FIG. 23A is a schematic of an exemplary gasketed lid, vessel, and collector assembly. FIG. 23B is a schematic of an exemplary gasketed lid comprising an air inlet, two buffer inlets configured to generate a circular flow pattern, a vent port, and a filling inlet that is a component of the lid system. FIG. 23C is a schematic of a vessel comprising, a mesh filter or a frit, and a valve that is a component of the vessel carousel. FIG. 23D is a schematic of the collector that is a component of the collection system.

FIG. 24A show the individual system components of an affinity-based purification apparatus. FIG. 24B show connectivity of the affinity-based purification apparatus comprising a staged linear system.

FIG. 24A show the individual system components of a charge-based purification apparatus. FIG. 24B show connectivity of the charge-based purification apparatus comprising a staged linear system.

FIG. 26A shows total protein analysis by BCA assay across fractions collected from 3 sequential cycles of affinity resin bead use and recycling demonstrating the ability to reproducibly recycle and reuse the affinity resin beads without compromising binding capacity and performance. FIG. 26B shows SDS-PAGE analysis across fractions collected from 3 sequential cycles of affinity resin bead use and recycling demonstrating the ability to reproducibly recycle and reuse the affinity resin beads without compromising binding capacity and performance.

FIG. 27A shows total protein analysis by BCA assay across fractions collected from 3 sequential cycles of affinity resin bead use and recycling demonstrating the ability to reproducibly recycle and reuse the affinity resin beads without compromising binding capacity and performance. FIG. 27B shows SDS-PAGE analysis across fractions collected from 3 sequential cycles of affinity resin bead use and recycling demonstrating the ability to reproducibly recycle and reuse the affinity resin beads without compromising binding capacity and performance.

FIG. 28A is an image showing a hybrid fluidic device comprising a parallel cross-flow channel, a permanent magnetic field, and two piezoelectric transducers. FIG. 28B is an image showing a hybrid fluidic device comprising an angled cross-flow channel, a permanent magnetic field, and two piezoelectric transducers. FIG. 28C is an image showing a hybrid fluidic device comprising a parallel cross-flow channel, a permanent magnetic field, and two selective dielectrophoretic electrodes. FIG. 28D is an image showing a hybrid fluidic device comprising an angled cross-flow channel, a permanent magnetic field, and two selective dielectrophoretic electrodes.

FIG. 40A shows an optical image of the fractions collected from the five outlets at 0V and 5 mL/min. FIG. 40B shows the absorbance spectra of the fractions collected from the five outlets at 0V and 5 mL/min. FIG. 40C shows an optical image of the fractions collected from the five outlets at 1000V and 10 mL/min in the presence of a pH gradient. FIG. 40D shows the absorbance spectra of the fractions collected from the five outlets at 1000V and 10 mL/min in the presence of a pH gradient. FIG. 40E shows the purification of the mixture resulting in fractions containing purified Rhodamine 6G (outlet 2, towards the cathode) and purified Fluorescein (outlet 4, toward the anode).

FIG. 41A shows isoelectric focusing free-flow electrophoresis of a mixture of Rhodamine 6G and Fluorescein at 500V and a flow rate of 3 mL/min. FIG. 41B shows isoelectric focusing free-flow electrophoresis of a mixture of Rhodamine 6G and Fluorescein at 700V and a flow rate of 5 mL/min. FIG. 41C shows isoelectric focusing free-flow electrophoresis of a mixture of Rhodamine 6G and Fluorescein at 900V and a flow rate of 10 mL/min.

FIG. 42A shows isoelectric focusing free-flow electrophoresis of a mixture of Basic Fuchsin (0.05 mg/mL, net charge of +3) and Fluorescein (0.25 mg/mL, net charge of −1) at 500V and a flow rate of 5 mL/min. FIG. 42B shows isoelectric focusing free-flow electrophoresis of a mixture of Crystal Violet (0.05 mg/mL, net charge of +3) and Fluorescein (0.25 mg/mL, net charge of −1) at 500V and a flow rate of 5 mL/min.

FIG. 44A shows isotachophoresis of a mixture of Rhodamine 6G (0.25 mg/mL, net charge of +1) and Fluorescein (0.25 mg/mL, net charge of −1) at 250V and a flow rate of 5 mL/min resulting in concentration of the two dyes into two discrete high resolution lines. FIG. 44B shows UV illumination of the results presented in FIG. 46A.

FIG. 45A shows the spectrophotometric analysis by BCA assay of the total protein concentration of the fractions derived from the five outlets at 0V and a flow rate of 10 mL/min. FIG. 45B shows the SDS-PAGE analysis of the fractions derived from the five outlets at 0V and a flow rate of 10 mL/min, showing the mixture present in outlet 3. FIG. 45C shows the spectrophotometric analysis by BCA assay of the total protein concentration of the fractions derived from the five outlets at 850V and a flow rate of 10 mL/min, showing a distribution of protein across outlets 2, 3, and 4. FIG. 45D shows the SDS-PAGE analysis of the fractions derived from the five outlets at 850V and a flow rate of 10 mL/min, showing the presence of purified Lysozyme in outlet 2 and purified BSA in outlet 4. FIG. 45E shows the theoretical electrophoretic migration direction of BSA (toward the anode) and Lysozyme (toward the cathode).

FIG. 46A shows the spectrophotometric analysis by BCA assay of the total protein concentration of the fractions derived from the five outlets at either (1) 0V, 5 mL/min, (2) 1000V, 5 mL/min, (3) 1500V, 5 mL/min, (4) 0V, 10 mL/min, or (5) 1000V, 10 mL/min. FIG. 46B shows the theoretical electrophoretic migration direction of hIgG (toward the anode, cathode and center) and Lysozyme (toward the cathode). FIG. 46C shows the SDS-PAGE analysis of the fractions derived from the five outlets at either (1) 0V, 5 mL/min, (2) 1000V, 5 mL/min, (3) 1500V, 5 mL/min, (4) 0V, 10 mL/min, or (5) 1000V, 10 mL/min.

FIG. 47A shows the spectrophotometric analysis by BCA assay of the total protein concentration of the fractions derived from the five outlets at 0V and 500V at a flow rate of 3 mL/min, showing a distribution of protein across outlets 2, 3, and 4 under applied voltage. FIG. 47B shows the spectrophotometric analysis by BCA assay of the total protein concentration of the fractions derived from the five outlets at 0V and 700V at a flow rate of 5 mL/min, showing a distribution of protein across outlets 2, 3, and 4 under applied voltage. FIG. 47C shows the spectrophotometric analysis by BCA assay of the total protein concentration of the fractions derived from the five outlets at 0V and 850V at a flow rate of 10 mL/min, showing a distribution of protein across outlets 2, 3, and 4 under applied voltage. FIG. 47D shows the SDS-PAGE analysis of the fractions derived from the five outlets at either (1) 0V or 500V at 3 mL/min, (2) 0V or 700V at 5 mL/min, or (3) 0V or 850V at 10 mL/min.

DETAILED DESCRIPTION

Figure 1:
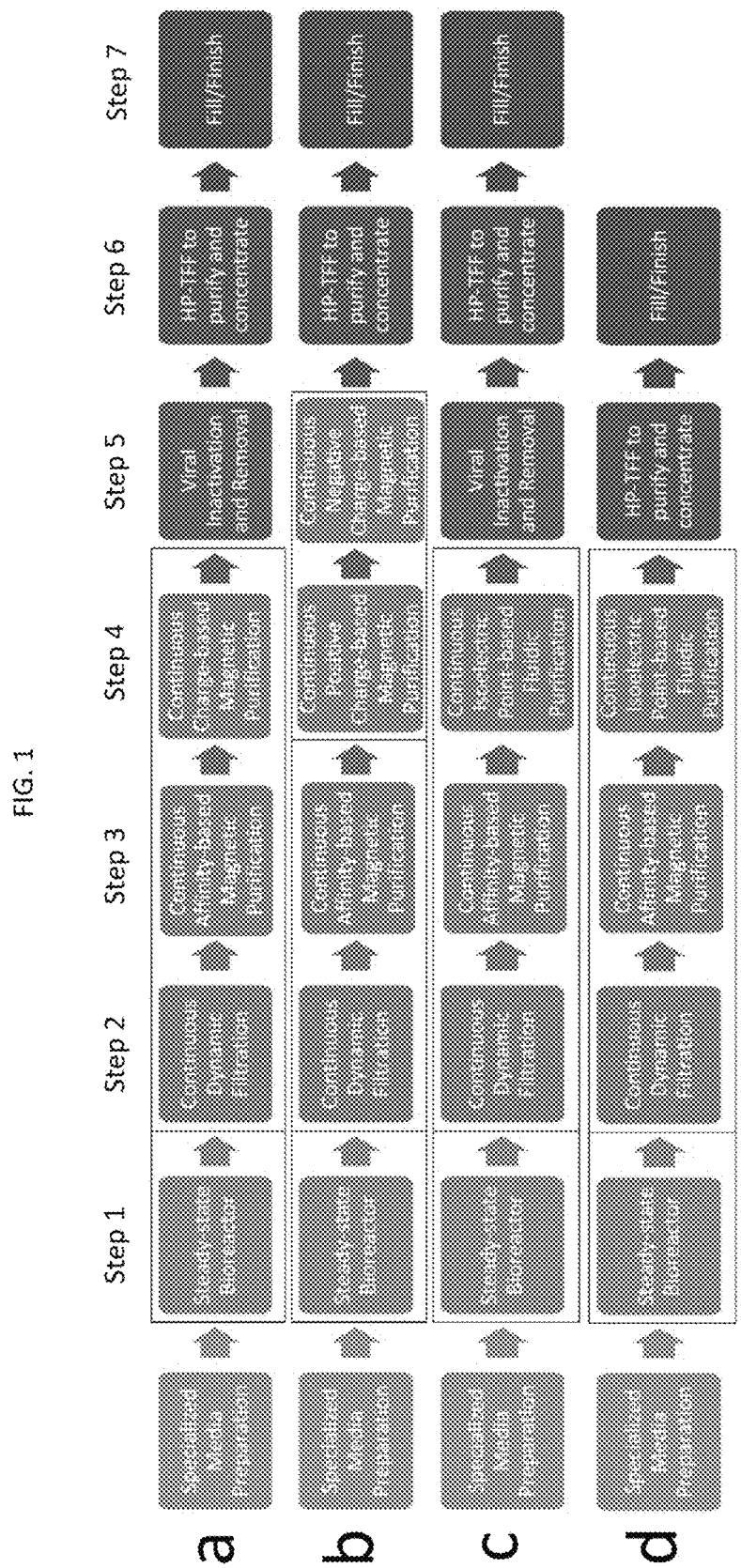
FIGS. 1A-1D show schematics of exemplary continuous process flows described herein.
Figure 2:
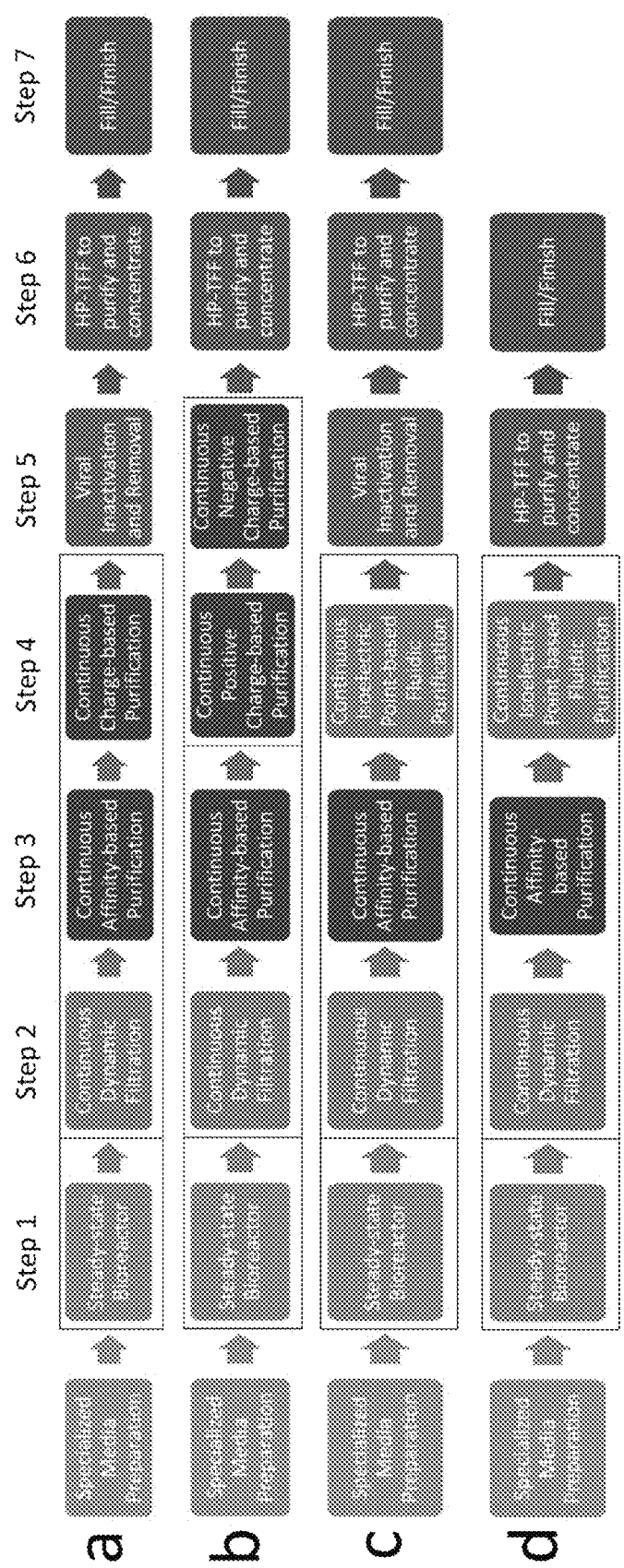
FIGS. 2A-2D show schematics of exemplary continuous process flows described herein.
Figure 3:
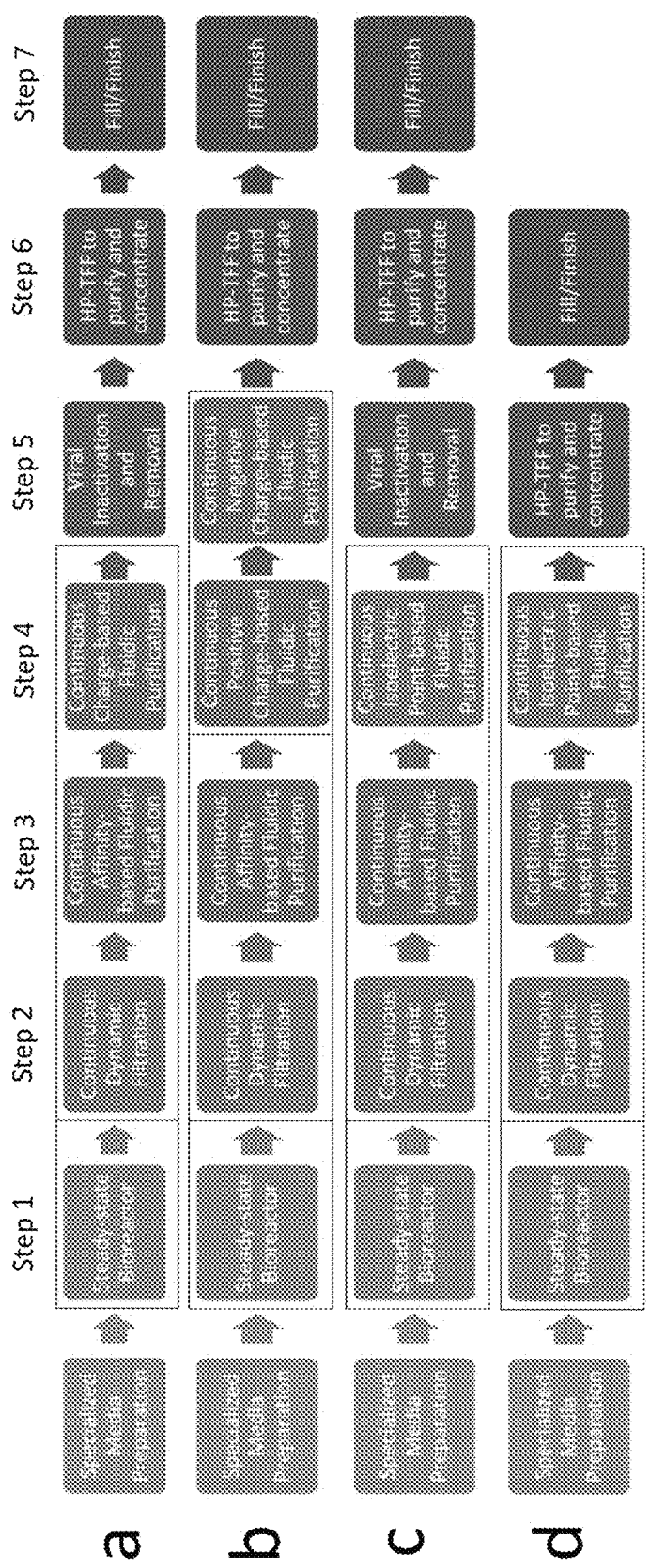
FIGS. 3A-3D show schematics of exemplary continuous process flows described herein.
Figure 4:
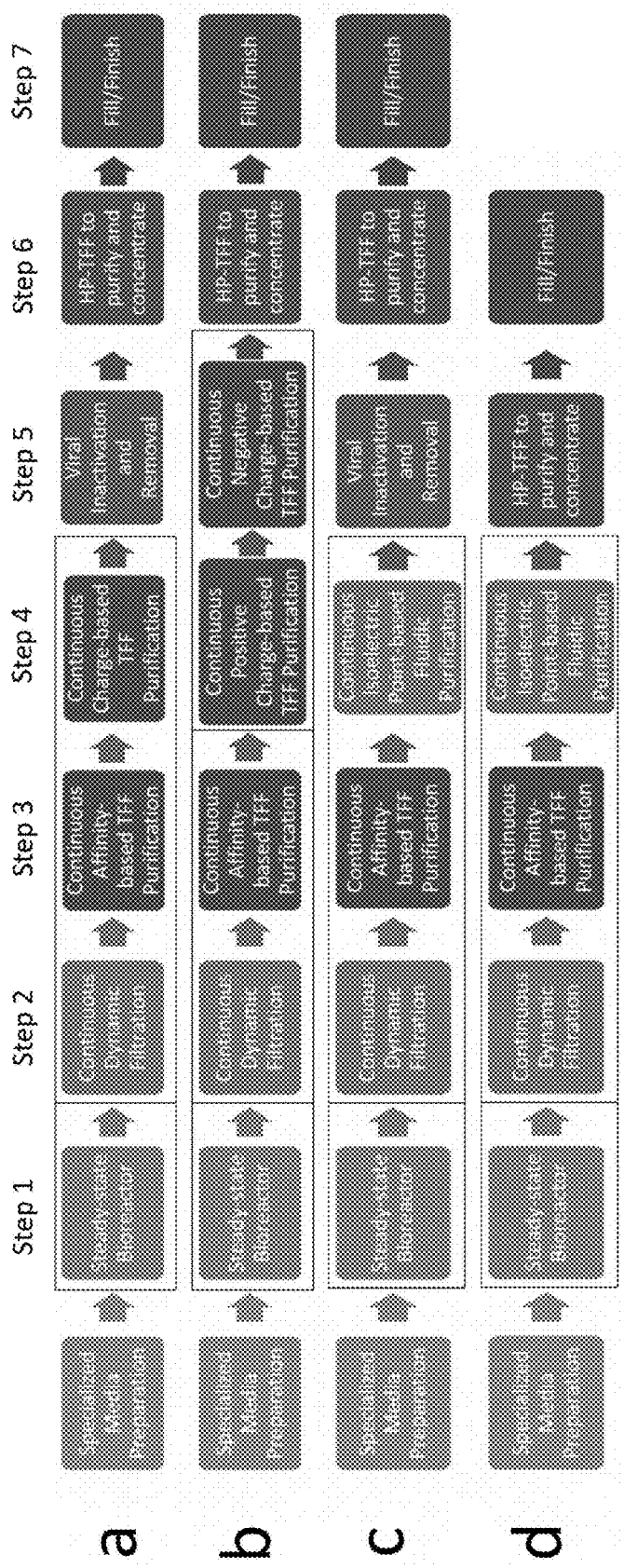
FIGS. 4A-4D show schematics of exemplary continuous process flows described herein.
Figure 5A:
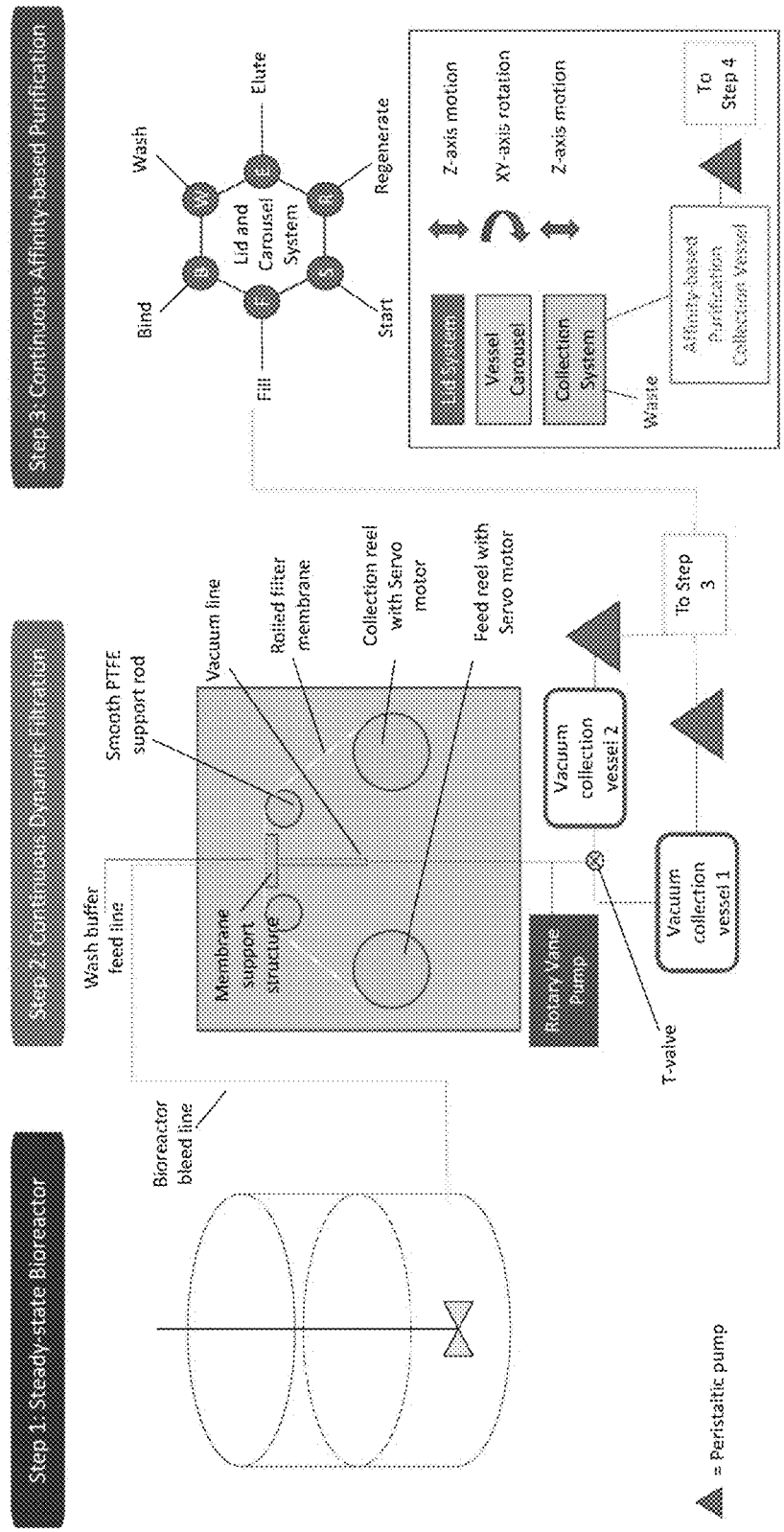
FIGS. 5A and 5B show an exemplary continuous process flow with design schematics for downstream purification modules described herein.
Figure 5B:
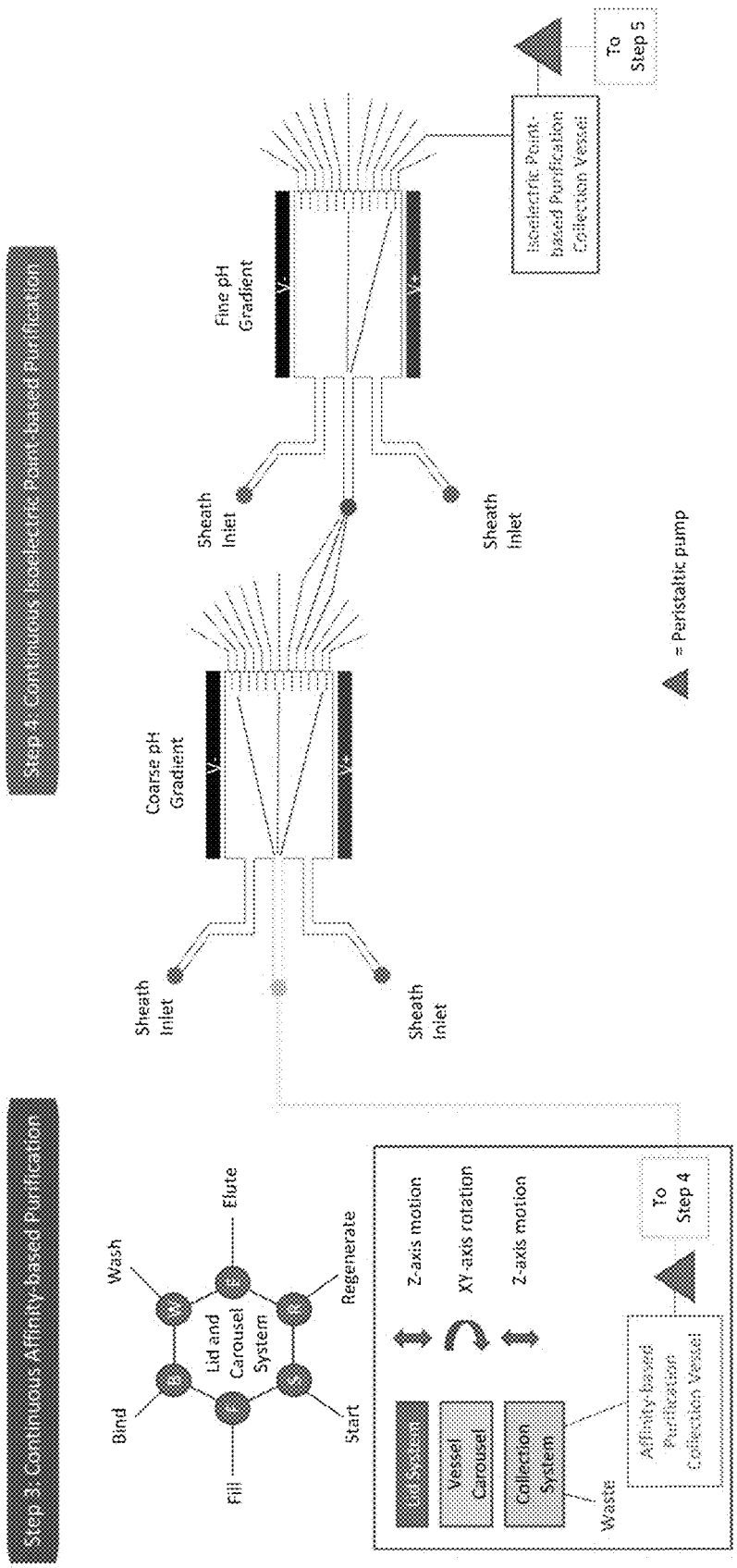
Figure 7B:
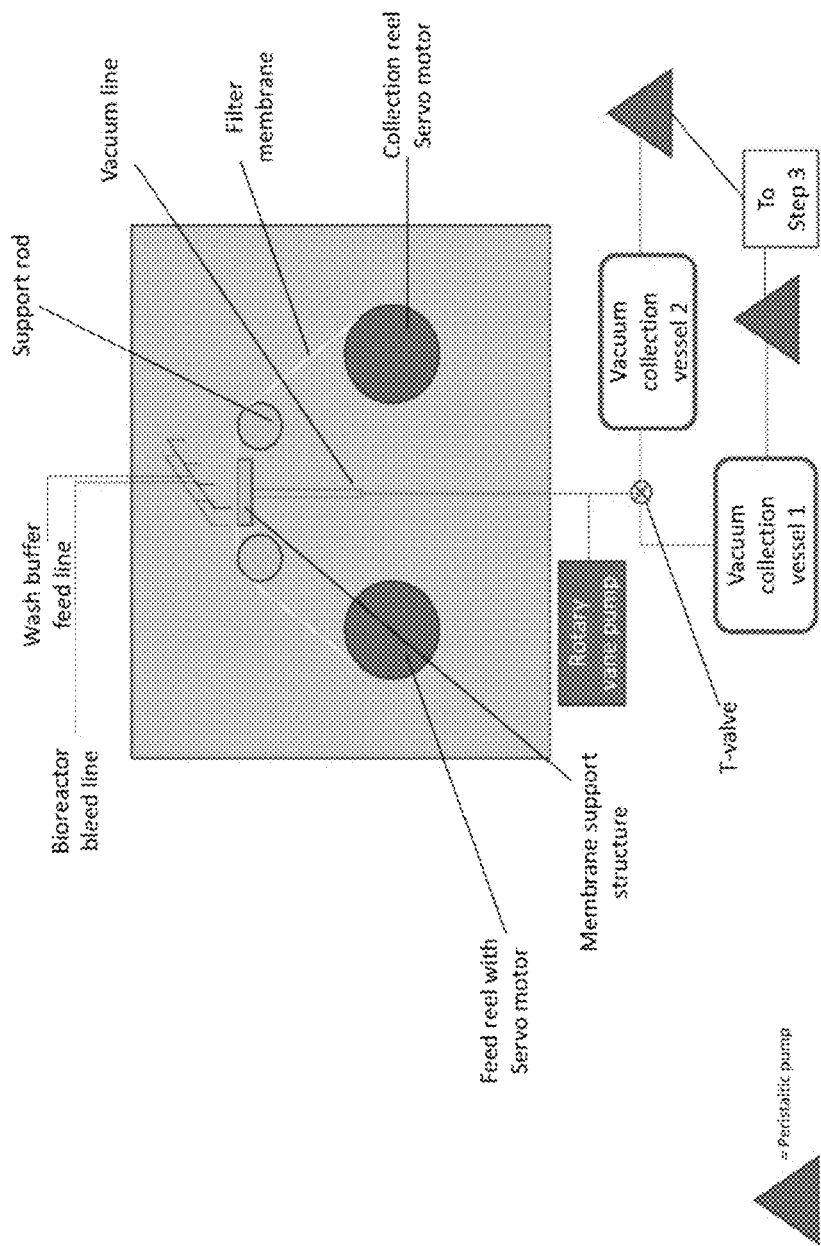
Figure 9A:
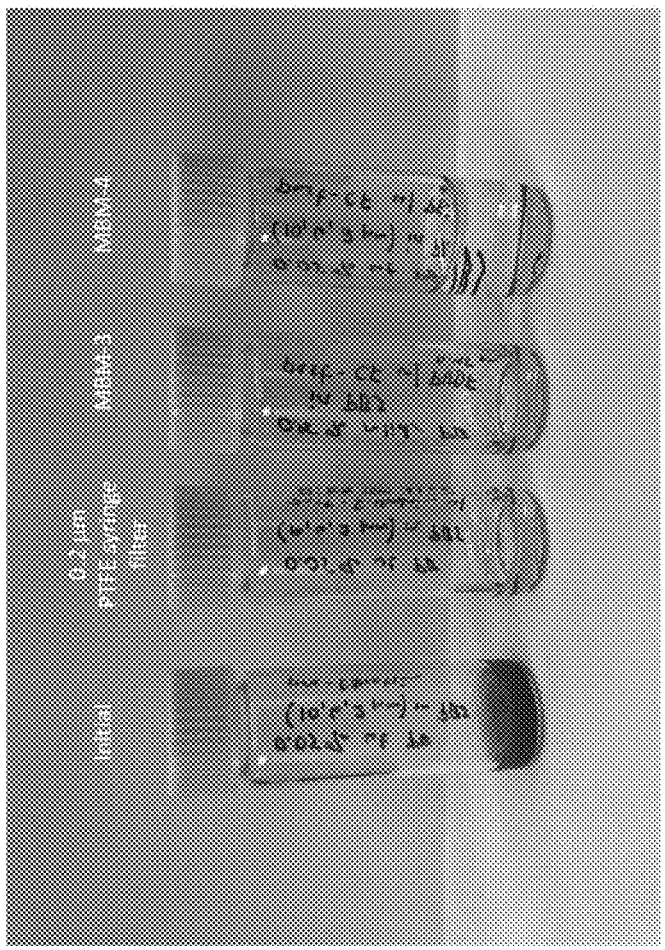
FIGS. 9A and 9B are images showing the removal of PolyBeads (0.05% solids; 2 µm (red), 6 µm (red), and 10 µm (blue) diameter) from a heterogeneous mixture in 1×PBS.
Figure 9B:
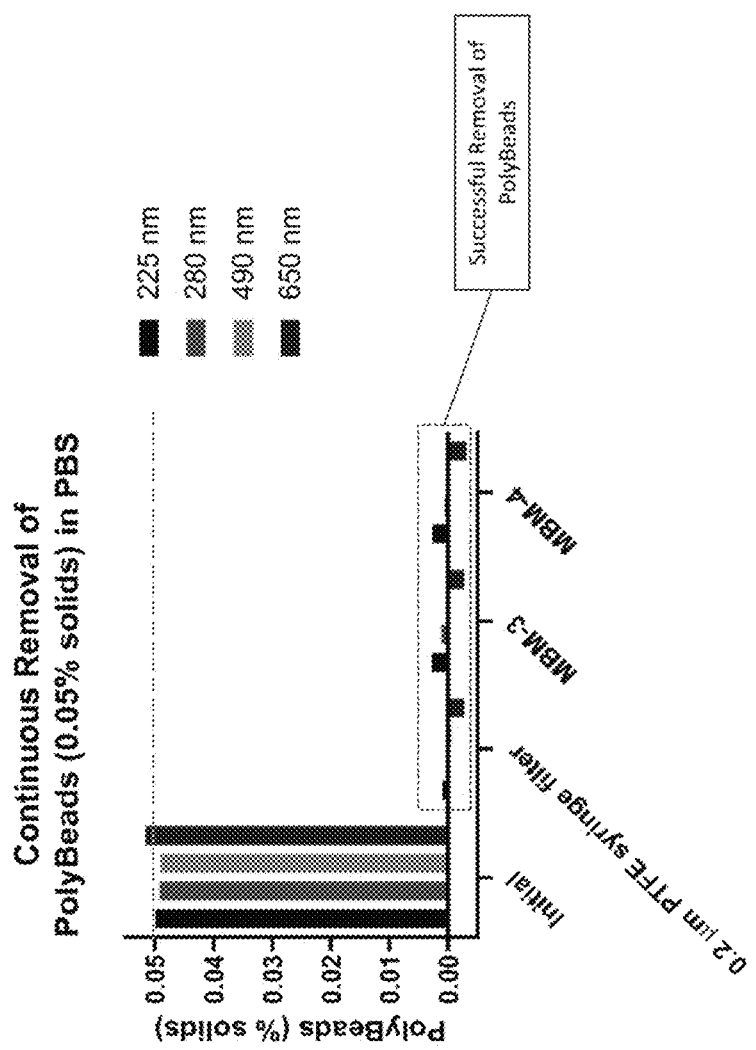
Figure 10A:
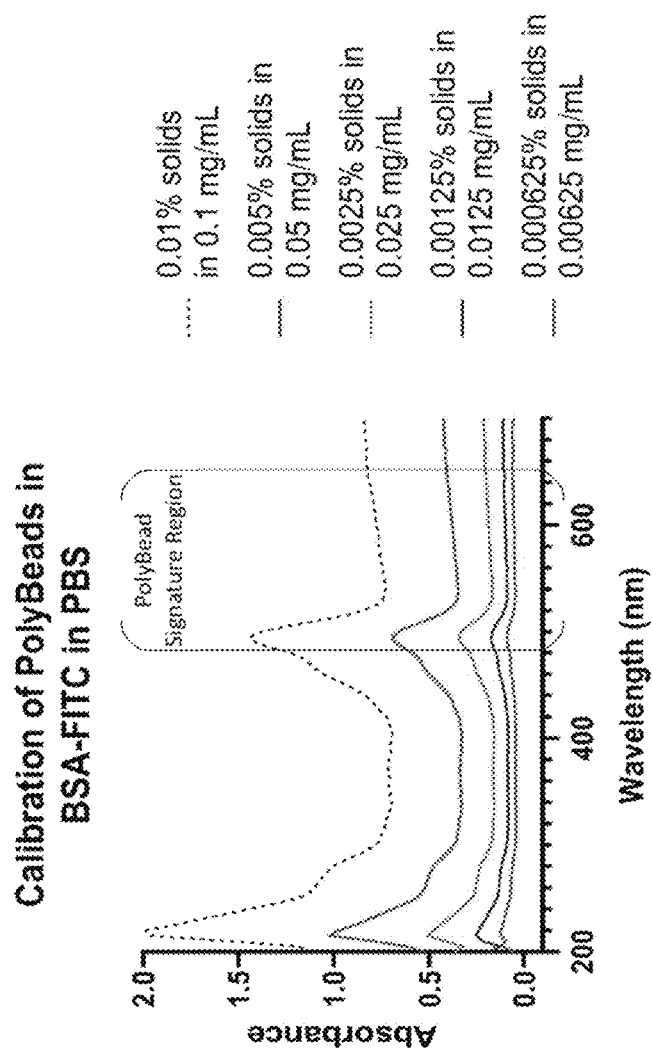
Figure 10B:
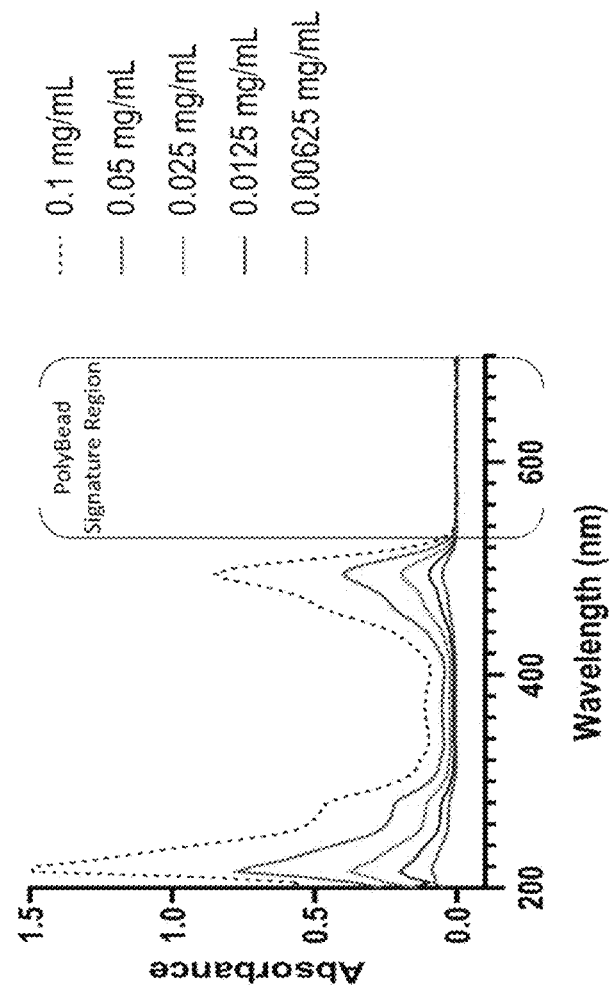
Figure 10C:
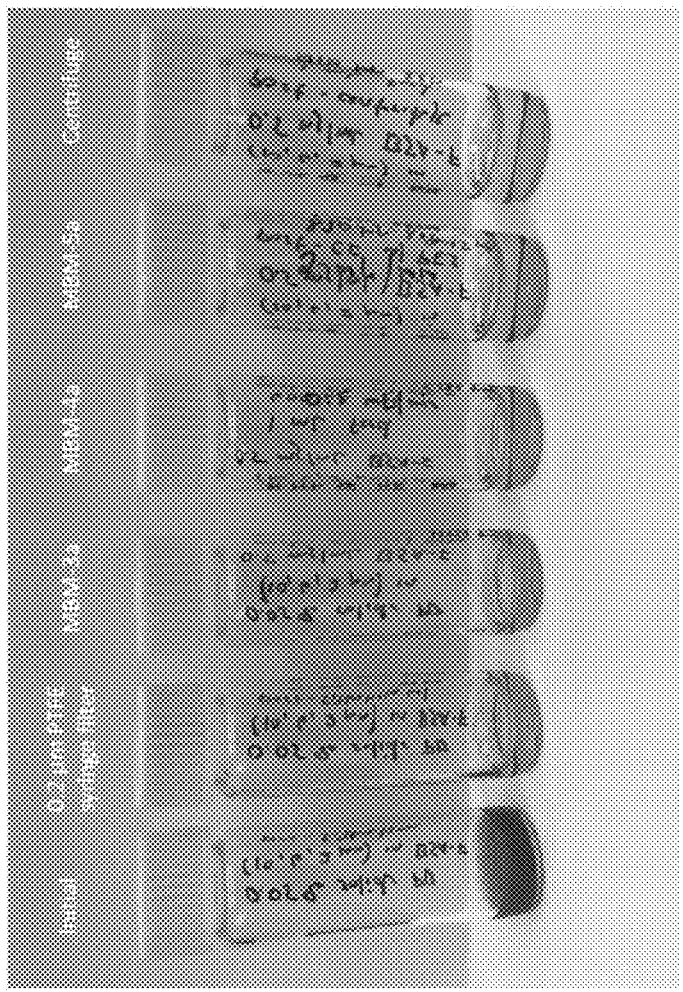

Provided herein is, inter alia, a continuous process for purifying a biological product. The presently claimed process provides for a number of advantages over current downstream methods and processes for purifying a biological product, for example, a protein or fragment thereof (a polypeptide) an antibody or fragment thereof, a cytokine, a chemokine, an enzyme, a growth factor, an oligonucleotide, a virus, an adenovirus, an adeno-associated virus, or a lentivirus. For example, without intent to be limiting, the process described herein provides a continuous bioprocess for purifying a monoclonal antibody that abrogates the problem of membrane fouling inherent to traditional multiple stage filtration processes (e.g. multiple stage tangential flow filtration or depth filtration) by having the initial stage of filtration comprise at least one dynamic filtration module, as described herein, to remove large impurities (e.g. cells, cellular debris, and aggregates). Further, the continuous process maintains throughput and yield, while significantly decreasing the production facility footprint, the time required for facility buildout and validation, the costs associated with facility buildout, and capital equipment expenditure, when compared to the traditional approaches of batch, single-use, or semi-continuous monoclonal antibody manufacturing.

The continuous bioprocessing as described herein affords smaller, more streamlined equipment (e.g., smaller bioreactor volumes and downstream bioprocess equipment) because the ability to operate continuously eliminates the need for the large process equipment required for the centrifugation, depth filtration, and column chromatography steps of traditional downstream bioprocessing, whose size is dictated by large bioreactor volumes. Further, the smaller, more streamlined equipment operating continuously affords the use of significantly smaller bioreactor(s) that produces monoclonal antibodies at steady-state. The continuous bioprocess as described herein may also significantly decrease operating expenditures, overall bioprocess line downtime, and biological product loss when compared to traditional monoclonal antibody manufacturing approaches. Finally, the process described herein for purifying a biological product is conducted in a system with a footprint that occupies significantly less square footage than current techniques, without sacrificing product throughput or yield on a kilogram/year basis. For example, the process for producing, purifying a monoclonal antibody as described herein is operated with a footprint that occupies up to about 30,000 square feet. In contrast, current mononclonal antibody production and downsteam processes require at least 200,000 square feet.

Continuous Process for Purifying a Biological Product Using a Dynamic Filtration Module, an Affinity-Based, Magnetic Purification Module, and at Least One of a Charge-Based, Magnetic Purification Module or an Isoelectric Point-Based, Fluidic Purification Module.

A continuous process for purifying a biological product is described; the process including continuously receiving, via an input line, a heterogeneous mixture containing the biological product, wherein the biological product includes, but is not limited to, a protein or fragment thereof (a polypeptide), an antibody or fragment thereof, a cytokine, a chemokine, an enzyme, or a growth factor. When purifying, the biological product (e.g., a monoclonal antibody) is substantially pure when it is at least 60%, 70%, 80%, 90%, 95%, or even 99%, by weight, free from impurities (cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

The process includes continuously removing large impurities from the heterogeneous mixture by dynamic filtration. Said dynamic filtration process includes at least one dynamic filtration module that continuously feeds the biological product from at least one output head in fluid communication with the input line to the dynamic filtration module under negative pressure, thereby producing a filtrate comprising the biological product. The dynamic filtration module may further include at least one additional input line to supply a wash buffer via a coaxial output head or a separate monoaxial output head.

In embodiments, the process described herein includes purifying a biological product that is continuously produced in a bioreactor (e.g., a fed-batch bioreactor, a perfusion bioreactor, a chemostat bioreactor). For example, the bioreactor includes a bioreactor feed line and an output bleed line to enable steady-state cell culture growth conditions, and the output bleed line functions as the input line to permit continuous fluid flow from the bioreactor to the dynamic filtration module.

As described herein, the process of continuously removing large impurities from the heterogeneous mixture (or mixture) does not include centrifugation, disk-stack centrifugation, depth filtration, static filtration, tangential flow filtration, a hydrocyclone, or any combination thereof. The term "static filtration" refers to a process in which the heterogeneous mixture being filtered remains static, meaning, for example, that the filter membrane (or depth filter) has a defined capacity, and the rate of filtration decreases as the membrane reaches its capacity (e.g., membrane pores become occluded). In a "static" (as opposed to "dynamic") filtration, the filter membrane remains stationary (does not move), and the flow (e.g., of the heterogeneous mixture) passes through the stationary filter membrane. These static filtration methods are common in the art and are simple and well-understood.

Unlike the static filtration methods commonly used in the art, the process herein describes a dynamic filtration module, wherein components of the dynamic filtration module move in a coordinated fashion (e.g., the membrane moves or advances in accordance with the flow rate of the entire process) to enable filtration to occur continuously across a fresh, unused target region of filter membrane. This eliminates membrane fouling or occlusion and permits control over the filter cake packing and thickness during operation.

The dynamic filtration module includes a filter membrane roll, a membrane support structure, at least one support rod or roller, a vacuum line, a vacuum system, and at least one vacuum collection vessel.

In embodiments, the filter membrane roll includes a rolled filter membrane, wherein the filter membrane, without intent to be limiting, comprises polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), hydrophilic PTFE, or any combination thereof.

The pore size of the rolled filter membrane depends on the biological product being purified. In examples, the rolled filter membrane has a pore size in the range from 0.1 µm to 1 µm. Alternatively, the pore size is in the range from about 0.2 µm to about 0.45 µm, or the pore size is less than about 0.45 µm. In other examples, when purifying an antibody, the pore size of the rolled filter membrane is in the range of 0.2 µm to about 0.45 µm.

The filter membrane roll has a width from about 10 mm to about 600 mm. The width of the filter membrane roll, for example, may depend on the size of the dynamic filtration system or the membrane support structure.

In embodiments, the filter membrane roll further functions as a feed reel that communicates with a collection reel, meaning the filter membrane originates from pre-fabricated roll and spans to an initially empty collecting roll, thus creating a reel-to-reel system. In aspects, the dynamic filtration module includes a rolled filter membrane extending between a feed reel and a collection reel, the filter membrane having a target region (e.g., an active target region) that is configured to receive the heterogeneous mixture. In examples, the feed reel motion is governed by a Servo motor coupled with a gear box to limit rotations per minute (RPM) by a ratio of 200:1 to enable low membrane transport velocities with high torque. The collection reel motion is governed by a Servo motor coupled with a gear box to limit RPM by a ratio of 200:1 to enable low membrane transport velocities with high torque. Further, the feed reel motor and the collection reel motor are controlled by a closed-loop controller that operates a feedback mechanism to ensure consistent velocity with the constantly changing diameters of the filter membrane roll on both the feed reel and the collection reel during operation. In examples, the feed reel and the collection reel operate in the same direction with equivalent velocities.

In embodiments, the transport velocity of the filter membrane ranges from about 0.1 mm/sec to about 100 mm/sec, preferably from about 0.1 mm/sec to about 10 mm/sec.

The membrane support structure of the dynamic filtration module includes a mechanically smooth contact surface derived from a material having a low static coefficient of friction (e.g. PTFE) and an opening that has continuity with the vacuum line. As used herein, the "membrane support structure" refers to a fabricated component that provides structural support to the active region of the filter membrane, to prevent deformation, as it traverses an area of negative pressure, resulting from the opening having continuity with the vacuum line. Further, as used herein, "mechanically smooth contact surface" refers to a surface having a low static coefficient of friction, thus creating a low frictional force opposing transport of the filter membrane, especially when wetted. The mechanically smooth contact surface may influence the ease at which the filter membrane moves in a dynamic fashion. The mechanically smooth contact surface may also be measured in surface roughness, where the lower the value the smoother the surface. Moreover, since rougher surfaces have more friction between them than smoother surfaces, the mechanically smooth contact surface, as used herein, refers to a surface having lower friction (i.e., a low static coefficient of friction).

In embodiments, the membrane support structure of the dynamic filtration module includes an opening. The opening for example, may include a mesh, at least one slot, at least one hole, a frit, a porous material, or any combination thereof. For example, the opening may include a series of regularly or irregularly spaced elements (e.g., a mesh, at least one slot, at least one hole, or any combination thereof). Moreover, the opening may include regularly spaced elements, for example the opening may include a series of equally spaced, parallel slots. Additionally, the opening can include one grate (e.g., a series of regularly or irregularly spaced elements as described above). In other examples, the opening can include more than one grate, with each grate perpendicular. The opening can be a collection of irregular or regular elements (e.g., a series of parallel slots). The opening can also include a mesh, which are of split-thickness or of full-thickness and may or may not be in parallel rows. The elements of the opening (e.g., a mesh, at least one slot, at least one hole, a frit, a porous material, or any combination thereof) may be of any desired thickness. For example, without intent to be limiting, the opening may include a mesh with a thickness of about 0.25 mm to about 5 mm.

The membrane support structure of the dynamic filtration module includes a temperature control mechanism. The temperature control mechanism maintains a temperature from about 4° C. to about 37° C. in the presence of evaporative cooling. For example, during purification of an antibody, the temperature control mechanism maintains a temperature from 15° C. to 37° C. Exemplary temperature control mechanisms include, but are not limited to, single loop controllers, multi-loop controllers, closed loop controllers, PID controllers, Peltier devices, resistive heating elements, and/or thermal chucks with circulating water/propylene glycol jackets.

In embodiments, the at least one support rod or roller of the dynamic filtration module has a mechanically smooth contact surface derived from a material having a low static coefficient of friction (e.g. PTFE, PFA). For example, the static coefficient of friction ranges from about 0.01 to about 0.1, or from about 0.01 to about 0.05, or from about 0.05 to about 0.1. In specific examples, the static coefficient of friction is 0.04. In examples, the dynamic filtration module includes at least one support rod or roller with a mechanically smooth contact surface to stabilize the motion of the filter membrane across the membrane support structure.

In embodiments, the dynamic filtration module includes at least one output head for modulating flow of the heterogeneous mixture and dispensing the heterogeneous mixture onto the target region (e.g., an active target region) of the filter membrane. In examples, the at least one output head is a tube or a slot die.

In some embodiments, the dynamic filtration module further includes at least one additional input line to supply a wash buffer via a coaxial output head, a separate monoaxial output head, a separate slot die output head, or a slot die output head with multiple openings.

In some embodiments, the dynamic filtration module includes elements known in the coating and converting industry, for example, without intent to be limiting, active or passive edge guides, tension control (e.g. a dancer), break and tension detectors, or any combination thereof.

In embodiments, the dynamic filtration module includes a vacuum system having continuity with the membrane support structure to apply negative pressure across the active target region of the filter membrane, where the negative pressure allows for active transport of the filter membrane across the membrane support structure and enables collection of the filtrate containing the biological product. In examples, the vacuum system of the dynamic filtration module maintains a gauge pressure of about −0.05 bar to about 0.98 bar for continuous filtration.

In embodiments, the dynamic filtration module further includes at least one vacuum collection vessel configured to collect the filtrate, and at least one sensor or detector. In aspects described herein, during the purification by dynamic filtration, the filtrate comprising the biological product is fed under negative pressure into a vacuum collection vessel capable of collecting from about 50 mL to about 100 L. In examples, the vacuum collection vessel capable of collecting the filtrate is from about 1 L to about 10 L. In other examples, the vacuum collection vessel capable of collecting the filtrate is from about 1 L to about 50 L.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 μm) in fluid communication with at least one second dynamic filtration apparatus having a rolled filter membrane with a small pore size (e.g., 0.2 µm), thereby producing a filtrate comprising the biological product.

The process described herein includes continuously transferring the filtrate to a first module capable of separating the solution into two or more fractions comprising at least one fraction containing the biological product. For example, separating the solution into two or more fractions, may include at least one fraction containing the biological product, and the at least one other fraction containing small impurities. As described herein, the first module comprises an affinity-based, magnetic purification apparatus. The "affinity-based, magnetic purification apparatus" refers to a purification technique based upon molecular, conformational binding interactions (e.g., ligand-receptor interactions) in which selective surface-immobilized ligands recognize and bind to the biological product to be purified. In examples, the first module has at least one first inlet and at least one first outlet and is configured to permit continuous fluid flow between the first inlet and the first outlet via a loop conveyor system or a pick and place robotics system.

In embodiments, the affinity-based, magnetic purification apparatus further includes a suspension of magnetic resin beads. The surface of the magnetic resin beads, for example, without intent to be limiting, is coupled with Protein A, Protein G, Protein L, an antigenic protein, a protein, a receptor, an antibody, or an aptamer. Continuous purification of biological products (e.g., a monoclonal antibody) with affinity magnetic resin beads can avoid the cumbersome processing steps of traditional affinity column chromatography (e.g., Protein A affinity chromatography).

In embodiments, the magnetic resin beads of the affinity-based, magnetic purification apparatus have a diameter of about 0.2 micron to about 200 micron. The diameter of the magnetic resin beads may depend on the biological product being purified and the flow rate of the process. Moreover, the magnetic resin beads may have a concentration ranging from 0.01% to 25% by weight. For example, the concentration of the magnetic resin beads may be about 1% to about 10% by weight. In other examples, the binding capacity of the magnetic resin beads is a function of the bead concentration, surface area-to-volume ratio, affinity ligand density, or any combination thereof. In yet other examples, the magnetic resin beads may be solid, porous, nanoporous, microporous, or any combination thereof.

The loop conveyer system may refer to, for example, a continuous or endless loop. The loop conveyer system is advantageous in that it allows for large volumes to move at high flow rates continuously and efficiently through the process, while affording a smaller footprint when compared to traditional affinity column chromatography systems (e.g., Protein A affinity chromatography). The biological products are conveyed directly on a track, so both regular and irregular shaped objects of all sizes can be configured for transport. In some aspects, the object is a transport vessel having a regular shape (e.g., a cube, a rectangular prism, a cylinder, a cone).

In embodiments, the loop conveyor system has at least two transport vessels charged with magnetic resin beads that are configured to continuously receive a filtrate comprising a mixture containing a biological product and subsequently transport the resulting heterogeneous mixture containing a biological product, magnetic resin beads, a buffer, or any combination thereof.

The pick and place robotics system may refer to, for example, at least one robot or robotic arm. The pick and place robotics system is advantageous in that it allows for large volumes to move at high flow rates continuously and efficiently through the process, while affording a smaller footprint when compared to traditional affinity column chromatography systems (e.g., Protein A affinity chromatography). The biological products contained in transport vessels are picked and placed, so regular shaped objects of all sizes can be configured for transport and stacking, with or without a handle. In some aspects, the object is a transport vessel having a regular shape (e.g., a cube, a rectangular prism).

In embodiments, the pick and place robotics system has at least two transport vessels charged with magnetic resin beads that are configured to continuously receive a filtrate comprising a mixture containing a biological product and subsequently transport the resulting heterogeneous mixture containing a biological product, magnetic resin beads, a buffer, or any combination thereof.

The affinity-based, magnetic purification module further includes at least one external magnetic field that may be used to attract, and thus separate, said magnetic resin beads from the heterogeneous mixture to enable washing within at least one of the at least two transport vessels. Further, the at least one external magnetic field may be used to attract, and thus separate, said magnetic resin beads from the heterogeneous mixture to enable elution of said biological product within at least one of the at least two transport vessels. Alternatively, the at least one external magnetic field may be used to enable recycling of said magnetic resin beads within at least one of the at least two transport vessels. In examples, mixing of the magnetic resin beads may be accomplished by placing the at least one transport vessel between two separate and opposing magnetic fields that toggle between states of on and off.

The process described herein also includes continuously transferring the fraction containing the biological product from the at least one first outlet of the first module to a second module having at least one inlet for receiving flow from the at least one first outlet of the first module, and the second module comprises a charge-based, magnetic purification apparatus. The "charge-based, magnetic purification apparatus" as used herein includes, for example, purifying biological molecules based on their surface charge, ionic character, electrostatic interactions, or isoelectric point. As described herein, the charge-based, magnetic purification comprises a positive charge-based, magnetic purification apparatus, a negative charge-based, magnetic purification apparatus, or combinations thereof. In examples, the second module has at least one second inlet and at least one second outlet and is configured to permit continuous fluid flow between the second inlet and the second outlet via a loop conveyor system or a pick and place robotics system.

In embodiments, the charge-based, magnetic purification apparatus (e.g., positive and/or negative charge-based, magnetic purification) further includes a suspension of magnetic resin beads. The surface of the magnetic resin beads, for example, may comprise cationic or anionic functionality configured to selectively associate with said biological product at a specific pH and ionic strength to enable positive charge-based, magnetic purification or negative charge-based, magnetic purification, respectively. Continuous purification of biological products (e.g., a monoclonal antibody) with ionic magnetic resin beads can avoid the cumbersome processing steps of traditional ion-exchange column chromatographies (e.g., cation exchange or anion exchange chromatographies).

In embodiments, the magnetic resin beads of the charge-based, magnetic purification apparatus have a diameter of about 0.2 micron to about 200 micron. The diameter of the magnetic resin beads may depend on the biological product being purified and the flow rate of the process. Moreover, the magnetic resin beads may have a concentration ranging from 0.01% to 25% by weight. For example, the concentration of the magnetic resin beads may be about 1% to about 10% by weight. In other examples, the charge or electrostatic association capacity of the magnetic resin beads is a function of the bead concentration, surface area-to-volume ratio, surface charge density, net charge, or any combination thereof. In yet other examples, the magnetic resin beads may be solid, porous, nanoporous, microporous, or any combination thereof.

The loop conveyer system may refer to, for example, a continuous or endless loop. The loop conveyer system is advantageous in that it allows for large volumes to move at high flow rates continuously and efficiently through the process, while affording a smaller footprint when compared to traditional ion-exchange column chromatography systems. The biological products are conveyed directly on a track, so both regular and irregular shaped objects of all sizes can be configured for transport. In some aspects, the object is a transport vessel having a regular shape (e.g., a cube, a rectangular prism, a cylinder, a cone).

In embodiments, the loop conveyer system has at least two transport vessels charged with magnetic resin beads that are configured to continuously receive a mixture containing a biological product and subsequently transport the resulting heterogeneous mixture containing a biological product, magnetic resin beads, a buffer, or any combination thereof.

The pick and place robotics system may refer to, for example, at least one robot or robotic arm. The pick and place robotics system is advantageous in that it allows for large volumes to move at high flow rates continuously and efficiently through the process, while affording a smaller footprint when compared to traditional ion-exchange chromatography systems. The biological products contained in transport vessels are picked and placed, so regular shaped objects of all sizes can be configured for transport and stacking, with or without a handle. In some aspects, the object is a transport vessel having a regular shape (e.g., a cube, a rectangular prism).

In embodiments, the pick and place robotics system has at least two transport vessels charged with magnetic resin beads that are configured to continuously receive a filtrate comprising a mixture containing a biological product and subsequently transport the resulting heterogeneous mixture containing a biological product, magnetic resin beads, a buffer, or any combination thereof.

The charge-based, magnetic purification module further includes at least one external magnetic field that may be used to attract, and thus separate, said magnetic resin beads from the heterogeneous mixture to enable washing within at least one of the at least two transport vessels. Further, the at least one external magnetic field may be used to attract, and thus separate, said magnetic resin beads from the heterogeneous mixture to enable dissociation and collection of said biological product within at least one of the at least two transport vessels. Alternatively, the at least one external magnetic field may be used to enable recycling of said magnetic resin beads within at least one of the at least two transport vessels. In examples, mixing of the magnetic resin beads may be accomplished by placing the at least one transport vessel between two separate and opposing magnetic fields that toggle between states of on and off.

In embodiments described herein, the magnetic resin beads of one or both of the first (affinity-based, magnetic purification) and/or second (charged-based, magnetic purification) module(s) are recycled and re-used. For example, the beads may be re-used at least 2, 3, 4, or more times for purifying a biological product.

Alternatively, the process described herein includes continuously transferring the fraction containing the biological product from the at least one first outlet of the first module to a second module having at least one inlet for receiving flow from the at least one first outlet of the first module, and the second module comprises a free-flow electrophoresis apparatus. The free-flow electrophoresis apparatus having a fluidic channel created between two parallel plates, an electric field or electric field gradient orthogonal to the fluid flow direction, and an aqueous ionic solution, may be used in lieu of or in addition to the charge-based, magnetic purification module(s) to purify the biological product (e.g., a monoclonal antibody).

In examples, the solution contacting surfaces of the two parallel plates comprise glass, ceramic, plastic, or any combination thereof. In some examples, the aqueous ionic solution may give rise to a pH gradient across the main separation channel. In other examples, the aqueous ionic solution may confer constant pH across the main separation channel.

In embodiments, the free-flow electrophoresis apparatus has at least one fluidic device comprising a fluidic channel created between two parallel plates, an electric field or electric field gradient orthogonal to the fluid flow direction, and a pH gradient. In examples, the isoelectric point-based, fluidic purification module includes at least one first fluidic device comprising a fluidic channel created between two parallel plates, an electric field or electric field gradient orthogonal to the fluid flow direction, and a coarse pH gradient across the main separation channel (in examples, a coarse pH gradient may be a pH range from about 2 to about 10); and at least one second fluidic device comprising a fluidic channel created between two parallel plates, an electric field or electric field gradient orthogonal to the fluid flow direction, and a fine pH gradient across the main separation channel (in examples, a fine pH gradient may be a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In other embodiments, the free-flow electrophoresis apparatus has at least one fluidic device comprising a fluidic channel created between two parallel plates, an electric field or electric field gradient orthogonal to the fluid flow direction, and no pH gradient (e.g. a constant pH across the main separation channel) to operate in a zone electrophoresis or charge separating mode of operation. In examples, the isoelectric point-based, fluidic purification module includes at least one first fluidic device comprising a fluidic channel created between two parallel plates, an electric field or electric field gradient orthogonal to the fluid flow direction, and constant basic pH (e.g., a pH of greater than 7); and at least one second fluidic device comprising a fluidic channel created between two parallel plates, an electric field or electric field gradient orthogonal to the fluid flow direction, and a constant acidic pH (e.g., a pH of less than 7).

In other embodiments, the free-flow electrophoresis apparatus has at least one fluidic device comprising a fluidic channel created between two parallel plates, an electric field or electric field gradient orthogonal to the fluid flow direction, and both an acidic pH gradient and a basic pH gradient separated by a spacer solution (e.g. NaCl solution) to operate in an isotachophoresis mode of operation.

In other embodiments, the isoelectric point-based, fluidic purification module includes at least one first free-flow electrophoresis apparatus comprising a fluidic channel created between two parallel plates and an electric field or electric field gradient orthogonal to the fluid flow direction, and at least one second free-flow electrophoresis apparatus comprising a fluidic channel created between two parallel plates and an electric field or electric field gradient orthogonal to the fluid flow direction, wherein each device connected in series and is capable of operating in an independent mode of operation to enable purification. For example, the at least one first free-flow electrophoresis apparatus may operate in an isoelectric focusing mode and the at least one second free-flow electrophoresis apparatus may operate in an isotachophoresis mode to increase separation resolution.

In other embodiments, the isoelectric point-based, fluidic purification module includes at least one first fluidic device comprising fluidic channel having at least one dielectrophoretic electrode capable of inducing a defined, unidirectional force; at least one second free-flow electrophoresis apparatus comprising a fluidic channel created between two parallel plates, an electric field or electric field gradient orthogonal to the fluid flow direction, and a coarse pH gradient across the main separation channel (e.g., a pH range from about 2 to about 10); and at least one third free-flow electrophoresis apparatus comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In embodiments, the isoelectric point-based fluidic purification apparatus further comprises at least two electrodes (e.g. platinum wire electrodes) to function as an anode or a cathode.

In embodiments, the backpressure within the isoelectric point-based fluidic purification apparatus is dependent on the channel geometry and dimensions, the inlet and outlet opening and/or tubing diameters, and the input flow rate. In examples, the backpressure ranges from about 0.5 psi to about 10 psi. In some examples, the backpressure is controlled by, for example, without intent to be limiting, a needle valve.

In embodiments, the isoelectric point-based fluidic purification apparatus further comprises at least one de-bubbler system to continuously remove $O_2$ and $H_2$ gas bubbles that evolve in the electrode channels under applied voltage. In some embodiments, removal of electrolysis bubbles is essential to enable continuous operation for substantially long periods of time. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar.

In embodiments, the isoelectric point-based fluidic purification apparatus further comprises an active cooling system or heat sink (e.g., a Peltier device, a thermal chuck with a circulating water/propylene glycol jacket) to enable temperature control and Joule heat dissipation. For example, the active cooling system may control cooling and/or heat dissipation in the range from about 4° C. to about 50° C., preferably from about 4° C. to about 37° C. Ideally, when isolating a biological product (e.g., a monoclonal antibody), the temperature is maintained at about 10° C. to about 25° C. In examples, the active cooling system comprises an aluminum thermal chuck containing a chilled, circulating water/propylene glycol jacket.

In embodiments, the isoelectric point-based, fluidic purification module includes at least one buffer or ampholyte system.

In embodiments, the isoelectric point-based, fluidic purification module includes at least one electrode solution. In some embodiments, the at least one electrode solution comprises an electrolyte solution configured to contact and enable the appropriate function of an anode or a cathode, for example, phosphoric acid and sodium hydroxide, respectively. In other embodiments, the at least one electrode solution comprises at least one ampholyte solution configured to contact and enable the appropriate function of an anode or a cathode, for example, Tris buffered saline flowing through the main separation channel, the anode channel, and the cathode channel.

In embodiments, the isoelectric point-based, fluidic purification module includes at least one sensor or detector. In examples, the at least one sensor or detector is positioned in-line. In some examples, the at least one sensor or detector includes, but is not limited to, a flow sensor, a temperature sensor, a conductivity sensor, a pH sensor, a refractive index detector, a UV detector, or a backpressure sensor.

In embodiments, the isoelectric point-based, fluidic purification module includes at least one liquid circuit breaker or disconnect downstream of the device and upstream of the at least one in-line sensor or detector to ensure the ability to perform sensing or detection in a voltage-free solution.

The presently claimed process provides for a number of advantages over current downstream methods and processes for purifying a biological product, for example, a protein or fragment thereof (a polypeptide), an antibody or fragment thereof, a cytokine, a chemokine, an enzyme, or a growth factor. For example, without intent to be limiting, the process described herein provides a continuous bioprocess for purifying a monoclonal antibody that maintains throughput and yield, while significantly decreasing the production facility footprint, the time required for facility buildout and validation, the costs associated with facility buildout, and capital equipment expenditure, when compared to the traditional approaches of batch, single-use, or semi-continuous monoclonal antibody manufacturing. The continuous bioprocessing as described herein affords smaller, more streamlined equipment (e.g., smaller bioreactor volumes and downstream bioprocess equipment) because the ability to operate continuously eliminates the need for the large process equipment required for the batch centrifugation, depth filtration, and column chromatography steps of traditional downstream bioprocessing, whose size is dictated by large bioreactor volumes. Further, the smaller, more streamlined equipment operating continuously affords the use of significantly smaller bioreactor(s) that produce monoclonal antibodies at steady-state. The continuous bioprocess as described herein may also significantly decrease operating expenditures, overall bioprocess line downtime, and biological product loss when compared to traditional monoclonal antibody manufacturing approaches. Finally, the process described herein for purifying a biological product is conducted in a system with a footprint that occupies significantly less square footage than current techniques, without sacrificing product throughput or yield on a kilograms/year basis.

Advantages of the process and methods described herein include the ability to remove large impurities (e.g., cells, cell debris, and aggregates) without membrane fouling or occlusion. Membrane fouling may refer to a process whereby the heterogeneous mixture is deposited on the membrane surface or in the membrane pores so that the membrane's performance is decreased over time, and thus creating a major limitation in the utility of traditional filtration systems. For example, it is known in the art that clarification of cells, cell debris and aggregates from cell culture media with traditional filtration or tangential flow filtration systems typically leads to fouling or occlusion of the filter membrane, thus rendering these methodologies unsuitable as a means to continuously remove large impurities from a heterogeneous mixture containing a biological product over long-term continuous processing. In contrast, the dynamic filtration apparatus described herein enables continuous removal of large impurities from a heterogeneous mixture containing a biological product without membrane fouling, as the active target region of the filter membrane is constantly being refreshed.

Additionally, because the entire process of producing and purifying the biological product may be continuous and can maintain a flow rate that ranges from about 0.1 mL/minute to about 50 mL/minute across the entirety of the process (e.g., about 5 mL/minute to about 10 mL/minute), the process equipment and overall process footprint is able to have a significantly smaller footprint than current standard processes, without sacrificing product throughput or yield on a kilogram/year basis. For example, the process for producing and purifying a monoclonal antibody as described herein is operated with a footprint that occupies up to about 30,000 square feet. In contrast, current mononclonal antibody production and downsteam processes require at least 200,000 square feet. In examples, the process of purifying the biological product has a flow rate that ranges from about 1 mL/minute to about 10 mL/minute. In some examples, the flow rate of the step of continuously removing large impurities from the heterogeneous mixture ranges from about 0.1 mL/minute to about 50 mL/minute. In other examples, the flow rate of the step of continuously removing large impurities from the heterogeneous mixture is equivalent to the flow rate from the bioreactor bleed line. In other examples, the process provides that the flow rate of the step of continuously transferring the filtrate to a first module ranges from about 0.1 mL/minute to about 50 mL/minute. In yet other examples, the process provides that the flow rate of the step of continuously transferring the fraction containing the biological product from the first outlet to a second module ranges from about 0.1 mL/minute to about 50 mL/minute.

An important advantage of the process and methods utilizing magnetic resin beads (e.g. magnetic agarose) described herein includes that these systems do not require traditional stationary phase or packed resin columns (e.g., for standard chromatographies) to be sanitized, recycled and/or regenerated. For example, these systems provide for recycling and/or regeneration of the magnetic resin beads to create a limitless surface area of the magnetic resin beads during operation, and in turn provides a continuous and cost-effective method. Put in another way, the modules described herein do not have a fixed binding or association capacity. In specific examples, the magnetic resin beads used during purification of the biological product, as described herein, are constantly being recycled and regenerated, and therefore able to accept flow from the previous step, either a dynamic filtration module or a purification module, without interruption of the flow from the bioreactor bleed line.

Put another way, the modules described in the present invention do not have to be left idle in order to be sanitized, regenerated and/or recycled after running, as they are continuously undergoing these steps. The method differs from current continuous chromatographic methods, in that current column chromatography methods have defined column capacity limitations due to resin packing constraints and thus require column switching of multiple packed columns to accept continuous input flow and enable regeneration and/or recycling of the columns that have reached full capacity. Another advantage of the methods described herein includes that the magnetic resin beads are not packed into a stationary phase, rather the magnetic resin beads have mobility. This increases the surface area of the resin beads that is available for binding or association, as substantially more of the magnetic resin bead surface is exposed and free to bind. Additionally, the resin beads in a packed column are exposed to a high pressure differential in order to generate flow through the column and damage from which is one of the reasons for less than desired column lifetime. The mobile resin beads in the presently described invention are subjected to substantially lower pressures which is much gentler on the fragile beads, resulting in longer lifetimes. Additionally, this mobility makes the magnetic resin beads more likely to be completed regenerated and returned to their initial condition. This further adds to the cost-effectiveness of the methods described herein, as the magnetic resin is utilized more efficiently.

An important advantage of the process and methods utilizing free-flow electrophoresis described herein includes that this system represents a "no product loss" process, in that, there is no need for the product to interact with a resin or other purifying moieties, as the separation occurs in aqueous solution according to the physicochemical properties of the target biological product via interaction with an electric field. Another advantage is observed in the resolving power of this approach, as a theoretically higher purity product is achievable when compared to traditional ion-exchange chromatographies. Additionally, the separation based on intrinsic physicochemical properties extends the utility of this approach for the purification a plethora of biological products, including, but not limited to, a protein or fragment thereof (a polypeptide), an antibody or fragment thereof, a cytokine, a chemokine, an enzyme, a growth factor, an oligonucleotide, a virus, an adenovirus, an adeno-associated virus (AAV), or a lentivirus.

Further, the modular approach affords flexibility in process design to accommodate a diverse range of biological products.

Continuous Process for Purifying a Biological Product Using a Dynamic Filtration Module, an Affinity-Based Purification Module, and at Least One of a Charge-Based Purification Module or an Isoelectric Point-Based, Fluidic Purification Module.

A continuous process for purifying a biological product is described; the process including continuously receiving, via an input line, a heterogeneous mixture containing the biological product, wherein the biological product includes, but is not limited to, a protein or fragment thereof (a polypeptide), an antibody or fragment thereof, a cytokine, a chemokine, an enzyme, or a growth factor. When purifying, the biological product (e.g., a monoclonal antibody) is substantially pure when it is at least about 60%, 70%, 80%, 90%, 95%, or even 99%, by weight, free from impurities (cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

The process includes continuously removing large impurities from the heterogeneous mixture by dynamic filtration. Said dynamic filtration process includes at least one dynamic filtration module that continuously feeds the biological product from at least one output head in fluid communication with the input line to the dynamic filtration module under negative pressure, thereby producing a filtrate comprising the biological product. The dynamic filtration module may further include at least one additional input line to supply a wash buffer via a coaxial output head or a separate monoaxial output head.

In embodiments, the process described herein includes purifying a biological product that is continuously produced in a bioreactor (e.g., a fed-batch bioreactor, a perfusion bioreactor, a chemostat bioreactor). For example, the bioreactor includes a bioreactor feed line and an output bleed line to enable steady-state cell culture growth conditions, and the output bleed line functions as the input line to permit continuous fluid flow from the bioreactor to the dynamic filtration module.

As described herein, the process of continuously removing large impurities from the heterogeneous mixture does not include centrifugation, disk-stack centrifugation, depth filtration, static filtration, tangential flow filtration, a hydrocyclone, or any combination thereof. The term "static filtration" refers to a process in which the heterogeneous mixture being filtered remains static, meaning, for example, that the filter membrane (or depth filter) has a defined capacity, and the rate of filtration decreases as the membrane reaches its capacity (e.g., membrane pores become occluded). In a "static" (as opposed to "dynamic") filtration, the filter membrane remains stationary (does not move), and the flow (e.g., of the heterogeneous mixture) passes through the stationary filter membrane. These static filtration methods are common in the art and are simple and well-understood.

Unlike the static filtration methods commonly used in the art, the process herein describes a dynamic filtration module, wherein components of the dynamic filtration module move in a coordinated fashion (e.g., the membrane moves or advances in accordance with the flow rate of the entire process) to enable filtration to occur continuously across a fresh, unused target region of filter membrane. This eliminates membrane fouling or occlusion and permits control over the filter cake packing and thickness during operation.

The dynamic filtration module includes a filter membrane roll, a membrane support structure, at least one support rod or roller, a vacuum line, a vacuum system, and at least one vacuum collection vessel.

For example, the filter membrane roll includes a rolled filter membrane, wherein the filter membrane, without intent to be limiting, comprises polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), hydrophilic PTFE, or any combination thereof.

The pore size of the rolled filter membrane depends on the biological product being purified. In examples, the rolled filter membrane has a pore size in the range from 0.1 μm to 1 μm. Alternatively, the pore size is in the range from about 0.2 μm to about 0.45 μm, or the pore size is less than about 0.45 μm. In other examples, when purifying an antibody, the pore size of the rolled filter membrane is in the range of 0.2 μm to about 0.45 μm.

The filter membrane roll has a width from about 10 mm to about 600 mm. The width of the filter membrane roll, for example, may depend on the size of the dynamic filtration system or the membrane support structure.

In embodiments, the filter membrane roll further functions as a feed reel that communicates with a collection reel, meaning the filter membrane originates from pre-fabricated roll and spans to an initially empty collecting roll, thus creating a reel-to-reel system. In aspects, the dynamic filtration module includes a rolled filter membrane extending between a feed reel and a collection reel, the filter membrane having an active target region that is configured to receive the heterogeneous mixture. In examples, the feed reel motion is governed by a Servo motor coupled with a gear box to limit rotations per minute (RPM) by a ratio of 200:1 to enable low membrane transport velocities with high torque. The collection reel motion is governed by a Servo motor coupled with a gear box to limit RPM by a ratio of 200:1 to enable low membrane transport velocities with high torque. Further, the feed reel motor and the collection reel motor are controlled by a closed-loop controller that operates a feedback mechanism to ensure consistent velocity with the constantly changing diameters of the filter membrane roll on both the feed reel and the collection reel during operation. In examples, the feed reel and the collection reel operate in the same direction with equivalent velocities.

In embodiments, the transport velocity of the filter membrane ranges from about 0.1 mm/sec to about 100 mm/sec, preferably from about 0.1 mm/sec to about 10 mm/sec.

The membrane support structure of the dynamic filtration module includes a mechanically smooth contact surface derived from a material having a low static coefficient of friction (e.g. PTFE) and an opening that has continuity with the vacuum line. As used herein, the "membrane support structure" refers to a fabricated component that provides structural support to the active region of the filter membrane, to prevent deformation, as it traverses an area of negative pressure, resulting from the opening having continuity with the vacuum line. Further, as used herein, "mechanically smooth contact surface" refers to a surface having a low static coefficient of friction, thus creating a low frictional force opposing transport of the filter membrane, especially when wetted. The mechanically smooth contact surface may influence the ease at which the filter membrane moves in a dynamic fashion. The mechanically smooth contact surface may also be measured in surface roughness, where the lower the value the smoother the surface. Moreover, since rougher surfaces have more friction between them than smoother surfaces, the mechanically smooth contact surface, as used herein, refers to a surface having lower friction (i.e., a low static coefficient of friction).

In embodiments, the membrane support structure of the dynamic filtration module includes an opening. The opening for example, may include a mesh, at least one slot, at least one hole, a frit, a porous material, or any combination thereof. For example, the opening may include a series of regularly or irregularly spaced elements (e.g., a mesh, at least one slot, at least one hole, or any combination thereof). Moreover, the opening may include regularly spaced elements, for example the opening may include a series of equally spaced, parallel slots. Additionally, the opening can include one grate (e.g., a series of regularly or irregularly spaced elements as described above). In other examples, the opening can include more than one grate, with each grate perpendicular. The opening can be a collection of irregular or regular elements (e.g., a series of parallel slots). The opening can also include a mesh, which are of split-thickness or of full-thickness and may or may not be in parallel rows. The elements of the opening (e.g., a mesh, at least one slot, at least one hole, a frit, a porous material, or any combination thereof) may be of any desired thickness. For example, without intent to be limiting, the opening may include a mesh with a thickness of about 0.25 mm to about 5 mm.

The membrane support structure of the dynamic filtration module includes a temperature control mechanism. The temperature control mechanism maintains a temperature from about 4° C. to about 37° C. in the presence of evaporative cooling. For example, during purification of an antibody, the temperature control mechanism maintains a temperature from about 15° C. to about 37° C. Exemplary temperature control mechanisms include, but are not limited to, single loop controllers, multi-loop controllers, closed loop controllers, PID controllers, Peltier devices, and/or thermal chucks with circulating water/propylene glycol jackets.

In embodiments, the at least one support rod or roller of the dynamic filtration module has a mechanically smooth contact surface derived from a material having a low static coefficient of friction (e.g. PTFE, PFA). In examples, the dynamic filtration module includes at least one support rod or roller with a mechanically smooth contact surface to stabilize the motion of the filter membrane across the membrane support structure.

In embodiments, the dynamic filtration module includes at least one output head for modulating flow of the heterogeneous mixture and dispensing the heterogeneous mixture onto the active target region of the filter membrane. In examples, the at least one output head is a tube or a slot die.

In some embodiments, the dynamic filtration module further includes at least one additional input line to supply a wash buffer via a coaxial output head, a separate monoaxial output head, a separate slot die output head, or a slot die output head with multiple openings.

In some embodiments, the dynamic filtration module includes elements known in the coating and converting industry, for example, without intent to be limiting, active or passive edge guides, tension control (e.g. a dancer), break and tension detectors, or any combination thereof.

In embodiments, the dynamic filtration module includes a vacuum system having continuity with the membrane support structure to apply negative pressure across the target region (e.g., active target region) of the filter membrane, where the negative pressure allows for active transport of the filter membrane across the membrane support structure and enables collection of the filtrate containing the biological product. In examples, the vacuum system of the dynamic filtration module maintains a gauge pressure of about −0.05 bar to about −0.98 bar for continuous filtration.

In embodiments, the dynamic filtration module further includes at least one vacuum collection vessel configured to collect the filtrate, and at least one sensor or detector. In aspects described herein, during the purification by dynamic filtration, the filtrate comprising the biological product is fed under negative pressure into a vacuum collection vessel capable of collecting from about 50 mL to about 100 L. In examples, the vacuum collection vessel capable of collecting the filtrate is from about 1 L to about 10 L. In other examples, the vacuum collection vessel capable of collecting the filtrate is from about 1 L to about 50 L.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 μm) in fluid communication with at least one second dynamic filtration apparatus having a rolled filter membrane with a small pore size (e.g., 0.2 μm), thereby producing a filtrate comprising the biological product.

The process described herein includes continuously transferring the filtrate to a first module capable of separating the solution into two or more fractions comprising at least one fraction containing the biological product. For example, separating the solution into two or more fractions, may include at least one fraction containing the biological product, and the at least one other fraction containing small impurities. As described herein, the first module comprises an affinity-based purification apparatus. The "affinity-based purification apparatus" refers to a purification technique based upon molecular, conformational binding interactions (e.g., ligand-receptor interactions) in which selective surface-immobilized ligands recognize and bind to the biological product to be purified. In examples, the first module has at least one first inlet and at least one first outlet and is configured to permit continuous fluid flow between the first inlet and the first outlet via a mechanical rotary system comprising a lid system, a vessel carousel, and a collection system.

In embodiments, the affinity-based purification apparatus further includes a suspension of resin beads. The surface of the resin beads, for example, without intent to be limiting, is coupled with Protein A, Protein G, Protein L, an antigenic protein, a protein, a receptor, an antibody, or an aptamer. Continuous purification of biological products (e.g., a monoclonal antibody) with affinity resin beads can avoid the cumbersome processing steps of traditional affinity column chromatography (e.g., Protein A affinity chromatography).

In embodiments, the resin beads of the affinity-based purification apparatus have a diameter of about 0.2 micron to about 200 micron. The diameter of the resin beads may depend on the biological product being purified and the flow rate of the process. Moreover, the resin beads may have a concentration ranging from 0.01% to 25% by weight. For example, the concentration of the magnetic resin beads may be about 1% to about 20% by weight. In other examples, the binding capacity of the resin beads is a function of the bead concentration, surface area-to-volume ratio, affinity ligand density, or any combination thereof. In yet other examples, the resin beads may be solid, porous, nanoporous, microporous, or any combination thereof.

In embodiments, the affinity-based purification module includes lid system having at least one gasketed lid, the at least one gasketed lid comprising at least one inlet to introduce a gas to enable control of positive head pressure, at least one vent port to enable equilibration to atmospheric pressure, at least one inlet to introduce a suspension of resin beads; at least one inlet to receive the filtrate containing a biological product, at least two inlets to introduce a buffer system to disperse the resin beads to enable washing of, elution from, or regeneration of said resin beads. In some embodiments, the at least one gasketed lid further comprises a port to accept an overhead stirring impeller to enable dispersion of the resin beads. In examples, the lid system has control of motion along the z-axis.

In embodiments, the affinity-based purification module includes a mechanical rotary system, for example, a carousel comprising at least two vessels charged with resin beads that are configured to continuously receive a mixture containing a biological product and subsequently transport the resulting heterogeneous mixture containing a biological product, resin beads, a buffer, or any combination thereof. In examples, the mechanical rotary system is configured to mate with the lid system to enable pressurization. In other examples, the mechanical rotary system has control of motion or rotation in the xy-plane.

In embodiments, the at least two vessels of the affinity-based purification module each have a supported, basement filter or filter membrane to enable retention of the resin beads during process steps of binding, de-binding, washing, elution, and regeneration. In examples, the at least two vessels further include a valve to control liquid flow.

In embodiments, the affinity-based purification module includes a collection system that interfaces with at least one of the at least two vessels of the mechanical rotary system to enable collection of waste, the fraction containing the biological product, or any combination thereof. In examples, the collection system has control of motion along the z-axis.

The process described herein also includes continuously transferring the fraction containing the biological product from the at least one first outlet of the first module to a second module having at least one inlet for receiving flow from the at least one first outlet of the first module, and the second module comprises a charge-based purification apparatus. The "charge-based purification apparatus" as used herein includes, for example, purifying biological molecules based on their surface charge, ionic character, electrostatic interactions, or isoelectric point. As described herein, the charge-based purification comprises a positive charge-based purification apparatus, a negative-charge based purification apparatus, or combinations thereof. In examples, the second module has at least one second inlet and at least one second outlet and is configured to permit continuous fluid flow between the second inlet and the second outlet via a mechanical rotary system comprising a lid system, a vessel carousel, and a collection system.

In embodiments, the charge-based purification apparatus (e.g., positive and/or negative charge-based purification) further includes a suspension of resin beads. The surface of the resin beads, for example, may comprise cationic or anionic functionality configured to selectively associate with said biological product at a specific pH and ionic strength to enable positive charge-based purification or negative charge-based purification, respectively. Continuous purification of biological products (e.g., a monoclonal antibody) with ionic resin beads can avoid the cumbersome processing steps of traditional ion-exchange column chromatographies (e.g., cation exchange or anion exchange chromatographies).

In embodiments, the resin beads of the charge-based purification apparatus have a diameter of about 0.2 micron to about 200 micron. The diameter of the resin beads may depend on the biological product being purified and the flow rate of the process. Moreover, the resin beads may have a concentration ranging from 0.01% to 25% by weight. For example, the concentration of the magnetic resin beads may be about 1% to about 20% by weight. In other examples, the charge or electrostatic association capacity of the resin beads is a function of the bead concentration, surface area-to-volume ratio, surface charge density, net charge, or any combination thereof. In yet other examples, the resin beads may be solid, porous, nanoporous, microporous, or any combination thereof.

In embodiments, the charge-based purification module includes lid system having at least one gasketed lid, the at least one gasketed lid comprising at least one inlet to introduce a gas to enable control of positive head pressure, at least one vent port to enable equilibration to atmospheric pressure, at least one inlet to introduce a suspension of resin beads; at least one inlet to receive the filtrate containing a biological product, at least two inlets to introduce a buffer system to disperse the resin beads to enable washing of, dissociation from, or regeneration of said resin beads. In some embodiments, the at least one gasketed lid further comprises a port to accept an overhead stirring impeller to enable dispersion of the resin beads. In examples, the lid system has control of motion along the z-axis.

In embodiments, the charge-based purification module includes a mechanical rotary system, for example, a carousel comprising at least two vessels charged with resin beads that are configured to continuously receive a mixture containing a biological product and subsequently transport the resulting heterogeneous mixture containing a biological product, resin beads, a buffer, or any combination thereof. In examples, the mechanical rotary system is configured to mate with the lid system to enable pressurization. In other examples, the mechanical rotary system has control of motion or rotation in the xy-plane.

In embodiments, the at least two vessels of the charge-based purification module each have a supported, basement filter or filter membrane to enable retention of the resin beads during process steps of association, dissociation, washing, and regeneration. In examples, the at least two vessels further include a valve to control liquid flow.

In embodiments, the charge-based purification module includes a collection system that interfaces with at least one of the at least two vessels of the mechanical rotary system to enable collection of waste, the fraction containing the biological product, or any combination thereof. In examples, the collection system has control of motion along the z-axis.

In embodiments described herein, the resin beads of one or both of the first (affinity-based purification) and/or second (charged-based purification) module(s) are recycled and re-used. For example, said beads may be re-used at least 2, 3, 4, or more times for purifying a biological product.

Alternatively, the process described herein includes continuously transferring the fraction containing the biological product from the at least one first outlet of the first module to a second module having at least one inlet for receiving flow from the at least one first outlet of the first module, and the second module comprises a free-flow electrophoresis apparatus. The free-flow electrophoresis apparatus having a fluidic channel created between two parallel plates, an electric field or electric field gradient orthogonal to the fluid flow direction, and an aqueous ionic solution, may be used in lieu of or in addition to the charge-based, magnetic purification module(s) to purify the biological product (e.g., a monoclonal antibody).

In examples, the solution contacting surfaces of the two parallel plates comprise glass, ceramic, plastic, or any combination thereof. In some examples, the aqueous ionic solution may give rise to a pH gradient across the main separation channel. In other examples, the aqueous ionic solution may confer constant pH across the main separation channel.

In embodiments, the free-flow electrophoresis apparatus has at least one fluidic device comprising a fluidic channel created between two parallel plates, an electric field or electric field gradient orthogonal to the fluid flow direction, and a pH gradient. In examples, the isoelectric point-based, fluidic purification module includes at least one first fluidic device comprising a fluidic channel created between two parallel plates, an electric field or electric field gradient orthogonal to the fluid flow direction, and a coarse pH gradient across the main separation channel (in examples, a coarse pH gradient may be a pH range from about 2 to about 10); and at least one second fluidic device comprising a fluidic channel created between two parallel plates, an electric field or electric field gradient orthogonal to the fluid flow direction, and a fine pH gradient across the main separation channel (in examples, a fine pH gradient may be a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In other embodiments, the free-flow electrophoresis apparatus has at least one fluidic device comprising a fluidic channel created between two parallel plates, an electric field or electric field gradient orthogonal to the fluid flow direction, and no pH gradient to operate in a zone electrophoresis or charge separating mode of operation. In examples, the isoelectric point-based, fluidic purification module includes at least one first fluidic device comprising a fluidic channel created between two parallel plates, an electric field or electric field gradient orthogonal to the fluid flow direction, and constant basic pH (e.g., a pH of greater than 7); and at least one second fluidic device comprising a fluidic channel created between two parallel plates, an electric field or electric field gradient orthogonal to the fluid flow direction, and a constant acidic pH (e.g., a pH of less than 7).

In other embodiments, the free-flow electrophoresis apparatus has at least one fluidic device comprising a fluidic channel created between two parallel plates, an electric field or electric field gradient orthogonal to the fluid flow direction, and both an acidic pH gradient and a basic pH gradient separated by a spacer solution (e.g. NaCl solution) to operate in an isotachophoresis mode of operation.

In other embodiments, the isoelectric point-based, fluidic purification module includes at least one first free-flow electrophoresis apparatus comprising a fluidic channel created between two parallel plates and an electric field or electric field gradient orthogonal to the fluid flow direction, and at least one second free-flow electrophoresis apparatus comprising a fluidic channel created between two parallel plates and an electric field or electric field gradient orthogonal to the fluid flow direction, wherein each device connected in series and is capable of operating in an independent mode of operation to enable purification. For example, the at least one first free-flow electrophoresis apparatus may operate in an isoelectric focusing mode and the at least one second free-flow electrophoresis apparatus may operate in an isotachophoresis mode to increase separation resolution.

In other embodiments, the isoelectric point-based, fluidic purification module includes at least one first fluidic device comprising fluidic channel having at least one dielectrophoretic electrode capable of inducing a defined, unidirectional force; at least one second free-flow electrophoresis apparatus comprising a fluidic channel created between two parallel plates, an electric field or electric field gradient orthogonal to the fluid flow direction, and a coarse pH gradient across the main separation channel (e.g., a pH range from about 2 to about 10); and at least one third free-flow electrophoresis apparatus comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In embodiments, the isoelectric point-based fluidic purification apparatus further comprises at least two electrodes (e.g. platinum wire electrodes) to function as an anode or a cathode.

In embodiments, the backpressure within the isoelectric point-based fluidic purification apparatus is dependent on the channel geometry and dimensions, the inlet and outlet opening and/or tubing diameters, and the input flow rate. In examples, the backpressure ranges from about 0.5 psi to about 10 psi. In some examples, the backpressure is controlled by, for example, without intent to be limiting, a needle valve.

In embodiments, the isoelectric point-based fluidic purification apparatus further comprises at least one de-bubbler system to continuously remove $O_2$ and $H_2$ gas bubbles that evolve in the electrode channels under applied voltage. In some embodiments, removal of electrolysis bubbles is essential to enable continuous operation for substantially long periods of time. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar.

In embodiments, the isoelectric point-based fluidic purification apparatus further comprises an active cooling system or heat sink (e.g., a Peltier device, a thermal chuck with a circulating water/propylene glycol jacket) to enable temperature control and Joule heat dissipation. For example, the active cooling system may control cooling and/or heat dissipation in the range from about 4° C. to about 50° C., preferably from about 4° C. to about 37° C. Ideally, when isolating a biological product (e.g., a monoclonal antibody), the temperature is maintained at about 10° C. to about 25° C. In examples, the active cooling system comprises an aluminum thermal chuck containing a chilled, circulating water/propylene glycol jacket.

In embodiments, the isoelectric point-based, fluidic purification module includes at least one buffer or ampholyte system.

In embodiments, the isoelectric point-based, fluidic purification module includes at least one electrode solution. In some embodiments, the at least one electrode solution comprises an electrolyte solution configured to contact and enable the appropriate function of an anode or a cathode, for example, phosphoric acid and sodium hydroxide, respectively. In other embodiments, the at least one electrode solution comprises at least one ampholyte solution configured to contact and enable the appropriate function of an anode or a cathode, for example, Tris buffered saline flowing through the main separation channel, the anode channel, and the cathode channel.

In embodiments, the isoelectric point-based, fluidic purification module includes at least one sensor or detector. In examples, the at least one sensor or detector is positioned in-line. In some examples, the at least one sensor or detector includes, but is not limited to, a flow sensor, a temperature sensor, a conductivity sensor, a pH sensor, a refractive index detector, a UV detector, or a backpressure sensor.

In embodiments, the isoelectric point-based, fluidic purification module includes at least one liquid circuit breaker or disconnect downstream of the device and upstream of the at least one in-line sensor or detector to ensure the ability to perform sensing or detection in a voltage-free solution.

The presently claimed process provides for a number of advantages over current downstream methods and processes for purifying a biological product, for example, a protein or fragment thereof (a polypeptide), an antibody or fragment thereof, a cytokine, a chemokine, an enzyme, or a growth factor. For example, without intent to be limiting, the process described herein provides a continuous bioprocess for purifying a monoclonal antibody that maintains throughput and yield, while significantly decreasing the production facility footprint, the time required for facility buildout and validation, the costs associated with facility buildout, and capital equipment expenditure, when compared to the traditional approaches of batch, single-use, or semi-continuous monoclonal antibody manufacturing. The continuous bioprocessing as described herein affords smaller, more streamlined equipment (e.g., smaller bioreactor volumes and downstream bioprocess equipment) because the ability to operate continuously eliminates the need for the large process equipment required for the centrifugation, depth filtration, and column chromatography steps of traditional downstream bioprocessing, whose size is dictated by large bioreactor volumes. Further, the smaller, more streamlined equipment operating continuously affords the use of significantly smaller bioreactor(s) that produce monoclonal antibodies at steady-state. The continuous bioprocess as described herein may also significantly decrease operating expenditures, overall bioprocess line downtime, and biological product loss when compared to traditional monoclonal antibody manufacturing approaches. Finally, the process described herein for purifying a biological product is conducted in a system with a footprint that occupies significantly less square footage than current techniques, without sacrificing product throughput or yield on a kilograms/year basis.

Advantages of the process and methods described herein include the ability to remove large impurities (e.g., cells, cell debris, and aggregates) without membrane fouling or occlusion. For example, it is known in the art that clarification of cells, cell debris and aggregates from cell culture media with traditional filtration or tangential flow filtration systems typically leads to fouling or occlusion of the filter membrane, thus rendering these methodologies unsuitable as a means to continuously remove large impurities from a heterogeneous mixture containing a biological product over long-term continuous processing. In contrast, the dynamic filtration apparatus described herein enables continuous removal of large impurities from a heterogeneous mixture containing a biological product without membrane fouling, as the active target region of the filter membrane is constantly being refreshed. Additionally, because the entire process of producing and purifying the biological product may be continuous and can maintain a flow rate that ranges from about 0.1 mL/minute to about 50 mL/minute across the entirety of the process, the process equipment and overall process footprint is able to have a significantly smaller footprint than current standard processes, without sacrificing product throughput or yield on a kilogram/year basis. For example, the process for producing and purifying a monoclonal antibody as described herein is operated with a footprint that occupies up to about 30,000 square feet. In contrast, current mononclonal antibody production and downsteam processes require at least 200,000 square feet. In examples, the process of purifying the biological product has a flow rate that ranges from about 1 mL/minute to about 10 mL/minute. In some examples, the flow rate of the step of continuously removing large impurities from the heterogeneous mixture ranges from about 0.1 mL/minute to about 50 mL/minute. In other examples, the flow rate of the step of continuously removing large impurities from the heterogeneous mixture is equivalent to the flow rate from the bioreactor bleed line. In other examples, the process provides that the flow rate of the step of continuously transferring the filtrate to a first module ranges from about 0.1 mL/minute to about 50 mL/minute. In yet other examples, the process provides that the flow rate of the step of continuously transferring the fraction containing the biological product from the first outlet to a second module ranges from about 0.1 mL/minute to about 50 mL/minute.

An important advantage of the process and methods utilizing resin beads (e.g. agarose) described herein includes that these systems do not require traditional stationary phase or packed resin columns (e.g., for standard chromatographies) to be sanitized, recycled and/or regenerated. For example, these systems provide for recycling and/or regeneration of the resin beads to create a limitless surface area of the resin beads during operation, and in turn provides a continuous and cost-effective method. Put in another way, the modules described herein do not have a fixed binding or association capacity. In specific examples, the resin beads used during purification of the biological product, as described herein, are constantly being recycled and regenerated, and therefore able to accept flow from the previous step, either a dynamic filtration module or a purification module, without interruption of the flow from the bioreactor bleed line. Put another way, the modules described in the present invention do not have to be left idle in order to be sanitized, regenerated and/or recycled after running, as they are continuously undergoing these steps. The method differs from current continuous chromatographic methods, in that current column chromatography methods have defined column capacity limitations due to column packing constraints and thus require column switching of multiple packed columns to accept continuous input flow and enable regeneration and/or recycling of the columns that have reached full capacity. Another advantage of the methods described herein includes the that the resin beads are not packed into a stationary phase, rather the resin beads have mobility. This increases the surface area of the resin beads that is available for binding or association, as substantially more of the resin bead surface is exposed and free to bind. Additionally, the resin beads in a packed column are exposed to a high pressure differential in order to generate flow through the column and damage from which is one of the reasons for less than desired column lifetime. The mobile resin beads in the presently described invention are subjected to substantially lower pressures which is much gentler on the fragile beads, resulting in longer lifetimes. Additionally, this mobility makes the resin beads more likely to be completed regenerated and returned to their initial condition. This further adds to the cost-effectiveness of the methods described herein, as the resin is utilized more efficiently.

An important advantage of the process and methods utilizing free-flow electrophoresis described herein includes that this system represents a "no product loss" process, in that, there is no need for the product to interact with a resin or other purifying moieties, as the separation occurs in aqueous solution according to the physicochemical properties of the target biological product via interaction with an electric field. Another advantage is observed in the resolving power of this approach, as a theoretically higher purity product is achievable when compared to traditional ion-exchange chromatographies. Additionally, the separation based on intrinsic physicochemical properties extends the utility of this approach for the purification a plethora of biological products, including, but not limited to, a protein or fragment thereof (a polypeptide), an antibody or fragment thereof, a cytokine, a chemokine, an enzyme, a growth factor, an oligonucleotide, a virus, an adenovirus, an adeno-associated virus (AAV), or a lentivirus.

Further, the modular approach affords flexibility in process design to accommodate a diverse range of biological products.

Continuous Process for Purifying a Biological Product Using a Dynamic Filtration Module, an Affinity-Based, Fluidic Purification Module, and at Least One of a Charge-Based, Fluidic Purification Module or an Isoelectric Point-Based, Fluidic Purification Module A continuous process for purifying a biological product is described; the process including continuously receiving, via an input line, a heterogeneous mixture containing the biological product, wherein the biological product includes, but is not limited to, a protein or fragment thereof (a polypeptide), an antibody or fragment thereof, a cytokine, a chemokine, an enzyme, or a growth factor. When purifying, the biological product (e.g., a monoclonal antibody) is substantially pure when it is at least about 60%, 70%, 80%, 90%, 95%, or even 99%, by weight, free from impurities (e.g., cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

The process includes continuously removing large impurities from the heterogeneous mixture by dynamic filtration. Said dynamic filtration process includes at least one dynamic filtration module that continuously feeds the biological product from at least one output head in fluid communication with the input line to the dynamic filtration module under negative pressure, thereby producing a filtrate comprising the biological product. The dynamic filtration module may further include at least one additional input line to supply a wash buffer via a coaxial output head or a separate monoaxial output head.

In embodiments, the process described herein includes purifying a biological product that is continuously produced in a bioreactor (e.g., a fed-batch bioreactor, a perfusion bioreactor, a chemostat bioreactor). For example, the bioreactor includes a bioreactor feed line and an output bleed line to enable steady-state cell culture growth conditions, and the output bleed line functions as the input line to permit continuous fluid flow from the bioreactor to the dynamic filtration module.

As described herein, the process of continuously removing large impurities from the heterogeneous mixture does not include centrifugation, disk-stack centrifugation, depth filtration, static filtration, tangential flow filtration, a hydrocyclone, or any combination thereof. The term "static filtration" refers to a process in which the heterogeneous mixture being filtered remains static, meaning for example that the filter membrane (or depth filter) has a defined capacity, and the rate of filtration decreases as the membrane reaches its capacity (e.g., membrane pores become occluded). In a "static" (as opposed to "dynamic") filtration, the filter membrane remains stationary (does not move), and the flow (e.g., of the heterogeneous mixture) passes through the stationary filter membrane. These static filtration methods are common in the art and are simple and well-understood.

Unlike the static filtration methods commonly used in the art, the process herein describes a dynamic filtration module, wherein components of the dynamic filtration module move in a coordinated fashion (e.g., the membrane moves or advances in accordance with the flow rate of the entire process) to enable filtration to occur continuously across a fresh, unused target region of filter membrane. This eliminates membrane fouling or occlusion and permits control over the filter cake packing and thickness during operation.

The dynamic filtration module includes a filter membrane roll, a membrane support structure, at least one support rod or roller, a vacuum line, a vacuum system, and at least one vacuum collection vessel.

In embodiments, the filter membrane roll includes a filter roll, wherein the filter membrane, without intent to be limiting, comprises polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), hydrophilic PTFE, or any combination thereof.

The pore size of the rolled filter membrane depends on the biological product being purified. In examples, the rolled filter membrane has a pore size in the range from 0.1 μm to 1 μm. Alternatively, the pore size is in the range from about 0.2 μm to about 0.45 μm, or the pore size is less than about 0.45 μm. In other examples, when purifying an antibody, the pore size of the rolled filter membrane is in the range of 0.2 μm to about 0.45 μm.

The filter membrane roll has a width from about 10 mm to about 600 mm. The width of the filter membrane roll, for example, may depend on the size of the dynamic filtration system or the membrane support structure.

In embodiments, the filter membrane roll further functions as a feed reel that communicates with a collection reel, meaning the filter membrane originates from pre-fabricated roll and spans to an initially empty collecting roll, thus creating a reel-to-reel system. In aspects, the dynamic filtration module includes a rolled filter membrane extending between a feed reel and a collection reel, the filter membrane having an active target region that is configured to receive the heterogeneous mixture. In examples, the feed reel motion is governed by a Servo motor coupled with a gear box to limit rotations per minute (RPM) by a ratio of 200:1 to enable low membrane transport velocities with high torque. The collection reel motion is governed by a Servo motor coupled with a gear box to limit RPM by a ratio of 200:1 to enable low membrane transport velocities with high torque. Further, the feed reel motor and the collection reel motor are controlled by a closed-loop controller that operates a feedback mechanism to ensure consistent velocity with the constantly changing diameters of the filter membrane roll on both the feed reel and the collection reel during operation. In examples, the feed reel and the collection reel operate in the same direction with equivalent velocities.

In embodiments, the transport velocity of the filter membrane ranges from about 0.1 mm/sec to about 100 mm/sec, preferably from about 0.1 mm/sec to about 10 mm/sec.

The membrane support structure of the dynamic filtration module includes a mechanically smooth contact surface derived from a material having a low static coefficient of friction (e.g. PTFE) and an opening that has continuity with the vacuum line. As used herein, the "membrane support structure" refers to a fabricated component that provides structural support to the active region of the filter membrane, to prevent deformation, as it traverses an area of negative pressure, resulting from the opening having continuity with the vacuum line. Further, as used herein, "mechanically smooth contact surface" refers to a surface having a low static coefficient of friction, thus creating a low frictional force opposing transport of the filter membrane, especially when wetted. The mechanically smooth contact surface may influence the ease at which the filter membrane moves in a dynamic fashion. The mechanically smooth contact surface may also be measured in surface roughness, where the lower the value the smoother the surface. Moreover, since rougher surfaces have more friction between them than smoother surfaces, the mechanically smooth contact surface, as used herein, refers to a surface having lower friction (i.e., a low static coefficient of friction).

In embodiments, the membrane support structure of the dynamic filtration module includes an opening. The opening for example, may include a mesh, at least one slot, at least one hole, a frit, a porous material, or any combination thereof. For example, the opening may include a series of regularly or irregularly spaced elements (e.g., a mesh, at least one slot, at least one hole, or any combination thereof). Moreover, the opening may include regularly spaced elements, for example the opening may include a series of equally spaced, parallel slots. Additionally, the opening can include one grate (e.g., a series of regularly or irregularly spaced elements as described above). In other examples, the opening can include more than one grate, with each grate perpendicular. The opening can be a collection of irregular or regular elements (e.g., a series of parallel slots). The opening can also include a mesh, which are of split-thickness or of full-thickness and may or may not be in parallel rows. The elements of the opening (e.g., a mesh, at least one slot, at least one hole, a frit, a porous material, or any combination thereof) may be of any desired thickness. For example, without intent to be limiting, the opening may include a mesh with a thickness of about 0.25 mm to about 5 mm.

The membrane support structure of the dynamic filtration module includes a temperature control mechanism. The temperature control mechanism maintains a temperature from about 4° C. to about 37° C. in the presence of evaporative cooling. For example, during purification of an antibody, the temperature control mechanism maintains a temperature from 15° C. to 37° C. Exemplary temperature control mechanisms include, but are not limited to, single loop controllers, multi-loop controllers, closed loop controllers, PID controllers, Peltier devices, resistive heating elements, and/or thermal chucks with circulating water jackets.

In embodiments, the at least one support rod or roller of the dynamic filtration module has a mechanically smooth contact surface derived from a material having a low static coefficient of friction (e.g. PTFE, PFA). In examples, the dynamic filtration module includes at least one support rod or roller with a mechanically smooth contact surface to stabilize the motion of the filter membrane across the membrane support structure.

In embodiments, the dynamic filtration module includes at least one output head for modulating flow of the heterogeneous mixture and dispensing the heterogeneous mixture onto the target region (e.g., active target region) of the filter membrane. In examples, the at least one output head is a tube or a slot die.

In some embodiments, the dynamic filtration module further includes at least one additional input line to supply a wash buffer via a coaxial output head, a separate monoaxial output head, a separate slot die output head, or a slot die output head with multiple openings.

In some embodiments, the dynamic filtration module includes elements known in the coating and converting industry, for example, without intent to be limiting, active or passive edge guides, tension control (e.g. a dancer), break and tension detectors, or any combination thereof.

In embodiments, the dynamic filtration module includes a vacuum system having continuity with the membrane support structure to apply negative pressure across the active target region of the filter membrane, where the negative pressure allows for active transport of the filter membrane across the membrane support structure and enables collection of the filtrate containing the biological product. In examples, the vacuum system of the dynamic filtration module maintains a gauge pressure of about −0.05 bar to about −0.98 bar for continuous filtration.

In embodiments, the dynamic filtration module further includes at least one vacuum collection vessel configured to collect the filtrate, and at least one sensor or detector. In aspects described herein, during the purification by dynamic filtration, the filtrate comprising the biological product is fed under negative pressure into a vacuum collection vessel capable of collecting from about 50 mL to about 100 L. In examples, the vacuum collection vessel capable of collecting the filtrate is from about 1 L to about 10 L. In other examples, the vacuum collection vessel capable of collecting the filtrate is from about 1 L to about 50 L.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 μm) in fluid communication with at least one second dynamic filtration apparatus having a rolled filter membrane with a small pore size (e.g., 0.2 μm), thereby producing a filtrate comprising the biological product.

The process described herein includes continuously transferring the filtrate to a first module capable of separating the solution into two or more fractions including at least one fraction containing the biological product. For example, separating the solution into two or more fractions, may include at least one fraction containing the biological product, and the at least one other fraction containing small impurities. As described herein, the first module comprises an affinity-based, fluidic purification apparatus. The "affinity-based, fluidic purification apparatus" refers to a purification technique based on utilizing molecular, conformational binding interactions (e.g., ligand-receptor interactions) in which selective surface-immobilized ligands recognize and bind to the biological product to be purified with at least one hybrid fluidic device or chip (e.g., microfluidic, mesofluidic, millifluidic, macrofluidic). In examples, the first module has at least one first inlet and at least one first outlet and is configured to permit continuous fluid flow between the first inlet and the first outlet.

In embodiments, the affinity-based, fluidic purification apparatus further includes a suspension of magnetic resin beads. The surface of the magnetic resin beads, for example, without intent to be limiting, is coupled with Protein A, Protein G, Protein L, an antigenic protein, a protein, a receptor, an antibody, or an aptamer. Continuous purification of biological products (e.g., a monoclonal antibody) with affinity magnetic resin beads can avoid the cumbersome processing steps of traditional affinity column chromatography (e.g., Protein A affinity chromatography).

In embodiments, the magnetic resin beads of the affinity-based, fluidic purification apparatus have a diameter of about 0.2 micron to about 200 micron. The diameter of the magnetic resin beads may depend on the biological product being purified and the flow rate of the process. Moreover, the magnetic resin beads may have a concentration ranging from 0.01% to 25% by weight. For example, the concentration of the magnetic resin beads may be about 1% by weight. In other examples, the binding capacity of the magnetic resin beads is a function of the bead concentration, surface area-to-volume ratio, affinity ligand density, or any combination thereof. In yet other examples, the magnetic resin beads may be solid, porous, nanoporous, microporous, or any combination thereof.

The at least one hybrid fluidic device or chip of the affinity-based, fluidic purification apparatus may refer to, for example, a microfluidic, a mesofluidic, a millifluidic, a macrofluidic device or chip, or any combination thereof. In some examples, the fluidic device or chip is a hybrid microfluidic device or chip, for example, a microfluidic device that combines the functionality of cross-flow fluid dynamics with magnetophoretic and dielectrophoretic capabilities, wherein the cross-flow fluid dynamics are governed by the microchannel design, the magnetophoresis is accomplished via an external magnetic field, and the dielectrophoresis is accomplished via a dielectrophoretic electrode. In aspects, the combination of the dielectrophoretic electrode and the external magnetic field is used to manipulate the flow path of the magnetic resin beads in the cross-flow microchannel to enable efficient purification at high flow rates (e.g., greater than 0.5 mL/min), a phenomenon not currently realized in the field of microfluidics in which flow rates are traditionally limited to μL/hr or μL/min. In other examples, the hybrid fluidic is a microfluidic device that combines the functionality of cross-flow fluid dynamics with magnetophoretic and acoustophoretic capabilities, wherein the cross-flow fluid dynamics are governed by the microchannel design, the magnetophoresis is accomplished via an external magnetic field, and the acoustophoresis is accomplished via a piezoelectric transducer or crystal. In aspects, the combination of the piezoelectric transducer and the external magnetic field is used to manipulate the flow path of the magnetic resin beads in the cross-flow microchannel to enable efficient purification at high flow rates (e.g., greater than 0.5 mL/min), a phenomenon not currently realized in the field of microfluidics in which flow rates are traditionally limited to μL/hr or μL/min.

In embodiments, the affinity-based, fluidic purification module further includes at least one tangential flow filtration system operated in fed-batch or perfusion mode to concentrate and buffer exchange the fraction containing the biological product.

The process as described herein also includes continuously transferring the fraction containing the biological product from the at least one first outlet of the first module to a second module having at least one inlet for receiving flow from the at least one first outlet of the first module, and the second module comprises a charge-based, fluidic purification apparatus. The "charge-based, fluidic purification apparatus" as used herein includes, for example, purifying biological molecules based on their surface charge, ionic character, electrostatic interactions, or isoelectric point with at least one hybrid fluidic device or chip (e.g., a microfluidic, a mesofluidic, a millifluidic, a macrofluidic device or chip, or any combination thereof). As described herein, the charge-based, fluidic purification comprises a positive charge-based, fluidic purification apparatus, negative charge-based, fluidic purification apparatus, or combinations thereof. In examples, the second module has at least one second inlet and at least one second outlet and is configured to permit continuous fluid flow between the second inlet and the second outlet.

In embodiments, the charge-based, fluidic purification apparatus further includes a suspension of magnetic resin beads. The surface of the magnetic resin beads, for example, may comprise cationic or anionic functionality configured to selectively associate with said biological product at a specific pH and ionic strength to enable positive charge-based, fluidic purification or negative charge-based, fluidic purification, respectively. Continuous purification of biological products (e.g., a monoclonal antibody) with ionic magnetic resin beads can avoid the cumbersome processing steps of traditional ion-exchange column chromatographies (e.g., cation exchange or anion exchange chromatographies).

In embodiments, the magnetic resin beads of the charge-based, fluidic purification apparatus have a diameter of about 0.2 micron to about 200 micron. The diameter of the magnetic resin beads may depend on the biological product being purified and the flow rate of the process. Moreover, the magnetic resin beads may have a concentration ranging from 0.01% to 25% by weight. For example, the concentration of the magnetic resin beads may be about 1% by weight. In other examples, the charge or electrostatic association capacity of the magnetic resin beads is a function of the bead concentration, surface area-to-volume ratio, surface charge density, net charge, or any combination thereof. In yet other examples, the magnetic resin beads may be solid, porous, nanoporous, microporous, or any combination thereof.

The at least one hybrid fluidic device or chip of the charge-based, fluidic purification apparatus may refer to, for example, a microfluidic, a mesofluidic, a millifluidic, a macrofluidic device or chip, or any combination thereof. In some examples, the fluidic device or chip is a hybrid microfluidic device or chip, for example, a microfluidic device that combines the functionality of cross-flow fluid dynamics with magnetophoretic and dielectrophoretic capabilities, wherein the cross-flow fluid dynamics are governed by the microchannel design, the magnetophoresis is accomplished via an external magnetic field, and the dielectrophoresis is accomplished via a dielectrophoretic electrode. In aspects, the combination of the dielectrophoretic electrode and the external magnetic field is used to manipulate the flow path of the magnetic resin beads in the cross-flow microchannel to enable efficient purification at high flow rates (e.g., greater than 0.5 mL/min), a phenomenon not currently realized in the field of microfluidics in which flow rates are traditionally limited to μL/hr or μL/min. In other examples, the hybrid fluidic is a microfluidic device that combines the functionality of cross-flow fluid dynamics with magnetophoretic and acoustophoretic capabilities, wherein the cross-flow fluid dynamics are governed by the microchannel design, the magnetophoresis is accomplished via an external magnetic field, and the acoustophoresis is accomplished via a piezoelectric transducer or crystal. In aspects, the combination of the piezoelectric transducer and the external magnetic field is used to manipulate the flow path of the magnetic resin beads in the cross-flow microchannel to enable efficient purification at high flow rates (e.g., greater than 0.5 mL/min), a phenomenon not currently realized in the field of microfluidics in which flow rates are traditionally limited to µL/hr or µL/min.

In embodiments, the charge-based, fluidic purification module further includes at least one tangential flow filtration system operated in fed-batch or perfusion mode to concentrate and buffer exchange the fraction containing the biological product.

In embodiments described herein, the magnetic resin beads of one or both of the first (affinity-based, fluidic purification) and/or second (charged-based, fluidic purification) modules are recycled and re-used. For example, the beads may be re-used at least 2, 3, 4, or more times for purifying a biological product.

Alternatively, the process described herein includes continuously transferring the fraction containing the biological product from the at least one first outlet of the first module to a second module having at least one inlet for receiving flow from the at least one first outlet of the first module, and the second module comprises a free-flow electrophoresis apparatus. The free-flow electrophoresis apparatus having a fluidic channel created between two parallel plates, an electric field or electric field gradient orthogonal to the fluid flow direction, and an aqueous ionic solution, may be used in lieu of or in addition to the charge-based, magnetic purification module(s) to purify the biological product (e.g., a monoclonal antibody).

In examples, the solution contacting surfaces of the two parallel plates comprise glass, ceramic, plastic, or any combination thereof. In some examples, the aqueous ionic solution may give rise to a pH gradient across the main separation channel. In other examples, the aqueous ionic solution may confer constant pH across the main separation channel.

In embodiments, the free-flow electrophoresis apparatus has at least one fluidic device comprising a fluidic channel created between two parallel plates, an electric field or electric field gradient orthogonal to the fluid flow direction, and a pH gradient. In examples, the isoelectric point-based, fluidic purification module includes at least one first fluidic device comprising a fluidic channel created between two parallel plates, an electric field or electric field gradient orthogonal to the fluid flow direction, and a coarse pH gradient across the main separation channel (in examples, a coarse pH gradient may be a pH range from about 2 to about 10); and at least one second fluidic device comprising a fluidic channel created between two parallel plates, an electric field or electric field gradient orthogonal to the fluid flow direction, and a fine pH gradient across the main separation channel (in examples, a fine pH gradient may be a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In other embodiments, the free-flow electrophoresis apparatus has at least one fluidic device comprising a fluidic channel created between two parallel plates, an electric field or electric field gradient orthogonal to the fluid flow direction, and no pH gradient to operate in a zone electrophoresis or charge separating mode of operation. In examples, the isoelectric point-based, fluidic purification module includes at least one first fluidic device comprising a fluidic channel created between two parallel plates, an electric field or electric field gradient orthogonal to the fluid flow direction, and constant basic pH (e.g., a pH of greater than 7); and at least one second fluidic device comprising a fluidic channel created between two parallel plates, an electric field or electric field gradient orthogonal to the fluid flow direction, and a constant acidic pH (e.g., a pH of less than 7).

In other embodiments, the free-flow electrophoresis apparatus has at least one fluidic device comprising a fluidic channel created between two parallel plates, an electric field or electric field gradient orthogonal to the fluid flow direction, and both an acidic pH gradient and a basic pH gradient separated by a spacer solution (e.g. NaCl solution) to operate in an isotachophoresis mode of operation.

In other embodiments, the isoelectric point-based, fluidic purification module includes at least one first free-flow electrophoresis apparatus comprising a fluidic channel created between two parallel plates and an electric field or electric field gradient orthogonal to the fluid flow direction, and at least one second free-flow electrophoresis apparatus comprising a fluidic channel created between two parallel plates and an electric field or electric field gradient orthogonal to the fluid flow direction, wherein each device connected in series and is capable of operating in an independent mode of operation to enable purification. For example, the at least one first free-flow electrophoresis apparatus may operate in an isoelectric focusing mode and the at least one second free-flow electrophoresis apparatus may operate in an isotachophoresis mode to increase separation resolution.

In other embodiments, the isoelectric point-based, fluidic purification module includes at least one first fluidic device comprising fluidic channel having at least one dielectrophoretic electrode capable of inducing a defined, unidirectional force; at least one second free-flow electrophoresis apparatus comprising a fluidic channel created between two parallel plates, an electric field or electric field gradient orthogonal to the fluid flow direction, and a coarse pH gradient across the main separation channel (e.g., a pH range from about 2 to about 10); and at least one third free-flow electrophoresis apparatus comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In embodiments, the isoelectric point-based fluidic purification apparatus further comprises at least two electrodes (e.g. platinum wire electrodes) to function as an anode or a cathode.

In embodiments, the backpressure within the isoelectric point-based fluidic purification apparatus is dependent on the channel geometry and dimensions, the inlet and outlet opening and/or tubing diameters, and the input flow rate. In examples, the backpressure ranges from about 0.5 psi to about 10 psi. In some examples, the backpressure is controlled by, for example, without intent to be limiting, a needle valve.

In embodiments, the isoelectric point-based fluidic purification apparatus further comprises at least one de-bubbler system to continuously remove $O_2$ and $H_2$ gas bubbles that evolve in the electrode channels under applied voltage. In some embodiments, removal of electrolysis bubbles is essential to enable continuous operation for substantially long periods of time. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar.

In embodiments, the isoelectric point-based fluidic purification apparatus further comprises an active cooling system or heat sink (e.g., a Peltier device, a thermal chuck with a circulating water/propylene glycol jacket) to enable temperature control and Joule heat dissipation. For example, the active cooling system may control cooling and/or heat dissipation in the range from about 4° C. to about 50° C., preferably from about 4° C. to about 37° C. Ideally, when isolating a biological product (e.g., a monoclonal antibody), the temperature is maintained at about 10° C. to about 25° C. In examples, the active cooling system comprises an aluminum thermal chuck containing a chilled, circulating water/propylene glycol jacket.

In embodiments, the isoelectric point-based, fluidic purification module includes at least one buffer or ampholyte system.

In embodiments, the isoelectric point-based, fluidic purification module includes at least one electrode solution. In some embodiments, the at least one electrode solution comprises an electrolyte solution configured to contact and enable the appropriate function of an anode or a cathode, for example, phosphoric acid and sodium hydroxide, respectively. In other embodiments, the at least one electrode solution comprises at least one ampholyte solution configured to contact and enable the appropriate function of an anode or a cathode, for example, Tris buffered saline flowing through the main separation channel, the anode channel, and the cathode channel.

In embodiments, the isoelectric point-based, fluidic purification module includes at least one sensor or detector. In examples, the at least one sensor or detector is positioned in-line. In some examples, the at least one sensor or detector includes, but is not limited to, a flow sensor, a temperature sensor, a conductivity sensor, a pH sensor, a refractive index detector, a UV detector, or a backpressure sensor.

In embodiments, the isoelectric point-based, fluidic purification module includes at least one liquid circuit breaker or disconnect downstream of the device and upstream of the at least one in-line sensor or detector to ensure the ability to perform sensing or detection in a voltage-free solution.

The presently claimed process provides for a number of advantages over current downstream methods and processes for purifying a biological product, for example, a protein or fragment thereof (a polypeptide), an antibody or fragment thereof, a cytokine, a chemokine, an enzyme, or a growth factor. For example, without intent to be limiting, the process described herein provides a continuous bioprocess for purifying a monoclonal antibody that maintains throughput and yield, while significantly decreasing the production facility footprint, the time required for facility buildout and validation, the costs associated with facility buildout, and capital equipment expenditure, when compared to the traditional approaches of batch, single-use, or semi-continuous monoclonal antibody manufacturing. The continuous bioprocessing as described herein affords smaller, more streamlined equipment (e.g., smaller bioreactor volumes and downstream bioprocess equipment) because the ability to operate continuously eliminates the need for the large process equipment required for the centrifugation, depth filtration, and column chromatography steps of traditional downstream bioprocessing, whose size is dictated by large bioreactor volumes. Further, the smaller, more streamlined equipment operating continuously affords the use of significantly smaller bioreactor(s) that produce monoclonal antibodies at steady-state. The continuous bioprocess as described herein may also significantly decrease operating expenditures, overall bioprocess line downtime, and biological product loss when compared to traditional monoclonal antibody manufacturing approaches. Finally, the process described herein for purifying a biological product is conducted in a system with a footprint that occupies significantly less square footage than current techniques, without sacrificing product throughput or yield on a kilograms/year basis.

Advantages of the process and methods described herein include the ability to remove large impurities (e.g., cells, cell debris, and aggregates) without membrane fouling or occlusion. For example, it is known in the art that clarification of cells, cell debris and aggregates from cell culture media with traditional filtration or tangential flow filtration systems typically leads to fouling or occlusion of the filter membrane, thus rendering these methodologies unsuitable as a means to continuously remove large impurities from a heterogeneous mixture containing a biological product over long-term continuous processing. In contrast, the dynamic filtration apparatus described herein enables continuous removal of large impurities from a heterogeneous mixture containing a biological product without membrane fouling, as the active target region of the filter membrane is constantly being refreshed. Additionally, because the entire process of producing and purifying the biological product may be continuous and can maintain a flow rate that ranges from about 0.1 mL/minute to about 50 mL/minute across the entirety of the process, the process equipment and overall process footprint is able to have a significantly smaller footprint than current standard processes, without sacrificing product throughput or yield on a kilogram/year basis. For example, the process for producing and purifying a monoclonal antibody as described herein is operated with a footprint that occupies up to about 30,000 square feet. In contrast, current mononclonal antibody production and downsteam processes require at least 200,000 square feet. In examples, the process of purifying the biological product has a flow rate that ranges from about 1 mL/minute to about 10 mL/minute. In some examples, the flow rate of the step of continuously removing large impurities from the heterogeneous mixture ranges from about 0.1 mL/minute to about 50 mL/minute. In other examples, the flow rate of the step of continuously removing large impurities from the heterogeneous mixture is equivalent to the flow rate from the bioreactor bleed line. In other examples, the process provides that the flow rate of the step of continuously transferring the filtrate to a first module ranges from about 0.1 mL/minute to about 50 mL/minute. In yet other examples, the process provides that the flow rate of the step of continuously transferring the fraction containing the biological product from the first outlet to a second module ranges from about 0.1 mL/minute to about 50 mL/minute. Further, the ability for the process of purifying the biological product at a flow rate that ranges from about 0.1 mL/minute to about 50 mL/minute with a hybrid microfluidic device, a phenomenon not currently realized in the field of microfluidics in which flow rates are traditionally limited to μL/hr or μL/min.

An important advantage of the process and methods utilizing magnetic resin beads (e.g. magnetic agarose) described herein includes that these systems do not require traditional stationary phase or packed resin columns (e.g., for standard chromatographies) to be sanitized, recycled and/or regenerated. For example, these systems provide for recycling and/or regeneration of the magnetic resin beads to create a limitless surface area of the magnetic resin beads during operation, and in turn provides a continuous and cost-effective method. Put in another way, the modules described herein do not have a fixed binding or association capacity. In specific examples, the magnetic resin beads used during purification of the biological product, as described herein, are constantly being recycled and regenerated, and therefore able to accept flow from the previous step, either a dynamic filtration module or a purification module, without interruption of the flow from the bioreactor bleed line. Put another way, the modules described in the present invention do not have to be left idle in order to be sanitized, regenerated and/or recycled after running, as they are continuously undergoing these steps. The method differs from current continuous chromatographic methods, in that current column chromatography methods have defined column capacity limitations due to resin packing constraints and thus require column switching of multiple packed columns to accept continuous input flow and enable regeneration and/or recycling of the columns that have reached full capacity. Another advantage of the methods described herein includes the that the magnetic resin beads are not packed into a stationary phase, rather the magnetic resin beads have mobility. This increases the surface area of the magnetic resin beads that is available for binding or association, as substantially more of the magnetic resin bead surface is exposed and free to bind. Additionally, the resin beads in a packed column are exposed to a high pressure differential in order to generate flow through the column and damage from which is one of the reasons for less than desired column lifetime. The mobile resin beads in the presently described invention are subjected to substantially lower pressures which is much gentler on the fragile beads, resulting in longer lifetimes. Additionally, this mobility makes the magnetic resin beads more likely to be completed regenerated and returned to their initial condition. This further adds to the cost-effectiveness of the methods described herein, as the resin is utilized more efficiently.

An important advantage of the process and methods utilizing free-flow electrophoresis described herein includes that this system represents a "no product loss" process, in that, there is no need for the product to interact with a resin or other purifying moieties, as the separation occurs in aqueous solution according to the physicochemical properties of the target biological product via interaction with an electric field. Another advantage is observed in the resolving power of this approach, as a theoretically higher purity product is achievable when compared to traditional ion-exchange chromatographies. Additionally, the separation based on intrinsic physicochemical properties extends the utility of this approach for the purification a plethora of biological products, including, but not limited to, a protein or fragment thereof (a polypeptide), an antibody or fragment thereof, a cytokine, a chemokine, an enzyme, a growth factor, an oligonucleotide, a virus, an adenovirus, an adeno-associated virus (AAV), or a lentivirus.

Further, the modular approach affords flexibility in process design to accommodate a diverse range of biological products.

Continuous Process for Purifying a Biological Product Using a Dynamic Filtration Module, an Affinity-Based TFF Purification Module, and at Least One of a Charge-Based TFF Purification Module or an Isoelectric Point-Based, Fluidic Purification Module A continuous process for purifying a biological product is described; the process including continuously receiving, via an input line, a heterogeneous mixture containing the biological product, wherein the biological product includes, but is not limited to, a protein or fragment thereof (a polypeptide), an antibody or fragment thereof, a cytokine, a chemokine, an enzyme, or a growth factor. When purifying, the biological product (e.g., a monoclonal antibody) is substantially pure when it is at least 60%, 70%, 80%, 90%, 95%, or even 99%, by weight, free from impurities (e.g., cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

The process includes continuously removing large impurities from the heterogeneous mixture by dynamic filtration. Said dynamic filtration process includes at least one dynamic filtration module that continuously feeds the biological product from at least one output head in fluid communication with the input line to the dynamic filtration module under negative pressure, thereby producing a filtrate comprising the biological product. The dynamic filtration module may further include at least one additional input line to supply a wash buffer via a coaxial output head or a separate monoaxial output head.

In embodiments, the process described herein includes purifying a biological product that is continuously produced in a bioreactor (e.g., a fed-batch bioreactor, a perfusion bioreactor, a chemostat bioreactor). For example, the bioreactor includes a bioreactor feed line and an output bleed line to enable steady-state cell culture growth conditions, and the output bleed line functions as the input line to permit continuous fluid flow from the bioreactor to the dynamic filtration module.

As described herein, the process of continuously removing large impurities from the heterogeneous mixture does not include centrifugation, disk-stack centrifugation, depth filtration, static filtration, tangential flow filtration, a hydrocyclone, or any combination thereof. The term "static filtration" refers to a process in which the heterogeneous mixture being filtered remains static, meaning for example that the filter membrane (or depth filter) has a defined capacity, and the rate of filtration decreases as the membrane reaches its capacity (e.g., membrane pores become occluded). In a "static" (as opposed to "dynamic") filtration, the filter membrane remains stationary (does not move), and the flow (e.g., of the heterogeneous mixture) passes through the stationary filter membrane. These static filtration methods are common in the art and are simple and well-understood.

Unlike the static filtration methods commonly used in the art, the process herein describes a dynamic filtration module, wherein components of the dynamic filtration module move in a coordinated fashion (e.g., the membrane moves or advances in accordance with the flow rate of the entire process) to enable filtration to occur continuously across a fresh, unused target region of filter membrane. This eliminates membrane fouling or occlusion and permits control over the filter cake packing and thickness during operation.

The dynamic filtration module includes a filter membrane roll, a membrane support structure, at least one support rod or roller, a vacuum line, a vacuum system, and at least one vacuum collection vessel.

In embodiments, the filter membrane roll includes a filter roll, wherein the filter membrane, without intent to be limiting, comprises polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), hydrophilic PTFE, or any combination thereof.

The pore size of the rolled filter membrane depends on the biological product being purified. In examples, the rolled filter membrane has a pore size in the range from 0.1 µm to 1 µm. Alternatively, the pore size is in the range from about 0.2 µm to about 0.45 µm, or the pore size is less than about 0.45 µm. In other examples, when purifying an antibody, the pore size of the rolled filter membrane is in the range of 0.2 µm to about 0.45 µm.

The filter membrane roll has a width from about 10 mm to about 600 mm. The width of the filter membrane roll, for example, may depend on the size of the dynamic filtration system or the membrane support structure.

In embodiments, the filter membrane roll further functions as a feed reel that communicates with a collection reel, meaning the filter membrane originates from pre-fabricated roll and spans to an initially empty collecting roll, thus creating a reel-to-reel system. In aspects, the dynamic filtration module includes a rolled filter membrane extending between a feed reel and a collection reel, the filter membrane having an active target region that is configured to receive the heterogeneous mixture. In examples, the feed reel motion is governed by a Servo motor coupled with a gear box to limit rotations per minute (RPM) by a ratio of 200:1 to enable low membrane transport velocities with high torque. The collection reel motion is governed by a Servo motor coupled with a gear box to limit RPM by a ratio of 200:1 to enable low membrane transport velocities with high torque. Further, the feed reel motor and the collection reel motor are controlled by a closed-loop controller that operates a feedback mechanism to ensure consistent velocity with the constantly changing diameters of the filter membrane roll on both the feed reel and the collection reel during operation. In examples, the feed reel and the collection reel operate in the same direction with equivalent velocities.

In embodiments, the transport velocity of the filter membrane ranges from about 0.1 mm/sec to about 100 mm/sec, preferably from about 0.1 mm/sec to about 10 mm/sec.

The membrane support structure of the dynamic filtration module includes a mechanically smooth contact surface derived from a material having a low static coefficient of friction (e.g. PTFE) and an opening that has continuity with the vacuum line. As used herein, the "membrane support structure" refers to a fabricated component that provides structural support to the active region of the filter membrane, to prevent deformation, as it traverses an area of negative pressure, resulting from the opening having continuity with the vacuum line. Further, as used herein, "mechanically smooth contact surface" refers to a surface having a low static coefficient of friction, thus creating a low frictional force opposing transport of the filter membrane, especially when wetted. The mechanically smooth contact surface may influence the ease at which the filter membrane moves in a dynamic fashion. The mechanically smooth contact surface may also be measured in surface roughness, where the lower the value the smoother the surface. Moreover, since rougher surfaces have more friction between them than smoother surfaces, the mechanically smooth contact surface, as used herein, refers to a surface having lower friction (i.e., a low static coefficient of friction).

In embodiments, the membrane support structure of the dynamic filtration module includes an opening. The opening for example, may include a mesh, at least one slot, at least one hole, a frit, a porous material, or any combination thereof. For example, the opening may include a series of regularly or irregularly spaced elements (e.g., a mesh, at least one slot, at least one hole, or any combination thereof). Moreover, the opening may include regularly spaced elements, for example the opening may include a series of equally spaced, parallel slots. Additionally, the opening can include one grate (e.g., a series of regularly or irregularly spaced elements as described above). In other examples, the opening can include more than one grate, with each grate perpendicular. The opening can be a collection of irregular or regular elements (e.g., a series of parallel slots). The opening can also include a mesh, which are of split-thickness or of full-thickness and may or may not be in parallel rows. The elements of the opening (e.g., a mesh, at least one slot, at least one hole, a frit, a porous material, or any combination thereof) may be of any desired thickness. For example, without intent to be limiting, the opening may include a mesh with a thickness of about 0.25 mm to about 5 mm.

The membrane support structure of the dynamic filtration module includes a temperature control mechanism. The temperature control mechanism maintains a temperature from 4° C. to 37° C. in the presence of evaporative cooling. For example, during purification of an antibody, the temperature control mechanism maintains a temperature from 15° C. to 37° C. Exemplary temperature control mechanisms include, but are not limited to, single loop controllers, multi-loop controllers, closed loop controllers, PID controllers, Peltier devices, resistive heating elements, and/or thermal chucks with circulating water jackets.

In embodiments, the at least one support rod or roller of the dynamic filtration module has a mechanically smooth contact surface derived from a material having a low static coefficient of friction (e.g. PTFE, PFA). In examples, the dynamic filtration module includes at least one support rod or roller with a mechanically smooth contact surface to stabilize the motion of the filter membrane across the membrane support structure.

In embodiments, the dynamic filtration module includes at least one output head for modulating flow of the heterogeneous mixture and dispensing the heterogeneous mixture onto the active target region of the filter membrane. In examples, the at least one output head is a tube or a slot die.

In some embodiments, the dynamic filtration module further includes at least one additional input line to supply a wash buffer via a coaxial output head, a separate monoaxial output head, a separate slot die output head, or a slot die output head with multiple openings.

In some embodiments, the dynamic filtration module includes elements known in the coating and converting industry, for example, without intent to be limiting, active or passive edge guides, tension control (e.g. a dancer), break and tension detectors, or any combination thereof.

In embodiments, the dynamic filtration module includes a vacuum system having continuity with the membrane support structure to apply negative pressure across the active target region of the filter membrane, where the negative pressure allows for active transport of the filter membrane across the membrane support structure and enables collection of the filtrate containing the biological product. In examples, the vacuum system of the dynamic filtration module maintains a gauge pressure of about −0.05 bar to about −0.98 bar for continuous filtration.

In embodiments, the dynamic filtration module further includes at least one vacuum collection vessel configured to collect the filtrate, and at least one sensor or detector. In aspects described herein, during the purification by dynamic filtration, the filtrate comprising the biological product is fed under negative pressure into a vacuum collection vessel capable of collecting from about 50 mL to about 100 L. In examples, the vacuum collection vessel capable of collecting the filtrate is from about 1 L to about 10 L. In other examples, the vacuum collection vessel capable of collecting the filtrate is from about 1 L to about 50 L.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 µm) in fluid communication with at least one second dynamic filtration apparatus having a rolled filter membrane with a small pore size (e.g., 0.2 µm), thereby producing a filtrate comprising the biological product.

The process described herein includes continuously transferring the filtrate to a first module capable of separating the solution into two or more fractions including at least one fraction containing the biological product. For example, separating the solution into two or more fractions, may include at least one fraction containing the biological product, and the at least one other fraction containing small impurities. As described herein, the first module comprises an affinity-based TFF purification apparatus. The "affinity-based TFF purification apparatus" refers to a purification technique based on utilizing molecular, conformational binding interactions (e.g., ligand-receptor interactions) in which selective surface-immobilized ligands recognize and bind to the biological product to be purified with at least one tangential flow filtration system. In examples, the first module has at least one first inlet and at least one first outlet and is configured to permit continuous fluid flow between the first inlet and the first outlet.

In embodiments, the affinity-based TFF purification apparatus further includes a suspension of resin beads. The surface of the resin beads, for example, without intent to be limiting, is coupled with Protein A, Protein G, Protein L, an antigenic protein, a protein, a receptor, an antibody, or an aptamer. Continuous purification of biological products (e.g., a monoclonal antibody) with affinity resin beads can avoid the cumbersome processing steps of traditional affinity column chromatography (e.g., Protein A affinity chromatography).

In embodiments, the resin beads of the affinity-based TFF purification apparatus have a diameter of about 10 micron to about 200 micron. The diameter of the resin beads may depend on the biological product being purified and the flow rate of the process. Moreover, the resin beads may have a concentration ranging from 0.01% to 25% by weight. For example, the concentration of the resin beads may be about 1% to about 20% by weight. In other examples, the binding capacity of the resin beads is a function of the bead concentration, surface area-to-volume ratio, affinity ligand density, or any combination thereof. In yet other examples, the resin beads may be solid, porous, nanoporous, microporous, or any combination thereof.

The at least one tangential flow filtration system of the affinity-based TFF purification apparatus may refer to, for example, a tangential flow, high performance tangential flow, or cross-flow filtration system having flat plate or hollow fiber membrane filtration geometries. In some examples, the tangential flow filtration system comprises a hollow fiber membrane filter. In aspects, the hollow fiber membrane material is selected from PES, modified PES (mPES), or mixed cellulose ester (MCE). In some aspects, the hollow fiber membrane may be charged (e.g., positively or negatively) or uncharged. In other aspects, the pore size of the hollow fiber membrane is selected from the range of about 10 kDa to about 1 µm. In yet other aspects, the inner diameter of the hollow fiber membrane is selected from the range of about 0.5 mm to about 5 mm.

The process as described herein also includes continuously transferring the fraction containing the biological product from the at least one first outlet of the first module to a second module having at least one inlet for receiving flow from the at least one first outlet of the first module, and the second module comprises a charge-based TFF purification apparatus. The charge-based TFF purification apparatus" as used herein includes, for example, purifying biological molecules based on their surface charge, ionic character, electrostatic interactions, or isoelectric point with at least one tangential flow filtration system. As described herein, the charge-based TFF purification comprises a positive charge-based TFF purification apparatus, negative charge-based TFF purification apparatus, or combinations thereof. In examples, the second module has at least one second inlet and at least one second outlet and is configured to permit continuous fluid flow between the second inlet and the second outlet.

In embodiments, the charge-based TFF purification apparatus further includes a suspension of resin beads. The surface of the resin beads, for example, may comprise cationic or anionic functionality configured to selectively associate with said biological product at a specific pH and ionic strength to enable positive charge-based purification or negative charge-based purification, respectively. Continuous purification of biological products (e.g., a monoclonal antibody) with ionic resin beads can avoid the cumbersome processing steps of traditional ion-exchange column chromatographies (e.g., cation exchange or anion exchange chromatographies).

In embodiments, the resin beads of the charge-based TFF purification apparatus have a diameter of about 10 micron to about 200 micron. The diameter of the resin beads may depend on the biological product being purified and the flow rate of the process. Moreover, the resin beads may have a concentration ranging from 0.01% to 25% by weight. For example, the concentration of the resin beads may be about 1% to about 20% by weight. In other examples, the charge or electrostatic association capacity of the resin beads is a function of the bead concentration, surface area-to-volume ratio, surface charge density, net charge, or any combination thereof.

The at least one tangential flow filtration system of the charge-based TFF purification apparatus may refer to, for example, a tangential flow, high performance tangential flow, or cross-flow filtration system having flat plate or hollow fiber membrane filtration geometries. In some examples, the tangential flow filtration system comprises a hollow fiber membrane filter. In aspects, the hollow fiber membrane material is selected from PES, modified PES (mPES), or mixed cellulose ester (MCE). In some aspects, the hollow fiber membrane may be charged (e.g., positively or negatively) or uncharged. In other aspects, the pore size of the hollow fiber membrane is selected from the range of about 10 kDa to about 1 µm. In yet other aspects, the inner diameter of the hollow fiber membrane is selected from the range of about 0.5 mm to about 5 mm.

In embodiments described herein, the resin beads of one or both of the first (affinity-based TFF purification) and/or second (charged-based TFF purification) modules are recycled and re-used. For example, the beads may be re-used at least 2, 3, 4, or more times for purifying a biological product.

Alternatively, the process described herein includes continuously transferring the fraction containing the biological product from the at least one first outlet of the first module to a second module having at least one inlet for receiving flow from the at least one first outlet of the first module, and the second module comprises a free-flow electrophoresis apparatus. The free-flow electrophoresis apparatus having a fluidic channel created between two parallel plates, an electric field or electric field gradient orthogonal to the fluid flow direction, and an aqueous ionic solution, may be used in lieu of or in addition to the charge-based, magnetic purification module(s) to purify the biological product (e.g., a monoclonal antibody).

In examples, the solution contacting surfaces of the two parallel plates comprise glass, ceramic, plastic, or any combination thereof. In some examples, the aqueous ionic solution may give rise to a pH gradient. In other examples, the aqueous ionic solution may confer constant pH.

In embodiments, the free-flow electrophoresis apparatus has at least one fluidic device comprising a fluidic channel created between two parallel plates, an electric field or electric field gradient orthogonal to the fluid flow direction, and a pH gradient. In examples, the isoelectric point-based, fluidic purification module includes at least one first fluidic device comprising a fluidic channel created between two parallel plates, an electric field or electric field gradient orthogonal to the fluid flow direction, and a coarse pH gradient across the main separation channel (in examples, a coarse pH gradient may be a pH range from about 2 to about 10); and at least one second fluidic device comprising a fluidic channel created between two parallel plates, an electric field or electric field gradient orthogonal to the fluid flow direction, and a fine pH gradient across the main separation channel (in examples, a fine pH gradient may be a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In other embodiments, the free-flow electrophoresis apparatus has at least one fluidic device comprising a fluidic channel created between two parallel plates, an electric field or electric field gradient orthogonal to the fluid flow direction, and no pH gradient to operate in a zone electrophoresis or charge separating mode of operation. In examples, the isoelectric point-based, fluidic purification module includes at least one first fluidic device comprising a fluidic channel created between two parallel plates, an electric field or electric field gradient orthogonal to the fluid flow direction, and constant basic pH (e.g., a pH of greater than 7); and at least one second fluidic device comprising a fluidic channel created between two parallel plates, an electric field or electric field gradient orthogonal to the fluid flow direction, and a constant acidic pH (e.g., a pH of less than 7).

In other embodiments, the free-flow electrophoresis apparatus has at least one fluidic device comprising a fluidic channel created between two parallel plates, an electric field or electric field gradient orthogonal to the fluid flow direction, and both an acidic pH gradient and a basic pH gradient separated by a spacer solution (e.g. NaCl solution) to operate in an isotachophoresis mode of operation.

In other embodiments, the isoelectric point-based, fluidic purification module includes at least one first free-flow electrophoresis apparatus comprising a fluidic channel created between two parallel plates and an electric field or electric field gradient orthogonal to the fluid flow direction, and at least one second free-flow electrophoresis apparatus comprising a fluidic channel created between two parallel plates and an electric field or electric field gradient orthogonal to the fluid flow direction, wherein each device connected in series and is capable of operating in an independent mode of operation to enable purification. For example, the at least one first free-flow electrophoresis apparatus may operate in an isoelectric focusing mode and the at least one second free-flow electrophoresis apparatus may operate in an isotachophoresis mode to increase separation resolution.

In other embodiments, the isoelectric point-based, fluidic purification module includes at least one first fluidic device comprising fluidic channel having at least one dielectrophoretic electrode capable of inducing a defined, unidirectional force; at least one second free-flow electrophoresis apparatus comprising a fluidic channel created between two parallel plates, an electric field or electric field gradient orthogonal to the fluid flow direction, and a coarse pH gradient across the main separation channel (e.g., a pH range from about 2 to about 10); and at least one third free-flow electrophoresis apparatus comprising a fluidic channel created between two parallel plates, an electric field or electric field gradient orthogonal to the fluid flow direction, and a fine pH gradient across the main separation channel (e.g., a pH range from about 5 to about 8). In examples, additional, subsequent fluidic devices or chips comprising a fluidic channel created between two parallel plates and an electric field or electric field gradient orthogonal to the fluid flow direction may be used to enable further refining of the pH gradient across the main separation channel (e.g., a pH range from about 7.1 to about 7.6).

In embodiments, the isoelectric point-based fluidic purification apparatus further comprises at least two electrodes (e.g. platinum wire electrodes) to function as an anode or a cathode.

In embodiments, the backpressure within the isoelectric point-based fluidic purification apparatus is dependent on the channel geometry and dimensions, the inlet and outlet opening and/or tubing diameters, and the input flow rate. In examples, the backpressure ranges from about 0.5 psi to about 10 psi. In some examples, the backpressure is controlled by, for example, without intent to be limiting, a needle valve.

In embodiments, the isoelectric point-based fluidic purification apparatus further comprises at least one de-bubbler system to continuously remove $O_2$ and $H_2$ gas bubbles that evolve in the electrode channels under applied voltage. In some embodiments, removal of electrolysis bubbles is essential to enable continuous operation for substantially long periods of time. In examples, the de-bubbler system utilizes a hydrophobic PTFE membrane to create a watertight seal atop the electrode channel that permits continuous removal of electrolysis bubbles at the point of generation by exposure to a vacuum system. In examples, the vacuum gauge pressure ranges from about −0.05 bar to about −0.4 bar.

In embodiments, the isoelectric point-based fluidic purification apparatus further comprises an active cooling system or heat sink (e.g., a Peltier device, a thermal chuck with a circulating water/propylene glycol jacket) to enable temperature control and Joule heat dissipation. For example, the active cooling system may control cooling and/or heat dissipation in the range from about 4° C. to about 50° C., preferably from 4° C. to about 37° C. Ideally, when isolating a biological product (e.g., a monoclonal antibody), the temperature is maintained at about 10° C. to about 25° C. In examples, the active cooling system comprises an aluminum thermal chuck containing a chilled, circulating water/propylene glycol jacket.

In embodiments, the isoelectric point-based, fluidic purification module includes at least one buffer or ampholyte system.

In embodiments, the isoelectric point-based, fluidic purification module includes at least one electrode solution. In some embodiments, the at least one electrode solution comprises an electrolyte solution configured to contact and enable the appropriate function of an anode or a cathode, for example, phosphoric acid and sodium hydroxide, respectively. In other embodiments, the at least one electrode solution comprises at least one ampholyte solution configured to contact and enable the appropriate function of an anode or a cathode, for example, Tris buffered saline flowing through the main separation channel, the anode channel, and the cathode channel.

In embodiments, the isoelectric point-based, fluidic purification module includes at least one sensor or detector. In examples, the at least one sensor or detector is positioned in-line. In some examples, the at least one sensor or detector includes, but is not limited to, a flow sensor, a temperature sensor, a conductivity sensor, a pH sensor, a refractive index detector, a UV detector, or a backpressure sensor.

In embodiments, the isoelectric point-based, fluidic purification module includes at least one liquid circuit breaker or disconnect downstream of the device and upstream of the at least one in-line sensor or detector to ensure the ability to perform sensing or detection in a voltage-free solution.

The presently claimed process provides for a number of advantages over current downstream methods and processes for purifying a biological product, for example, a protein or fragment thereof (a polypeptide), an antibody or fragment thereof, a cytokine, a chemokine, an enzyme, or a growth factor. For example, without intent to be limiting, the process described herein provides a continuous bioprocess for purifying a monoclonal antibody that maintains throughput and yield, while significantly decreasing the production facility footprint, the time required for facility buildout and validation, the costs associated with facility buildout, and capital equipment expenditure, when compared to the traditional approaches of batch, single-use, or semi-continuous monoclonal antibody manufacturing. The continuous bioprocessing as described herein affords smaller, more streamlined equipment (e.g., smaller bioreactor volumes and downstream bioprocess equipment) because the ability to operate continuously eliminates the need for the large process equipment required for the centrifugation, depth filtration, and column chromatography steps of traditional downstream bioprocessing, whose size is dictated by large bioreactor volumes. Further, the smaller, more streamlined equipment operating continuously affords the use of significantly smaller bioreactor(s) that produce monoclonal antibodies at steady-state. The continuous bioprocess as described herein may also significantly decrease operating expenditures, overall bioprocess line downtime, and biological product loss when compared to traditional monoclonal antibody manufacturing approaches. Finally, the process described herein for purifying a biological product is conducted in a system with a footprint that occupies significantly less square footage than current techniques, without sacrificing product throughput or yield on a kilograms/year basis.

Advantages of the process and methods described herein include the ability to remove large impurities (e.g., cells, cell debris, and aggregates) without membrane fouling or occlusion. For example, it is known in the art that clarification of cells, cell debris and aggregates from cell culture media with traditional filtration or tangential flow filtration systems typically leads to fouling or occlusion of the filter membrane, thus rendering these methodologies unsuitable as a means to continuously remove large impurities from a heterogeneous mixture containing a biological product over long-term continuous processing. In contrast, the dynamic filtration apparatus described herein enables continuous removal of large impurities from a heterogeneous mixture containing a biological product without membrane fouling, as the active target region of the filter membrane is constantly being refreshed. Additionally, because the entire process of producing and purifying the biological product may be continuous and can maintain a flow rate that ranges from about 0.1 mL/minute to about 50 mL/minute across the entirety of the process, the process equipment and overall process footprint is able to have a significantly smaller footprint than current standard processes, without sacrificing product throughput or yield on a kilogram/year basis. For example, the process for producing and purifying a monoclonal antibody as described herein is operated with a footprint that occupies up to about 30,000 square feet. In contrast, current mononclonal antibody production and downsteam processes require at least 200,000 square feet. In examples, the process of purifying the biological product has a flow rate that ranges from about 1 mL/minute to about 10 mL/minute. In some examples, the flow rate of the step of continuously removing large impurities from the heterogeneous mixture ranges from about 0.1 mL/minute to about 50 mL/minute. In other examples, the flow rate of the step of continuously removing large impurities from the heterogeneous mixture is equivalent to the flow rate from the bioreactor bleed line. In other examples, the process provides that the flow rate of the step of continuously transferring the filtrate to a first module ranges from about 0.1 mL/minute to about 50 mL/minute. In yet other examples, the process provides that the flow rate of the step of continuously transferring the fraction containing the biological product from the first outlet to a second module ranges from about 0.1 mL/minute to about 50 mL/minute.

An important advantage of the process and methods utilizing resin beads (e.g. agarose) described herein includes that these systems do not require traditional stationary phase or packed resin columns (e.g., for standard chromatographies) to be sanitized, recycled and/or regenerated. For example, these systems provide for recycling and/or regeneration of the resin beads to create a limitless surface area of the resin beads during operation, and in turn provides a continuous and cost-effective method. Put in another way, the modules described herein do not have a fixed binding or association capacity. In specific examples, the resin beads used during purification of the biological product, as described herein, are constantly being recycled and regenerated, and therefore able to accept flow from the previous step, either a dynamic filtration module or a purification module, without interruption of the flow from the bioreactor bleed line. Put another way, the modules described in the present invention do not have to be left idle in order to be sanitized, regenerated and/or recycled after running, as they are continuously undergoing these steps. The method differs from current continuous chromatographic methods, in that current column chromatography methods have defined column capacity limitations due to resin packing constraints and thus require column switching of multiple packed columns to accept continuous input flow and enable regeneration and/or recycling of the columns that have reached full capacity. Another advantage of the methods described herein includes the that the resin beads are not packed into a stationary phase, rather the resin beads have mobility. This increases the surface area of the resin beads that is available for binding or association, as substantially more of the resin bead surface is exposed and free to bind. Additionally, the resin beads in a packed column are exposed to a high pressure differential in order to generate flow through the column and damage from which is one of the reasons for less than desired column lifetime. The mobile resin beads in the presently described invention are subjected to substantially lower pressures which is much gentler on the fragile beads, resulting in longer lifetimes. Additionally, this mobility makes the resin beads more likely to be completed regenerated and returned to their initial condition. This further adds to the cost-effectiveness of the methods described herein, as the resin is utilized more efficiently.

An important advantage of the process and methods utilizing free-flow electrophoresis described herein includes that this system represents a "no product loss" process, in that, there is no need for the product to interact with a resin or other purifying moieties, as the separation occurs in aqueous solution according to the physicochemical properties of the target biological product via interaction with an electric field. Another advantage is observed in the resolving power of this approach, as a theoretically higher purity product is achievable when compared to traditional ion-exchange chromatographies. Additionally, the separation based on intrinsic physicochemical properties extends the utility of this approach for the purification a plethora of biological products, including, but not limited to, a protein or fragment thereof (a polypeptide), an antibody or fragment thereof, a cytokine, a chemokine, an enzyme, a growth factor, an oligonucleotide, a virus, an adenovirus, an adeno-associated virus (AAV), or a lentivirus.

Further, the modular approach affords flexibility in process design to accommodate a diverse range of biological products.

Dynamic Filtration Module

Provided herein is a dynamic filtration module for continuously removing large impurities from a biological product in a heterogeneous mixture, for example, a filtrate containing a biological product is generated by removing cell, cells debris, and aggregates from a heterogeneous mixture derived from a bioreactor operating at steady-state (FIGS. 6A-6B and 7A-7B). Unlike the static filtration methods commonly used in the art, the components of the dynamic filtration module move in a coordinated fashion (e.g., the membrane moves or advances in accordance with the flow rate of the entire process) to enable filtration to occur continuously across a fresh, unused target region of filter membrane. This eliminates membrane fouling or occlusion and permits control over the filter cake packing and thickness during operation.

The dynamic filtration module includes a filter membrane roll, a membrane support structure, at least one support rod or roller, at least one vacuum line, a vacuum system, and at least one vacuum collection vessel. As shown in FIGS. 6A-6B and 7A-7B, the feed reel comprises a filter membrane that is disposed on a filter membrane roll, wherein the filter membrane, supported by two mechanically smooth support rods, passes over the mechanically smooth membrane support structure, which includes an opening. As the heterogeneous mixture is delivered from the output head to the active target region of the filter membrane, the filter membrane continues to move and advance the filter membrane toward the collection reel, while a vacuum line, in continuity with the opening of the membrane support structure, maintains a negative pressure, allowing separation and removal of the cells, cell debris, and aggregates, thus creating a filtrate containing the biological product.

The dynamic filtration module enables removal of large impurities (e.g., cells, cell debris, and aggregates), from the heterogeneous mixture to yield a filtrate containing the biological product and associated small impurities (e.g., host cell proteins, undesired proteins and peptides, undesired antibodies, undesired nucleic acids and oligonucleotides, viruses, undesired nucleic acids or oligonucleotides, salts, buffer components, surfactants, sugars, metallic contaminants, leachables, media components, and/or naturally-occurring organic molecules with which it is naturally associated) without centrifugation, depth filtration, static filtration, or any combination thereof.

The dynamic filtration module described herein provides for a small footprint and requires appropriate materials selection for tubing, connectors, the membrane support structure, and the filter membrane (e.g., polymer type, pore size) to enable filtration with high yield, low protein binding, and minimal solution contact and residence times.

The dynamic filtration module includes a rolled filter membrane extending between a feed reel and a collection reel, wherein the filter membrane has an active target region that is configured to receive the heterogeneous mixture. In examples, the filter membrane of the filter membrane roll is made of a suitable material, including, but not limited to, polyethersulfone (PES), hydrophilic polysulfone, cellulose ester, cellulose acetate, polyvinylidene fluoride (PVDF), hydrophilic PVDF, polycarbonate, nylon, polytetrafluoroethylene (PTFE), or hydrophilic PTFE.

In embodiments, the pore size of the rolled filter membrane depends on the biological product being purified. In examples, the rolled filter membrane has a pore size in the range from 0.1 µm to 1 µm. Alternatively, the pore size is in the range from about 0.2 µm to about 0.45 µm, or the pore size is less than about 0.45 µm. In other examples, when purifying an antibody, the pore size of the rolled filter membrane is in the range of 0.2 µm to about 0.45 µm.

In embodiments, the filter membrane roll has a width from about 10 mm to about 600 mm. The width of the filter membrane roll, for example, may depend on factors such as the size of the dynamic filtration system and the size of the membrane support structure.

In embodiments, the filter membrane roll further functions as a feed reel that communicates with a collection reel, meaning the filter membrane originates from pre-fabricated roll and spans to an initially empty collecting roll, thus creating a reel-to-reel system. In operation, the heterogeneous mixture is continuously applied from the output head to a fresh, unused region of the filter membrane (also referred to herein as the active target region) created by the transport of the filter membrane as it is moved at an appropriate rate from the feed reel to the collection reel, thus collecting the used portions of filter membrane. In examples, the feed reel motion is governed by a Servo motor coupled with a gear box to limit rotations per minute (RPM) by a ratio of 200:1 to enable low membrane transport velocities with high torque. The collection reel motion is governed by a Servo motor coupled with a gear box to limit RPM by a ratio of 200:1 to enable low membrane transport velocities with high torque. Further, the feed reel motor and the collection reel motor are controlled by a closed-loop controller that operates a feedback mechanism to ensure consistent velocity with the constantly changing diameters of the filter membrane roll on both the feed reel and the collection reel during operation. In examples, the feed reel and the collection reel operate in the same direction with equivalent velocities. Other methods of filter membrane transport from the feed reel to the collection reel can be contemplated by those of skill in the art of the coating and converting industry.

In embodiments, the filter membrane transport velocity within the dynamic filtration module is selected to enable high flow rates (high throughput), while maintaining high yield (recovery). In examples, the transport velocity of the filter membrane ranges from about 0.1 mm/sec to about 100 mm/sec, preferably from about 0.1 mm/sec to about 10 mm/sec.

Additionally, the dynamic filtration module includes a membrane support structure (FIG. 8) to support the active target region of the filter membrane as it experiences negative pressure. The membrane support structure is positioned between the feed reel and the collection reel, has a mechanically smooth contact surface derived from a material having a low static coefficient of friction (e.g. PTFE), and has an opening that has continuity with the vacuum line. For example, as used herein, "mechanically smooth contact surface" refers to a surface having a low static coefficient of friction, thus creating a low frictional force opposing transport of the filter membrane, especially when wetted. The mechanically smooth contact surface may influence the ease at which the filter membrane moves in a dynamic fashion. The mechanically smooth contact surface may also be measured in surface roughness, where the lower the value the smoother the surface. Moreover, since rougher surfaces have more friction between them than smoother surfaces, the mechanically smooth contact surface, as used herein, refers to a surface having lower friction (i.e., a low static coefficient of friction).

In embodiments, the membrane support structure of the dynamic filtration module includes an opening. The opening for example, may include a mesh, at least one slot, at least one hole, a frit, a porous material, or any combination thereof. For example, the opening may include a series of regularly or irregularly spaced elements (e.g., a mesh, at least one slot, at least one hole, or any combinations thereof). Moreover, the opening may include regularly spaced elements, for example the opening may include a series of equally spaced, parallel slots. Additionally, the opening can include one grate (e.g., a series of regularly or irregularly spaced elements as described above). In other examples, the opening can include more than one grate, with each grate perpendicular. The opening can be a collection of irregular or regular elements (e.g., a series of parallel slots). The opening can also include a mesh, which are of split-thickness or of full-thickness and may or may not be in parallel rows. The elements of the opening (e.g., a mesh, at least one slot, at least one hole, a frit, a porous material, or any combinations thereof) may be of any desired thickness. For example, without intent to be limiting, the opening may include a mesh with a thickness of about 0.25 mm to about 5 mm.

Additionally, temperature control of the membrane support structure and its connection to the at least one vacuum collection vessel to counteract evaporative cooling is also provided, which avoids clogging, fouling, solution freezing, changes in solution viscosity, and denaturation (or precipitation) of the biological product (e.g., a protein or fragment thereof (a polypeptide), an antibody or fragment thereof, a cytokine, a chemokine, an enzyme, or a growth factor). The temperature control mechanism maintains a temperature from about 4° C. to about 37° C. For example, during purification of an antibody, the temperature control mechanism maintains a temperature from about 15° C. to about 37° C. Exemplary temperature control mechanisms include, but are not limited to, single loop controllers, multi-loop controllers, closed loop controllers, PID controllers, Peltier devices, resistive heating elements, and/or thermal chucks with circulating water jackets.

In embodiments, the at least one support rod or roller of the dynamic filtration module has a mechanically smooth contact surface derived from a material having a low static coefficient of friction (e.g. PTFE, PFA). For example, as used herein, "mechanically smooth contact surface" refers to a surface having a low static coefficient of friction, the creating a low frictional force opposing transport of the filter membrane. The mechanically smooth contact surface may influence the ease at which the filter membrane moves in a dynamic fashion. The mechanically smooth contact surface may also be measured in surface roughness, where the lower the value the smoother the surface. Moreover, since rougher surfaces have more friction between them than smoother surfaces, the mechanically smooth contact surface, as used herein, refers to a surface having lower friction (i.e., a low static coefficient of friction). Alternatively, the at least one support rod may further include a bearing, for example, a sleeve bearing with a mechanically smooth contact surface to reduce friction and tension on the filter membrane. Additionally, the at least one support rod or roller having a mechanically smooth contact surface may rotate to reduce and tension on the filter membrane.

In embodiments, the dynamic filtration module includes at least one output head for modulating flow of the heterogeneous mixture and dispensing the heterogeneous mixture onto the active target region of the filter membrane. In examples, the at least one output head is a tube or a slot die.

Within the dynamic filtration module, the input flow rate matches the bleed rate of the bioreactor operating at steady-state, wherein said bleed rate confers reasonably high throughput (e.g., consistent with or greater than traditional biopharmaceutical manufacturing throughput on a kilogram/year basis). In specific examples, multiple heads may be used to manage flow rate, as well as xy rastering or rθ rastering heads, with or without motion along the z-axis.

The dynamic filtration module incorporates the negative pressure of a vacuum system, which as described herein, the pressure value may be selected to enable efficient filtration, while maintaining desired filter membrane transport mobility to achieve high throughput and yield. In embodiments, the vacuum system of the dynamic filtration module maintains a gauge pressure of about −0.05 bar to about −0.98 bar for continuous filtration.

In some embodiments, a wash zone is provided in addition and subsequent to the feed zone (e.g., the bioreactor bleed solution input line and output head dispensing area or filter membrane active target region). The wash zone comprises a wash buffer that is supplied from an additional input line via a coaxial output head, a separate monoaxial output head, a separate slot die output head, or a slot die output head with multiple opening.

In some embodiments, the dynamic filtration module includes elements known in the coating and converting industry, for example, without intent to be limiting, active or passive edge guides, tension control (e.g. a dancer), break and tension detectors, or any combination thereof.

In embodiments, the process of continuously removing large impurities (e.g., cells, cell debris, and aggregates) from the heterogeneous mixture by dynamic filtration comprises a multiple stage filtration with at least two discrete rolled filter membranes with different pore sizes. In examples, this multiple stage dynamic filtration process includes at least one first dynamic filtration apparatus having a rolled filter membrane with a large pore size (e.g., 0.45 μm) in fluid communication with at least one second dynamic filtration apparatus having a rolled filter membrane with a small pore size (e.g., 0.2 μm), thereby producing a filtrate comprising the biological product.

As described herein, the dynamic filtration module provides for yields of biological product that are comparable or higher than standard purification (centrifugation) processes on a kilogram/year basis. The dynamic filtration module also allows for the ability to feed the next step from the at least one vacuum collection vessel that may be under negative pressure or allowed to equilibrate to atmospheric pressure. Materials incorporated and selected for the dynamic filtration module include connectors, tubing, filter membrane, membrane support structure, vacuum collection vessel(s), all of which, alone or in combination, minimize friction and yield loss due to protein adsorption and are known by those skilled in the art.

Unlike the static filtration methods commonly used in the art, the components of the dynamic filtration module move in a coordinated fashion (e.g., the membrane moves or advances in accordance with the flow rate of the heterogeneous mixture from the input line) to enable continuous, unimpeded and unfouled filtration.

Affinity-Based, Magnetic Purification Module Having a Loop Conveyor System

Provided herein is an affinity-based, magnetic purification module for separating a heterogeneous mixture into two or more fractions, at least one fraction containing a biological product. The module includes at least one inlet and at least one outlet configured to permit continuous fluid flow between the at least one inlet and the at least one outlet and wherein the flow rate may be, for example, consistent and constant during steady-state operation. Moreover, the affinity-based, magnetic purification module includes a suspension of affinity magnetic resin beads, wherein the magnetic resin bead surface, without intent to be limiting, is coupled to Protein A, Protein G, Protein L, an antigenic protein, a protein, a receptor, an antibody, or an aptamer configured to selectively bind said biological product.

The affinity-based, magnetic purification module includes a loop conveyor system comprising at least two transport vessels charged with affinity magnetic resin beads that are configured to continuously receive a heterogeneous mixture containing a biological product and subsequently transport the resulting heterogeneous mixture containing a biological product, affinity magnetic resin beads, a buffer, or any combination thereof; at least one external magnetic field to attract, and thus separate, said magnetic resin beads from the heterogeneous mixture to enable washing; at least one external magnetic field to attract, and thus separate, said magnetic resin beads from the heterogeneous mixture to enable elution of said biological product; at least one external magnetic field to enable recycling of said magnetic resin beads; at least one binding/wash buffer system; at least one low pH elution buffer system; at least one magnetic resin bead regeneration buffer system; at least one aspirator system to remove waste solution from the at least two transport vessels; at least one collection vessel; at least one sensor or detector; and at least one fluid handling pump.

Figure 14:
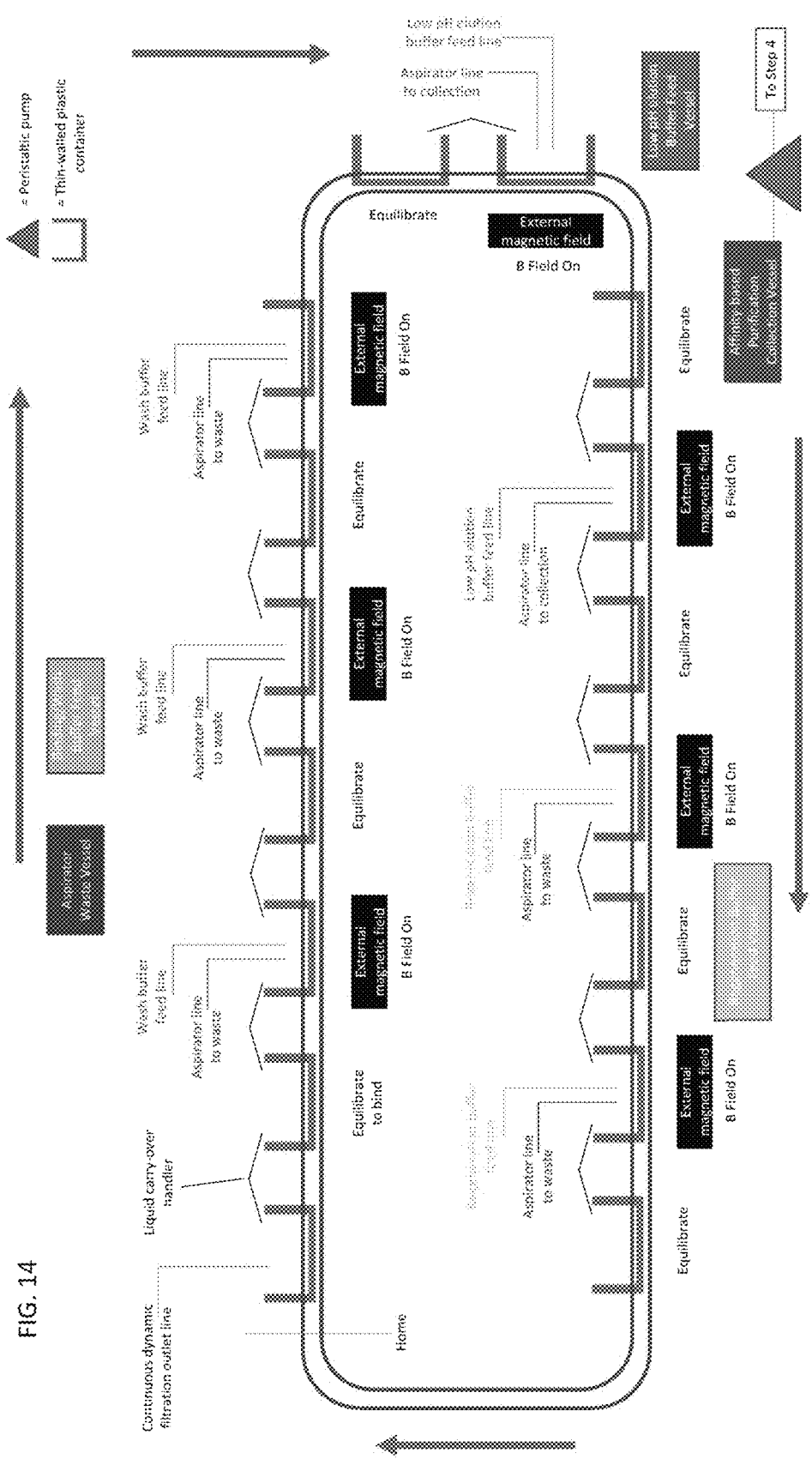
FIG. 14 shows an exemplary design schematic of an affinity-based, magnetic purification apparatus comprising a loop conveyor system and at least one magnetic field that is permanently "on".
Figure 15:
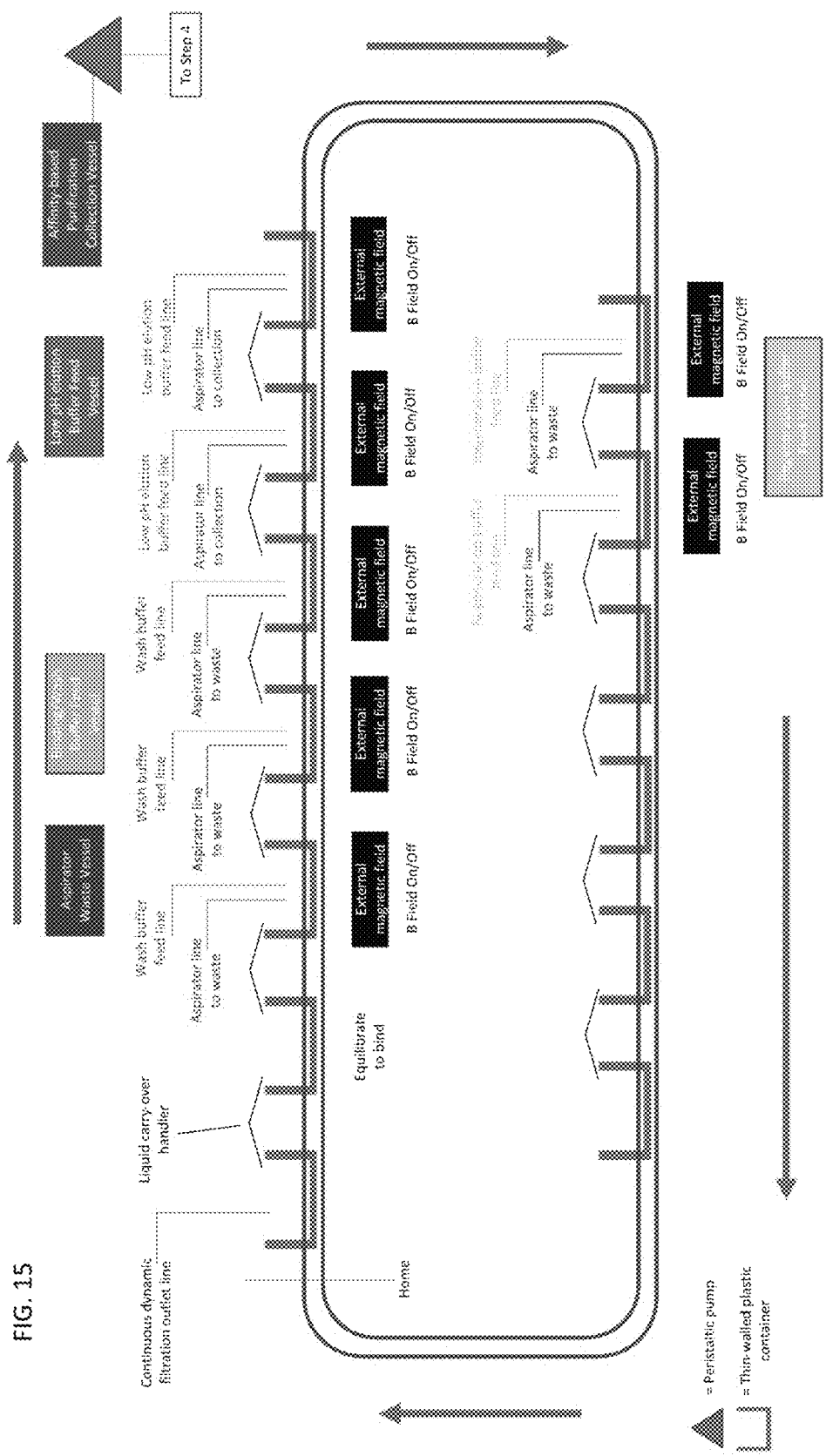
FIG. 15 shows an exemplary design schematic of an affinity-based, magnetic purification apparatus comprising a loop conveyor system and at least one magnetic field capable of "on/off" toggling.

The equipment design of the affinity-based, magnetic purification module (FIGS. 14-15) enables for automated and continuous, biological magnetic purification, as compared to a batch process or a semi-continuous process and provides for a small footprint.

The magnetic field strength and field effect are dependent on the transport vessel wall thickness and material type, proximity to the wall of the transport vessel on a loop conveyor track, magnetic resin bead size, concentration, saturation magnetization, and magnetic susceptibility, and solution viscosity. In embodiments, the magnetic field strength ranges from about 0.01 Tesla to about 1 Tesla (e.g., up to about 1 Tesla). In examples, the magnetic field is generated by a permanent magnet (e.g., a Neodymium magnet). The permanent magnet may be positioned within 5 mm, or preferably within 1 mm of the vessel wall. In other examples, the magnetic field is generated by an electromagnet. In yet other examples, mixing of the magnetic resin beads may be accomplished by placing the at least one transport vessel between two separate and opposing magnetic fields that toggle between states of on and off.

As described herein, the affinity-based, magnetic purification module includes a suspension of magnetic resin beads, in which the concentration depends on the desired binding capacity or the desired solution viscosity. Alternatively, the affinity-based, magnetic purification module magnetic resin bead size is micron to sub-micron and is dependent on the binding capacity needs, which is a function of the surface area-to-volume ratio required to enable adequate fluid dynamics for equilibration and affinity interactions, for example, solution viscosity dependency and surface ligand density dependency, respectively.

The transport vessel number and size depends on input flow rate, magnetic resin bead binding capacity, and binding equilibration time. The transport vessel material and wall thickness are dependent on the strength and close proximity of the magnetic field.

The material selection for the magnetic resin beads of the affinity-based, magnetic purification module is important for negligible leachables and to provide for robust stability to enable recycling and reuse. The magnetic resin beads may be solid, porous, nanoporous, microporous, or any combination thereof.

The binding/wash buffer is dependent on the biological product (e.g., monoclonal antibody) of interest and small impurities to be removed. Other considerations for the binding/wash buffer including pH, ionic strength, use of surfactants, and use of organic and/or inorganic salts are also contemplated in the binding/wash buffer. Moreover, additional transport vessels and replicate conveyor track positions may also be required to effectively wash.

The elution buffer is dependent on the binding affinity (e.g., strength of the non-covalent interactions) between the magnetic resin bead surface ligands and the biological product (e.g., monoclonal antibody) of interest. For example, the elution buffer may vary pH, ionic strength, use of surfactants, use of organic and/or inorganic salts, use of multiple elution buffer compositions (e.g., to increase yield, and which might require additional transport vessels and replicate conveyor track positions). Moreover, additional transport vessels and replicate conveyor track positions may also be required to effectively elute.

The dwell time for each stage in conveyor track progression is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The affinity-based, magnetic purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the affinity-based, magnetic purification module utilizes a mobile affinity resin capable of in situ regeneration and recycling to enable more efficient use of the resin and to enable continuous processing in a small-footprint without concerns of traditional column capacity limitations.

Affinity-Based, Magnetic Purification Module Having a Pick and Place Robotics System Provided herein is an affinity-based, magnetic purification module for separating a mixture into two or more fractions, at least one fraction containing a biological product. The module includes at least one inlet and at least one outlet configured to permit continuous fluid flow between the at least one inlet and the at least one outlet and wherein the flow rate may be, for example, consistent and constant during steady-state operation. Moreover, the affinity-based, magnetic purification module includes a suspension of affinity magnetic resin beads, wherein the magnetic resin bead surface, without intent to be limiting, is coupled to Protein A, Protein G, Protein L, an antigenic protein, a protein, a receptor, an antibody, or an aptamer configured to selectively bind said biological product.

The affinity-based, magnetic purification module includes a pick and place robotics system comprising at least two transport vessels charged with affinity magnetic resin beads that are configured to continuously receive a mixture containing a biological product and subsequently transport the resulting heterogeneous mixture containing a biological product, affinity magnetic resin beads, a buffer, or any combination thereof; at least one external magnetic field to attract, and thus separate, said magnetic resin beads from the heterogeneous mixture to enable washing; at least one external magnetic field to attract, and thus separate, said magnetic resin beads from the heterogeneous mixture to enable elution of said biological product; at least one external magnetic field to enable recycling of said magnetic resin beads; at least one binding/wash buffer system; at least one low pH elution buffer system; at least one magnetic resin bead regeneration buffer system; at least one aspirator system to remove waste solution from the at least two transport vessels; at least one collection vessel; at least one sensor or detector; and at least one fluid handling pump.

The equipment design of the affinity-based, magnetic purification module (FIG. 18) enables for automated and continuous, biological magnetic purification, as compared to a batch process or a semi-continuous process and provides for a small footprint.

The magnetic field strength and field effect are dependent on the transport vessel wall thickness and material type, proximity to the wall of the placed transport vessel, magnetic resin bead size, concentration, saturation magnetization, and magnetic susceptibility, and solution viscosity. In embodiments, the magnetic field strength ranges from about 0.01 Tesla to about 1 Tesla (e.g., up to about 1 Tesla). In examples, the magnetic field is generated by a permanent magnet (e.g., a Neodymium magnet). The permanent magnet may be positioned within 5 mm, or preferably within 1 mm of the vessel wall. In other examples, the magnetic field is generated by an electromagnet. In yet other examples, mixing of the magnetic resin beads may be accomplished by placing the at least one transport vessel between two separate and opposing magnetic fields that toggle between states of on and off.

As described herein, the affinity-based, magnetic purification module includes a suspension of magnetic resin beads, in which the concentration depends on the desired binding capacity or the desired solution viscosity. Alternatively, the affinity-based, magnetic purification module magnetic resin bead size is micron to sub-micron and is dependent on the binding capacity needs, which is a function of the surface area-to-volume ratio required to enable adequate fluid dynamics for equilibration and affinity interactions, for example, solution viscosity dependency and surface ligand density dependency, respectively.

The transport vessel number and size depends on input flow rate, magnetic resin bead binding capacity, and binding equilibration time. The transport vessel material and wall thickness are dependent on the strength and close proximity of the magnetic field.

The material selection for the magnetic resin beads of the affinity-based, magnetic purification module is important for negligible leachables and to provide for robust stability to enable recycling and reuse. The magnetic resin beads may be solid, porous, nanoporous, microporous, or any combination thereof.

The binding/wash buffer is dependent on the biological product (e.g., monoclonal antibody) of interest and small impurities to be removed. Other considerations for the binding/wash buffer including pH, ionic strength, use of surfactants, and use of organic and/or inorganic salts are also contemplated in the binding/wash buffer. Moreover, additional transport vessels and replicate pick and place positions may also be required to effectively wash.

The elution buffer is dependent on the binding affinity (e.g., strength of the non-covalent interactions) between the magnetic resin bead surface ligands and the biological product (e.g., monoclonal antibody) of interest. For example, the elution buffer may vary pH, ionic strength, use of surfactants, use of organic and/or inorganic salts, use of multiple elution buffer compositions (e.g., to increase yield, and which might require additional transport vessels and replicate conveyor track positions). Moreover, additional transport vessels and replicate pick and place positions may also be required to effectively elute.

The dwell time for each stage in the progression of the transport vessel through the pick and place process is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The affinity-based, purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the affinity-based, magnetic purification module utilizes a mobile affinity resin capable of in situ regeneration and recycling to enable more efficient use of the resin and to enable continuous processing in a small-footprint without concerns of traditional column capacity limitations.

Positive Charge-Based, Magnetic Purification Module Having a Loop Conveyor System As described herein, a positive charge-based, magnetic purification module for separating a mixture into two or more fractions, at least one fraction containing a biological product is included. The positive charge-based, magnetic purification module includes at least one inlet and at least one outlet configured to permit continuous fluid flow between the at least one inlet and the at least one outlet and wherein the flow rate may be, for example, consistent and constant during steady-state operation. Moreover, the positive charge-based, magnetic purification module includes a suspension of cationic magnetic resin beads, wherein the magnetic resin bead surface comprises cationic functionality configured to selectively associate with said biological product at a specific pH and ionic strength.

The positive charge-based, magnetic purification module includes a loop conveyor system comprising at least two transport vessels charged with cationic magnetic resin beads that are configured to continuously receive a mixture containing a biological product and subsequently transport the resulting heterogeneous mixture containing a biological product, cationic magnetic resin beads, a buffer, or any combination thereof; at least one external magnetic field to attract, and thus separate, said magnetic resin beads from the heterogeneous mixture to enable washing; at least one external magnetic field to attract, and thus separate, said magnetic resin beads from the heterogeneous mixture to enable dissociation of said biological product; at least one external magnetic field to enable recycling of said magnetic resin beads; at least one association/wash buffer system, at least one dissociation buffer system; at least one magnetic resin bead regeneration buffer system; at least one aspirator system to remove waste solution from the at least two transport vessels; at least one collection vessel; at least one sensor or detector; and at least one fluid handling pump.

Figure 16:
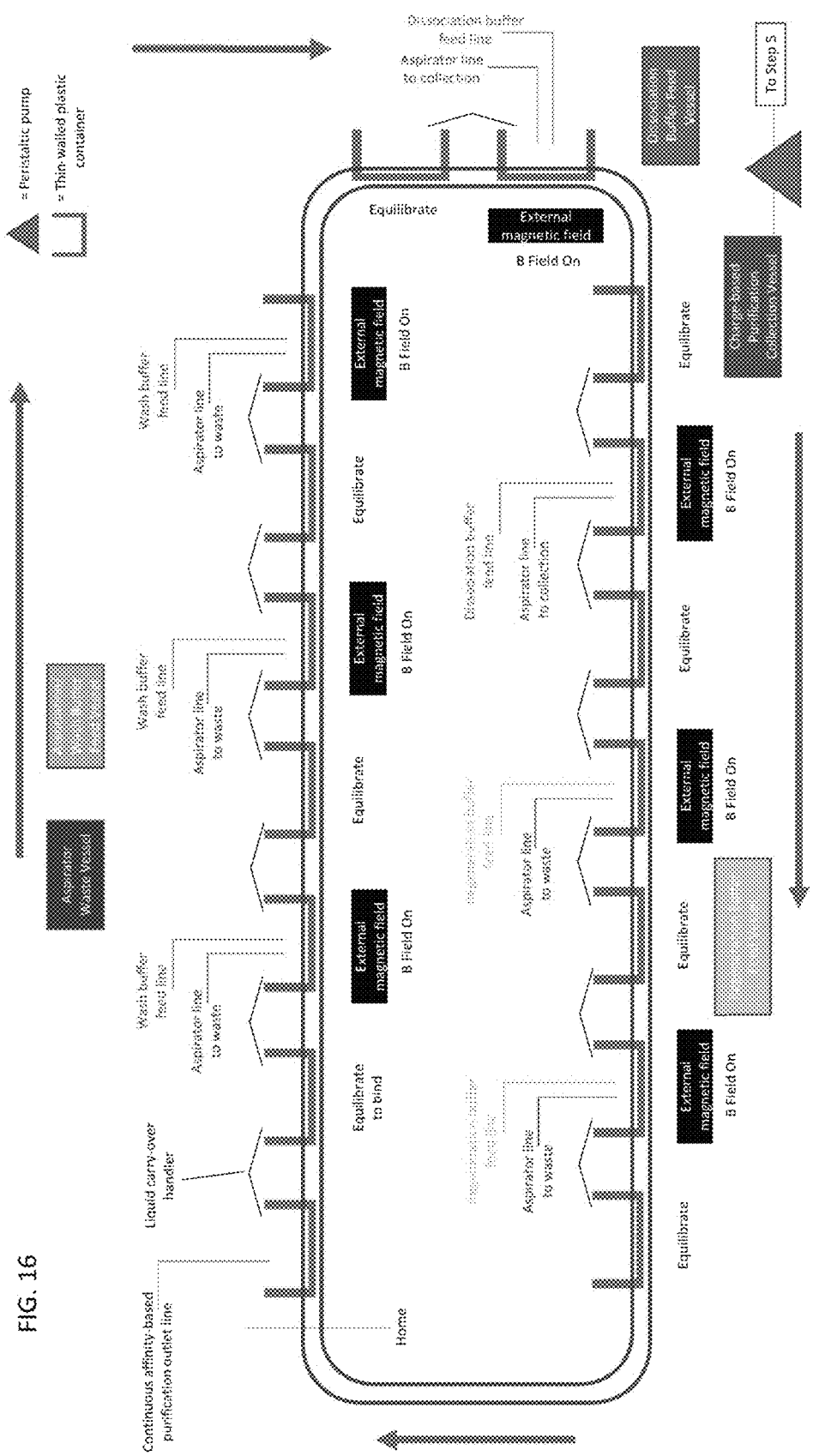
FIG. 16 shows an exemplary design schematic of a charge-based, magnetic purification apparatus comprising a loop conveyor system and at least one magnetic field that is permanently "on".
Figure 17:
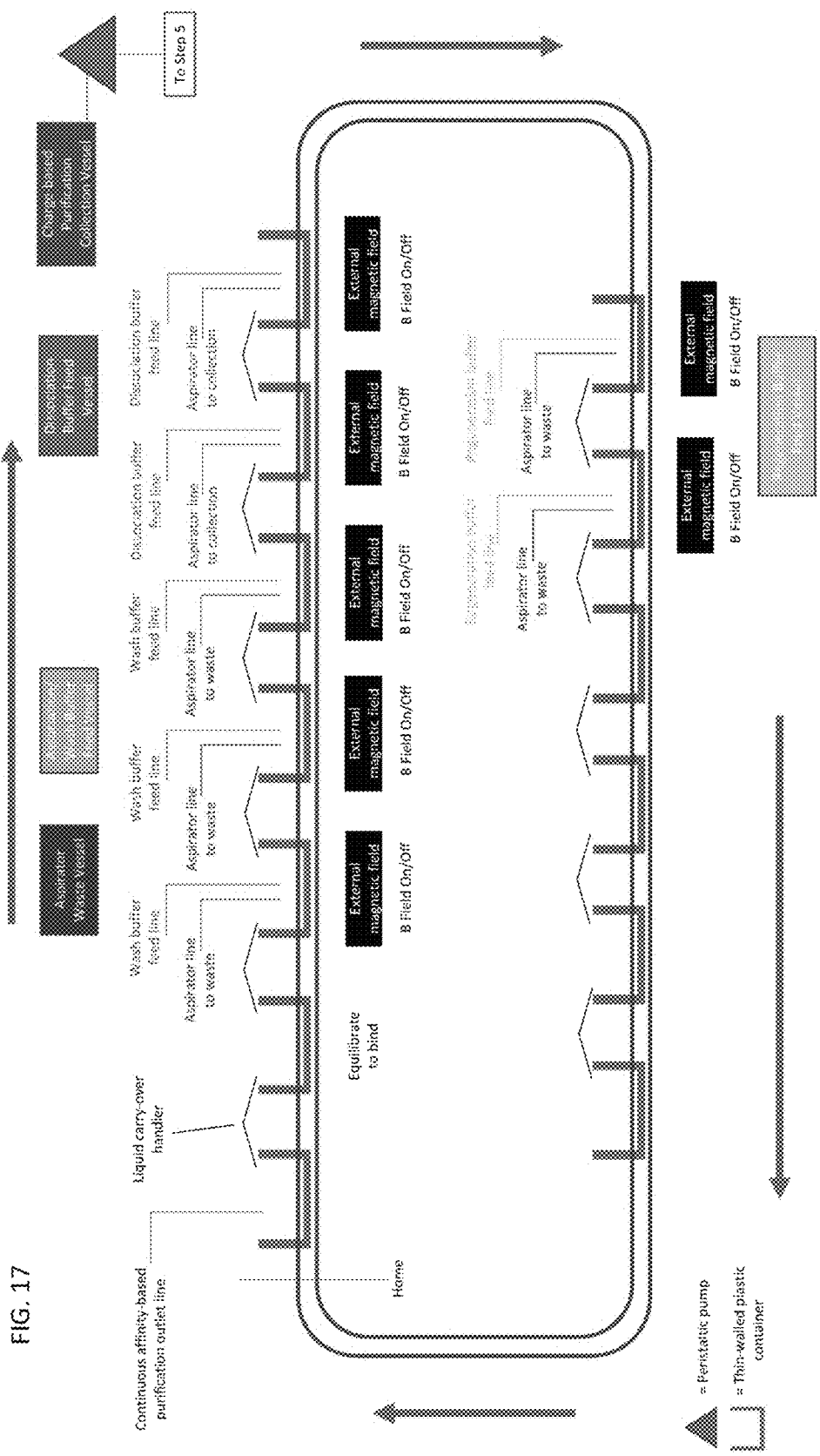
FIG. 17 shows an exemplary design schematic of a charge-based, magnetic purification apparatus comprising a loop conveyor system and at least one magnetic field capable of "on/off" toggling.

The equipment design for the positive charge-based, magnetic purification module (FIGS. 16-17) enables for automated and continuous, biological magnetic purification as compared to a batch process or a semi-continuous process and provides for a small footprint.

The magnetic field strength and field effect are dependent on the transport vessel wall thickness and material type, proximity to the wall of the transport vessel on a loop conveyor track, magnetic resin bead size, concentration, saturation magnetization, and magnetic susceptibility, and solution viscosity. In embodiments, the magnetic field strength ranges from about 0.01 Tesla to about 1 Tesla (e.g., up to about 1 Tesla). In examples, the magnetic field is generated by a permanent magnet (e.g., a Neodymium magnet). The permanent magnet may be positioned within 5 mm, or preferably within 1 mm of the vessel wall. In other examples, the magnetic field is generated by an electromagnet. In yet other examples, mixing of the magnetic resin beads may be accomplished by placing the at least one transport vessel between two separate and opposing magnetic fields that toggle between states of on and off.

As described herein, the positive charge-based, magnetic purification module includes a suspension of magnetic resin beads, in which the concentration depends on the desired charge or electrostatic association capacity or the desired solution viscosity. Alternatively, the positive charge-based, magnetic purification module magnetic resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The transport vessel number and size depends on input flow rate, magnetic resin bead charge or electrostatic association capacity, and association equilibration time. The transport vessel material and wall thickness is dependent on the strength and close proximity of the magnetic field.

The material selection for the magnetic resin beads of the positive charge-based, magnetic purification module is important for negligible leachables and to provide for robust stability to enable recycling and reuse. The magnetic resin beads may be solid, porous, nanoporous, microporous, or any combination thereof.

Within the positive charge-based, magnetic purification module, the cationic surface selection is an important consideration and may include cationic polymers, net positively charged peptides or proteins, amine functionality. Further, the cationic surface selection is based on achieving appropriate electrostatic interactions and stability between the positively charged bead surface and the biological product within a defined buffer (pH and ionic strength).

The association/wash buffer of the positive charge-based, magnetic purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional transport vessels and replicate conveyor track positions may also be required to effectively wash.

The dissociation buffer of the positive charge-based, magnetic purification module is dependent on the strength of the electrostatic interactions between the cationic magnetic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional transport vessels and replicate conveyor track positions). In other examples, multiple dissociation buffers varying pH, ionic strength, or any combination thereof, are utilized sequentially to create a gradient dissociation effect. Moreover, additional transport vessels and replicate conveyor track positions may also be required to effectively dissociate.

The dwell time for each stage in conveyor track progression of the positive charge-based, magnetic purification module is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The positive charge-based, purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the positive charge-based, magnetic purification module utilizes a mobile affinity resin capable of in situ regeneration and recycling to enable more efficient use of the resin and to enable continuous processing in a small-footprint without concerns of traditional column capacity limitations.

Positive Charge-Based, Magnetic Purification Module Having a Pick and Place Robotics System As described herein, a positive charge-based, magnetic purification module for separating a mixture into two or more fractions, at least one fraction containing a biological product is included. The positive charge-based, magnetic purification module includes at least one inlet and at least one outlet configured to permit continuous fluid flow between the at least one inlet and the at least one outlet and wherein the flow rate may be, for example, consistent and constant during steady-state operation. Moreover, the positive charge-based, magnetic purification module includes a suspension of cationic magnetic resin beads, wherein the magnetic resin bead surface comprises cationic functionality configured to selectively associate with said biological product at a specific pH and ionic strength.

The positive charge-based, magnetic purification module includes a pick and place robotics system comprising at least two transport vessels charged with cationic magnetic resin beads that are configured to continuously receive a mixture containing a biological product and subsequently transport the resulting heterogeneous mixture containing a biological product, cationic magnetic resin beads, a buffer, or any combination thereof; at least one external magnetic field to attract, and thus separate, said magnetic resin beads from the heterogeneous mixture to enable washing; at least one external magnetic field to attract, and thus separate, said magnetic resin beads from the heterogeneous mixture to enable dissociation of said biological product; at least one external magnetic field to enable recycling of said magnetic resin beads; at least one association/wash buffer system, at least one dissociation buffer system; at least one magnetic resin bead regeneration buffer system; at least one aspirator system to remove waste solution from the at least two transport vessels; at least one collection vessel; at least one sensor or detector; and at least one fluid handling pump.

The equipment design for the positive charge-based, magnetic purification module (FIG. 19) enables for automated and continuous, biological magnetic purification as compared to a batch process or a semi-continuous process and provides for a small footprint.

The magnetic field strength and field effect are dependent on the transport vessel wall thickness and material type, proximity to the wall of the transport vessel on a loop conveyor track, magnetic resin bead size, concentration, saturation magnetization, and magnetic susceptibility, and solution viscosity. In embodiments, the magnetic field strength ranges from about 0.01 Tesla to about 1 Tesla (e.g., up to about 1 Tesla). In examples, the magnetic field is generated by a permanent magnet (e.g., a Neodymium magnet). The permanent magnet may be positioned within 5 mm, or preferably within 1 mm of the vessel wall. In other examples, the magnetic field is generated by an electromagnet. In yet other examples, mixing of the magnetic resin beads may be accomplished by placing the at least one transport vessel between two separate and opposing magnetic fields that toggle between states of on and off.

As described herein, the positive charge-based, magnetic purification module includes a suspension of magnetic resin beads, in which the concentration depends on the desired charge or electrostatic association capacity or the desired solution viscosity. Alternatively, the positive charge-based, magnetic purification module magnetic resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The transport vessel number and size depends on input flow rate, magnetic resin bead charge or electrostatic association capacity, and association equilibration time. The transport vessel material and wall thickness is dependent on the strength and close proximity of the magnetic field.

The material selection for the magnetic resin beads of the positive charge-based, magnetic purification module is important for negligible leachables and to provide for robust stability to enable recycling and reuse. The magnetic resin beads may be solid, porous, nanoporous, microporous, or any combination thereof.

Within the positive charge-based, magnetic purification module, the cationic surface selection is an important consideration and may include cationic polymers, net positively charged peptides or proteins, amine functionality. Further, the cationic surface selection is based on achieving appropriate electrostatic interactions and stability between the positively charged bead surface and the biological product within a defined buffer (pH and ionic strength).

The association/wash buffer of the positive charge-based, magnetic purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional transport vessels and replicate pick and place positions may also be required to effectively wash.

The dissociation buffer of the positive charge-based, magnetic purification module is dependent on the strength of the electrostatic interactions between the cationic magnetic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional transport vessels and replicate conveyor track positions). In other examples, multiple dissociation buffers varying pH, ionic strength, or any combination thereof, are utilized sequentially to create a gradient dissociation effect. Moreover, additional transport vessels and replicate pick and place positions may also be required to effectively dissociate.

The dwell time for each stage in the progression of the transport vessel through the pick and place process of the positive charge-based, magnetic purification module is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The positive charge-based, magnetic purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the positive charge-based, magnetic purification module utilizes a mobile affinity resin capable of in situ regeneration and recycling to enable more efficient use of the resin and to enable continuous processing in a small-footprint without concerns of traditional column capacity limitations.

Negative Charge-Based, Magnetic Purification Module Having a Loop Conveyor System As described herein, a negative charge-based, magnetic purification module for separating a mixture into two or more fractions, at least one fraction containing a biological product is included. The negative charge-based, magnetic purification module includes at least one inlet and at least one outlet configured to permit continuous fluid flow between the at least one inlet and the at least one outlet and wherein the flow rate may be, for example, consistent and constant during steady-state operation. Moreover, the negative charge-based, magnetic purification module includes a suspension of anionic magnetic resin beads, wherein the magnetic resin bead surface comprises anionic functionality configured to selectively associate with said biological product at a specific pH and ionic strength.

The negative charge-based, magnetic purification module includes a loop conveyor system comprising at least two transport vessels charged with anionic magnetic resin beads that are configured to continuously receive a mixture containing a biological product and subsequently transport the resulting heterogeneous mixture containing a biological product, anionic magnetic resin beads, a buffer, or any combination thereof; at least one external magnetic field to attract, and thus separate, said magnetic resin beads from the heterogeneous mixture to enable washing; at least one external magnetic field to attract, and thus separate, said magnetic resin beads from the heterogeneous mixture to enable dissociation of said biological product; at least one external magnetic field to enable recycling of said magnetic resin beads; at least one association/wash buffer system; at least one dissociation buffer system; at least one magnetic resin bead regeneration buffer system; at least one aspirator system to remove waste solution from the at least two transport vessels; at least one collection vessel; at least one sensor or detector; and at least one fluid handling pump.

The equipment design for the negative charge-based, magnetic purification module (FIGS. 16-17) enables for automated and continuous, biological magnetic purification as compared to a batch process or a semi-continuous process and provides for a small footprint.

The magnetic field strength and field effect are dependent on the transport vessel wall thickness and material type, proximity to the wall of the transport vessel on a loop conveyor track, magnetic resin bead size, concentration, saturation magnetization, and magnetic susceptibility, and solution viscosity. In embodiments, the magnetic field strength ranges from about 0.01 Tesla to about 1 Tesla (e.g., up to about 1 Tesla). In examples, the magnetic field is generated by a permanent magnet (e.g., a Neodymium magnet). The permanent magnet may be positioned within 5 mm, or preferably within 1 mm of the vessel wall. In other examples, the magnetic field is generated by an electromagnet. In yet other examples, mixing of the magnetic resin beads may be accomplished by placing the at least one transport vessel between two separate and opposing magnetic fields that toggle between states of on and off.

As described herein, the negative charge-based, magnetic purification module includes a suspension of magnetic resin beads, in which the concentration depends on the desired charge or electrostatic association capacity or the desired solution viscosity. Alternatively, the negative charge-based, magnetic purification module magnetic resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The transport vessel number and size depends on input flow rate, magnetic resin bead charge or electrostatic association capacity, and association equilibration time. The transport vessel material and wall thickness is dependent on the strength and close proximity of the magnetic field.

The material selection for the magnetic resin beads of the negative charge-based, magnetic purification module is important for negligible leachables and to provide for robust stability to enable recycling and reuse. The magnetic resin beads may be solid, porous, nanoporous, microporous, or any combination thereof.

Within the negative charge-based, magnetic purification module, the anionic surface selection is an important consideration and may include anionic polymers, net negatively charged peptides or proteins, oligonucleotides, carboxyl functionality. Further, the selection is based on achieving appropriate electrostatic interactions and stability between the negatively charged bead surface and the biological product within a defined buffer (pH and ionic strength).

The association/wash buffer of the negative charge-based, magnetic purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional transport vessels and replicate conveyor track positions may also be required to effectively wash.

The dissociation buffer of the negative charge-based, magnetic purification module is dependent on the strength of the electrostatic interactions between the anionic magnetic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional transport vessels and replicate conveyor track positions). In other examples, multiple dissociation buffers varying pH, ionic strength, or any combination thereof, are utilized sequentially to create a gradient dissociation effect. Moreover, additional transport vessels and replicate conveyor track positions may also be required to effectively dissociate.

The dwell time for each stage in conveyor track progression of the negative charge-based, magnetic purification module is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The negative charge-based, magnetic purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the negative charge-based, magnetic purification module utilizes a mobile affinity resin capable of in situ regeneration and recycling to enable more efficient use of the resin and to enable continuous processing in a small-footprint without concerns of traditional column capacity limitations.

Negative Charge-Based, Magnetic Purification Module Having a Pick and Place Robotics System As described herein, a negative charge-based, magnetic purification module for separating a mixture into two or more fractions, at least one fraction containing a biological product is included. The negative charge-based, magnetic purification module includes at least one inlet and at least one outlet configured to permit continuous fluid flow between the at least one inlet and the at least one outlet and wherein the flow rate may be, for example, consistent and constant during steady-state operation. Moreover, the negative charge-based, magnetic purification module includes a suspension of anionic magnetic resin beads, wherein the magnetic resin bead surface comprises anionic functionality configured to selectively associate with said biological product at a specific pH and ionic strength.

The negative charge-based, magnetic purification module includes a pick and place robotics system comprising at least two transport vessels charged with anionic magnetic resin beads that are configured to continuously receive a mixture containing a biological product and subsequently transport the resulting heterogeneous mixture containing a biological product, anionic magnetic resin beads, a buffer, or any combination thereof; at least one external magnetic field to attract, and thus separate, said magnetic resin beads from the heterogeneous mixture to enable washing; at least one external magnetic field to attract, and thus separate, said magnetic resin beads from the heterogeneous mixture to enable dissociation of said biological product; at least one external magnetic field to enable recycling of said magnetic resin beads; at least one association/wash buffer system; at least one dissociation buffer system; at least one magnetic resin bead regeneration buffer system; at least one aspirator system to remove waste solution from the at least two transport vessels; at least one collection vessel; at least one sensor or detector; and at least one fluid handling pump.

The equipment design for the negative charge-based, magnetic purification module (FIG. 19) enables for automated and continuous, biological magnetic purification as compared to a batch process or a semi-continuous process and provides for a small footprint.

The magnetic field strength and field effect are dependent on the transport vessel wall thickness and material type, proximity to the wall of the transport vessel on a loop conveyor track, magnetic resin bead size, concentration, saturation magnetization, and magnetic susceptibility, and solution viscosity. In embodiments, the magnetic field strength ranges from about 0.01 Tesla to about 1 Tesla (e.g., up to about 1 Tesla). In examples, the magnetic field is generated by a permanent magnet (e.g., a Neodymium magnet). The permanent magnet may be positioned within 5 mm, or preferably within 1 mm of the vessel wall. In other examples, the magnetic field is generated by an electromagnet. In yet other examples, mixing of the magnetic resin beads may be accomplished by placing the at least one transport vessel between two separate and opposing magnetic fields that toggle between states of on and off.

As described herein, the negative charge-based, magnetic purification module includes a suspension of magnetic resin beads, in which the concentration depends on the desired charge or electrostatic association capacity or the desired solution viscosity. Alternatively, the negative charge-based, magnetic purification module magnetic resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The transport vessel number and size depends on input flow rate, magnetic resin bead charge or electrostatic association capacity, and association equilibration time. The transport vessel material and wall thickness is dependent on the strength and close proximity of the magnetic field.

The material selection for the magnetic resin beads of the negative charge-based, magnetic purification module is important for negligible leachables and to provide for robust stability to enable recycling and reuse. The magnetic resin beads may be solid, porous, nanoporous, microporous, or any combination thereof.

Within the negative charge-based, magnetic purification module, the anionic surface selection is an important consideration and may include anionic polymers, net negatively charged peptides or proteins, oligonucleotides, carboxyl functionality. Further, the selection is based on achieving appropriate electrostatic interactions and stability between the negatively charged bead surface and the biological product within a defined buffer (pH and ionic strength).

The association/wash buffer of the negative charge-based, magnetic purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional transport vessels and replicate pick and place positions may also be required to effectively wash.

The dissociation buffer of the negative charge-based, magnetic purification module is dependent on the strength of the electrostatic interactions between the anionic magnetic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional transport vessels and replicate conveyor track positions). In other examples, multiple dissociation buffers varying pH, ionic strength, or any combination thereof, are utilized sequentially to create a gradient dissociation effect. Moreover, additional transport vessels and replicate pick and place positions may also be required to effectively dissociate.

The dwell time for each stage in the progression of the transport vessel through the pick and place process of the negative charge-based, magnetic purification module is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The negative charge-based, purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the negative charge-based, magnetic purification module utilizes a mobile affinity resin capable of in situ regeneration and recycling to enable more efficient use of the resin and to enable continuous processing in a small-footprint without concerns of traditional column capacity limitations.

Affinity-Based Purification Module Having a Mechanical Rotary System

Provided herein is an affinity-based purification module for separating a mixture into two or more fractions, at least one fraction containing a biological product. The module includes at least one inlet and at least one outlet configured to permit continuous fluid flow between the at least one inlet and the at least one outlet and wherein the flow rate may be, for example, consistent and constant during steady-state operation. Moreover, the affinity-based purification module includes a suspension of affinity resin beads, wherein the resin bead surface, without intent to be limiting, is coupled to Protein A, Protein G, Protein L, an antigenic protein, a protein, a receptor, an antibody, or an aptamer configured to selectively bind said biological product.

The affinity-based purification module includes a lid system capable of motion along the z-axis having at least one gasketed lid, the at least one gasketed lid comprising at least one inlet to introduce a gas to enable control of positive head pressure, at least one vent port to enable equilibration to atmospheric pressure, at least one inlet to introduce a suspension of resin beads, at least one inlet to receive the filtrate containing a biological product to enable binding, at least two inlets to introduce a buffer system to disperse the resin beads to enable washing of, elution from, or regeneration of said resin beads; a mechanical rotary system capable of motion in the xy-plane, for example, a carousel comprising at least two vessels charged with resin beads that are configured to continuously receive a mixture containing a biological product and subsequently transport the resulting heterogeneous mixture containing a biological product, resin beads, a buffer, or any combination thereof; a collection system capable of motion along the z-axis that interfaces with at least one of the at least two vessels of the mechanical rotary system to enable collection of waste, the fraction containing the biological product, or any combination thereof; at least one gas; at least one binding/wash buffer system; at least one elution buffer system; at least one resin bead regeneration buffer system; at least one collection vessel; at least one sensor or detector; and, at least one fluid handling pump.

The equipment design of the affinity-based purification module (FIGS. 21 and 23) enables for automated and continuous, biological purification, as compared to a batch process or a semi-continuous process and provides for a small footprint.

As described herein, the affinity-based purification module includes a suspension of resin beads, in which the concentration depends on the desired binding capacity or the desired solution viscosity. Alternatively, the affinity-based purification module resin bead size is micron to sub-micron and is dependent on the binding capacity needs, which is a function of the surface area-to-volume ratio required to enable adequate fluid dynamics for equilibration and affinity interactions, for example, solution viscosity dependency and surface ligand density dependency, respectively.

The vessel number and size depends on input flow rate, resin bead binding capacity, and binding equilibration time. The vessel material is selected to limit protein binding.

The filter or filter membrane material and pore size of the vessel depends on the resin bead diameter and the biological product of interest. The filter or filter membrane materials is selected to limit protein binding.

The material selection for the resin beads of the affinity-based purification module is important for negligible leachables and to provide for robust stability to enable recycling and reuse. The resin beads may be solid, porous, nanoporous, microporous, or any combination thereof.

The binding/wash buffer is dependent on the biological product (e.g., monoclonal antibody) of interest and small impurities to be removed. Other considerations for the binding/wash buffer including pH, ionic strength, use of surfactants, and use of organic and/or inorganic salts are also contemplated in the binding/wash buffer. Moreover, additional vessels and replicate carousel positions may also be required to effectively wash.

The elution buffer is dependent on the binding affinity (e.g., strength of the non-covalent interactions) between the resin bead surface ligands and the biological product (e.g., monoclonal antibody) of interest. For example, the elution buffer may vary pH, ionic strength, use of surfactants, use of organic and/or inorganic salts, use of multiple elution buffer compositions (e.g., to increase yield, and which might require additional vessels and replicate carousel positions). Moreover, additional vessels and replicate carousel positions or additional elutions may also be required to effectively elute.

The dwell time for each stage in the progression of the vessel through the rotary process is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The affinity-based, purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the affinity-based purification module utilizes a mobile affinity resin capable of in situ regeneration and recycling to enable more efficient use of the resin and to enable continuous processing in a small-footprint without concerns of traditional column capacity limitations.

Positive Charge-Based Purification Module Having a Mechanical Rotary System

As described herein, a positive charge-based purification module for separating a mixture into two or more fractions, at least one fraction containing a biological product is included. The positive charge-based purification module includes at least one inlet and at least one outlet configured to permit continuous fluid flow between the at least one inlet and the at least one outlet and wherein the flow rate may be, for example, consistent and constant during steady-state operation. Moreover, the positive charge-based purification module includes a suspension of cationic resin beads, wherein the resin bead surface comprises cationic functionality configured to selectively associate with said biological product at a specific pH and ionic strength.

The positive charge-based purification module includes a lid system capable of motion along the z-axis having at least one gasketed lid, the at least one gasketed lid comprising at least one inlet to introduce a gas to enable control of positive head pressure, at least one vent port to enable equilibration to atmospheric pressure, at least one inlet to introduce a suspension of resin beads, at least one inlet to receive the filtrate containing a biological product to enable association, at least two inlets to introduce a buffer system to disperse the resin beads to enable washing of, dissociation from, or regeneration of said resin beads; a mechanical rotary system capable of motion in the xy-plane, for example, a carousel comprising at least two vessels charged with resin beads that are configured to continuously receive a mixture containing a biological product and subsequently transport the resulting heterogeneous mixture containing a biological product, resin beads, a buffer, or any combination thereof; a collection system capable of motion along the z-axis that interfaces with at least one of the at least two vessels of the mechanical rotary system to enable collection of waste, the fraction containing the biological product, or any combination thereof; at least one gas; at least one association/wash buffer system; at least one dissociation buffer system; at least one resin bead regeneration buffer system; at least one collection vessel; at least one sensor or detector; and, at least one fluid handling pump.

The equipment design for the positive charge-based purification module (FIGS. 22-23) enables for automated and continuous, biological purification as compared to a batch process or a semi-continuous process and provides for a small footprint.

As described herein, the positive charge-based purification module includes cationic resin beads, in which the concentration depends on the desired charge or electrostatic association capacity or the desired solution viscosity. Alternatively, the positive charge-based purification module resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The vessel number and size depends on input flow rate, resin bead charge or electrostatic association capacity, and association equilibration time. The vessel material is selected to limit protein binding.

The filter or filter membrane material and pore size of the vessel depends on the resin bead diameter and the biological product of interest. The filter or filter membrane materials is selected to limit protein binding.

The material selection for the resin beads of the positive charge-based purification module is important for negligible leachables and to provide for robust stability to enable recycling and reuse. The resin beads may be solid, porous, nanoporous, microporous, or any combination thereof.

Within the positive charge-based purification module, the cationic surface selection is an important consideration and may include cationic polymers, net positively charged peptides or proteins, amine functionality. Further, the selection is based on achieving appropriate electrostatic interactions and stability between the positively charged bead surface and the biological product within a defined buffer (pH and ionic strength).

The association/wash buffer of the positive charge-based purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional vessels and replicate carousel positions may also be required to effectively wash.

The dissociation buffer of the positive charge-based purification module is dependent on the strength of the electrostatic interactions between the anionic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional vessels and replicate carousel positions). In other examples, multiple dissociation buffers varying pH, ionic strength, or any combination thereof, are utilized sequentially to create a gradient dissociation effect. Moreover, additional vessels and replicate carousel positions or additional dissociations may also be required to effectively dissociate.

The dwell time for each stage in the progression of the vessel through the rotary process is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The positive charge-based purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the positive charge-based purification module utilizes a mobile affinity resin capable of in situ regeneration and recycling to enable more efficient use of the resin and to enable continuous processing in a small-footprint without concerns of traditional column capacity limitations.

Negative Charge-Based Purification Module Having a Mechanical Rotary System

As described herein, a negative charge-based purification module for separating a mixture into two or more fractions, at least one fraction containing a biological product is included. The negative charge-based purification module includes at least one inlet and at least one outlet configured to permit continuous fluid flow between the at least one inlet and the at least one outlet and wherein the flow rate may be, for example, consistent and constant during steady-state operation. Moreover, the negative charge-based purification module includes a suspension of anionic resin beads, wherein the resin bead surface comprises anionic functionality configured to selectively associate with said biological product at a specific pH and ionic strength.

The negative charge-based purification module includes a lid system capable of motion along the z-axis having at least one gasketed lid, the at least one gasketed lid comprising at least one inlet to introduce a gas to enable control of positive head pressure, at least one vent port to enable equilibration to atmospheric pressure, at least one inlet to introduce a suspension of resin beads, at least one inlet to receive the filtrate containing a biological product to enable association, at least two inlets to introduce a buffer system to disperse the resin beads to enable washing of, dissociation from, or regeneration of said resin beads; a mechanical rotary system capable of motion in the xy-plane, for example, a carousel comprising at least two vessels charged with resin beads that are configured to continuously receive a mixture containing a biological product and subsequently transport the resulting heterogeneous mixture containing a biological product, resin beads, a buffer, or any combination thereof; a collection system capable of motion along the z-axis that interfaces with at least one of the at least two vessels of the mechanical rotary system to enable collection of waste, the fraction containing the biological product, or any combination thereof; at least one gas; at least one association/wash buffer system; at least one dissociation buffer system; at least one resin bead regeneration buffer system; at least one collection vessel; at least one sensor or detector; and, at least one fluid handling pump.

The equipment design for the negative charge-based purification module (FIGS. 22-23) enables for automated and continuous, biological purification as compared to a batch process or a semi-continuous process and provides for a small footprint.

As described herein, the negative charge-based purification module includes a suspension of resin beads, in which the concentration depends on the desired charge or electrostatic association capacity or the desired solution viscosity. Alternatively, the negative charge-based purification module resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The vessel number and size depends on input flow rate, resin bead charge or electrostatic association capacity, and association equilibration time. The vessel material is selected to limit protein binding.

The filter or filter membrane material and pore size of the vessel depends on the resin bead diameter and the biological product of interest. The filter or filter membrane materials is selected to limit protein binding.

The material selection for the resin beads of the negative charge-based purification module is important for negligible leachables and to provide for robust stability to enable recycling and reuse. The resin beads may be solid, porous, nanoporous, microporous, or any combination thereof.

Within the negative charge-based purification module, the anionic surface selection is an important consideration and may include anionic polymers, net negatively charged peptides or proteins, oligonucleotides, carboxyl functionality. Further, the selection is based on achieving appropriate electrostatic interactions and stability between the negatively charged bead surface and the biological product within a defined buffer (pH and ionic strength).

The association/wash buffer of the negative charge-based purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional vessels and replicate carousel positions may also be required to effectively wash.

The dissociation buffer of the negative charge-based purification module is dependent on the strength of the electrostatic interactions between the anionic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional vessels and replicate carousel positions). In other examples, multiple dissociation buffers varying pH, ionic strength, or any combination thereof, are utilized sequentially to create a gradient dissociation effect. Moreover, additional vessels and replicate carousel positions or additional dissociations may also be required to effectively dissociate.

The dwell time for each stage in the progression of the vessel through the rotary process is dependent on flow rate, equilibration times, and throughput volume. Moreover, depending on buffer composition and pH, viral inactivation and removal during the wash steps is also contemplated, and would thus eliminate the need for a separate viral inactivation and removal process step, for example, when purifying a monoclonal antibody.

The negative charge-based purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the negative charge-based, magnetic purification module utilizes a mobile affinity resin capable of in situ regeneration and recycling to enable more efficient use of the resin and to enable continuous processing in a small-footprint without concerns of traditional column capacity limitations.

Affinity-Based Purification Module Having a Staged Linear System

Provided herein is an affinity-based purification module for separating a mixture into two or more fractions, at least one fraction containing a biological product. The module includes at least one inlet and at least one outlet configured to permit continuous fluid flow between the at least one inlet and the at least one outlet and wherein the flow rate may be, for example, consistent and constant during steady-state operation. Moreover, the affinity-based purification module includes a suspension of affinity resin beads, wherein the resin bead surface, without intent to be limiting, is coupled to Protein A, Protein G, Protein L, an antigenic protein, a protein, a receptor, an antibody, or an aptamer configured to selectively bind said biological product.

The affinity-based purification module includes at least one gasketed lid system having at least one inlet to introduce a gas to enable control of positive head pressure, at least one vent port to enable equilibration to atmospheric pressure, at least one inlet to introduce a suspension of resin beads, at least one inlet to receive the filtrate containing a biological product to enable binding, at least two inlets to introduce a buffer system to disperse the resin beads to enable washing of, elution from, or regeneration of said resin beads; a staged linear system comprising at least two vessels charged with mobile resin beads that are configured to continuously receive a mixture containing a biological product and subsequently process the resulting heterogeneous mixture containing a biological product, resin beads, a buffer, or any combination thereof; a collection system connected to at least one of the at least two vessels of the staged linear system to enable collection of waste, the fraction containing the biological product, or any combination thereof; at least one gas; at least one binding/wash buffer system; at least one elution buffer system; at least one resin bead regeneration buffer system; at least one collection vessel; at least one sensor or detector; and, at least one fluid handling pump.

The equipment design of the affinity-based purification module (FIGS. 24A and 24B) enables for automated and continuous, biological purification, as compared to a batch process or a semi-continuous process and provides for a small footprint.

As described herein, the affinity-based purification module includes a suspension of resin beads, in which the concentration depends on the desired binding capacity or the desired solution viscosity. Alternatively, the affinity-based purification module resin bead size is micron to sub-micron and is dependent on the binding capacity needs, which is a function of the surface area-to-volume ratio required to enable adequate fluid dynamics for equilibration and affinity interactions, for example, solution viscosity dependency and surface ligand density dependency, respectively.

The vessel number and size depends on input flow rate, resin bead binding capacity, and binding equilibration time. The vessel material is selected to limit protein binding.

The filter or filter membrane material and pore size of the vessel depends on the resin bead diameter and the biological product of interest. The filter or filter membrane materials is selected to limit protein binding.

The material selection for the resin beads of the affinity-based purification module is important for negligible leachables and to provide for robust stability to enable recycling and reuse. The resin beads may be solid, porous, nanoporous, microporous, or any combination thereof.

The binding/wash buffer is dependent on the biological product (e.g., monoclonal antibody) of interest and small impurities to be removed. Other considerations for the binding/wash buffer including pH, ionic strength, use of surfactants, and use of organic and/or inorganic salts are also contemplated in the binding/wash buffer. Moreover, additional vessels and replicate carousel positions may also be required to effectively wash.

The elution buffer is dependent on the binding affinity (e.g., strength of the non-covalent interactions) between the resin bead surface ligands and the biological product (e.g., monoclonal antibody) of interest. For example, the elution buffer may vary pH, ionic strength, use of surfactants, use of organic and/or inorganic salts, use of multiple elution buffer compositions (e.g., to increase yield, and which might require additional vessels and replicate carousel positions). Moreover, additional elutions may also be required to effectively elute.

Depending on buffer composition and pH, viral inactivation and removal during the wash steps is also contemplated, and would thus eliminate the need for a separate viral inactivation and removal process step, for example, when purifying a monoclonal antibody.

The affinity-based, purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the affinity-based purification module utilizes a mobile affinity resin capable of in situ regeneration and recycling to enable more efficient use of the resin and to enable continuous processing in a small-footprint without concerns of traditional column capacity limitations.

Positive Charge-Based Purification Module Having a Staged Linear System

Provided herein is a positive charge-based purification module for separating a mixture into two or more fractions, at least one fraction containing a biological product. The module includes at least one inlet and at least one outlet configured to permit continuous fluid flow between the at least one inlet and the at least one outlet and wherein the flow rate may be, for example, consistent and constant during steady-state operation. Moreover, the positive charge-based purification module includes a suspension of affinity resin beads, wherein the resin bead surface, without intent to be limiting, is coupled to Protein A, Protein G, Protein L, an antigenic protein, a protein, a receptor, an antibody, or an aptamer configured to selectively bind said biological product.

The positive charge-based purification module includes at least one gasketed lid system having at least one inlet to introduce a gas to enable control of positive head pressure, at least one vent port to enable equilibration to atmospheric pressure, at least one inlet to introduce a suspension of resin beads, at least one inlet to receive the filtrate containing a biological product, at least two inlets to introduce a buffer system to disperse the resin beads to enable washing of, dissociation from, or regeneration of said resin beads; a staged linear system comprising at least two vessels charged with mobile resin beads that are configured to continuously receive a mixture containing a biological product and subsequently process the resulting heterogeneous mixture containing a biological product, resin beads, a buffer, or any combination thereof; a collection system connected to at least one of the at least two vessels of the staged linear system to enable collection of waste, the fraction containing the biological product, or any combination thereof; at least one gas; at least one binding/wash buffer system; at least one elution buffer system; at least one resin bead regeneration buffer system; at least one collection vessel; at least one sensor or detector; and, at least one fluid handling pump.

The equipment design of the positive charge-based purification module (FIGS. 24A and 24B) enables for automated and continuous, biological purification, as compared to a batch process or a semi-continuous process and provides for a small footprint.

As described herein, the positive charge-based purification module includes cationic resin beads, in which the concentration depends on the desired charge or electrostatic association capacity or the desired solution viscosity. Alternatively, the positive charge-based purification module resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The vessel number and size depends on input flow rate, resin bead charge or electrostatic association capacity, and association equilibration time. The vessel material is selected to limit protein binding.

The filter or filter membrane material and pore size of the vessel depends on the resin bead diameter and the biological product of interest. The filter or filter membrane materials is selected to limit protein binding.

The material selection for the resin beads of the positive charge-based purification module is important for negligible leachables and to provide for robust stability to enable recycling and reuse. The resin beads may be solid, porous, nanoporous, microporous, or any combination thereof.

Within the positive charge-based purification module, the cationic surface selection is an important consideration and may include cationic polymers, net positively charged peptides or proteins, amine functionality. Further, the selection is based on achieving appropriate electrostatic interactions and stability between the positively charged bead surface and the biological product within a defined buffer (pH and ionic strength).

The association/wash buffer of the positive charge-based purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional vessels and replicate carousel positions may also be required to effectively wash.

The dissociation buffer of the positive charge-based purification module is dependent on the strength of the electrostatic interactions between the anionic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional vessels and replicate carousel positions). In other examples, multiple dissociation buffers varying pH, ionic strength, or any combination thereof, are utilized sequentially to create a gradient dissociation effect. Moreover, additional dissociations may also be required to effectively dissociate.

Depending on buffer composition and pH, viral inactivation and removal during the wash steps is also contemplated, and would thus eliminate the need for a separate viral inactivation and removal process step, for example, when purifying a monoclonal antibody.

The positive charge-based purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the positive charge-based purification module utilizes a mobile affinity resin capable of in situ regeneration and recycling to enable more efficient use of the resin and to enable continuous processing in a small-footprint without concerns of traditional column capacity limitations.

Negative Charge-Based Purification Module Having a Staged Linear System

Provided herein is a negative charge-based purification module for separating a mixture into two or more fractions, at least one fraction containing a biological product. The module includes at least one inlet and at least one outlet configured to permit continuous fluid flow between the at least one inlet and the at least one outlet and wherein the flow rate may be, for example, consistent and constant during steady-state operation. Moreover, the negative charge-based purification module includes a suspension of affinity resin beads, wherein the resin bead surface, without intent to be limiting, is coupled to Protein A, Protein G, Protein L, an antigenic protein, a protein, a receptor, an antibody, or an aptamer configured to selectively bind said biological product.

The negative charge-based purification module includes at least one gasketed lid system having at least one inlet to introduce a gas to enable control of positive head pressure, at least one vent port to enable equilibration to atmospheric pressure, at least one inlet to introduce a suspension of resin beads, at least one inlet to receive the filtrate containing a biological product, at least two inlets to introduce a buffer system to disperse the resin beads to enable washing of, dissociation from, or regeneration of said resin beads; a staged linear system comprising at least two vessels charged with mobile resin beads that are configured to continuously receive a mixture containing a biological product and subsequently process the resulting heterogeneous mixture containing a biological product, resin beads, a buffer, or any combination thereof; a collection system connected to at least one of the at least two vessels of the staged linear system to enable collection of waste, the fraction containing the biological product, or any combination thereof; at least one gas; at least one binding/wash buffer system; at least one elution buffer system; at least one resin bead regeneration buffer system; at least one collection vessel; at least one sensor or detector; and, at least one fluid handling pump.

The equipment design of the negative charge-based purification module (FIGS. 25A and 25B) enables for automated and continuous, biological purification, as compared to a batch process or a semi-continuous process and provides for a small footprint.

As described herein, the negative charge-based purification module includes a suspension of resin beads, in which the concentration depends on the desired charge or electrostatic association capacity or the desired solution viscosity. Alternatively, the negative charge-based purification module resin bead size is micron to sub-micron and is dependent on the charge or electrostatic association capacity needs, which is a function of the surface area-to-volume ratio required to enable adequate fluid dynamics for equilibration and charge or electrostatic interactions, for example, solution viscosity dependency and surface charge density dependency, respectively.

The vessel number and size depends on input flow rate, resin bead charge or electrostatic association capacity, and association equilibration time. The vessel material is selected to limit protein binding.

The filter or filter membrane material and pore size of the vessel depends on the resin bead diameter and the biological product of interest. The filter or filter membrane materials is selected to limit protein binding.

The material selection for the resin beads of the negative charge-based purification module is important for negligible leachables and to provide for robust stability to enable recycling and reuse. The resin beads may be solid, porous, nanoporous, microporous, or any combination thereof.

Within the negative charge-based purification module, the anionic surface selection is an important consideration and may include anionic polymers, net negatively charged peptides or proteins, oligonucleotides, carboxyl functionality. Further, the selection is based on achieving appropriate electrostatic interactions and stability between the negatively charged bead surface and the biological product within a defined buffer (pH and ionic strength).

The association/wash buffer of the negative charge-based purification module is dependent on the biological product of interest (e.g., a monoclonal antibody) and small impurities to be removed. The pH, ionic strength, use of surfactants, and use of organic and/or inorganic salts is also contemplated in the association/wash buffer. Moreover, additional vessels and replicate carousel positions may also be required to effectively wash.

The dissociation buffer of the negative charge-based purification module is dependent on the strength of the electrostatic interactions between the anionic resin bead surface functionality and the biological product (e.g., monoclonal antibody) of interest. For example, the dissociation buffer may vary pH, ionic strength, use of surfactants, use of organic and/or inorganic salts, use of multiple dissociation buffer compositions (e.g., to increase yield, and which might require additional vessels and replicate carousel positions). In other examples, multiple dissociation buffers varying pH, ionic strength, or any combination thereof, are utilized sequentially to create a gradient dissociation effect. Moreover, additional dissociations may also be required to effectively dissociate.

Depending on buffer composition and pH, viral inactivation and removal during the wash steps is also contemplated, and would thus eliminate the need for a separate viral inactivation and removal process step, for example, when purifying a monoclonal antibody.

The negative charge-based purification module may include in-line sampling ports for in-process analytical testing and/or in-line analytical measurement techniques. Further, the in-line analytical measurement techniques (e.g., flow sensors, optical density measurement devices, UV detectors, RI detectors) may be used to enable feedback control mechanisms with the process.

Unlike the traditional packed column chromatography and column-switching chromatography methods commonly used in the art, the negative charge-based, magnetic purification module utilizes a mobile affinity resin capable of in situ regeneration and recycling to enable more efficient use of the resin and to enable continuous processing in a small-footprint without concerns of traditional column capacity limitations.

Affinity-Based, Fluidic Purification Module

As provided herein, an affinity-based, fluidic purification module for separating a mixture into two or more fractions, at least one fraction containing a biological product is described. The affinity-based, fluidic purification module includes at least one inlet and at least one outlet configured to permit continuous fluid flow between the at least one inlet and the at least one outlet and wherein the flow rate may be, for example, consistent and constant during steady-state operation. Moreover, the affinity-based, fluidic purification module includes a suspension of affinity magnetic resin beads, wherein the magnetic resin bead surface, without intent to be limiting, is coupled to Protein A, Protein G, Protein L, an antigenic protein, a protein, a receptor, an antibody, or an aptamer configured to selectively bind said biological product.

Figure 28:
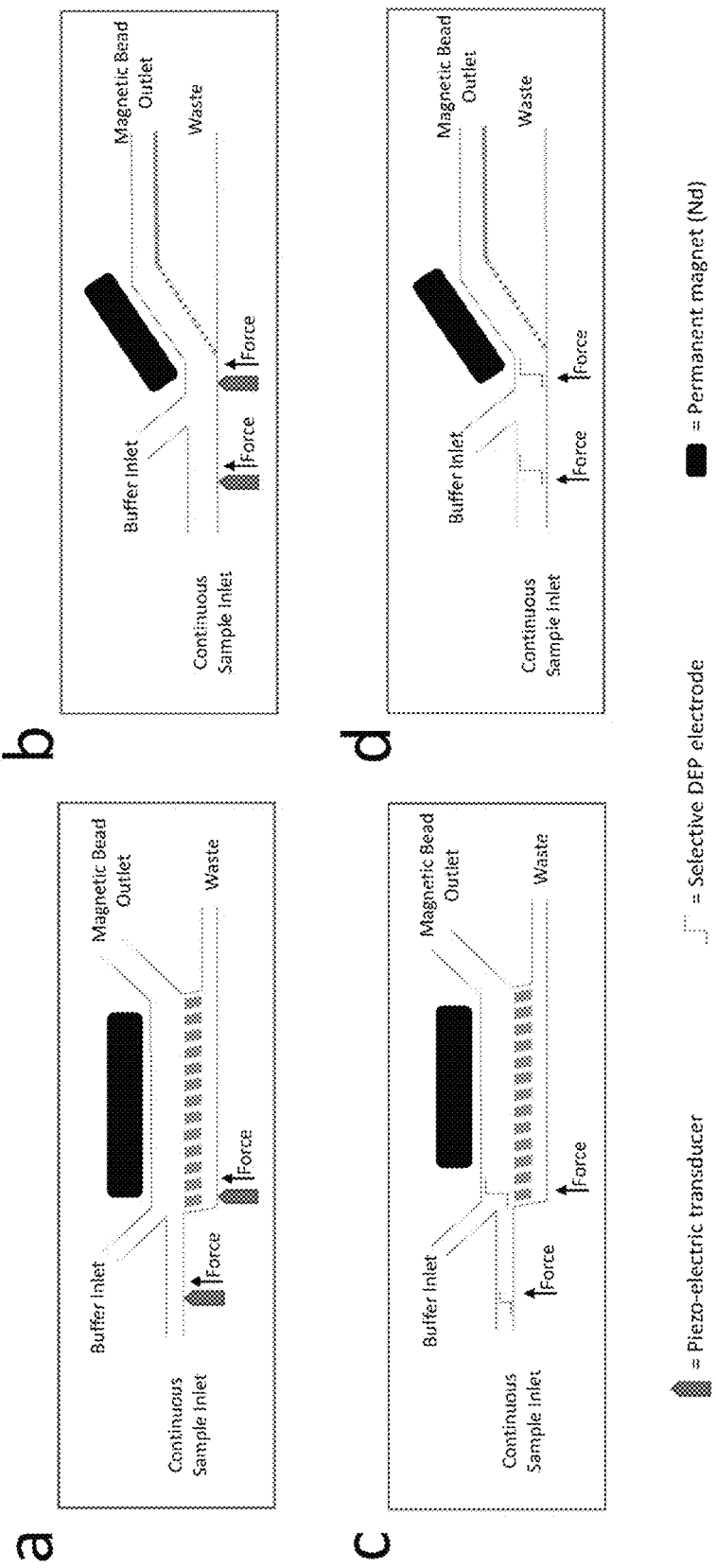
FIGS. 28A-28D are a series of images showing exemplary designs of hybrid fluidic devices.

The affinity-based, fluidic purification module includes at least one equilibration vessel to allow for binding of the biological product to the magnetic resin bead surface; at least one low pH equilibration vessel to allow for de-binding of the biological product from the magnetic resin bead surface; at least one first hybrid cross-flow fluidic device or chip (e.g., a microfluidic, a mesofluidic, a millifluidic, a macrofluidic device or chip, or any combination thereof) comprising at least one magnetic field and at least one of a piezoelectric component or a dielectrophoretic electrode configured to generate or induce a unidirectional force to manipulate the flow path of the magnetic resin beads in said heterogeneous mixture, and a cross-flow channel to separate the magnetic resin beads bound to the biological product from small impurities in the heterogeneous mixture (FIG. 28); at least one second hybrid cross-flow fluidic device or chip (e.g., a microfluidic, a mesofluidic, a millifluidic, a macrofluidic device or chip, or any combination thereof) comprising at least one magnetic field and at least one of a piezoelectric component or a dielectrophoretic electrode configured to generate or induce a unidirectional force to manipulate the flow path of said magnetic resin beads from said biological product, and a cross-flow channel to separate the magnetic resin beads from said biological product (FIG. 28); at least two buffer systems; at least one magnetic resin bead regeneration buffer system; at least one regeneration equilibration vessel configured to enable recycling of said magnetic resin beads; at least one collection vessel; at least one sensor or detector; and, at least one fluid handling pump.

Figure 29:
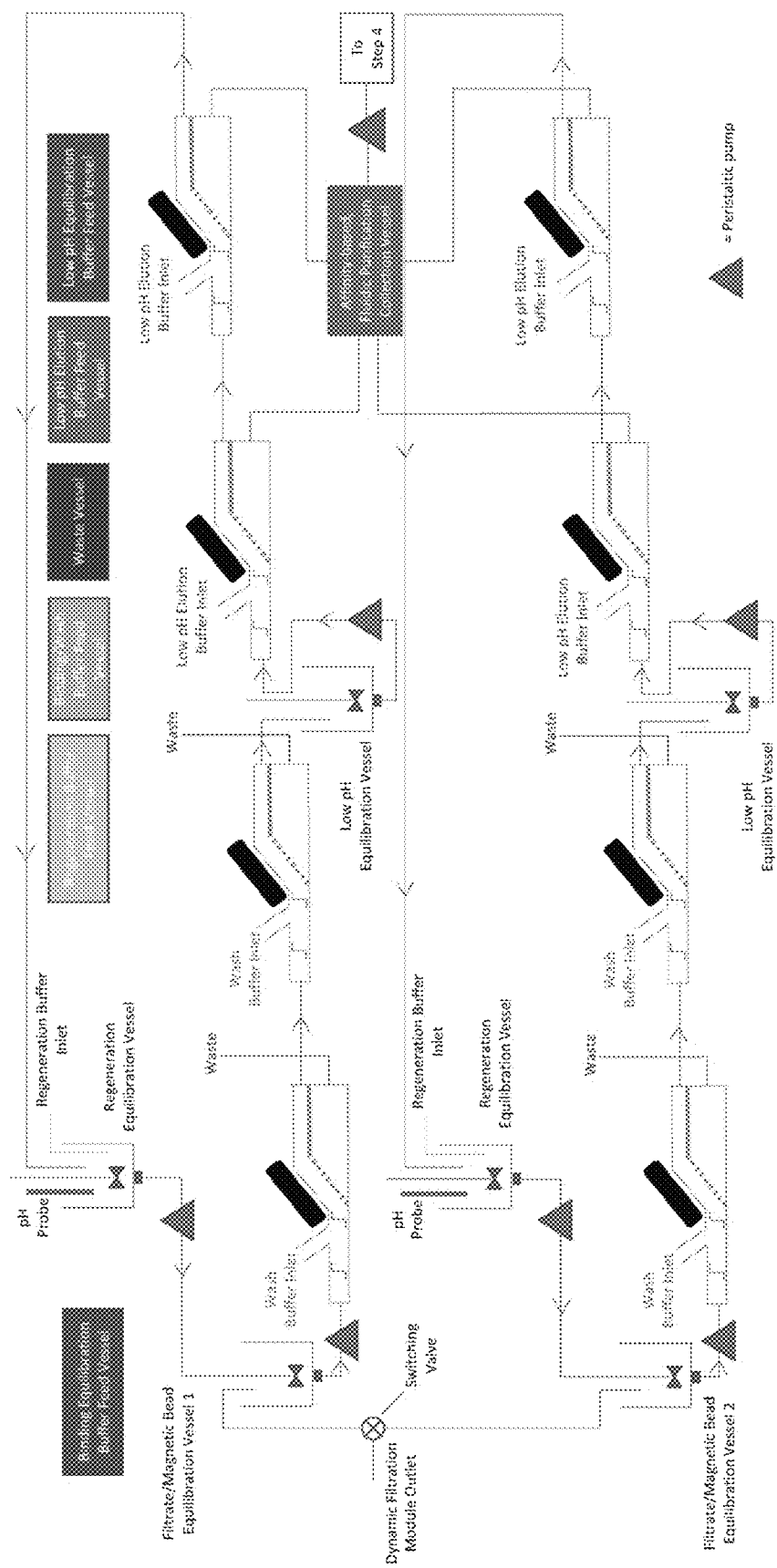
FIG. 29 shows an exemplary design schematic of an affinity-based, fluidic purification apparatus.

The equipment design for the affinity-based, fluidic purification module (FIG. 29) enables continuous, biological magnetic purification and provides for a small footprint.

The at least one equilibration vessel volume and agitation capabilities of the affinity-based, fluidic purification module consider the input flow rate and throughput, equilibration time and agitation rate to enable binding kinetics, and magnetic resin bead concentration and binding capacity. The equilibration buffer for the affinity-based, fluidic purification module is dependent on the biological product of interest (e.g., a monoclonal antibody) and the small impurities to be removed. Considerations for the buffer include pH, ionic strength, use of surfactants, or use of organic and/or inorganic salts.

The cross-flow channel size of the affinity-based, fluidic purification module is dependent on the solution viscosity, magnetic resin bead concentration, input flow rate and throughput volume. The piezoelectric or acoustic actuator considers the physical location and the energy (e.g., frequency) to enable desired magnetic resin bead deflection or manipulation of the magnetic resin bead flow path, and the piezoelectric crystal type. The dielectrophoretic electrodes consider selective-type and design to enable desired magnetic resin bead deflection, the number of electrodes and spacing to enable desired bead deflection, the voltage applied to enable desired bead deflection, and the electrode material.

The magnetic field strength and field effect are dependent on the flow rate and magnetic resin bead concentration, size, saturation magnetization, and magnetic susceptibility, and/or the proximity to the cross-flow channel. In embodiments, the magnetic field strength ranges from about 0.01 Tesla to about 1 Tesla (e.g., up to about 1 Tesla). The magnetic resin bead concentration is dependent on the desired binding capacity, desired solution viscosity, and the magnetic resin bead size is dependent on the surface area-to-volume ratio to enable adequate fluid dynamics for equilibration and affinity interactions, for example, solution viscosity dependency and surface ligand density dependency, respectively. In embodiments, the magnetic resin beads have sub-micron to micron diameters.

The material selection of the affinity-based, fluidic purification module is important for negligible leachables and robust stability to enable recycling and reuse of the affinity-based, fluidic purification module. The magnetic resin beads may be solid, porous, nanoporous, microporous, or any combination thereof.

The at least one low pH equilibration vessel volume and agitation capabilities of the affinity-based, fluidic purification module consider the input flow rate and throughput, equilibration time to enable de-binding kinetics, a low pH elution buffer at 10× to enable dilution during equilibration time to arrive at 1× final buffer salt concentration. The low pH elution buffer is dependent on the binding affinity of biological product of interest (e.g., a monoclonal antibody) for the magnetic resin bead surface ligand, and variations may include pH, ionic strength, or use of organic and/or inorganic salts.

The throughput of the affinity-based, fluidic purification module may be increased by multiplexing multiple fluidic devices or chips, in series or in parallel. Moreover, multiple fluidic devices or chips in series or in parallel may be required to enable complete purification. Additionally, a regeneration equilibration vessel might require a permanent magnetic field and a waste line to maintain correct concentration of magnetic resin beads and allow for effective recycling. Viral inactivation and removal may be accomplished during the low pH elution buffer equilibration and subsequent fluidic processing steps depending on buffer composition and pH.

The affinity-based, fluidic purification module may include at least one tangential flow filtration system operated in fed-batch or perfusion mode to concentrate and buffer exchange the fraction containing the biological product.

The affinity-based, fluidic purification module may include in-line sampling ports for in-process analytical testing and/or in-line analytical measurement techniques. Further, the in-line analytical measurement techniques (e.g., flow sensors, pressure sensors, optical density measurement devices, UV detectors, RI detectors) may be used to enable feedback control mechanisms with the process.

Unlike the traditional packed column chromatography and column-switching chromatography methods commonly used in the art, the affinity-based, fluidic purification module utilizes a mobile affinity resin capable of in situ regeneration and recycling to enable more efficient use of the resin and to enable continuous processing in a small-footprint without concerns of traditional column capacity limitations.

Positive Charge-Based, Fluidic Purification Module

As provided herein, a positive charge-based, fluidic purification module for separating a mixture into two or more fractions, at least one fraction containing a biological product is described. The positive charge-based, fluidic purification module includes at least one inlet and at least one outlet configured to permit continuous fluid flow between the at least one inlet and the at least one outlet and wherein the flow rate may be, for example, consistent and constant during steady-state operation. Moreover, the positive charge-based, fluidic purification module includes a suspension of cationic magnetic resin beads, wherein the magnetic resin bead surface comprises cationic functionality configured to selectively associate with said biological product based on charge or electrostatic interactions at a specific pH and ionic strength.

The positive charge-based, fluidic purification module includes at least one association equilibration vessel to allow for charge or electrostatic association of the biological product with the magnetic resin bead surface; at least one dissociation equilibration vessel to allow for dissociation of the biological product from the magnetic resin bead surface; at least one first hybrid cross-flow fluidic device or chip (e.g., a microfluidic, a mesofluidic, a millifluidic, a macrofluidic device or chip, or any combination thereof) comprising at least one magnetic field and at least one of a piezoelectric component or a dielectrophoretic electrode configured to generate or induce a unidirectional force to manipulate the flow path of the magnetic resin beads in said heterogeneous mixture, and a cross-flow channel to separate the magnetic resin beads bound to the biological product from small impurities in the heterogeneous mixture (FIG. 28); at least one second hybrid cross-flow fluidic device or chip (e.g., a microfluidic, a mesofluidic, a millifluidic, a macrofluidic device or chip, or any combination thereof) comprising at least one magnetic field and at least one of a piezoelectric component or a dielectrophoretic electrode configured to generate or induce a unidirectional force to manipulate the flow path of said magnetic resin beads from said biological product, and a cross-flow channel to separate the magnetic resin beads from said biological product (FIG. 28); at least two buffer systems; at least one magnetic resin bead regeneration buffer system; at least one regeneration equilibration vessel configured to enable recycling of said magnetic resin beads; at least one collection vessel; at least one sensor or detector; and, at least one fluid handling pump.

Figure 30:
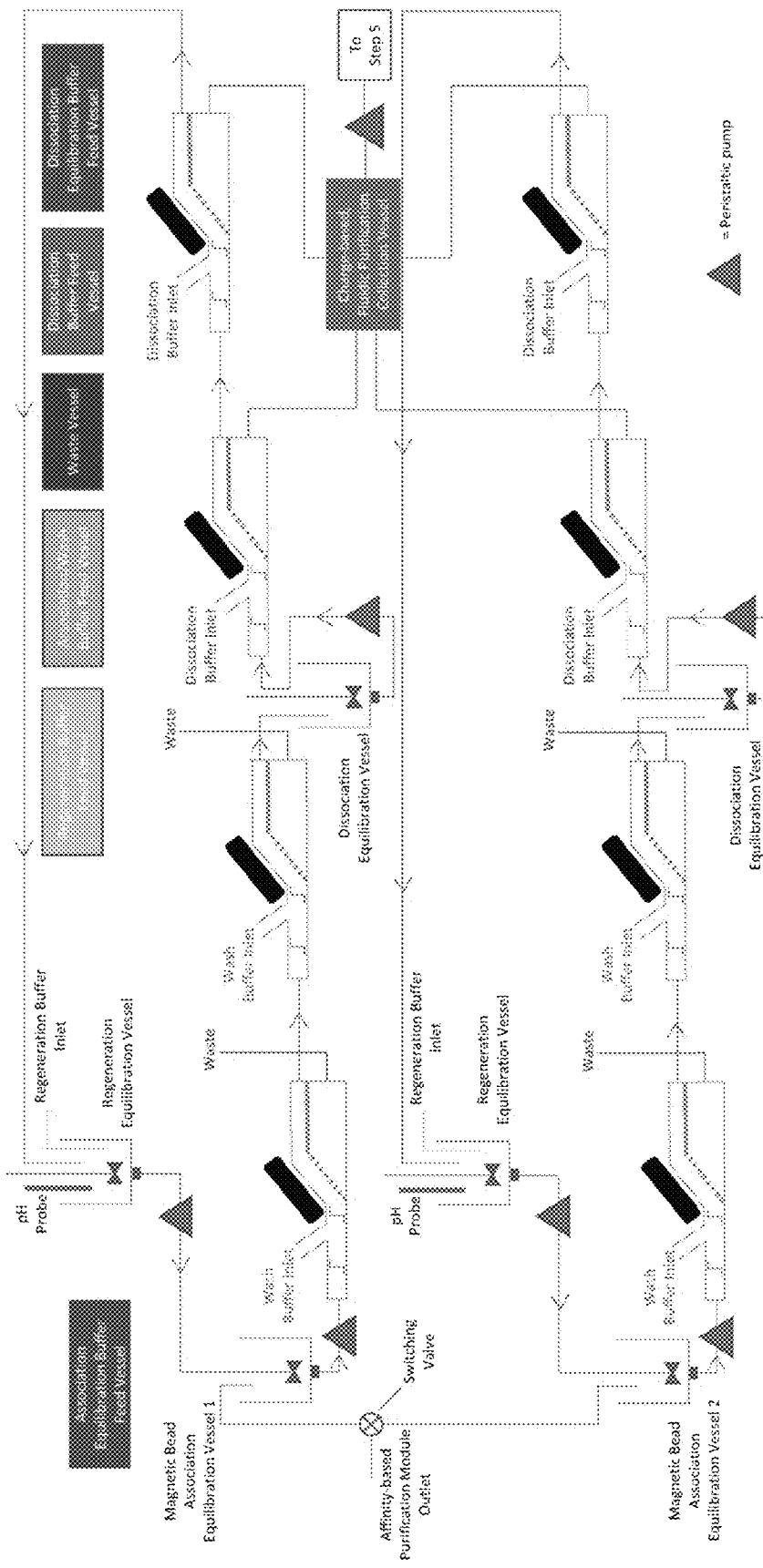
FIG. 30 shows an exemplary design schematic of a charge-based, fluidic purification apparatus.

The equipment design for the positive charge-based, fluidic purification module (FIG. 30) enables continuous, biological magnetic purification and provides for a small footprint.

The at least one association equilibration vessel volume and agitation capabilities of the positive charge-based, fluidic purification module consider the input flow rate and throughput, equilibration time and agitation rate to enable association kinetics, and magnetic resin bead concentration and charge or electrostatic association capacity. The association buffer for the positive charge-based, fluidic purification module is dependent on the biological product of interest (e.g., a monoclonal antibody) and the small impurities to be removed. Considerations for the buffer include pH, ionic strength, use of surfactants, or use of organic and/or inorganic salts, specifically to maintain favorable charge or electrostatic interactions between the target monoclonal antibody and positively charged bead surface.

The cross-flow channel size of the positive charge-based, fluidic purification module is dependent on the solution viscosity and magnetic resin bead concentration, and input flow rate and throughput volume. The piezoelectric or acoustic actuator considers the physical location and the energy (e.g., frequency) to enable desired magnetic resin bead deflection or manipulation of the magnetic resin bead flow path, and the piezoelectric crystal type. The dielectrophoretic electrodes consider selective-type and design to enable desired magnetic resin bead deflection, the number of electrodes and spacing to enable desired bead deflection, the voltage applied to enable desired bead deflection, and the electrode material.

The magnetic field strength and field effect are dependent on the flow rate and magnetic resin bead concentration, size, saturation magnetization, and magnetic susceptibility, and/ or the proximity to the cross-flow channel. In embodiments, the magnetic field strength ranges from about 0.01 Tesla to about 1 Tesla (e.g., up to about 1 Tesla). The magnetic resin bead concentration is dependent on the desired charge or electrostatic association capacity, desired solution viscosity, and the magnetic resin bead size is dependent on the surface area-to-volume ratio required to enable adequate fluid dynamics for equilibration and charge or electrostatic interactions, for example, solution viscosity dependency and surface charge density dependency, respectively. In embodiments, the magnetic resin beads have sub-micron to micron diameters.

The material selection of the positive charge-based, fluidic purification module is important for negligible leachables and robust stability to enable recycling and reuse in the positive charge-based, fluidic purification module.

The cationic surface selection for the positive charge-based, fluidic purification module is important and may include cationic polymers, net positively charged peptides or proteins, amine functionality, and selection is based on achieving appropriate charge or electrostatic interactions and association stability between the positively charged bead surface and the biological product within a defined buffer (pH and ionic strength).

The at least one dissociation equilibration vessel volume and agitation capabilities of the positive charge-based, fluidic purification module consider the input flow rate and throughput, equilibration time to enable dissociation kinetics, a dissociation buffer at 10× to enable dilution during equilibration time to arrive at 1× final buffer salt concentration. The dissociation buffer is dependent on the strength of the charge or electrostatic interactions between the biological product of interest (e.g., a monoclonal antibody) and the magnetic resin bead cationic surface, and variations may include pH, ionic strength, use of surfactants, or use of organic and/or inorganic salts. In embodiments, multiple dissociation equilibration vessels comprising discrete buffers varying pH, ionic strength, or any combination thereof, are utilized sequentially to create a gradient dissociation effect.

The throughput of the positive charge-based, fluidic purification module may be increased by multiplexing multiple fluidic devices or chips, in series or in parallel. Moreover, multiple fluidic devices or chips in series or in parallel may be required to enable complete purification. Additionally, a regeneration equilibration vessel might require a permanent magnetic and a waste line to maintain correct concentration of magnetic resin beads and allow for effective recycling. Viral inactivation and removal may be accomplished during the association or dissociation buffer equilibration and subsequent fluidic processing steps depending on buffer composition and pH.

The positive charge-based, fluidic purification module may include at least one tangential flow filtration system operated in fed-batch or perfusion mode to concentrate and buffer exchange the fraction containing the biological product.

The positive charge-based, fluidic purification module may include in-line sampling ports for in-process analytical testing and/or in-line analytical measurement techniques. Further, the in-line analytical measurement techniques (e.g., flow sensors, pressure sensors, optical density measurement devices, UV detectors, RI detectors) may be used to enable feedback control mechanisms with the process.

Unlike the traditional packed column chromatography and column-switching chromatography methods commonly used in the art, the positive charge-based, fluidic purification module utilizes a mobile affinity resin capable of in situ regeneration and recycling to enable more efficient use of the resin and to enable continuous processing in a small-footprint without concerns of traditional column capacity limitations.

Negative Charge-Based, Fluidic Purification Module

As provided herein, a negative charge-based, fluidic purification module for separating a mixture into two or more fractions, at least one fraction containing a biological product is described. The negative charge-based, fluidic purification module includes at least one inlet and at least one outlet configured to permit continuous fluid flow between the at least one inlet and the at least one outlet and wherein the flow rate may be, for example, consistent and constant during steady-state operation. Moreover, the negative charge-based, fluidic purification module includes a suspension of anionic magnetic resin beads, wherein the magnetic resin bead surface comprises anionic functionality configured to selectively associate with said biological product based on charge or electrostatic interactions at a specific pH and ionic strength.

The negative charge-based, fluidic purification module includes at least one association equilibration vessel to allow for charge or electrostatic association of the biological product with the magnetic resin bead surface; at least one dissociation equilibration vessel to allow for dissociation of the biological product from the magnetic resin bead surface; at least one first hybrid cross-flow fluidic device or chip (e.g., a microfluidic, a mesofluidic, a millifluidic, a macrofluidic device or chip, or any combination thereof) comprising at least one magnetic field and at least one of a piezoelectric component or a dielectrophoretic electrode configured to generate or induce a unidirectional force to manipulate the flow path of the magnetic resin beads in said heterogeneous mixture, and a cross-flow channel to separate the magnetic resin beads bound to the biological product from small impurities in the heterogeneous mixture (FIG. 28); at least one second hybrid cross-flow fluidic device or chip (e.g., a microfluidic, a mesofluidic, a millifluidic, a macrofluidic device or chip, or any combination thereof) comprising at least one magnetic field and at least one of a piezoelectric component or a dielectrophoretic electrode configured to generate or induce a unidirectional force to manipulate the flow path of said magnetic resin beads from said biological product, and a cross-flow channel to separate the magnetic resin beads from said biological product (FIG. 28); at least two buffer systems; at least one magnetic resin bead regeneration buffer system; at least one regeneration equilibration vessel configured to enable recycling of said magnetic resin beads; at least one collection vessel; at least one sensor or detector; and, at least one fluid handling pump.

The equipment design for the negative charge-based, fluidic purification module (FIG. 30) enables continuous, biological magnetic purification and provides for a small footprint.

The at least one association equilibration vessel volume and agitation capabilities of the negative charge-based, fluidic purification module consider the input flow rate and throughput, equilibration time and agitation rate to enable association kinetics, and magnetic resin bead concentration and charge or electrostatic association capacity. The buffer for the negative charge-based, fluidic purification module is dependent on the biological product of interest (e.g., a monoclonal antibody) and the small impurities to be removed. Considerations for the buffer include pH, ionic strength, use of surfactants, or use of organic and/or inorganic salts, specifically to maintain favorable charge or electrostatic interactions between the target monoclonal antibody and negatively charged bead surface.

The cross-flow channel size of the negative charge-based, fluidic purification module is dependent on the solution viscosity and magnetic resin bead concentration, and input flow rate and throughput volume. The piezoelectric or acoustic actuator considers the physical location and the energy (e.g., frequency) to enable desired magnetic resin bead deflection or manipulation of the magnetic resin bead flow path, and the piezoelectric crystal type. The dielectrophoretic electrodes consider selective-type and design to enable desired magnetic resin bead deflection, the number of electrodes and spacing to enable desired bead deflection, the voltage applied to enable desired bead deflection, and the electrode material.

The magnetic field strength and field effect are dependent on the flow rate and magnetic resin bead concentration, size, saturation magnetization, and magnetic susceptibility, and/or the proximity to the cross-flow channel. In embodiments, the magnetic field strength ranges from about 0.01 Tesla to about 1 Tesla (e.g., up to about 1 Tesla). The magnetic resin bead concentration is dependent on the desired charge or electrostatic association capacity, desired solution viscosity, and the magnetic resin bead size is dependent on the surface area-to-volume ratio required to enable adequate fluid dynamics for equilibration and charge or electrostatic interactions, for example, solution viscosity dependency and surface charge density dependency, respectively. In embodiments, the magnetic resin beads have sub-micron to micron diameters.

The material selection of the negative charge-based, fluidic purification module is important for negligible leachables and robust stability to enable recycling and reuse in the negative charge-based, fluidic purification module.

The anionic surface selection for the negative charge-based, fluidic purification module is important and may include anionic polymers, net negatively charged peptides or proteins, carboxyl functionality, and selection is based on achieving appropriate charge or electrostatic interactions and association stability between the negatively charged bead surface and the biological product within a defined buffer (pH and ionic strength).

The at least one dissociation equilibration vessel volume and agitation capabilities of the negative charge-based, fluidic purification module consider the input flow rate and throughput, equilibration time to enable dissociation kinetics, a dissociation buffer at 10× to enable dilution during equilibration time to arrive at 1× final buffer salt concentration. The dissociation buffer is dependent on the strength of the charge or electrostatic interactions between the biological product of interest (e.g., a monoclonal antibody) and the magnetic resin bead anionic surface, and variations may include pH, ionic strength, use of surfactants, or use of organic and/or inorganic salts. In embodiments, multiple dissociation equilibration vessels comprising discrete buffers varying pH, ionic strength, or any combination thereof, are utilized sequentially to create a gradient dissociation effect.

The throughput of the negative charge-based, fluidic purification module may be increased by multiplexing multiple fluidic devices or chips, in series or in parallel. Moreover, multiple fluidic devices or chips in series or in parallel may be required to enable complete purification. Additionally, a regeneration equilibration vessel might require a permanent magnetic and a waste line to maintain correct concentration of magnetic resin beads and allow for effective recycling. Viral inactivation and removal may be accomplished during the association or dissociation buffer equilibration and subsequent fluidic processing steps depending on buffer composition and pH.

The negative charge-based, fluidic purification module may include at least one tangential flow filtration system operated in fed-batch or perfusion mode to concentrate and buffer exchange the fraction containing the biological product.

The negative charge-based, fluidic purification module may include in-line sampling ports for in-process analytical testing and/or in-line analytical measurement techniques. Further, the in-line analytical measurement techniques (e.g., flow sensors, pressure sensors, optical density measurement devices, UV detectors, RI detectors) may be used to enable feedback control mechanisms with the process.

Unlike the traditional packed column chromatography and column-switching chromatography methods commonly used in the art, the negative charge-based, magnetic purification module utilizes a mobile affinity resin capable of in situ regeneration and recycling to enable more efficient use of the resin and to enable continuous processing in a small-footprint without concerns of traditional column capacity limitations.

Affinity-Based TFF Purification Module

As provided herein, an affinity-based TFF purification module for separating a mixture into two or more fractions, at least one fraction containing a biological product is described. The affinity-based TFF purification module includes at least one inlet and at least one outlet configured to permit continuous fluid flow between the at least one inlet and the at least one outlet and wherein the flow rate is consistent and constant during steady-state operation. Moreover, the affinity-based TFF purification module includes a suspension of affinity resin beads, wherein the resin bead surface, without intent to be limiting, is coupled to Protein A, Protein G, Protein L, an antigenic protein, a protein, a receptor, an antibody, or an aptamer configured to selectively bind said biological product.

The affinity-based TFF purification module includes at least one equilibration vessel to allow for binding of the biological product to the resin bead surface and at least one first tangential flow filtration system comprising a hollow fiber membrane filter to separate the resin beads bound to the biological product from small impurities in the heterogeneous mixture; at least one low pH equilibration vessel to allow for de-binding of the biological product from the resin bead surface and at least one second tangential flow filtration system comprising a hollow fiber membrane filter to separate the resin beads from said unbound biological product; at least one regeneration equilibration vessel and at least one third tangential flow filtration system comprising a hollow fiber membrane filter to concentrate and buffer exchange the resin beads to enable their recycling and reuse; at least one collection vessel and at least one fourth tangential flow filtration system to allow for concentration and buffer exchange of the biological product; at least two buffer systems; at least one resin bead recycling buffer system; at least one sensor or detector; and, at least one fluid handling pump.

Figure 31:
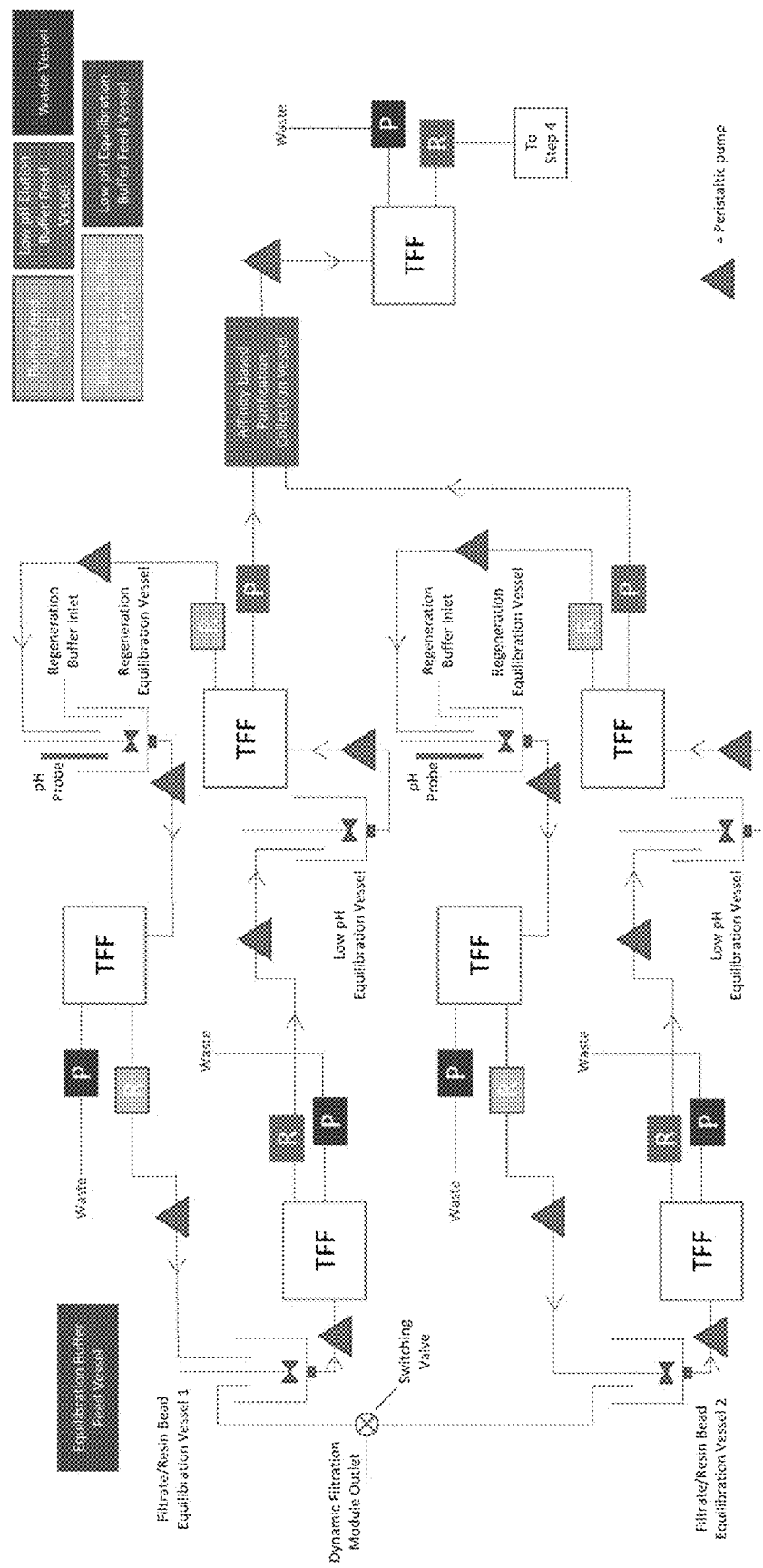
FIG. 31 shows an exemplary design schematic of an affinity-based purification apparatus comprising at least one tangential flow filtration systems.

The equipment design for the affinity-based TFF purification module (FIG. 31) enables continuous, biological purification and provides for a small footprint.

The at least one equilibration vessel volume and agitation capabilities of the affinity-based TFF purification module consider the input flow rate and throughput, equilibration time and agitation rate to enable binding kinetics, and resin bead concentration and binding capacity. The equilibration buffer for the affinity-based TFF purification module is dependent on the biological product of interest (e.g., a monoclonal antibody) and the small impurities to be removed. Considerations for the buffer include pH, ionic strength, use of surfactants, or use of organic and/or inorganic salts.

The hollow fiber membrane filter length and surface area of the affinity-based TFF purification module is dependent on the solution viscosity, small impurities and resin bead concentration, and input flow rate and throughput volume. The hollow fiber membrane material is selected from low protein binding materials, including, but not limited to, PES, mPES, or MCE. The pore size of the hollow fiber membrane is selected from the range of about 10 kDa to about 1 μm. The inner diameter of the hollow fiber membrane is selected from the range of about 0.5 mm to about 5 mm.

The resin bead concentration is dependent on the desired binding capacity, desired solution viscosity, and the resin bead size is dependent on the surface area-to-volume ratio to enable adequate fluid dynamics for equilibration and affinity interactions, for example, solution viscosity dependency and surface ligand density dependency, respectively. In embodiments, the resin beads have micron diameters.

The resin bead selection of the affinity-based TFF purification module is important for negligible leachables and robust stability to enable recycling and reuse of the affinity-based purification module.

The at least one low pH equilibration vessel volume and agitation capabilities of the affinity-based TFF purification module consider the input flow rate and throughput, equilibration time to enable de-binding kinetics, and a low pH elution buffer, for example, a low pH elution buffer at 10× to enable dilution during equilibration time to arrive at 1× final buffer salt concentration. The low pH elution buffer is dependent on the binding affinity of biological product of interest (e.g., a monoclonal antibody) for the resin bead surface ligand, and variations may include pH, ionic strength, or use of organic and/or inorganic salts.

The at least one regeneration equilibration vessel of the affinity-based TFF purification module is used in combination with the at least one third tangential flow filtration system to allow for concentration and buffer exchange of the resin beads to return the resin beads to their initial condition, thus, enabling recycling and reuse of the resin beads.

The at least one collection vessel of the affinity-based TFF purification module is used in combination with the at least one fourth tangential flow filtration system to allow for concentration and buffer exchange of the fraction containing the biological product.

In embodiments, the at least one equilibration vessel, the at least one low pH equilibration vessel, and the at least one regeneration equilibration vessel of the affinity-based TFF purification module may comprise a single vessel that is transitioned between the corresponding tangential flow filtration systems to enable purification and regeneration of the resin beads with appropriate buffers, while maintaining continuous flow of the filtrate via at least one additional vessel on a parallel flow path.

In embodiments, the regeneration of the resin beads may be accomplished with the at least one low pH equilibration vessel and the at least one second tangential flow filtration system of the affinity-based TFF purification module configured to comprise both the low pH elution buffer and the regeneration buffer to enable purification, concentration and buffer exchange, thus regenerating the resin beads without necessitating a separate regeneration equilibration vessel and corresponding tangential flow filtration system.

Viral inactivation and/or removal may be accomplished during the low pH elution buffer equilibration and subsequent fluidic processing steps depending on buffer composition and pH.

The affinity-based TFF purification module may include in-line sampling ports for in-process analytical testing and/or in-line analytical measurement techniques. Further, the in-line analytical measurement techniques (e.g., flow sensors, pressure sensors, optical density measurement devices, UV detectors, RI detectors) may be used to enable feedback control mechanisms with the process.

Unlike the traditional packed column chromatography and column-switching chromatography methods commonly used in the art, the affinity-based TFF purification module utilizes a mobile affinity resin capable of in situ regeneration and recycling to enable more efficient use of the resin and to enable continuous processing in a small-footprint without concerns of traditional column capacity limitations.

Positive Charge-Based TFF Purification Module

As provided herein, a positive charge-based TFF purification module for separating a mixture into two or more fractions, at least one fraction containing a biological product is described. The positive charge-based TFF purification module includes at least one inlet and at least one outlet configured to permit continuous fluid flow between the at least one inlet and the at least one outlet and wherein the flow rate is consistent and constant during steady-state operation. Moreover, the positive charge-based TFF purification module includes a suspension of cationic resin beads, wherein the resin bead surface comprises cationic functionality configured to selectively associate with said biological product based on charge or electrostatic interactions at a specific pH and ionic strength.

The positive charge-based TFF purification module includes at least one association equilibration vessel to allow for charge or electrostatic association of the biological product with the resin bead surface and at least one first tangential flow filtration system comprising a hollow fiber membrane filter to separate the resin beads associated with the biological product from small impurities in the heterogeneous mixture; at least one dissociation equilibration vessel to allow for dissociation of the biological product from the resin bead surface and at least one second tangential flow filtration system comprising a hollow fiber membrane filter to separate the resin beads from said dissociated biological product; at least one regeneration equilibration vessel and at least one third tangential flow filtration system comprising a hollow fiber membrane filter to concentrate and buffer exchange the resin beads to enable their recycling and reuse; at least one collection vessel and at least one fourth tangential flow filtration system to allow for concentration and buffer exchange of the biological product; at least two buffer systems; at least one resin bead recycling buffer system; at least one sensor or detector; and, at least one fluid handling pump.

Figure 32:
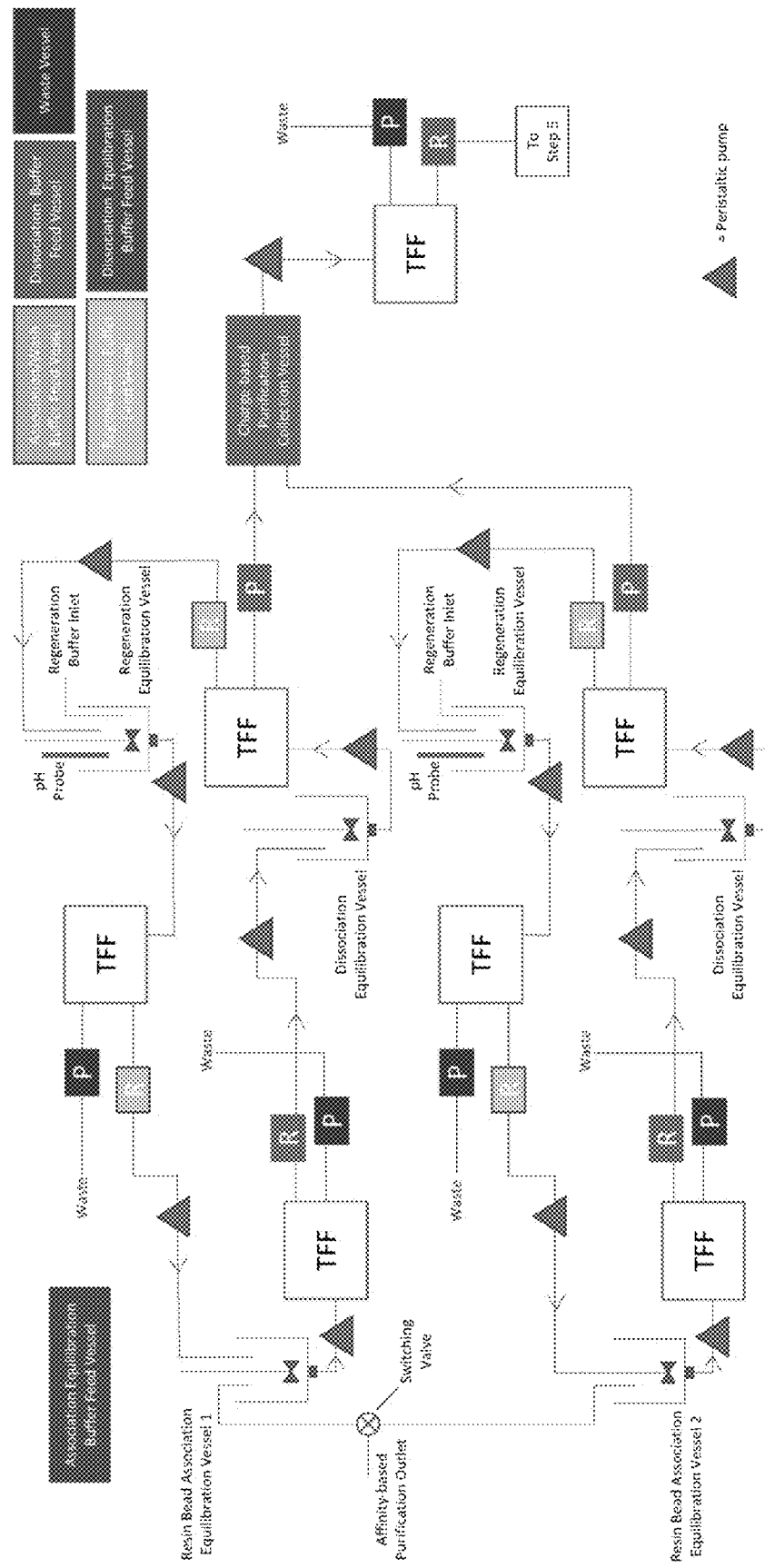
FIG. 32 shows an exemplary design schematic of a charge-based purification apparatus comprising at least one tangential flow filtration systems.

The equipment design for the positive charge-based TFF purification module (FIG. 32) enables continuous, biological purification and provides for a small footprint.

The at least one association equilibration vessel volume and agitation capabilities of the positive charge-based TFF purification module consider the input flow rate and throughput, equilibration time and agitation rate to enable association kinetics, and resin bead concentration and charge or electrostatic association capacity. The association buffer for the positive charge-based TFF purification module is dependent on the biological product of interest (e.g., a monoclonal antibody) and the small impurities to be removed. Considerations for the buffer include pH, ionic strength, use of surfactants, or use of organic and/or inorganic salts, specifically to maintain favorable charge or electrostatic interactions between the target monoclonal antibody and positively charged bead surface.

The hollow fiber membrane filter length and surface area of the positive charge-based TFF purification module is dependent on the solution viscosity, small impurities and resin bead concentration, and input flow rate and throughput volume. The hollow fiber membrane material is selected from low protein binding materials, including, but not limited to, PES, mPES, or MCE. The pore size of the hollow fiber membrane is selected from the range of about 10 kDa to about 1 µm. The inner diameter of the hollow fiber membrane is selected from the range of about 0.5 mm to about 5 mm.

The resin bead selection of the positive charge-based TFF purification module is important for negligible leachables and robust stability to enable recycling and reuse in the positive charge-based TFF purification module.

The cationic surface selection for the positive charge-based TFF purification module is important and may include cationic polymers, net positively charged peptides or proteins, amine functionality, and selection is based on achieving appropriate charge or electrostatic interactions and association stability between the positively charged bead surface and the biological product within a defined buffer (pH and ionic strength).

The at least one dissociation equilibration vessel volume and agitation capabilities of the positive charge-based TFF purification module consider the input flow rate and throughput, equilibration time to enable dissociation kinetics, and a dissociation buffer, for example, a dissociation buffer at 10× to enable dilution during equilibration time to arrive at 1× final buffer salt concentration. The dissociation buffer is dependent on the strength of the charge or electrostatic interactions between the biological product of interest (e.g., a monoclonal antibody) and the resin bead cationic surface, and variations may include pH, ionic strength, use of surfactants, or use of organic and/or inorganic salts. In some aspects, multiple dissociation equilibration vessels are utilized with multiple tangential flow filtration systems to achieve a gradient dissociation, for example, a pH gradient or an ionic strength gradient.

The at least one regeneration equilibration vessel of the positive charge-based TFF purification module is used in combination with the at least one third tangential flow filtration system to allow for concentration and buffer exchange of the resin beads to return the resin beads to their initial condition, thus, enabling recycling and reuse of the resin beads.

The at least one collection vessel of the positive charge-based TFF purification module is used in combination with the at least one fourth tangential flow filtration system to allow for concentration and buffer exchange of the fraction containing the biological product.

In embodiments, the at least one association equilibration vessel, the at least one dissociation equilibration vessel, and the at least one regeneration equilibration vessel of the positive charge-based TFF purification module may comprise a single vessel that is transitioned between the corresponding tangential flow filtration systems to enable purification and regeneration of the resin beads with appropriate buffers, while maintaining continuous flow of the filtrate via at least one additional vessel on a parallel flow path.

In embodiments, the regeneration of the resin beads may be accomplished with solely the at least one dissociation equilibration vessel and the at least one second tangential flow filtration system of the positive charge-based TFF purification module configured to comprise both the low pH elution buffer and the regeneration buffer to enable purification, concentration and buffer exchange, thus regenerating the resin beads without necessitating a separate regeneration equilibration vessel and corresponding tangential flow filtration system.

Viral inactivation and/or removal may be accomplished during the association or dissociation buffer equilibration and subsequent fluidic processing steps depending on buffer composition and pH.

The positive charge-based TFF purification module may include in-line sampling ports for in-process analytical testing and/or in-line analytical measurement techniques. Further, the in-line analytical measurement techniques (e.g., flow sensors, pressure sensors, optical density measurement devices, UV detectors, RI detectors) may be used to enable feedback control mechanisms with the process.

Unlike the traditional packed column chromatography and column-switching chromatography methods commonly used in the art, the positive charge-based TFF purification module utilizes a mobile affinity resin capable of in situ regeneration and recycling to enable more efficient use of the resin and to enable continuous processing in a small-footprint without concerns of traditional column capacity limitations.

Negative Charge-Based TFF Purification Module

As provided herein, a negative charge-based TFF purification module for separating a mixture into two or more fractions, at least one fraction containing a biological product is described. The negative charge-based TFF purification module includes at least one inlet and at least one outlet configured to permit continuous fluid flow between the at least one inlet and the at least one outlet and wherein the flow rate is consistent and constant during steady-state operation. Moreover, the negative charge-based TFF purification module includes a suspension of anionic resin beads, wherein the resin bead surface comprises anionic functionality configured to selectively associate with said biological product based on charge or electrostatic interactions at a specific pH and ionic strength.

The negative charge-based TFF purification module includes at least one association equilibration vessel to allow for charge or electrostatic association of the biological product with the resin bead surface and at least one first tangential flow filtration system comprising a hollow fiber membrane filter to separate the resin beads associated with the biological product from small impurities in the heterogeneous mixture; at least one dissociation equilibration vessel to allow for dissociation of the biological product from the resin bead surface and at least one second tangential flow filtration system comprising a hollow fiber membrane filter to separate the resin beads from said dissociated biological product; at least one regeneration equilibration vessel and at least one third tangential flow filtration system comprising a hollow fiber membrane filter to concentrate and buffer exchange the resin beads to enable their recycling and reuse; at least one collection vessel and at least one fourth tangential flow filtration system to allow for concentration and buffer exchange of the biological product; at least two buffer systems; at least one resin bead recycling buffer system; at least one sensor or detector; and, at least one fluid handling pump.

The equipment design for the negative charge-based TFF purification module (FIG. 32) enables continuous, biological purification and provides for a small footprint.

The at least one association equilibration vessel volume and agitation capabilities of the negative charge-based TFF purification module consider the input flow rate and throughput, equilibration time and agitation rate to enable association kinetics, and resin bead concentration and charge or electrostatic association capacity. The association buffer for the negative charge-based TFF purification module is dependent on the biological product of interest (e.g., a monoclonal antibody) and the small impurities to be removed. Considerations for the buffer include pH, ionic strength, use of surfactants, or use of organic and/or inorganic salts, specifically to maintain favorable charge or electrostatic interactions between the target monoclonal antibody and negatively charged bead surface.

The hollow fiber membrane filter length and surface area of the negative charge-based TFF purification module is dependent on the solution viscosity, small impurities and resin bead concentration, and input flow rate and throughput volume. The hollow fiber membrane material is selected from low protein binding materials, including, but not limited to, PES, mPES, or MCE. The pore size of the hollow fiber membrane is selected from the range of about 10 kDa to about 1 μm. The inner diameter of the hollow fiber membrane is selected from the range of about 0.5 mm to about 5 mm.

The resin bead selection of the negative charge-based TFF purification module is important for negligible leachables and robust stability to enable recycling and reuse in the negative charge-based purification module.

The anionic surface selection for the negative charge-based TFF purification module is important and may include anionic polymers, net negatively charged peptides or proteins, carboxyl functionality, and selection is based on achieving appropriate charge or electrostatic interactions and association stability between the negatively charged bead surface and the biological product within a defined buffer (pH and ionic strength).

The at least one dissociation equilibration vessel volume and agitation capabilities of the negative charge-based TFF purification module consider the input flow rate and throughput, equilibration time to enable dissociation kinetics, and a dissociation buffer, for example, a dissociation buffer at 10× to enable dilution during equilibration time to arrive at 1× final buffer salt concentration. The dissociation buffer is dependent on the strength of the charge or electrostatic interactions between the biological product of interest (e.g., a monoclonal antibody) and the resin bead anionic surface, and variations may include pH, ionic strength, use of surfactants, or use of organic and/or inorganic salts. In some aspects, multiple dissociation equilibration vessels are utilized with multiple tangential flow filtration systems to achieve a gradient dissociation, for example, a pH gradient or an ionic strength gradient.

The at least one regeneration equilibration vessel of the negative charge-based TFF purification module is used in combination with the at least one third tangential flow filtration system to allow for concentration and buffer exchange of the resin beads to return the resin beads to their initial condition, thus, enabling recycling and reuse of the resin beads.

The at least one collection vessel of the negative charge-based TFF purification module is used in combination with the at least one fourth tangential flow filtration system to allow for concentration and buffer exchange of the fraction containing the biological product.

In embodiments, the at least one association equilibration vessel, the at least one dissociation equilibration vessel, and the at least one regeneration equilibration vessel of the negative charge-based TFF purification module may comprise a single vessel that is transitioned between the corresponding tangential flow filtration systems to enable purification and regeneration of the resin beads with appropriate buffers, while maintaining continuous flow of the filtrate via at least one additional vessel on a parallel flow path.

In embodiments, the regeneration of the resin beads may be accomplished with solely the at least one dissociation equilibration vessel and the at least one second tangential flow filtration system of the negative charge-based TFF purification module configured to comprise both the low pH elution buffer and the regeneration buffer to enable purification, concentration and buffer exchange, thus regenerating the resin beads without necessitating a separate regeneration equilibration vessel and corresponding tangential flow filtration system.

Viral inactivation and/or removal may be accomplished during the association or dissociation buffer equilibration and subsequent fluidic processing steps depending on buffer composition and pH.

The negative charge-based TFF purification module may include in-line sampling ports for in-process analytical testing and/or in-line analytical measurement techniques. Further, the in-line analytical measurement techniques (e.g., flow sensors, pressure sensors, optical density measurement devices, UV detectors, RI detectors) may be used to enable feedback control mechanisms with the process.

Unlike the traditional packed column chromatography and column-switching chromatography methods commonly used in the art, the negative charge-based TFF purification module utilizes a mobile affinity resin capable of in situ regeneration and recycling to enable more efficient use of the resin and to enable continuous processing in a small-footprint without concerns of traditional column capacity limitations.

Isoelectric Point-Based, Fluidic Purification Module

As provided herein, an isoelectric point-based, fluidic purification module for separating a mixture into two or more fractions, at least one fraction containing a biological product is described. The isoelectric point-based, fluidic purification module includes at least one inlet and at least one outlet configured to permit continuous fluid flow between the at least one inlet and the at least one outlet and wherein the flow rate may be, for example, consistent and constant during steady-state operation.

Figure 33:
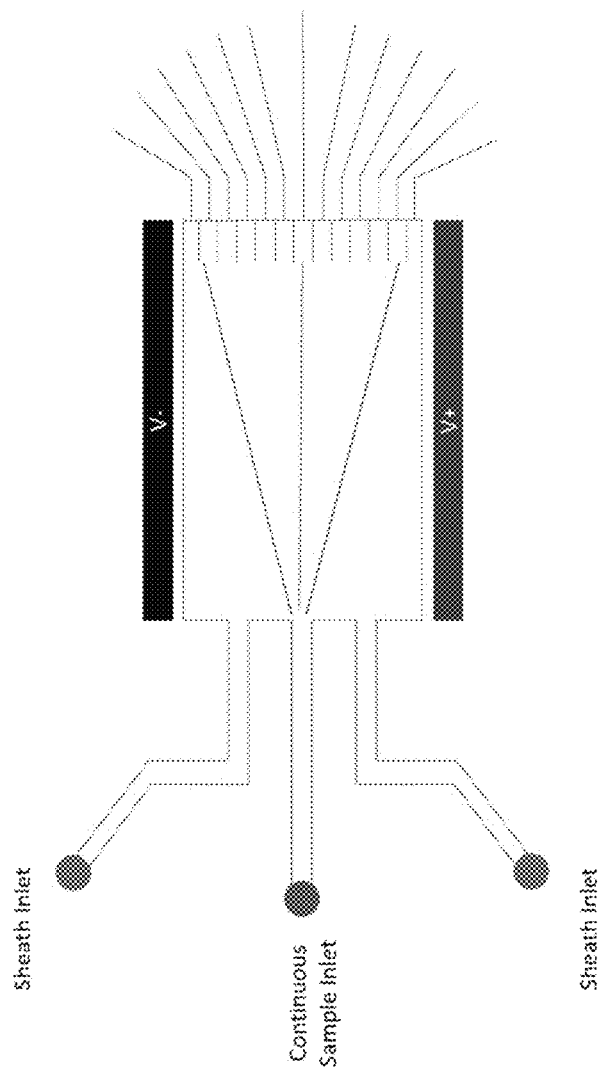
FIG. 33 shows an exemplary design schematic of an isoelectric point-based, fluidic purification apparatus comprising a fluidic device having a channel created between two parallel plates, an electric field orthogonal to the direction of the fluid flow, and an aqueous ionic solution.

In embodiments, the isoelectric point-based fluidic purification module includes at least one free-flow electrophoresis apparatus comprising a fluidic device (e.g., a mesofluidic, a millifluidic, a macrofluidic device, or any combination thereof) having a fluidic channel created between two parallel plates; an electric field or electric field gradient orthogonal to the fluid flow direction; an aqueous ionic solution (FIG. 33); at least one de-bubbling or de-gassing system to remove electrolysis bubbles near the point of generation by a vacuum system to create a bubble-free main separation channel and to enable continuous, long-term operation; at least one liquid circuit breaker; at least one buffer or ampholyte system; at least one electrode solution; at least one sensor or detector; at least one fluid handling pump; and at least one collection vessel.

Figure 34:
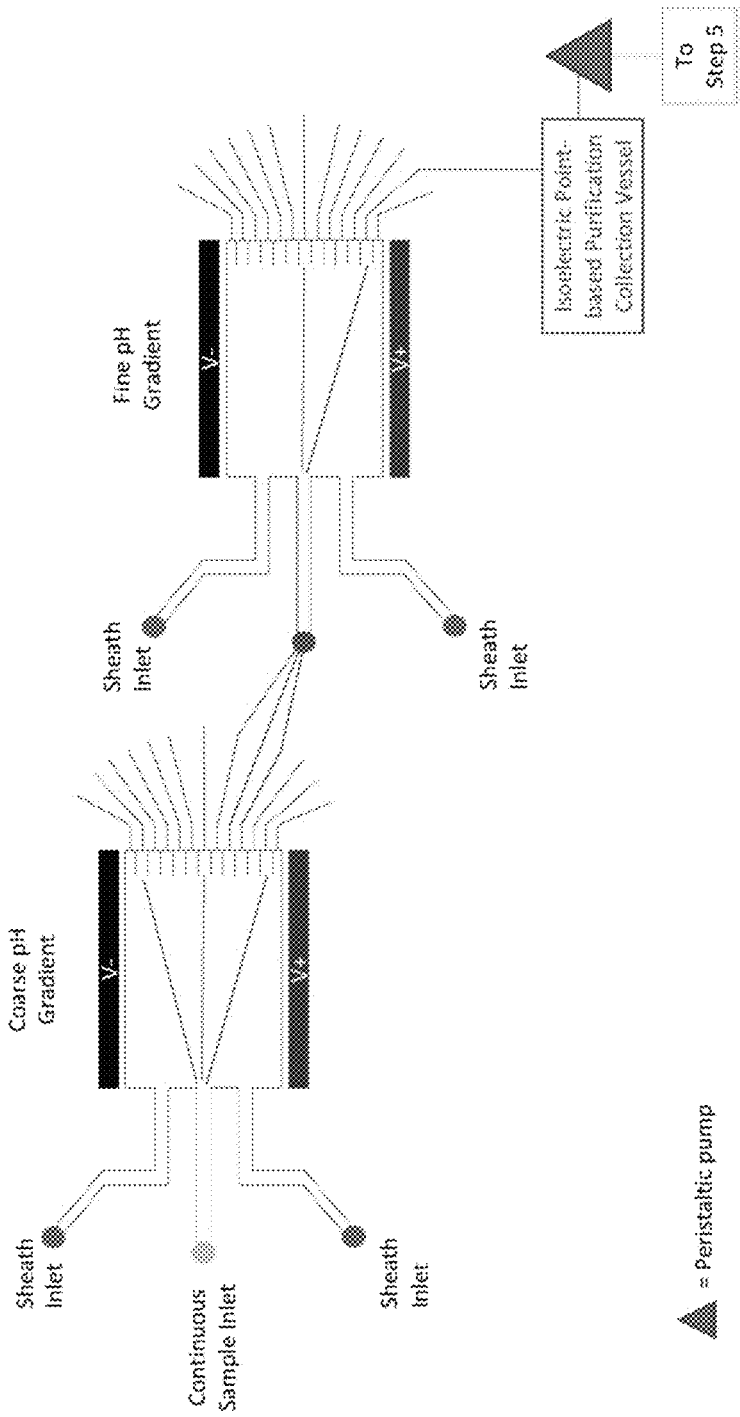
FIG. 34 shows an exemplary design schematic of a free-flow electrophoresis apparatus comprising a first fluidic device having a channel created between two parallel plates, an electric field orthogonal to the direction of the fluid flow, and a coarse pH gradient, and that is connected to a second fluidic device having a channel created between two parallel plates, an electric field orthogonal to the direction of the fluid flow, and a fine pH gradient, wherein the apparatus is capable of operating in isoelectric focusing mode.
Figure 35:
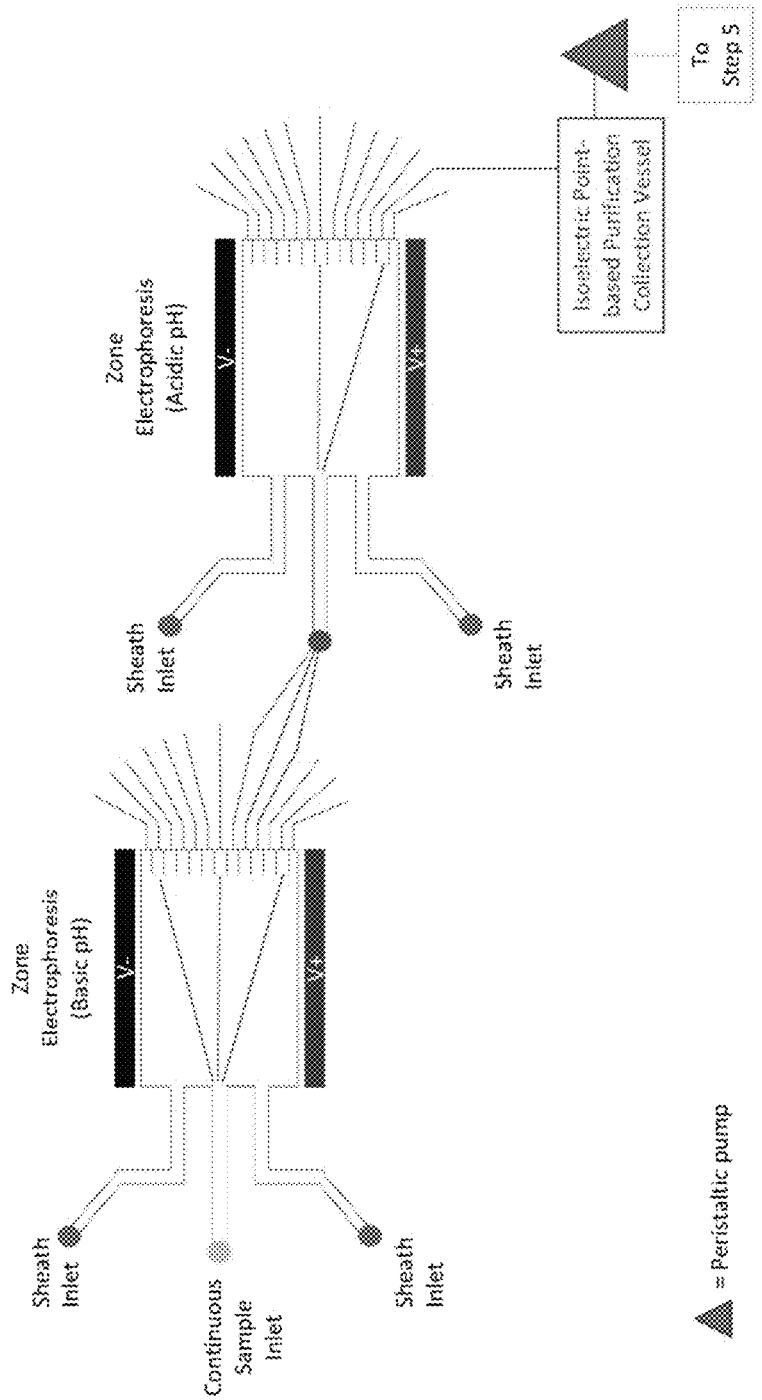
FIG. 35 shows an exemplary design schematic of a free-flow electrophoresis apparatus comprising a first fluidic device having a channel created between two parallel plates, an electric field orthogonal to the direction of the fluid flow, and a constant basic pH across the main separation channel, that is connected to a second fluidic device having a channel created between two parallel plates, an electric field orthogonal to the direction of the fluid flow, and a constant acidic pH across the main separation channel, wherein the apparatus is capable of operating in zone electrophoresis mode.
Figure 36:
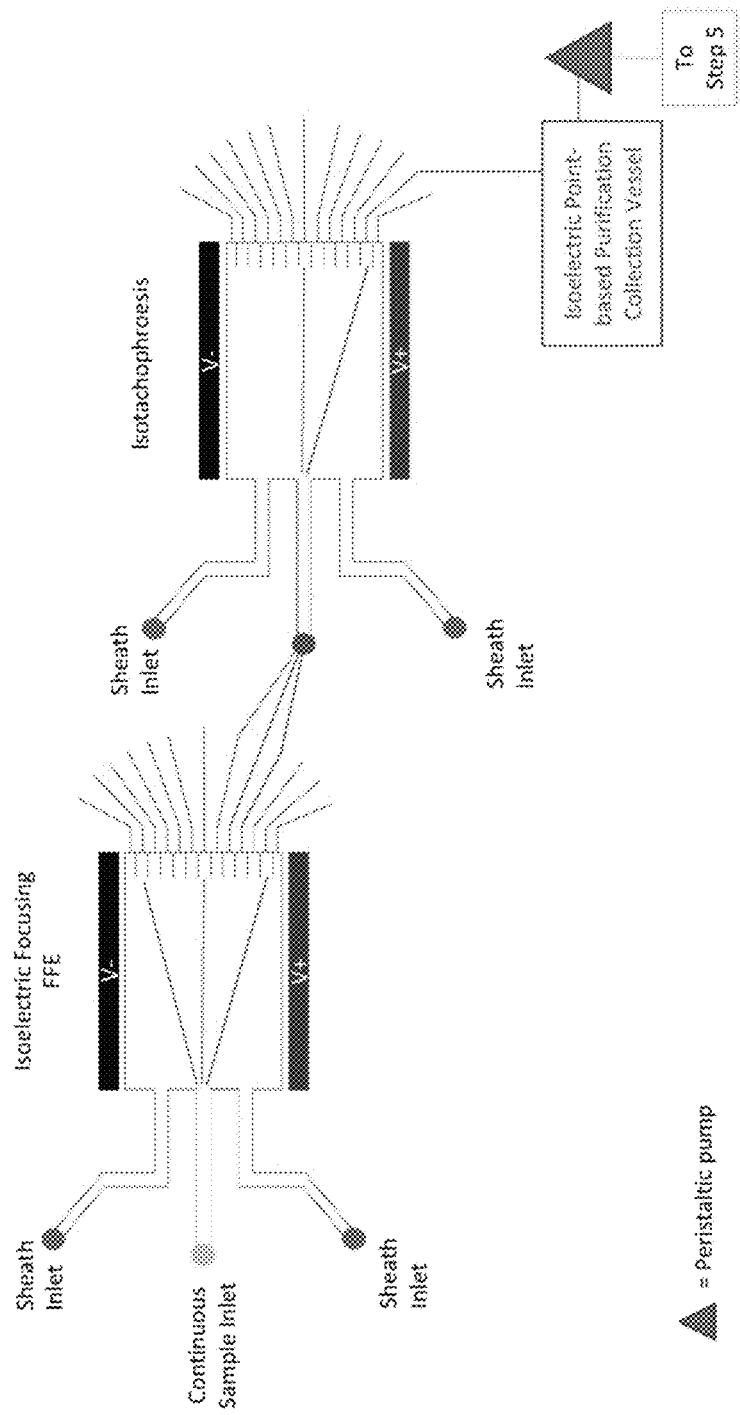
FIG. 36 shows an exemplary design schematic of a free-flow electrophoresis apparatus comprising a first fluidic device having a channel created between two parallel plates and an electric field orthogonal to the direction of the fluid flow capable of operating in isoelectric focusing mode that is connected to a second fluidic device having a channel created between two parallel plates and an electric field orthogonal to the direction of the fluid flow capable of operating in isotachophoresis mode.

In other embodiments, the isoelectric point-based, fluidic purification module includes at least one first free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, an aqueous ionic solution; and at least one second free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and an aqueous ionic solution; wherein each free-flow electrophoresis apparatus is connected in series and is capable of operating in an independent mode of operation to enable purification (FIGS. 34-36). For example, without intent to be limiting, the at least one first free-flow electrophoresis apparatus may operate in an isoelectric focusing mode and the at least one second free-flow electrophoresis apparatus may operate in an isotachophoresis mode to increase separation resolution.

In embodiments, the isoelectric point-based, fluidic purification module comprises at least one first free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and a coarse pH gradient across the main separation channel (e.g., a pH range from about 2 to about 10); and at least one second free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and a fine pH gradient across the main separation channel (e.g., a pH range from about 5 to about 8); at least one de-bubbling or de-gassing system; at least one liquid circuit breaker; at least one buffer or ampholyte system; at least one electrode solution; at least one collection vessel; at least one sensor or detector; and at least one fluid handling pump (FIG. 34). In examples, the at least one first free-flow electrophoresis apparatus and the at least one second free-flow electrophoresis apparatus are connected in series and operated in an isoelectric focusing modes.

In embodiments, the isoelectric point-based, fluidic purification module comprises at least one first free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and constant basic pH across the main separation channel with no pH gradient (e.g., a pH of greater than 7); and at least one second free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and a constant acidic pH across the main separation channel with no pH gradient (e.g., a pH of less than 7); at least one de-bubbling or de-gassing system; at least one liquid circuit breaker; at least one buffer or ampholyte system; at least one electrode solution; at least one collection vessel; at least one sensor or detector; and at least one fluid handling pump (FIG. 35). In examples, the at least one first free-flow electrophoresis apparatus and the at least one second free-flow electrophoresis apparatus are connected in series and operated in zone electrophoresis modes.

In embodiments, the isoelectric point-based, fluidic purification module comprises at least one first free-flow electrophoresis apparatus comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and a pH gradient across the main separation channel (e.g., a pH range from about 4 to about 9); and at least one second free-flow electrophoresis apparatus comprising a fluidic device (e.g., a mesofluidic, a millifluidic, a macrofluidic device, or any combination thereof) comprising a fluidic channel created between two parallel plates, an electric field or electric field gradient orthogonal to the fluid flow direction, and both an acidic pH gradient and a basic pH gradient separated by a spacer solution (e.g. NaCl solution); at least one de-bubbling or de-gassing system; at least one liquid circuit breaker; at least one buffer or ampholyte system; at least one electrode solution; at least one collection vessel; at least one sensor or detector; and at least one fluid handling pump (FIG. 36). In examples, the at least one first free-flow electrophoresis apparatus and the at least one second free-flow electrophoresis apparatus are connected in series and operated in an isoelectric focusing mode and an isotachophoresis mode, respectively.

Figure 37:
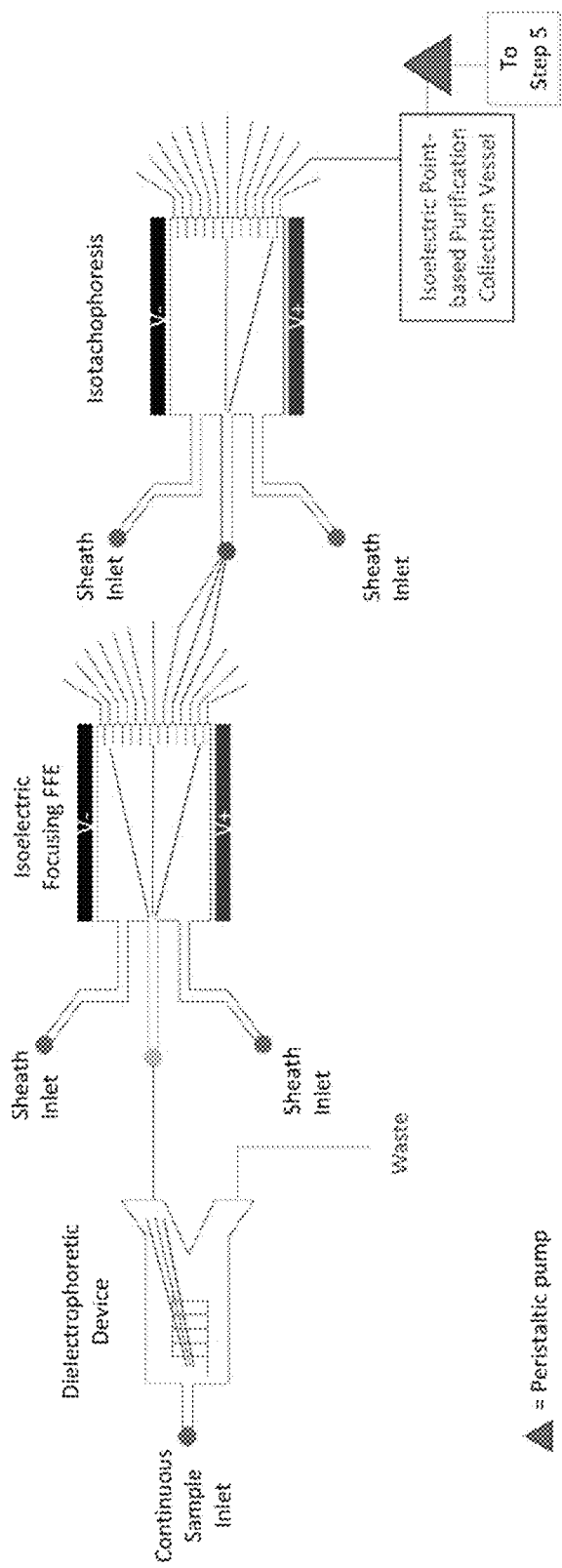
FIG. 37 shows an exemplary design schematic of a free-flow electrophoresis apparatus comprising a first fluidic device having a channel with a selective dielectrophoretic electrode to pre-sort a mixture that is connected to a second fluidic device having a channel created between two parallel plates and an electric field orthogonal to the direction of the fluid flow capable of operating in isoelectric focusing mode that is connected to a third fluidic device having a channel created between two parallel plates and an electric field orthogonal to the direction of the fluid flow capable of operating in isotachophoresis mode.

Alternatively, the isoelectric point-based, fluidic purification module includes at least one first fluidic device (e.g., a mesofluidic, a millifluidic, a macrofluidic device, or any combination thereof) comprising a fluidic channel having at least one dielectrophoretic electrode capable of inducing a defined, unidirectional force; at least one second fluidic device comprising a free-flow electrophoresis apparatus having a fluidic channel created between two parallel plates, an electric field or electric field gradient orthogonal to the fluid flow direction, and a pH gradient across the main separation channel (e.g., a pH range from about 4 to about 9); and at least one third fluidic device comprising a free-flow electrophoresis apparatus having a fluidic channel created between two parallel plates, an electric field or electric field gradient orthogonal to the fluid flow direction, and both an acidic pH gradient and a basic pH gradient separated by a spacer solution (e.g. NaCl solution); at least one de-bubbling or de-gassing system; at least one liquid circuit breaker; at least one buffer or ampholyte system; at least one electrode solution; at least one collection vessel; at least one sensor or detector; and at least one fluid handling pump (FIG. 37). In examples, the at least one first fluidic device having at least one selective dielectrophoretic electrode, the at least one second fluidic device comprising a free-flow electrophoresis apparatus and the at least one third fluidic device comprising a free-flow electrophoresis apparatus are connected in series and operated in manner to pre-sort the mixture containing a biological product prior to purification via an isoelectric focusing mode and an isotachophoresis mode by the second and third fluidic devices or chips, respectively.

In embodiments, additional, subsequent free-flow electrophoresis apparatuses comprising a fluidic device (e.g., a mesofluidic, a millifluidic, a macrofluidic device, or any combination thereof) having a fluidic channel created between two parallel plates, an electric field or electric field gradient orthogonal to the fluid flow direction, and an aqueous ionic solution may be used to enable enhanced separation resolution. For example, without intent to be limiting, an additional free-flow electrophoresis apparatus having an ampholyte solution capable of generating a refined pH gradient across the main separation channel (e.g., a pH range from about 7.1 to about 7.6), may be used to increase the separation resolution of a monoclonal antibody.

The equipment design for the isoelectric point-based, fluidic purification module (FIGS. 33-37) enables continuous, biological purification and provides for a small footprint.

In embodiments, the isoelectric point-based fluidic purification apparatus further comprises at least two electrodes (e.g. platinum wire electrodes) to function as an anode or a cathode.

In embodiments, the isoelectric point-based, fluidic purification apparatus includes at least one electrode solution. In some embodiments, the at least one electrode solution comprises an electrolyte solution configured to contact and enable the appropriate function of an anode or a cathode, for example, sulfuric acid and sodium hydroxide, respectively. In other embodiments, the at least one electrode solution comprises the same ampholyte composition as is present in the main separation channel configured to enable the appropriate function of an anode or a cathode, for example, Tris buffered saline flowing through the main separation channel, the anode channel, and the cathode channel.

Figure 38:
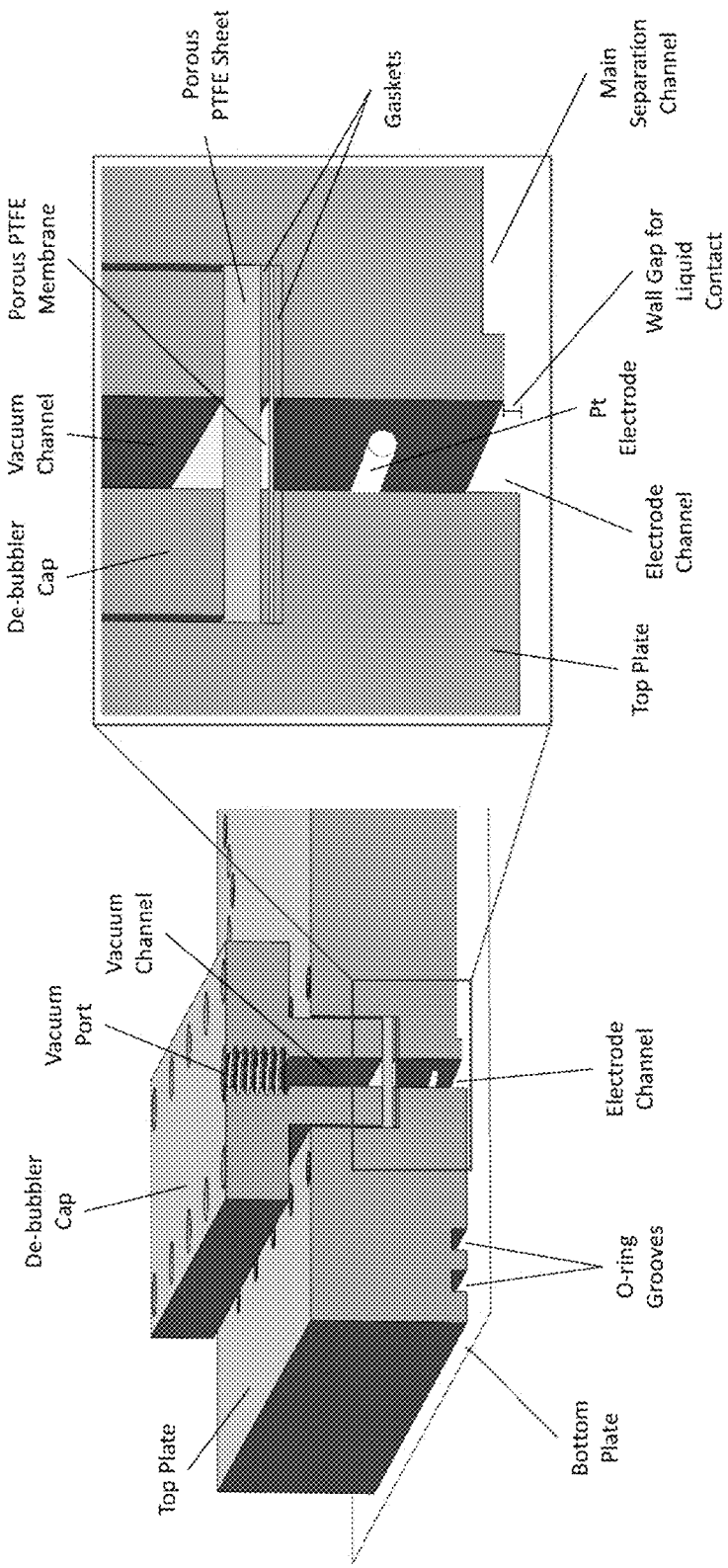
FIG. 38 shows the design of an exemplary de-bubbling and de-gassing system that removes electrolysis bubbles directly from the electrode channels to create a bubble-free main separation channel.

In embodiments, the isoelectric point-based fluidic purification apparatus further comprises at least one de-bubbler system to continuously remove, via a vacuum system, $O_2$ and $H_2$ gas bubbles that evolve in the electrode channels under applied voltage (FIG. 38). In some embodiments, removal of electrolysis bubbles is essential to enable continuous operation for substantially long periods of time. Removal of the electrolysis bubbles directly from the electrode channels creates a bubble-free main separation channel. In examples, the de-bubbler system utilizes a hydrophobic PTFE membrane to create a water-tight seal atop the electrode channel that permits continuous removal of electrolysis bubbles at the point of generation by exposure to a vacuum system. In examples, the vacuum gauge pressure ranges from about −0.05 bar to about −0.4 bar.

The fluidic channel dimensions and the applied voltage across the channel to generate the orthogonal electric field or electric field gradient to enable protein separation at high flow rates (e.g., greater than 1 mL/min) may necessitate the implementation of a robust active cooling system or heat sink to dissipate Joule heat and maintain desired operating temperatures, for example, between about 4° C. and about 50° C., preferably from 4° C. to about 37° C., to ensure thermostability of the biological product (e.g., a monoclonal antibody). For example, the active cooling system may comprise an aluminum thermal chuck containing a chilled, circulating water/propylene glycol jacket with a feedback control loop to maintain a constant temperature ranging from about 10° C. to about 25° C. Further, the dimensions of the channel are critical parameters to enable adequate protein separation and is dependent on the number of proteins to be separated and their range of their respective isoelectric points.

The backpressure within the isoelectric point-based fluidic purification apparatus is dependent on the channel geometry and dimensions, the inlet and outlet opening and/or tubing diameters, and the input flow rate. In examples, the backpressure ranges from about 0.5 psi to about 10 psi. In some examples, the backpressure is controlled by, for example, without intent to be limiting, a needle valve.

Figure 39:
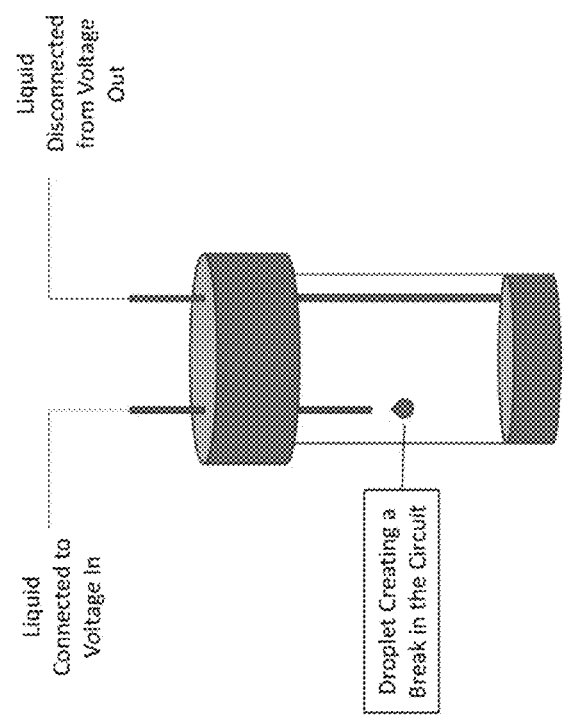
FIG. 39 shows an exemplary liquid circuit breaker that creates a break in the solution connected to applied voltage flowing from the outlet of a free-flow electrophoresis apparatus to at least one in-line sensor or detector.

In order to perform in-line sensing and detection, for example, with a flow sensor, a temperature sensor, a conductivity sensor, a pH sensor, a refractive index detector, a UV detector, a backpressure sensor, or any combination thereof, the solution must be voltage-free. In embodiments, the isoelectric point-based, fluidic purification module includes at least one liquid circuit breaker or disconnect downstream of the fluidic device and upstream of the at least one in-line sensor or detector to ensure the ability to perform sensing or detection in a voltage-free solution (FIG. 39).

The throughput of the isoelectric point-based, fluidic purification module may be increased by multiplexing multiple free-flow electrophoresis apparatuses, in series or in parallel. Moreover, multiple fluidic devices or chips in series or in parallel may be required to enable adequate purification. Viral inactivation and removal may be accomplished during the isoelectric point-based fluidic processing steps.

The isoelectric point-based, fluidic purification module may include in-line sampling ports for in-process analytical testing and/or in-line analytical measurement techniques are contemplated. Further, the in-line analytical measurement techniques (e.g., flow sensors, temperature sensors, pH sensors, conductivity sensors, pressure sensors, optical density measurement devices, UV detectors, RI detectors) may be used to enable feedback control mechanisms with the process.

Continuous Dynamic Filtration Approaches

The transport velocity of the rolled filter membrane across the membrane support structure may be constant or may change in response to a feedback mechanism (e.g., rotary encoder, a traction encoder wheel) that accounts for differences between the feed reel and the collection reel diameter arising from changes in the filter membrane thickness or diameter during operation. Alternatively, the transport of the rolled filter membrane across the membrane support structure may be stepped, wherein the vacuum is removed during the stepping and then reapplied following the stepping. In this mode of operation, the at least one output head may have an xy rastering or rθ rastering capability, motion along the z-axis, and/or at least one additional dynamic filtration apparatus operating in parallel may be utilized to maintain continuous operation. Moreover, the stepping phenomenon may also be accomplished by having a pick and place robotics system place individual membranes (e.g., a circular membrane piece) onto the membrane support structure, wherein the vacuum is removed during the pick and place mechanics and then reapplied following the placement. In this mode of operation, the at least one output head may have an xy rastering or rθ rastering capability, motion along the z-axis, and/or at least one additional dynamic filtration apparatus operating in parallel may be utilized to maintain continuous operation. Furthermore, modes of operation in which the filtrate is generated through utilizing positive pressure to drive a heterogeneous mixture across the filter membrane are also contemplated herein. For example, without intent to be limiting, when the dynamic filtration apparatus comprises a pick and place robotics system to place individual membranes, an xy rastering output head with motion along the z-axis may be used to make contact with the membrane surface to force a heterogeneous mixture across the membrane. Methods of pre-wetting the filter membrane to increase transport across the membrane is also contemplated herein. The at least one vacuum collection vessel may be used until full and subsequently equilibrated to atmospheric pressure or may be continuously emptied while under vacuum during operation. Additionally, the use of at least one additional dynamic filtration apparatus operated in parallel to enable continuous processing is also contemplated herein. Similarly, the dynamic filtration apparatus may comprise multiple feed reels of different types of filter membrane (e.g., material and/or pore size) that can be layered and transported at the same velocity across the active target region to provide enhanced filtration.

Continuous Loop Conveyor Apparatus Approaches

The at least one magnetic field in the continuous loop conveyor apparatuses performing the affinity-based, magnetic purification and/or charge-based, magnetic purification steps may be generated by an electromagnet or a permanent magnetic (e.g., a Neodymium magnet). The magnetic field may be applied as an on/off toggle or as permanently on (FIGS. 14, 15, 16, 17). When the magnetic field is generated by an electromagnet, on/off toggling may be accomplished by turning the electromagnet on or off. When the magnetic field is generated by a permanent magnet, on/off toggling may be accomplished by mechanically changing the placement of the magnet from far to within close proximity, for example, within 5 mm of the transport vessel wall surface. Alternatively, when the magnetic field is generated by a permanent magnet, on/off toggling may be accomplished by transport the vessel into and out of close proximity (e.g., within 5 mm) of the magnet. Further, the loop conveyor apparatuses may include multiple, discrete magnetic field locations, wherein said discrete magnetic field locations within the apparatuses may further require shielding. Additionally, mixing of the magnetic resin beads may be accomplished by placing the at least one transport vessel between two separate and opposing magnetic fields that toggle between states of on and off. Additionally, the use of at least one additional affinity-based, magnetic purification or charge-based, magnetic purification apparatus connected in parallel to enable continuous processing is also contemplated herein.

Continuous Pick and Place Robotics Apparatus Approaches

Figure 18:
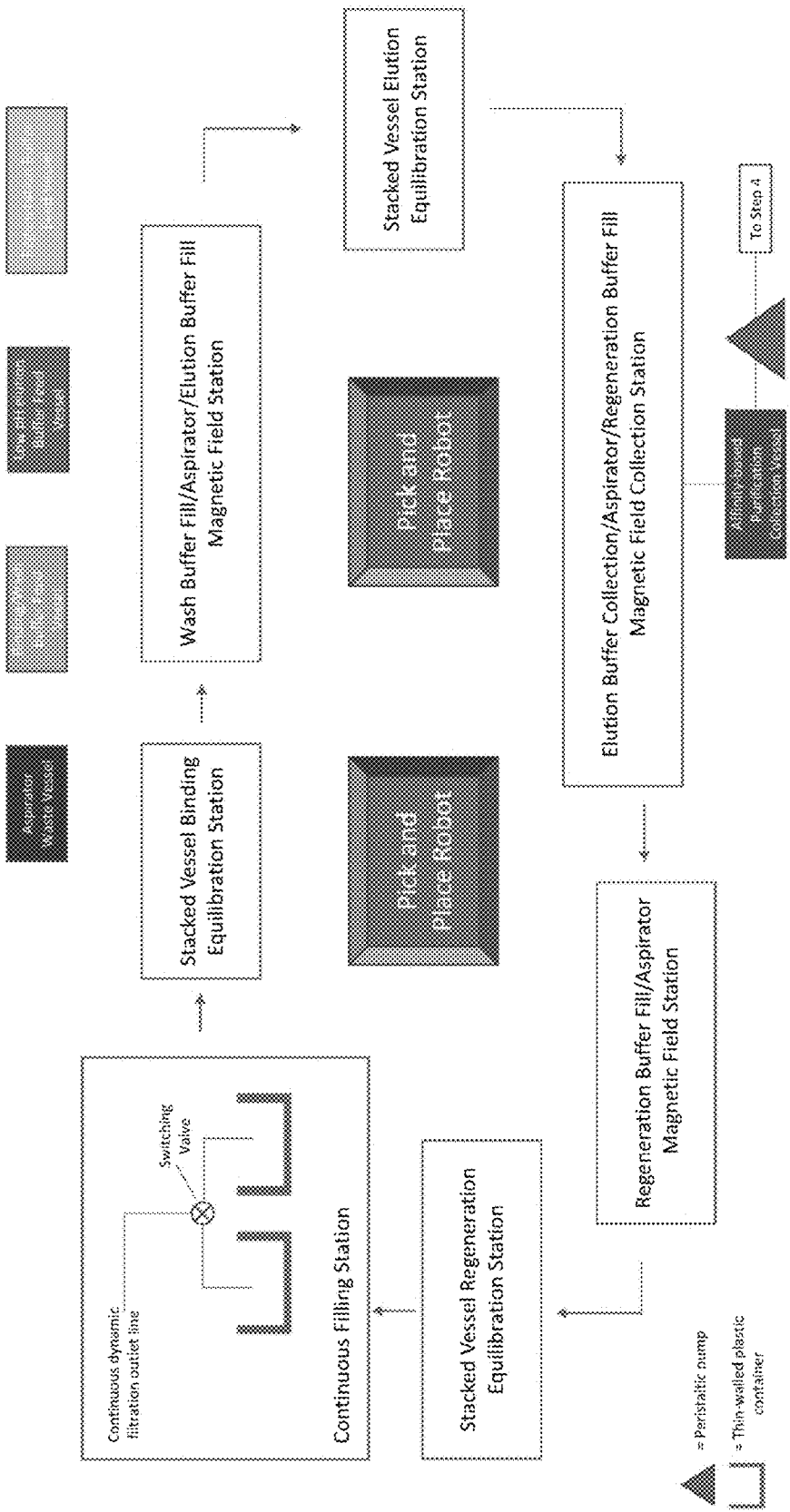
FIG. 18 shows an exemplary design schematic of an affinity-based, magnetic purification apparatus comprising a pick and place robotics system and at least one magnetic field.
Figure 19:
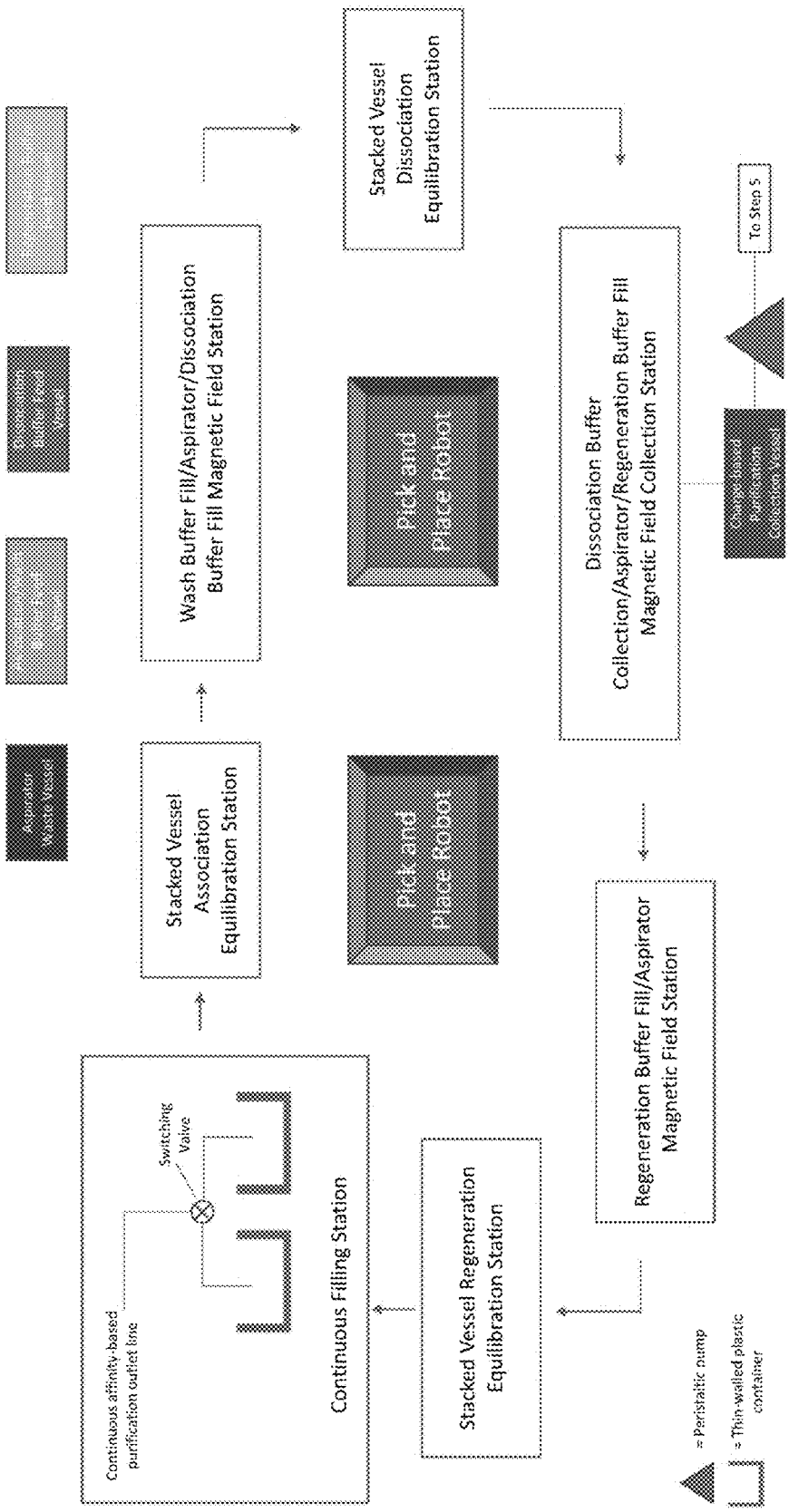
FIG. 19 shows an exemplary design schematic of a charge-based, magnetic purification apparatus comprising a pick and place robotics system and at least one magnetic field.

The at least one magnetic field in the continuous pick and place robotics apparatuses performing the affinity-based, magnetic purification and/or charge-based, magnetic purification steps may be generated by an electromagnet or a permanent magnetic (e.g., a Neodymium magnet). The magnetic field may be applied as an on/off toggle or as permanently on (FIGS. 18 and 19). When the magnetic field is generated by an electromagnet, on/off toggling may be accomplished by turning the electromagnet on or off. When the magnetic field is generated by a permanent magnet, on/off toggling may be accomplished by mechanically changing the placement of the magnet from far to within close proximity, for example, within 5 mm of the transport vessel wall surface. Alternatively, when the magnetic field is generated by a permanent magnet, on/off toggling may be accomplished by transport the vessel into and out of close proximity (e.g., within 5 mm) of the magnet. Further, the loop conveyor apparatuses may include multiple, discrete magnetic field locations, wherein said discrete magnetic field locations within the apparatuses may further require shielding. Additionally, mixing of the magnetic resin beads may be accomplished by placing the at least one transport vessel between two separate and opposing magnetic fields that toggle between states of on and off. Additionally, the use of at least one additional affinity-based, magnetic purification or charge-based, magnetic purification apparatus connected in parallel to enable continuous processing is also contemplated herein.

Continuous Mechanical Rotary System Apparatus Approaches

Figure 21:
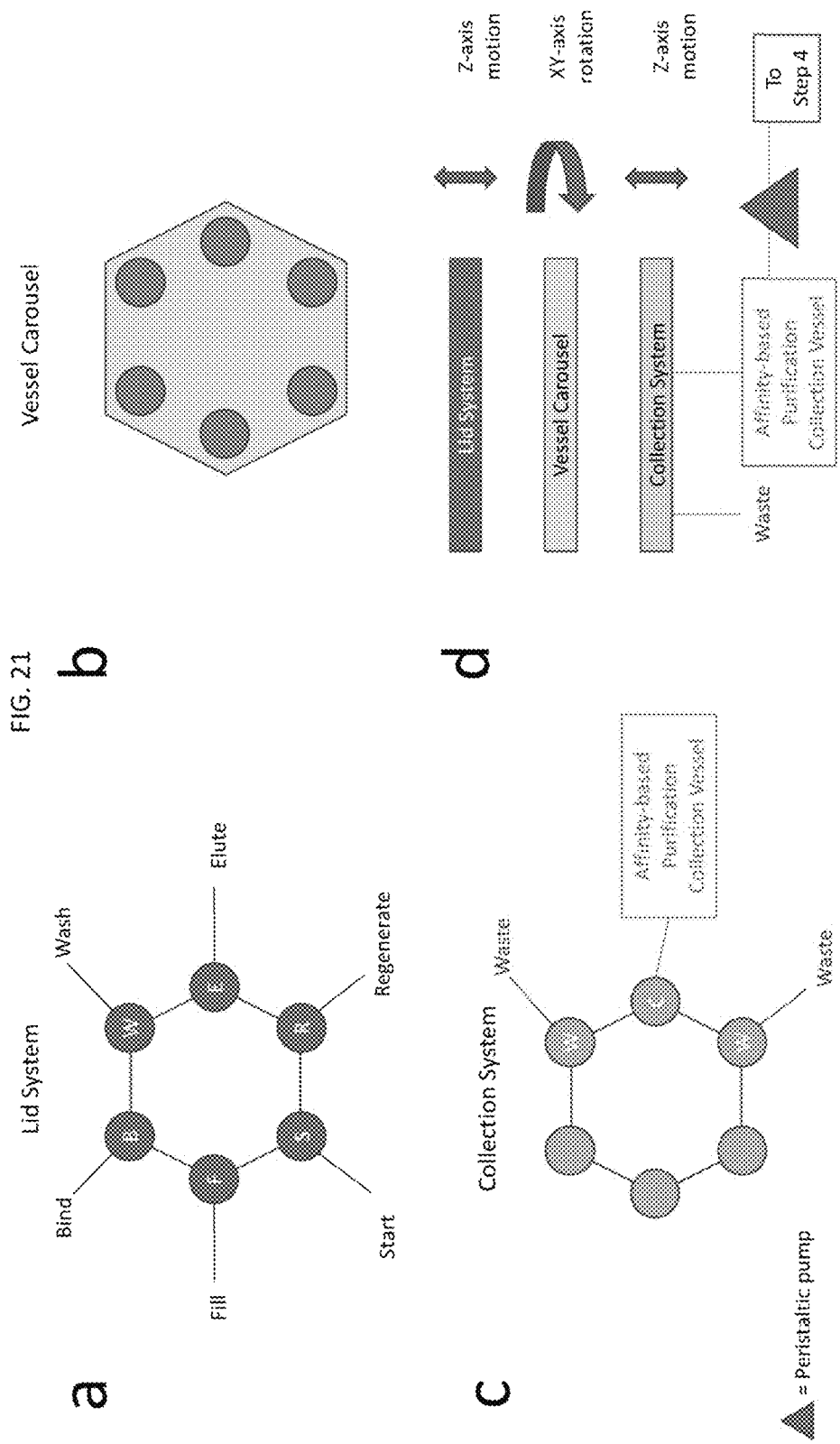
FIGS. 21A-21D show an exemplary design of an affinity-based purification apparatus comprising a mechanical rotary system.
Figure 22:
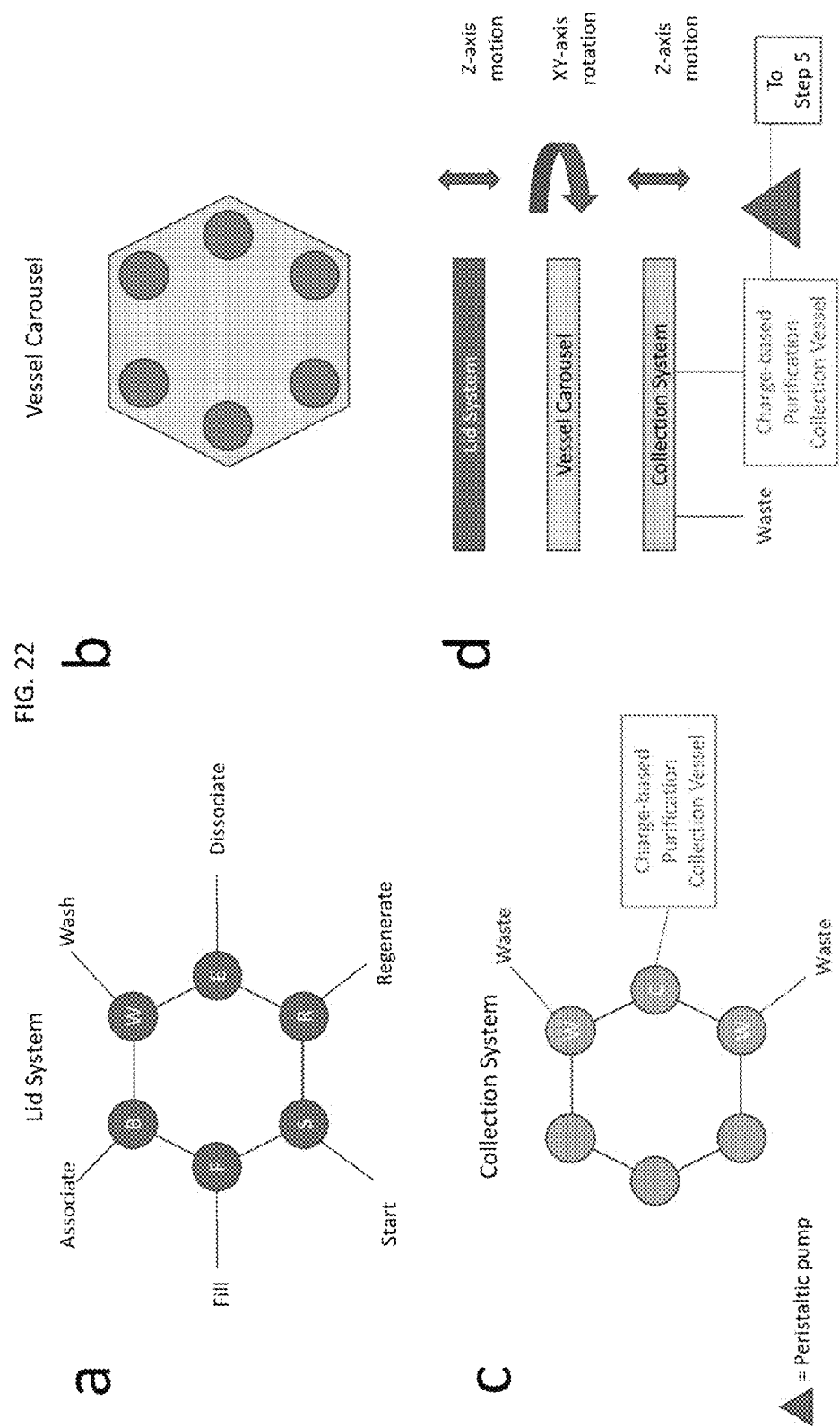
FIGS. 22A-22D show an exemplary design of a charge-based purification apparatus comprising a mechanical rotary system.
Figure 23:
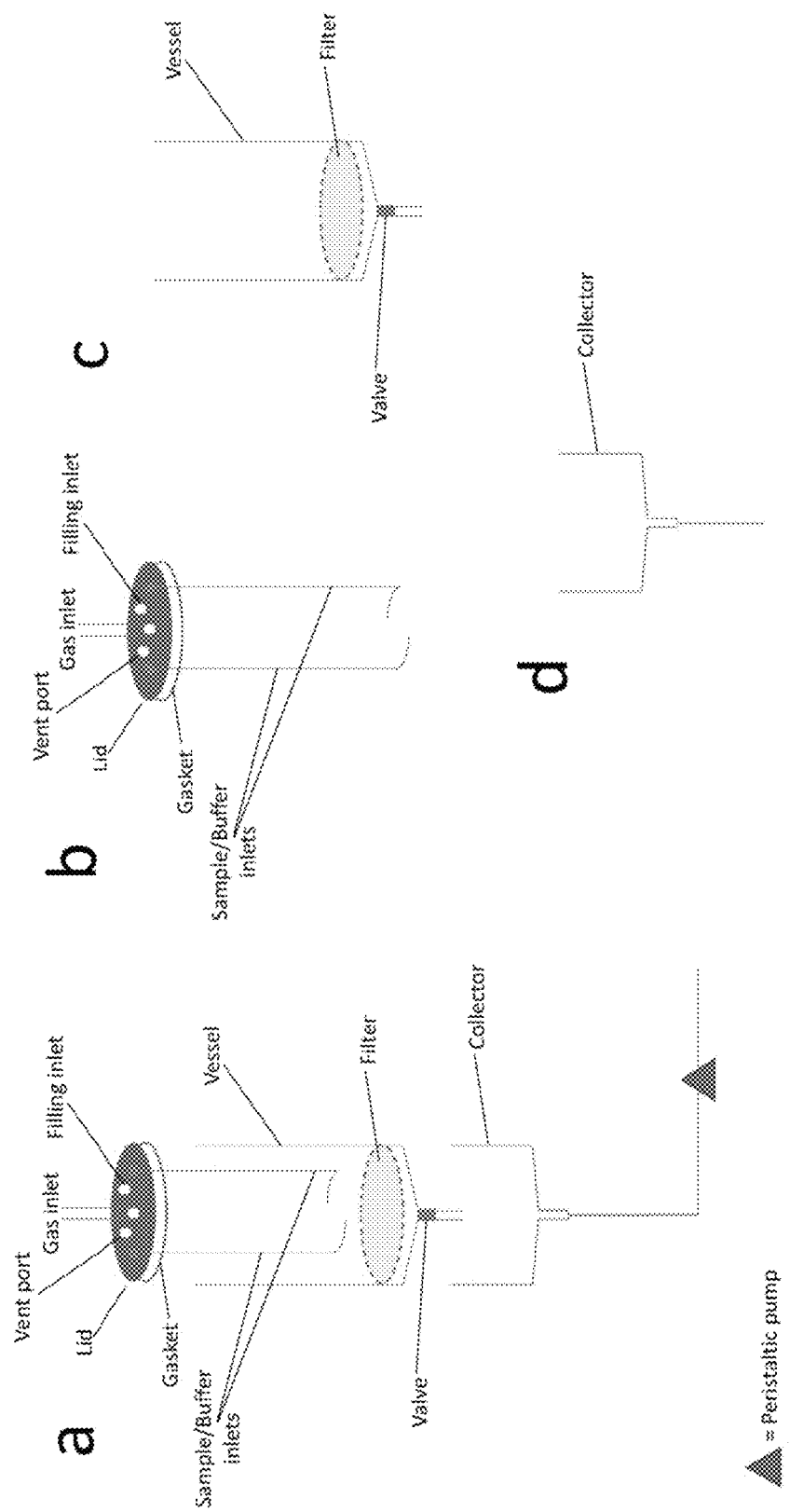
FIGS. 23A-23D show the individual system components of an affinity-based purification or a charge-based purification apparatus.

A seal between the at least one gasketed lid and vessel assembly of the continuous mechanical rotary apparatus performing the affinity-based purification and/or charge-based purification steps system may be formed by a mechanism designed to compress the gasket and ensure the lid is fixed in a sealed 3-dimensional geometry (FIGS. 21-23). In embodiments, the mechanism used to form the seal is a clamping system or interlocking system. In some embodiments, the mechanism used to form the seal is a screw cap system. In other embodiments, the seal is formed by mechanically pressing the lid down uniformly onto the vessel from the top with a motorized system. In aspects, a mechanical system or a robotics system may be utilized to ensure that the seal is reproducibly formed and broken in a reversible and repetitive manner over multiple cycles to enable continuous operation. For example, a leak test after pressurization can be used to analyze the integrity of the seal. Further, the buffer inlets of the at least one lid may be positioned to create a circular or vortex-like mixing flow pattern. Additionally, the use of at least one additional affinity-based purification or charge-based purification apparatus connected in parallel to enable continuous processing is also contemplated herein.

Continuous Staged Linear System Apparatus Approaches

Figure 24:
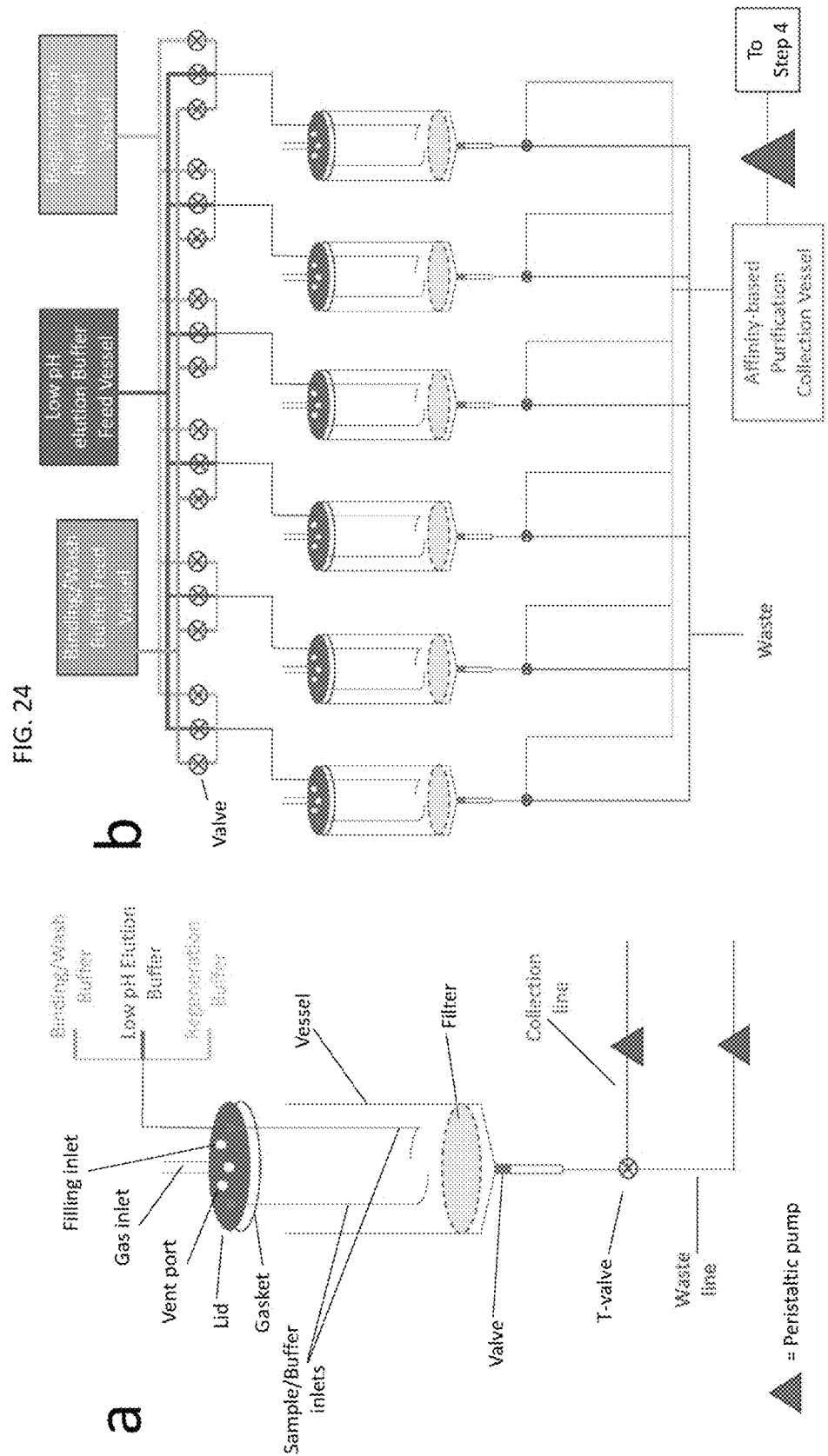
FIGS. 24A and 24B show an exemplary design of an affinity-based purification apparatus comprising a staged linear system.
Figure 25:
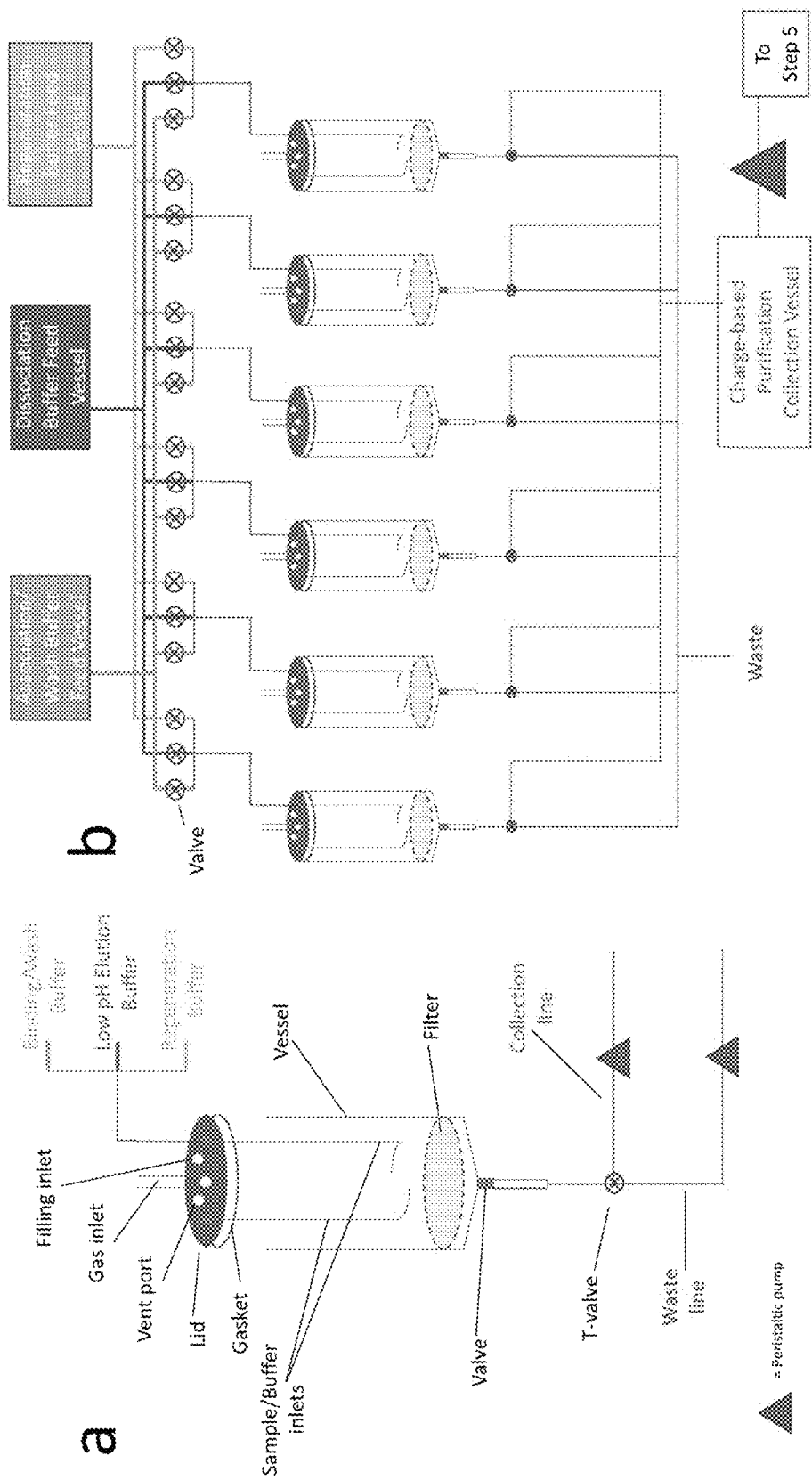
FIGS. 25A and 25B show an exemplary design of an affinity-based purification apparatus comprising a staged linear system.
Figure 26A:
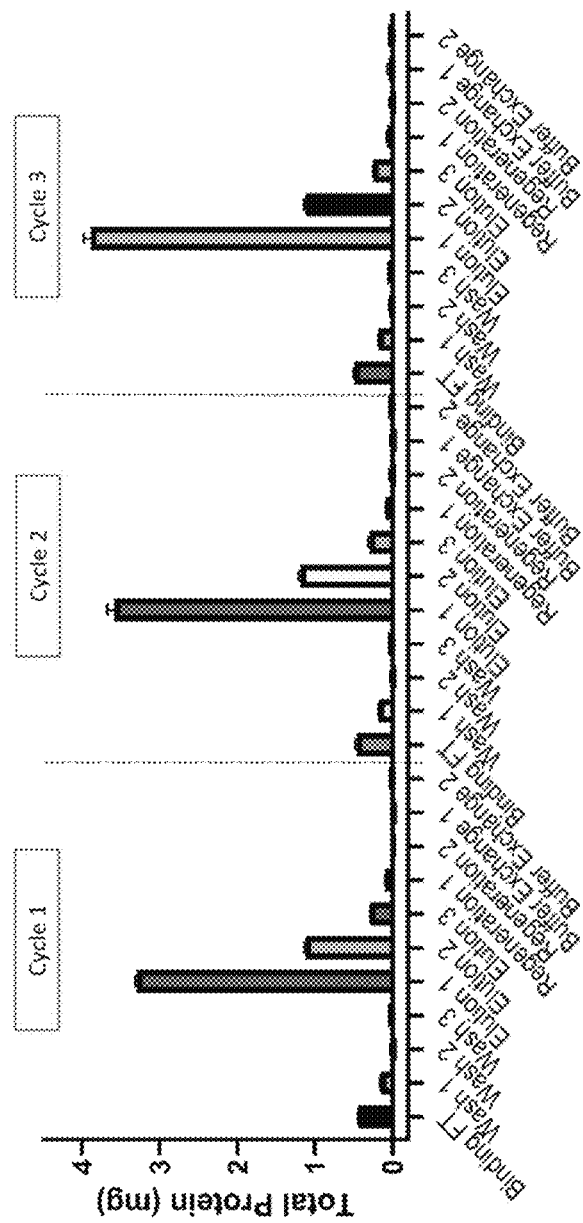
FIGS. 26A and 26B shows the affinity-based purification of a solution of hIgG (2 g/L input concentration) performed with an affinity-based purification apparatus charged with Protein A-coated agarose resin beads.
Figure 26B:
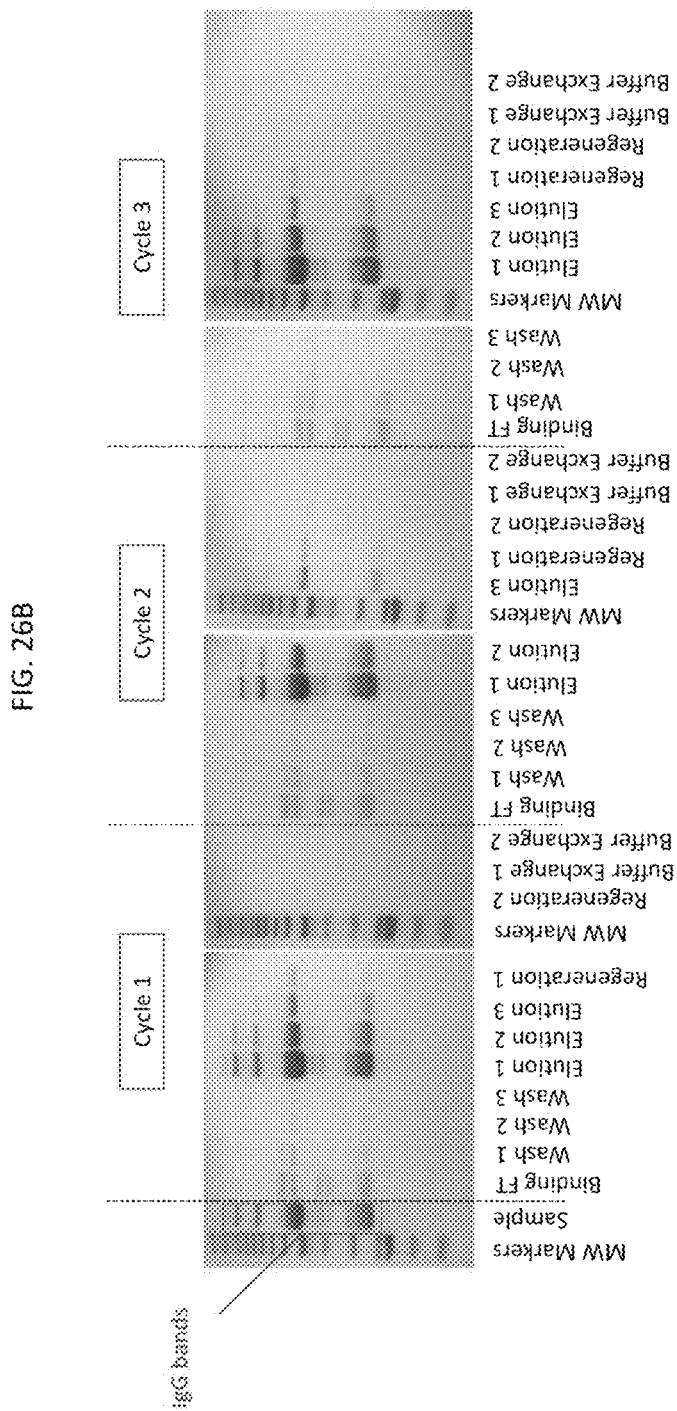

The vessels in a staged linear system are configured to receive continuous input flow. The process steps of binding, washing, elution, and regeneration (for affinity-based purification) and association, washing, dissociation, and regeneration (for charge-based purification) are accomplished via connection of each vessel to manifold capable of automated liquid handling (FIGS. 24-25). In embodiments, each vessel in the staged linear system may be configured to perform different process steps at the same time to enable continuous operation. For example, without intent to be limiting, one vessel may be performing a binding process step while another vessel is performing an elution process step.

Continuous Hybrid Fluidic Device Approaches

The at least one magnetic field in the continuous hybrid fluidic device (FIG. 28) performing the affinity-based, fluidic purification and/or charge-based, fluidic purification steps may be generated by an electromagnet, a permanent magnet (e.g., a Neodymium magnet) or a patterned magnet. The independent permanent magnets may require local shielding. Moreover, to achieve high flow rates, the combination of the magnetic components and the piezoelectric components or the combination of the magnetic components and the dielectrophoretic components may require precise placement. Additional cross-flow channel designs are contemplated. Alternatively, T-junction channel designs are also contemplated. Moreover, a coarse/fine screen approach to select a biological product of interest (e.g., a monoclonal antibody) based on isoelectric point. Further, multiple elutions or dissociations is considered. The equilibration vessels may be batch, fed-batch, continuous feed and bleed vessels, or plug flow reactors with the appropriate residence times. Additionally, increasing the throughput of the affinity-based, fluidic purification or the charge-based, fluidic purification module by multiplexing multiple fluidic devices or chips, in series or in parallel. Moreover, the use of at least one additional affinity-based, fluidic purification or charge-based, fluidic purification apparatus connected in parallel to enable continuous processing is also contemplated herein.

Continuous Tangential Flow Filtration Approaches

The equilibration vessels in the affinity-based TFF purification and charge-based TFF purification modules (FIGS. 31-32) may be batch, fed-batch, continuous feed and bleed vessels, or plug flow reactors with the appropriate residence times. The use of additional tangential flow filtration systems to enable continuous operation, buffer exchange, diafiltration, ultrafiltration/diafiltration, microfiltration/diafiltration, and/or concentration is also contemplated herein.

Continuous Free-Flow Electrophoresis Approaches

An electric field orthogonal to the direction of fluid flow may be used for purification of a biological product (e.g., a monoclonal antibody) in an aqueous ionic solution and/or pH gradient, for example, in the free-flow electrophoresis apparatus comprising a fluidic channel created between two parallel plates, an electric field or electric field gradient orthogonal to the fluid flow direction, and an aqueous ionic solution and/or pH gradient, as described herein (FIGS. 33-37). The fluidic channel dimensions are dependent on flow rate, throughput volume, time to achieve separation, diffusive band broadening, magnitude of the electric field, and are further dependent on cooling system capabilities to dissipate Joule heat. Moreover, the channel design may have multiple inlets to generate a pH gradient by delivering one or more buffer or ampholyte systems. An applied voltage may be dependent on the flow rate, pH gradient, the biological product charge and/or isoelectric point (e.g., monoclonal antibody isoelectric point), or the cooling system capabilities to dissipate Joule heat. Various buffer and/or ampholyte systems are dependent on the biological product of interest (e.g., monoclonal antibody of interest) and its unique isoelectric point (pI) and are thus selected to modulate its charge. Control of pH and ionic strength and use of organic salts, inorganic salts, acids, bases, zwitter-ions, and/or ampholytes within the buffer and/or ampholyte system to establish a continuous pH gradient effect across the channel is contemplated. Alternatively, the pH gradient may be stratified via multiple inlets delivering discrete buffer and/or ampholyte systems to achieve a desired gradient, for example, without intent to be limiting, a continuous gradient or a stepwise gradient. Moreover, a combination of coarse and fine pH gradients may be necessary to purify solely the biological product (e.g., monoclonal antibody). Considerations regarding a robust cooling mechanism to enable sufficient heat transfer (e.g., a Peltier device, a thermal chuck with a circulating water/propylene glycol jacket) are also contemplated. Multiplexing of free-flow electrophoresis apparatuses may accommodate higher input flow rates, and thus higher throughput. Also, the potential to further remove residual inactivated virus during the isoelectric point-based, fluidic purification steps is contemplated.

Incorporation of Standard Semi-Continuous, Industry Downstream Processes

Figure 48:
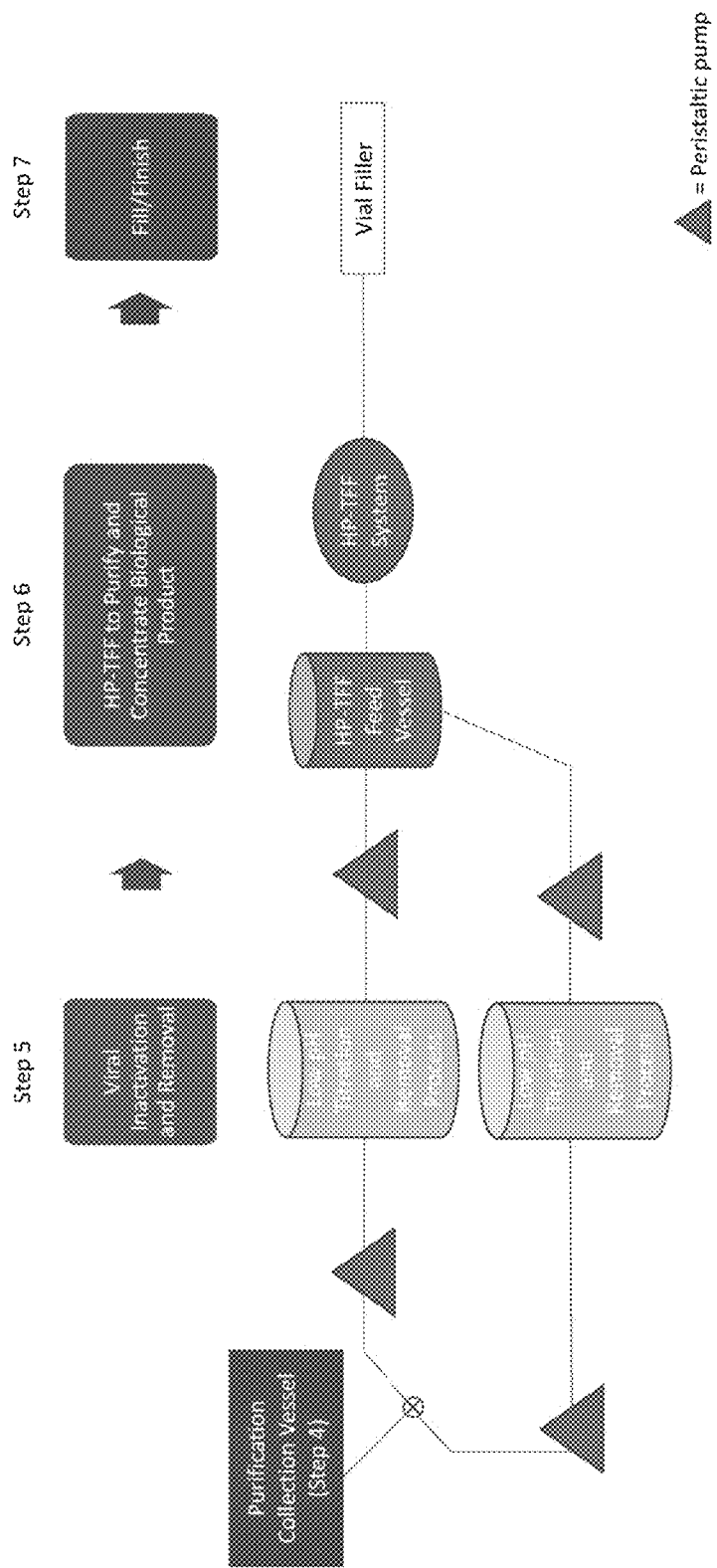
FIG. 48 shows an exemplary a schematic of connecting a charge-based, magnetic, a charge-based, a charge-based fluidic, a charge-based TFF, or an isoelectric point-based purification module to an exemplary semi-continuous process, described herein, utilizing standard industry downstream processing equipment run in fed-batch or perfusion mode to prepare the biological product for fill-finish.
Figure 49:
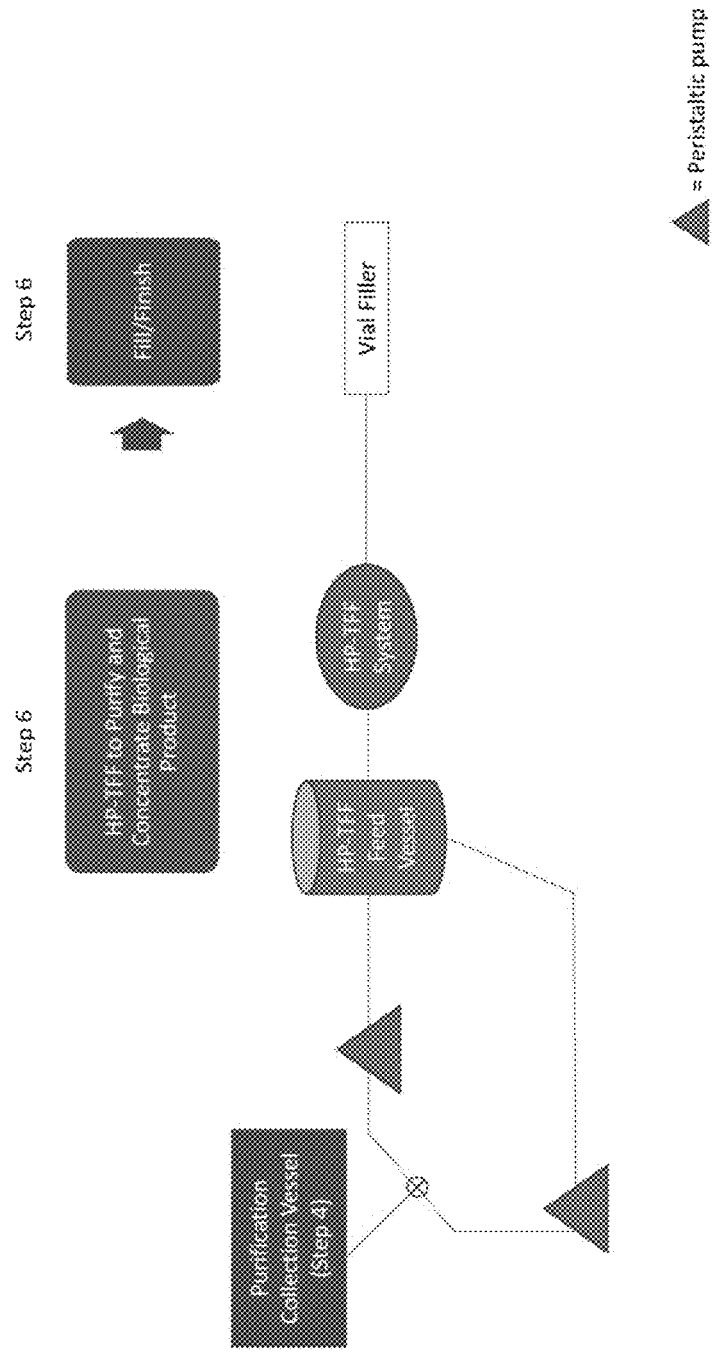
FIG. 49 shows an exemplary a schematic of connecting a charge-based, magnetic, a charge-based, a charge-based fluidic, a charge-based TFF, or an isoelectric point-based purification module to an exemplary semi-continuous process, described herein, utilizing standard industry downstream processing equipment run in fed-batch or perfusion mode to prepare the biological product for fill-finish in the absence of an independent viral inactivation and removal process step.

To enable a turn-key, end-to-end process (e.g., from bioreactor-based monoclonal antibody production through obtaining the biological product in final form), standard semi-continuous industry downstream process equipment (and steps) may be further added to the process described herein to further purify, buffer exchange, and concentrate the purified biological product (e.g., a monoclonal antibody) (FIGS. 48 and 49).

A designated virus inactivation and filtration step may or may not be necessary if virus inactivation and removal is adequately accomplished by modules (e.g., wherein LRV>4 for MVM and MuLV viruses). That said, the addition of a designated virus inactivation and filtration step is contemplated herein.

Depending on the purity of the biological product (e.g., monoclonal antibody purity) achieved by the continuous process modules described herein, off-the-shelf tangential flow filtration (TFF), ultrafiltration/diafiltration (UF/DF), or high performance tangential flow filtration (HP-TFF) technologies run in fed-batch or perfusion mode may be used to further purify, buffer exchange, or concentrate the final biological product prior to fill-finish operations, which may include, vial filling, lyophilization, filter sterilization, terminal sterilization, or combinations thereof. Moreover, in-line sampling ports for in-process analytical testing and/or in-line analytical measurement techniques are contemplated.

Methods

Provided herein are methods of continuously purifying a biological product from a heterogeneous mixture derived from a bioreactor producing said biological product at steady-state comprising utilizing the process described herein. As used herein, the terms "steady-state" or "dynamic equilibrium" may refer to a system or process that remains steady over time in the presence or absence of perturbations. For example, a bioreactor that produces said biological product at steady-state provides that the expression host cell, for example, a mammalian cell (e.g., CHO cell) or a bacterial cell (e.g., *E. coli*) can be grown in a physiological steady-state under constant environmental conditions. In this steady state, growth occurs at a constant specific cell culture growth rate and all culture parameters remain constant (culture volume, dissolved oxygen concentration, nutrient and product concentrations, pH, cell density, etc.). In addition, environmental conditions can be controlled by the feedback mechanisms (e.g., a feed/bleed system) inherent to the bioreactor (e.g., a fed-batch, a perfusion, or a chemostat bioreactor) in order to maintain the steady-state production of the biological product over time. The cell density, for example, remains constant over time. In other examples, the protein concentration remains constant overtime.

A method of continuously purifying a biological product from a heterogeneous mixture derived from a bioreactor producing said biological product at steady-state comprising utilizing at least one of the modules described herein (for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module) is disclosed.

Additionally, a method of purifying a biological product from a heterogeneous mixture derived from a bioreactor producing said biological product comprising utilizing at least one of the modules described herein (for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module) is also disclosed. For example, at least one of the modules described herein (for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module) may replace or be used in addition to a traditional purification technique utilized in current batch, single-use, or semi-continuous processes known in the art.

Alternatively, a method of purifying a biological product from a mixture not derived from a bioreactor producing said biological product comprising utilizing at least one of the modules described herein (for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module) is also disclosed. For example, at least one of the modules described herein (for example, the dynamic filtration module, the affinity-based, magnetic purification module, the positive charge-based, magnetic purification module, the negative charge-based, magnetic purification module, the affinity-based purification module, the positive charge-based purification module, the negative charge-based purification module, the affinity-based, fluidic purification module, the positive charge-based, fluidic purification module, the negative charge-based, fluidic purification module, the affinity-based TFF purification module, the positive charge-based TFF purification module, the negative charge-based TFF purification module, and/or the isoelectric point-based, fluidic purification module) may replace or be used in addition to a traditional purification technique utilized in current batch, single-use, or semi-continuous processes known in the art.

As described herein, the term "module" or "modular" may refer to separate distinct parts (e.g., the dynamic filtration module, the affinity-based, magnetic purification module, the positive charge-based, magnetic purification module, the negative charge-based, magnetic purification module, the affinity-based, fluidic purification module, the positive charge-based, fluidic purification module, the negative charge-based, fluidic purification module and/or the isoelectric point-based, fluidic purification module) that may be used alone, or in any combination. Moreover, the process may include one or more of any of the above-described modules. The term "modular" may refer to and mean a structure which is constructed from a plurality of modular units and which may be constructed in a wide variety of structural forms. For example, the modular units can be connected together in the form of a transport system or a continuous fluid handling system. Moreover, in-line sampling ports for in-process analytical testing and/or in-line analytical measurement techniques are contemplated within each of the modules.

General Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices, and materials similar or equivalent to those described herein can be used in the practice of this invention. The following definitions are provided to facilitate understanding of certain terms used frequently herein and are not meant to limit the scope of the present disclosure.

Unless specifically stated or obvious from context, as used herein, the term "or" is understood to be inclusive. Unless specifically stated or obvious from context, as used herein, the terms "a," "an," and "the" are understood to be singular or plural.

The term "about" when used in reference to numerical ranges, cutoffs, or specific values is used to indicate that the recited values may vary by up to as much as 25% from the listed value. As many of the numerical values used herein are experimentally determined, it should be understood by those skilled in the art that such determinations can, and often times will, vary among different experiments. The values used herein should not be considered unduly limiting by virtue of this inherent variation. The term "about" is used to encompass variations of ±25% or less, variations of ±20% or less, variations of 10% or less, variations of ±5% or less, variations of ±1% or less, variations of ±0.5% or less, or variations of ±0.1% or less from the specified value. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Ranges provided herein are understood to be shorthand for all of the values within the range. For example, a range of 1 to 60 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 60 may comprise 1 to 10, 1 to 20, 1 to 30, and 1 to 40 in one direction, or 50 to 40, 50 to 30, 50 to 20, and 50 to 10 in the other direction.

The term "subject" as used herein refers to a living member of the animal kingdom. In embodiments, the subject is a member of a species comprising individuals who may naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs, horses, cats, livestock (such as pigs, bovines, donkeys, mules, bison, goats, camels, and sheep). In embodiments, the subject is a human.

The terms "within close proximity to" or "within close proximity of" as used herein refers to a distance of less than about 1 cm, for example, less than about 5 mm (meaning, for example, the distance between a magnet or a magnetic field and a transport vessel wall or a cross-flow channel).

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The terms "mechanically smooth" or "substantially smooth" are used interchangeably herein to describe a contact surface of a material having a low static coefficient of friction of about 0.01 to about 0.1.

The terms "hybrid fluidic device" or "hybrid fluidic chip" are used interchangeably herein to describe a fluid flow device or chip that combines cross-flow channel dynamics, magnetophoretic dynamics, and, either acoustophoretic or dielectrophoretic dynamics together to manipulate magnetic resin beads at high flow rate. Further, hybrid fluidic devices may also include electrokinetic or capillary flow dynamics. In some aspects herein, a hybrid fluidic device or chip comprises a cross-flow channel, at least one magnetic field, and at least one piezoelectric component (e.g., piezoelectric crystal). In other aspects herein, a hybrid fluidic device or chip comprises a cross-flow channel, at least one magnetic field, and at least one dielectrophoretic electrode. Hybrid fluidic devices or chips may be microfluidic, mesofluidic, millifluidic, macrofluidic, or any combination thereof. For example, without intent to be limiting, a hybrid fluidic device can be a microfluidic device comprising a cross-flow channel, at least one magnetic field, and at least one dielectrophoretic electrode.

The terms "tangential flow filtration (TFF) system," "high performance tangential flow filtration (HP-TFF) system," and "cross-flow filtration system (CFF)" are used interchangeably herein, to refer to an equipment and controls system wherein a sample solution is fed from a feed vessel in a flow path parallel to a porous membrane face allowing one fraction to pass orthogonally through a membrane (e.g., permeate), while the remainder of the sample solution is recirculated back to the sample feed vessel (e.g., retentate) to enable purification of the sample solution by microfiltration, ultrafiltration, diafiltration, or any combination thereof. The membrane may be either a flat plate or hollow fiber geometry, charged or uncharged. Further, tangential flow filtration and cross-flow filtration systems are defined as one-dimensional systems used to purify biomolecules by separation based on a tenfold difference in hydrodynamic size. In contrast, high performance tangential flow filtration systems are defined as two-dimensional systems that purify biomolecules by separation based on both differences in charge characteristics and a tenfold difference in hydrodynamic size.

The terms "microfilter," "microfiltrate" or "microfiltration" as used herein, refer to a TFF process utilizing a membrane with a pore size greater than 0.1 micron to concentrate resin beads.

The terms "ultrafilter" or "ultrafiltrate" or "ultrafiltration" as used herein, refers to a TFF process utilizing a membrane with a pore size less than 0.1 micron to concentrate a biological product (e.g., a protein or fragment thereof (a polypeptide), an antibody or fragment thereof, a cytokine, a chemokine, an enzyme, or a growth factor).

The terms "diafilter," "diafiltrate" or "diafiltration" as used herein, refers to a TFF process in which a retentate produced by microfiltration or ultrafiltration is diluted with buffer solution and subsequently re-microfiltered or re-ultrafiltered, respectively, to further purify the retentate or enable buffer exchange.

The term "diavolume" as used herein, refers to the volume of diafiltration buffer utilized in the unit TFF operation compared to the initial retentate volume.

The terms "free-flow electrophoresis" and "isoelectric point-based, fluidic purification" are used interchangeably herein to a continuous flow process of separating a biological product based upon its charge, its isoelectric point, its electrophoretic mobility, or any combination thereof. In some aspects herein, free flow electrophoresis has different modes of operation, including, but not limited to, isoelectric focusing (IEF-FFE), zone electrophoresis (ZE-FFE), isotachophoresis, or any combination thereof.

The term "isoelectric point" or "pI" as used herein refers to the pH at which a protein is charge neutral or has no net electrical charge.

A pH gradient, as used herein may refer to a "coarse pH gradient" or a "fine pH gradient." For example, a coarse pH gradient refers to a pH range (or gradient) of a pH from about 2 to about 10, or from about 2 to about 9, or from about 2 to about 8, or from 2 to about 7, or from 2 to about 5, or from 2 to about 4, or from about 2 to about 3. Moreover, a coarse pH gradient may be a pH range from about 5 to about 8. Alternatively, a fine pH gradient refers to a pH gradient (e.g., a pH change) within 1 pH unit. For example, the pH range may be from about 7.0 to about 8.0, or from about 7.1 to about 8.0, or from about 7.2 to about 8.0, or from about 7.3 to about 8.0, or from about 7.4 to about 8.0, or from about 7.4 to about 8.0, or from about 7.5 to about 8.0, or from about 7.6 to about 8.0, or from about 7.7 to about 8.0, or from about 7.8 to about 8.0, or from about 7.9 to about 8.0. Alternatively, the pH range in a fine pH gradient may range from about 7.0 to about 7.5, or from about 7.1 to about 7.5, or from about 7.3 to about 7.5, or from about 7.4 to about 7.5 Moreover, the pH range may be from about 7.1 to about 7.6.

The term "ampholyte" as used herein refers to an amphoteric electrolyte or an electrolyte that has both acid and base functionality. In some aspects herein, ampholytes comprise amphoteric organic buffer salts or amino acids that are utilized to establish a pH gradient in an isoelectric point-based, fluidic purification apparatus. For example, without intent to be limiting, ampholytes comprise, Tris, HEPES, MES, glycine, histidine, arginine, glutamic acid, or any combination thereof.

The term "antibody" herein is used in the broadest sense and encompasses polypeptides or proteins that comprise or consist of antibody domains, which are understood as constant and/or variable domains of the heavy and/or light chains of immunoglobulins, with or without a linker sequence. The term encompasses various antibody structures, including but not limited to monoclonal antibodies, polyclonal antibodies, multi-specific antibodies such as bispecific antibodies, and antibody fragments. The term "monoclonal antibody" as used herein refers to identical antibodies or antibody fragments produced by a single clone of cells or cell line that have binding affinity and specificity for a target antigen. Antibody domains may be of native structure or modified by mutagenesis or derivatization. Further, the term "immunoglobulin" refers to a protein having the structure of a naturally occurring antibody. For example, immunoglobulins of the IgG class are heterotetrameric glycoproteins of about 150,000 Daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. An immunoglobulin of the IgG class essentially consists of two F(ab) domains and an Fc domain, linked via the immunoglobulin hinge region. The heavy chain of an immunoglobulin may be assigned to one of five types, namely, IgG, IgM, IgA, IgE, and IgD immunoglobulin isotypes derived from any animal (e.g., any of the animals conventionally used, for example, sheep, rabbits, goats, or mice) which may be further divided into subtypes, such as IgG1, IgG2, or IgG2a. Preferably, the antibody comprises a monoclonal antibody (e.g., a human monoclonal antibody).

The term "valent" as used herein refers the presence of a specified number of binding sites in an antibody molecule. As such, the terms "bivalent," "trivalent," and "multivalent" denote the presence of two binding sites, three binding sites, and multiple binding sites, respectively, in an antibody molecule. The term "monovalent" as used herein with respect to a binding site of an antibody shall refer to a molecule comprising only one binding site directed against a target antigen. The term "valency" is thus understood as the number of binding sites directed against the same target antigen, either specifically binding to the same or different epitopes of an antigen.

The term "monospecific antibody" as used herein means the ability of a single antibody to have the capability to selectively bind to a single, discrete target with specificity and high affinity. The specificity and high affinity means that the monospecific antibody predominantly binds to one discrete target antigen of interest, while manifesting negligible binding to other molecules in a sample solution. A specific binding site is typically not cross-reactive with other targets, however, the specific binding site may specifically bind to one or more epitopes, isoforms, or variants of the target. The specific binding means that binding is selective in terms of target identity, for example, high binding affinity or avidity. Selective binding is usually achieved if the binding constant or binding dynamics to a target antigen is preferably at least 100-fold, and more preferably at least 1000-fold compared to binding constant or binding dynamics to an antigen or molecule which is not the target antigen. As used herein, the term "high affinity" refers to a binding interaction of antibody with the target antigen having an equilibrium dissociation constant ($K_D$) less than or equal to 10-6 M (micromolar affinity), preferably less than 10-9 M (nanomolar affinity), and more preferably less than 10-12 M (picomolar affinity). As used herein, "no substantial cross-reactivity" means that an antibody does not recognize or specifically bind an antigen different from the actual target antigen of the molecule, particularly when compared to that target antigen. For example, an antibody may bind less than about 10% to less than about 5% to an antigen different from the actual target antigen or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen. Monospecific antibodies can be one of four types, specifically, human, humanized, chimeric, and murine, and can be derived from IgG, IgM, IgA, IgE, IgD immunoglobulin isotypes and subtypes. Further, monospecific antibodies can have monovalent, bivalent, trivalent, or multivalent binding sites for the target antigen of interest. Similarly, the term "bispecific antibody" as used herein means the ability of a single antibody having the capability to selectively bind to two different and discrete targets with specificity and high affinity for each target independently. In aspects, the specificity and high affinity means that the bispecific antibody predominantly binds to the two different and discrete target antigens of interest, while manifesting negligible binding to other molecules in a sample solution. Moreover, the term "trispecific antibody" as used herein means the ability of a single antibody having the capability to selectively bind to three different and discrete targets with specificity and high affinity for each target independently. In aspects, the specificity and high affinity means that the trispecific antibody predominantly binds to the three different and discrete target antigens of interest, while manifesting negligible binding to other molecules in a sample solution. Further, multispecific antibodies can include or be formed from antibody fragments.

The term "antibody fragment" as used herein refers to a molecule other than an intact antibody that comprises a portion of an intact antibody that binds the antigen to which the intact antibody binds. Non-limiting examples of antibody fragments include, monovalent IgG, linear antibodies, single-chain antibody molecules, Fv, scFv, scFv-Fc, F(ab), F(ab)2, scF(ab), F(ab)-scFv fusion, F(ab)-(scFv)2 fusion, F(ab)-scFv-Fc, cross-F(ab), nanobodies, minibodies, diabodies, scFv-Fc diabodies, and/or affibodies. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full-length antibodies.

The term "chimeric antibody" refers to an antibody in which a portion of the heavy and/or light chain is derived from a particular source or species, while the remainder of the heavy and/or light chain is derived from a different source or species, usually prepared by recombinant DNA techniques. Chimeric antibodies may comprise a rabbit or murine variable region and a human constant region. Other forms of "chimeric antibodies" are those in which the constant region has been modified or changed from that of the original antibody to generate the properties according to the present invention. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art (Morrison S L, et al., PNAS, 81:6851-6855, (1984)).

The term "human antibody" as used herein is an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies, the term "human antibody" as used herein also comprises such antibodies which are modified in the constant region, for example, by "class switching".

The terms "recombinant antibody" and "recombinant human antibody", as used herein, are intended to include all human antibodies that are prepared, expressed, created, or isolated by recombinant means, such as antibodies isolated from an expression host cell, for example, without intent to be limiting, a mammalian cell (e.g., HEK 293, NSO or CHO cell) or a bacterial cell (e.g., E. coli), or from an animal (e.g., a mouse) that is transgenic for human immunoglobulin genes or antibodies expressed using a recombinant expression vector transfected into a host cell. Such recombinant human antibodies have variable and constant regions in a rearranged form. The recombinant human antibodies according to the present invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo. The term "recombinant" as used herein shall mean "being prepared by genetic engineering" or "the result of genetic engineering", for example, specifically employing heterologous sequences incorporated in a recombinant vector or recombinant host cell.

The term "humanized antibody" refers to a chimeric antibody comprising amino acid residues from non-human hypervariable regions and amino acid residues from human framework regions (FRs) which has undergone humanization. In certain embodiments, a humanized antibody will comprise substantially all of at least one, and typically two, variable domains, in which all or substantially all of the hypervariable regions (e.g., CDRs) correspond to those of a non-human antibody, and all or substantially all of the FRs correspond to those of a human antibody. A humanized antibody optionally may comprise at least a portion of an antibody constant region derived from a human antibody. Other forms of humanized antibodies encompassed by the present invention are those in which the constant region has been additionally modified or changed from that of the original antibody to generate the new properties, for example, Fc receptor binding.

The terms "purify," "purified," "purifying," or "purification" as used herein refer to methods by which impurities are removed from a biological product (e.g., nucleic acid, protein, antibody products and the like) in a heterogeneous mixture. In aspects, the impurities are cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated. In some aspects, the terms "large impurity" or "large impurities" as used herein, refer to cells, cell debris, and/or aggregates. In other aspects, the terms "small impurity" or "small impurities" as used herein refer to host cell proteins, undesired proteins and peptides, undesired nucleic acids and oligonucleotides, viruses, salts, buffer components, surfactants, sugars, metallic contaminants, leachables, media components, and/or naturally-occurring organic molecules with which it is naturally associated. Purified biological products are at least 60% by weight (dry weight) the product of interest. Preferably, the preparation is at least 75%, more preferably at least 90%, and most preferably at least 99%, by weight the product of interest. For example, a purified antibody is one that is at least 90%, 91%, 92%, 93%, 94%, 95%, 98%, 99%, or 100% (w/w) of the desired antibody by weight. Purity is measured by any appropriate standard method, for example, by a column chromatography. Purified also defines a degree of sterility that is safe for administration to a subject, e.g., lacking infectious, toxic, or immunogenic agents. Similarly, by "substantially pure" means a biological product (e.g., nucleic acid, protein, antibody products and the like) that has been separated from the components that naturally accompany it. Typically, the biological product (e.g., an antibody, a protein, a polypeptide and the like) is substantially pure when it is at least 60%, 70%, 80%, 90%, 95%, or even 99%, by weight, free from impurities (e.g., cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

The terms "isolate," "isolated," or "isolation" as used herein refer to methods by which a desired biological product (e.g., nucleic acid, protein, antibody products and the like) is specifically selected and separated from undesired products in a heterogeneous mixture. Further, an "isolated antibody," as used herein, is intended to refer to an antibody that is substantially free of other antibodies having different antigenic specificities (e.g., an isolated antibody that specifically binds CD20 and is substantially free of antibodies that specifically bind antigens other than CD20). Moreover, an isolated antibody may be substantially free of impurities (e.g., cells, cellular debris, aggregates, host cell proteins, undesired proteins and peptides, undesired antibodies, undesired nucleic acids and oligonucleotides, viruses, salts, buffer components, surfactants, sugars, metallic contaminants, leachables, media components, and/or naturally-occurring organic molecules with which it is naturally associated).

The terms "peptide," "polypeptide," and "protein" are used interchangeably herein to refer to a polymer of amino acids, wherein the polymer may in embodiments be conjugated to a moiety that does not consist of amino acids. The terms also apply to amino acid polymers in which one or more amino acid residue is an artificial chemical mimetic of a corresponding naturally occurring amino acid, as well as to naturally occurring amino acid polymers and non-naturally occurring amino acid polymers. A "fusion" or "fusion protein" refers to a chimeric protein encoding two or more separate protein sequences that are recombinantly expressed or chemically synthesized as a single moiety The term "nucleic acid" as described herein refers to nucleotides (e.g., deoxyribonucleotides, ribonucleotides, and 2'-modified nucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid (e.g., polynucleotides) contemplated herein include any types of RNA (e.g., mRNA, siRNA, miRNA, and guide RNA) and any types of DNA (e.g., genomic DNA, plasmid DNA, and minicircle DNA), and any fragments thereof. Further, as described herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides and/or ribonucleotides, and/or analogs, derivatives, or modifications thereof. Different polynucleotides may have different three-dimensional structures, and may perform various functions, known or unknown. Non-limiting examples of polynucleotides include genomic DNA, a genome, a mitochondrial DNA, a gene, a gene fragment, an exon, an intron, intergenic DNA (including, without limitation, heterochromatic DNA), double stranded DNA (dsDNA), messenger RNA (mRNA), transfer RNA, enhancer RNA (eRNA), micro RNA, interfering RNA (RNAi), small interfering RNA (siRNA), ribosomal RNA, a ribozyme, cDNA, a recombinant polynucleotide, a branched polynucleotide, a plasmid, a vector, an aptamer, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

The term "amino acid," as used herein, encompasses both naturally-occurring amino acids and non-naturally-occurring amino acids. For the purposes of this disclosure, the naturally occurring amino acids comprises the twenty naturally occurring L-amino acids. These 20 amino acids can be split into those that have neutral charges, positive charges, and negative charges. For reference, the "neutral" amino acids are listed along with their respective three-letter and single-letter code and polarity: Alanine: (Ala, A) nonpolar, neutral; Asparagine: (Asn, N) polar, neutral; Cysteine: (Cys, C) nonpolar, neutral; Glutamine: (Gln, Q) polar, neutral; Glycine: (Gly, G) nonpolar, neutral; Isoleucine: (Ile, I) nonpolar, neutral; Leucine: (Leu, L) nonpolar, neutral; Methionine: (Met, M) nonpolar, neutral; Phenylalanine: (Phe, F) nonpolar, neutral; Proline: (Pro, P) nonpolar, neutral; Serine: (Ser, S) polar, neutral; Threonine: (Thr, T) polar, neutral; Tryptophan: (Trp, W) nonpolar, neutral; Tyrosine: (Tyr, Y) polar, neutral; Valine: (Val, V) nonpolar, neutral; and Histidine: (His, H) polar, positive (10%) neutral (90%). The "positively" charged amino acids are: Arginine: (Arg, R) polar, positive; and Lysine: (Lys, K) polar, positive. The "negatively" charged amino acids are: Aspartic acid: (Asp, D) polar, negative; and Glutamic acid: (Glu, E) polar, negative. Examples of non-naturally occurring amino acids include, but are not limited to, D-amino acids (i.e., an amino acid of an opposite chirality to the naturally-occurring form), N-α-methyl amino acids, C-α-methyl amino acids, β-methyl amino acids and D- or L-β-amino acids. Other non-naturally occurring amino acids include, for example, β-alanine (β-Ala), norleucine (Nle), norvaline (Nva), homoarginine (Har), 4-aminobutyric acid (γ-Abu), 2-aminoisobutyric acid (Aib), 6-aminohexanoic acid (ε-Ahx), ornithine (orn), sarcosine, α-amino isobutyric acid, 3-aminopropionic acid, 2,3-diaminopropionic acid (2,3-diaP), D- or L-phenylglycine, D-(trifluoromethyl)-phenylalanine, and D-p-fluorophenylalanine.

The term "continuous" or "semi-continuous" refers to a process by which the production and purification of a biological product is performed substantially with or without interruption or with minor interruption or with unintended interruption for prolonged periods of time. For example, the process transferring the bioreactor bleed solution to the dynamic filtration module is done without interruption, or with minor interruption. In other examples, the process of removing impurities from a heterogeneous mixture by dynamic filtration and transferring the filtrate (containing the biological product) to a first module (e.g., affinity-based purification module) is done without interruption, or with minor interruption. Moreover, the process of transferring the solution from the first module to a second module (e.g., charge-based purification) is done without interruption, or with minor interruption. In yet other examples, the product stream from dynamic filtration through the first module, through the second module, and/or subsequent steps is done without interruption, or with minor interruption. In other words, a subsequent unit operation can start processing the product stream before a first unit operation has finished processing the product stream.

As used in reference to the dynamic filtration and/or purification processes (affinity-based, magnetic purification, charge-based, magnetic purification, affinity-based purification, charge-based purification, affinity-based, fluidic purification, charge-based fluidic purification, the affinity-based TFF purification module, the charge-based TFF purification module, and/or isoelectric point-based purification processes) of the present invention, "continuous" means that the processes are physically and logistically integrated so as to permit operation without interruption of the fluid flow derived from a steady-state bioreactor for a prolonged period of time. The processes of the present invention are capable of continuous operation, for example, for prolonged periods ranging from 1 day to several months without interrupting the operation or sequence of the processes. The term continuous, as used in reference to the processes of the disclosed invention, is also understood to mean that a process is not performed in a batch-wise manner or in a truly continuous manner. For example, a process comprising a hold-up volume may be deemed continuous if the process is able to operate without interrupting the fluid flow derived from the bioreactor bleed line. As used in the present invention, the processes are operated for a continuous period greater than 2, 3, 4, 5, 6, or 7 days, 2, 3, 4, 5, 6, 7 or 8 weeks, or 3, 4, 5, 6 or more months.

The terms "semi-continuous" and "intermittent" mean that one or more of the processes or elements of an integrated system operate in a discontinuous or batch-wise manner, for example, fed-batch modes of operation, while other processes or elements of the integrated system operate in a continuous manner.

The methods and processes described herein may be continuous, semi-continuous, or not continuous. Minor (and/or unintended interruptions, and/or intended interruptions) interruptions, for example, may include tears or breaks (e.g., within the filter membrane of the dynamic filtration module). For example, a tear or break in the filter membrane may include any alteration which affects the integrity of the filter membrane to perform its function. Any blockage or obstruction within any of the ports, tubing, devices, or apparatuses throughout the system may be considered a minor interruption. Other minor interruptions contemplated include overfilled containers/vessels or underfilled vessels/containers. A malfunction of the magnet or magnetic field used during purification may also constitute a minor interruption. A malfunction of loop conveyer system used during purification may also constitute a minor interruption. A malfunction of pick and place robotics system used during purification may also constitute a minor interruption. A malfunction of mechanical rotary system used during purification may also constitute a minor interruption. A malfunction of in-line analytical measurement instruments, for example, sensors or detectors used during purification may also constitute a minor interruption. A malfunction of feedback control mechanisms, for example, PID or closed loop controllers, used during purification may also constitute a minor interruption.

The term "integrated," as used in reference to multiple apparatuses, modules, systems and/or processes, means that the apparatuses, modules, systems and/or processes are physically and logistically connected so as to constitute a unified system capable of operating continuously. In the context of the system of the present invention, which is directed to an integrated continuous or semi-continuous system for producing a purified biological product, an integrated system will connect different components directly and in a manner sufficient to maintain continuous flow between the different components of the system.

The term "weight percent" or "% (w/w)" refers to a percentage of a component in a solution that is calculated on the basis of weight for the component and the solvent. For example, a 1% (w/w) solution of a component would have 1 g of the component dissolved in a 100 g of solvent. The term "volume percent" or "% (v/v)" refers to a percentage of a component in a solution that is calculated on the basis of volume for the component and the solvent. For example, a 1% (v/v) solution of a component would have 1 ml of the component dissolved in a 100 ml of solvent.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1: Method of Continuous Production and Purification of Monoclonal Antibodies Having a Dynamic Filtration Module, an Affinity-Based, Magnetic Purification Module, and a Free-Flow Electrophoresis Module Etanercept is continuously produced in a chemostat bioreactor operating at steady-state at a titre of 4 g/L. The heterogeneous mixture containing etanercept, large impurities, and small impurities is transferred to a dynamic filtration module via a single output head in communication with the input line (perfusion bioreactor bleed line) at a flow rate of 10 mL/min. Large impurities are removed by dynamic filtration (0.45 µm PES, rolled filter membrane; mechanically smooth membrane support structure with a parallel slotted opening and temperature control; a wash zone; a membrane transport velocity of 1 mm/sec; a vacuum gauge pressure of −0.9 bar; 2 vacuum collection vessel with a controllable T-valve) to yield a filtrate containing etanercept and small impurities. Once the first vacuum collection vessel reaches capacity, the flow is diverted to the second vacuum collection vessel and the first vacuum collection vessel is equilibrate to atmospheric pressure.

The filtrate is transferred from the first vacuum collection vessel (atmospheric pressure equilibrated) to the inlet of the affinity-based, magnetic purification module at a flow rate of 10 mL/min via a tubing connection and a peristaltic pump. The filtrate enters a thin-walled, transport vessel charged with 2% by weight Protein A-coated magnetic resin beads (40 µm), suspended in a binding/wash buffer (0.025 M Tris, 0.15 M NaCl; pH 7), at the home position of a loop conveyor system. Once the transport vessel is filled, the transport vessel moves to an equilibration zone to bind for 30 minutes, while the next transport vessel continues to receive the continuous filtrate flow. Following the binding of antibodies to Protein A-coated magnetic resin beads, the transport vessel moves to a permanent magnetic field zone to allow the magnetic resin beads to migrate toward the wall of the tranport vessel. The solution containing small impurities is removed by aspiration and sent to a waste vessel. Binding/wash buffer (0.025 M Tris, 0.15 M NaCl; pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Binding/wash buffer is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Binding/wash buffer is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Low pH elution buffer (0.1 M glycine, pH 2.0) is added and the transport vessel moves to an equilibration zone to enable elution. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Low pH elution buffer (0.1 M glycine, pH 2.0) is added and the transport vessel moves to an equilibration zone to enable elution. The transport vessel moves to a permanent magnetic field zone to allow the magnetic resin beads to migrate toward a single wall of the tranport vessel. The solution is removed by aspiration and sent to a collection vessel. Regeneration buffer (0.25 M Tris; pH 8.5) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Binding/wash buffer (0.025 M Tris, 0.15 M NaCl; pH 7) is added and the transport vessel moves to an equilibration zone to enable buffer exchange to return the magnetic resin beads to their initial condition to complete recycling.

The affinity-purified antibody solution is transferred from the collection vessel to the inlet of the isoelectric point-based, fluidic purification module at a flow rate of 10 mL/min via a tubing connection and a peristaltic pump. The solution enters a first free-flow electrophoresis apparatus comprising an ampholyte solution designed to achieve a stable, linear pH gradient between pH 4 and pH 9 under applied voltage to enable operation in an isoelectric focusing mode, a de-bubbling and de-gassing system to enable continuous, long-term operation, an active cooling system to remove Joule heat and maintain a temperature between 4° C. and 37° C., and a liquid circuit breaker to enable in-line process monitoring. This goal of this first apparatus is to separate residual host cell proteins (pI of 4-7 and 9-10) from antibodies (pI of 7-9) into at least two fractions at the outlets of the apparatus. The outlet(s) containing the antibody fraction become(s) the inlet of a second free-flow electrophoresis apparatus connected in series, while the outlet(s) containing host cell proteins are sent to waste collection. The antibody fraction enters the second free-flow electrophoresis apparatus comprising two separate ampholyte solutions and a spacer solution designed to enable operation in a highly resolving isotachophoresis mode, a de-bubbling and de-gassing system to enable continuous, long-term operation, an active cooling system to remove Joule heat and maintain a temperature between 4° C. and 37° C., and a liquid circuit breaker to enable in-line process monitoring. This goal of this first apparatus is to separate residual host cell antibodies (pI of 7-9) from Etanercept (pI of 7.9) into at least two fractions at the outlets of the apparatus. The outlet(s) containing purified Etanercept is collected, while the outlet(s) containing antibody impurities are sent to waste collection.

The purified and isolated etanercept solution is transferred from the collection vessel to the a high performance tangential flow filtration (HP-TFF) vessel at a flow rate of 5 mL/min via a tubing connection and a peristaltic pump to enable HP-TFF to be performed semi-continuously in fed-batch mode. HP-TFF is performed to buffer exchange and further purify the ritxumab (difiltration with 10 diavolulmes) and then concentrate to enable subsequent vial filling of the rententate containing the purified etanercept.

This process is performed continuously for 3 months after reaching steady-state cell culture growth conditions.

Example 2: Method of Continuous Production and Purification of Monoclonal Antibodies Having a Dynamic Filtration Module, an Affinity-Based Purification Module, and a Free-Flow Electrophoresis Module Etanercept is continuously produced in a chemostat bioreactor operating at steady-state at a titre of 4 g/L. The heterogeneous mixture containing etanercept, large impurities, and small impurities is transferred to a dynamic filtration module via a single output head in communication with the input line (perfusion bioreactor bleed line) at a flow rate of 10 mL/min. Large impurities are removed by dynamic filtration (0.45 µm PES, rolled filter membrane; mechanically smooth membrane support structure with a parallel slotted opening and temperature control; a wash zone; a membrane transport velocity of 1 mm/sec; a vacuum gauge pressure of −0.9 bar; 2 vacuum collection vessel with a controllable T-valve) to yield a filtrate containing etanercept and small impurities. Once the first vacuum collection vessel reaches capacity, the flow is diverted to the second vacuum collection vessel and the first vacuum collection vessel is equilibrate to atmospheric pressure.

The filtrate is transferred from the first vacuum collection vessel (atmospheric pressure equilibrated) to the inlet of the affinity-based purification module at a flow rate of 10 mL/min via a tubing connection and a peristaltic pump. Through a gasketed lid system, the filtrate enters a vessel in a carousel charged with a 40 mL dense slurry of Protein A-coated resin beads (90 µm) suspended in a binding/wash buffer (0.025 M Tris, 0.15 M NaCl, pH 7), at the fill position of a mechanical rotary system. Once the vessel is filled, the vessel moves to an equilibration position to allow binding for 30 minutes, while the next vessel continues to receive the continuous filtrate flow. Following the binding of antibodies to Protein A-coated resin beads, the vessel moves to a wash position to remove the solution containing small impurities by pressure driven flow through the basement porous membrane and direct it to waste collection. Binding/wash buffer (0.025 M Tris, 0.15 M NaCl; pH 7) is added to resuspend the resin beads and enable washing for 5 minutes. The wash solution is removed by pressure driven flow through the basement porous membrane and is directed to waste collection. This wash process is repeated four times to effectively wash the resin beads. Following the washing of the Protein A-coated resin beads, the vessel moves to an elution position to elute the captured etanercept by pressure driven flow through the basement porous membrane and direct it to a collection vessel. Low pH elution buffer (0.1 M glycine; pH 2.0) is added to resuspend the resin beads and is equilibrated for 5 minutes to enable de-binding and elution of etanercept. The eluate is removed by pressure driven flow through the basement porous membrane and is directed to a collection vessel. This elution process is repeated four times to effectively elute the etanercept from the resin beads. Following the elution of etanercept from resin beads, the vessel moves to a regeneration position to enable recycling of the resin beads. Regeneration buffer (0.25 M Tris; pH 8.5) is added to resuspend the resin beads and is equilibrated for 5 minutes to enable regeneration of the resin beads. This regeneration process is repeated two times to effectively regenerate the resin beads. Binding/wash buffer (0.025 M Tris, 0.15 M NaCl; pH 7) is added and is equilibrated for 5 minutes to enable buffer exchange to return the resin beads to their initial condition to complete recycling. This buffer exchange is repeated two times and represents the final aspect of regeneration and recycling process.

The affinity-purified antibody solution is transferred from the collection vessel to the inlet of the isoelectric point-based, fluidic purification module at a flow rate of 10 mL/min via a tubing connection and a peristaltic pump. The solution enters a first free-flow electrophoresis apparatus comprising an ampholyte solution designed to achieve a stable, linear pH gradient between pH 4 and pH 9 under applied voltage to enable operation in an isoelectric focusing mode, a de-bubbling and de-gassing system to enable continuous, long-term operation, an active cooling system to remove Joule heat and maintain a temperature between 4° C. and 37° C., and a liquid circuit breaker to enable in-line process monitoring. This goal of this first apparatus is to separate residual host cell proteins (pI of 4-7 and 9-10) from antibodies (pI of 7-9) into at least two fractions at the outlets of the apparatus. The outlet(s) containing the antibody fraction become(s) the inlet of a second free-flow electrophoresis apparatus connected in series, while the outlet(s) containing host cell proteins are sent to waste collection. The antibody fraction enters the second free-flow electrophoresis apparatus comprising two separate ampholyte solutions and a spacer solution designed to enable operation in a highly resolving isotachophoresis mode, a de-bubbling and de-gassing system to enable continuous, long-term operation, an active cooling system to remove Joule heat and maintain a temperature between 4° C. and 37° C., and a liquid circuit breaker to enable in-line process monitoring. This goal of this first apparatus is to separate residual host cell antibodies (pI of 7-9) from Etanercept (pI of 7.9) into at least two fractions at the outlets of the apparatus. The outlet(s) containing purified Etanercept is collected, while the outlet(s) containing antibody impurities are sent to waste collection.

The purified and isolated etanercept solution is transferred from the collection vessel to the a high performance tangential flow filtration (HP-TFF) vessel at a flow rate of 5 mL/min via a tubing connection and a peristaltic pump to enable HP-TFF to be performed semi-continuously in fed-batch mode. HP-TFF is performed to buffer exchange and further purify the ritxumab (difiltration with 10 diavolulmes) and then concentrate to enable subsequent vial filling of the rententate containing the purified etanercept.

This process is performed continuously for 3 months after reaching steady-state cell culture growth conditions.

Example 3: Method of Continuous Production and Purification of Monoclonal Antibodies Having a Dynamic Filtration Module, an Affinity-Based, Magnetic Purification Module, and a Charge-Based, Magnetic Purification Module Etanercept is continuously produced in a chemostat bioreactor operating at steady-state at a titre of 4 g/L. The heterogeneous mixture containing etanercept, large impurities, and small impurities is transferred to a dynamic filtration module via a single output head in communication with the input line (chemostat bioreactor bleed line) at a flow rate of 5 mL/min. Large impurities are removed by dynamic filtration (0.45 μm PES, rolled filter membrane; mechanically smooth membrane support structure with a parallel slotted opening and temperature control; a wash zone; a membrane transport velocity of 2 mm/sec; a vacuum of 6 Torr; 2 vacuum collection vessel with a controllable T-valve) to yield a filtrate containing etanercept and small impurities. Once the first vacuum collection vessel reaches capacity, the flow is diverted to the second vacuum collection vessel and the first vacuum collection vessel is equilibrate to atmospheric pressure.

The filtrate is transferred from the first vacuum collection vessel (atmospheric pressure equilibrated) to the inlet of the affinity-based, magnetic purification module at a flow rate of 5 mL/min via a tubing connection and a peristaltic pump. The filtrate enters a thin-walled, transport vessel charged with 2% by weight Protein A-coated magnetic resin beads (40 μm), suspended in a binding/wash buffer (0.025 M Tris, 0.15 M NaCl, 0.05% Tween-20; pH 7), at the home position of a loop conveyor system. Once the transport vessel is filled, the transport vessel moves to an equilibration zone to bind for 30 minutes, while the next transport vessel continues to receive the continuous filtrate flow. Following the binding of antibodies to Protein A-coated magnetic resin beads, the transport vessel moves to a permanent magnetic field zone to allow the magnetic resin beads to migrate toward the wall of the tranport vessel. The solution is removed by aspiration and sent to a waste vessel. Binding/wash buffer (0.025 M Tris, 0.15 M NaCl, 0.05% Tween-20; pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Binding/wash buffer is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Binding/wash buffer is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Low pH elution buffer (0.1 M glycine, 0.05% Tween-20, pH 2.0) is added and the transport vessel moves to an equilibration zone to enable elution. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Low pH elution buffer (0.1 M glycine, 0.05% Tween-20, pH 2.0) is added and the transport vessel moves to an equilibration zone to enable elution. The transport vessel moves to a permanent magnetic field zone to allow the magnetic resin beads to migrate toward a single wall of the tranport vessel. The solution is removed by aspiration and sent to a collection vessel. Regeneration buffer (0.25 M Tris, 0.05% Tween-20; pH 8.5) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Regeneration buffer is added and the transport vessel moves to an equilibration zone to enable magnetic resin bead recycling.

The affinity-purified antibody solution is adjusted to pH 7 and transferred from the collection vessel to the inlet of the positive charge-based, magnetic purification module at a flow rate of 5 mL/min via a tubing connection and a peristaltic pump. The solution enters a thin-walled, transport vessel charged with 2% by weight cationic magnetic resin beads (40 µm), suspended in an association/wash buffer (0.025 M Tris, 0.05% Tween-20, pH 7), at the home position of a loop conveyor system. Once the transport vessel is filled, the transport vessel moves to an equilibration zone to enable charge or electrostatic association for 30 minutes, while the next transport vessel continues to receive the continuous affinity-purified antibody solution flow. Following the association of antibodies with the cationic magnetic resin beads, the transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Association/wash buffer (0.025 M Tris, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Association/wash buffer (0.025 M Tris, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Association/wash buffer (0.025 M Tris, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Dissociation buffer (0.1 M Tris, 0.1 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Dissociation buffer (0.025 M Tris, 0.15 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Dissociation buffer (0.025 M Tris, 0.2 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Dissociation buffer (0.025 M Tris, 0.25 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Regeneration buffer (0.025 M Tris, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Regeneration buffer (0.025 M Tris, 0.05% Tween-20, pH 7) is added and the transport vessel moves to an equilibration zone to enable magnetic resin bead recycling.

The positive charge-purified antibody solution is buffer exchanged by tangential flow filtration to 0.05 M phosphate, pH 7 and subsequently transferred from the collection vessel to the inlet of the negative charge-based, magnetic purification module at a flow rate of 5 mL/min via a tubing connection and a peristaltic pump. The solution enters a thin-walled, transport vessel charged with 2% by weight anionic magnetic resin beads (40 µm), suspended in an association/wash buffer (0.05 M phosphate, 0.05% Tween-20, pH 7), at the home position of a loop conveyor system. Once the transport vessel is filled, the transport vessel moves to an equilibration zone to enable charge or electrostatic association for 30 minutes, while the next transport vessel continues to receive the continuous positive charge-purified antibody solution flow. Following the association of antibodies with the anionic magnetic resin beads, the transport vessel moves to a permanent magnetic field zone to allow the magnetic resin beads to migrate toward the wall of the tranport vessel. The solution is removed by aspiration and sent to a waste vessel. Association/wash buffer (0.05 M phosphate, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Association/wash buffer (0.05 M phosphate, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Association/wash buffer (0.05 M phosphate, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Dissociation buffer (0.05 M phosphate, 0.1 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Dissociation buffer (0.05 M phosphate, 0.15 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Dissociation buffer (0.05 M phosphate, 0.2 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Dissociation buffer (0.05 M phosphate, 0.25 M NaCl, 0.05% Tween-20, pH 7) is added and the transport vessel moves to an equilibration zone to enable dissociation. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a collection vessel. Regeneration buffer (0.05 M phosphate, 0.05% Tween-20, pH 7) is added and the transport vessel moves to an equilibration zone to enable washing. The transport vessel moves to a permanent magnetic field zone to allow the magnetic resin beads to mix between two separate and opposing magnetic fields that toggle between states of on and off and subsequently migrate toward a single wall of the tranport vessel. The solution is removed by aspiration and sent to a waste vessel. Regeneration buffer (0.05 M phosphate, 0.05% Tween-20, pH 7) is added and the transport vessel moves to an equilibration zone to enable magnetic resin bead recycling.

The negative charge-purified and isolated etanercept solution is transferred from the collection vessel to the a high performance tangential flow filtration (HP-TFF) vessel at a flow rate of 5 mL/min via a tubing connection and a peristaltic pump to enable HP-TFF to be performed semi-continuously in fed-batch mode. HP-TFF is performed to buffer exchange and further purify the ritxumab (difiltration with 10 diavolulmes) and then concentrate to enable subsequent vial filling of the rententate containing the purified etanercept.

This process is performed continuously for 3 months after reaching steady-state cell culture growth conditions.

Figure 11:
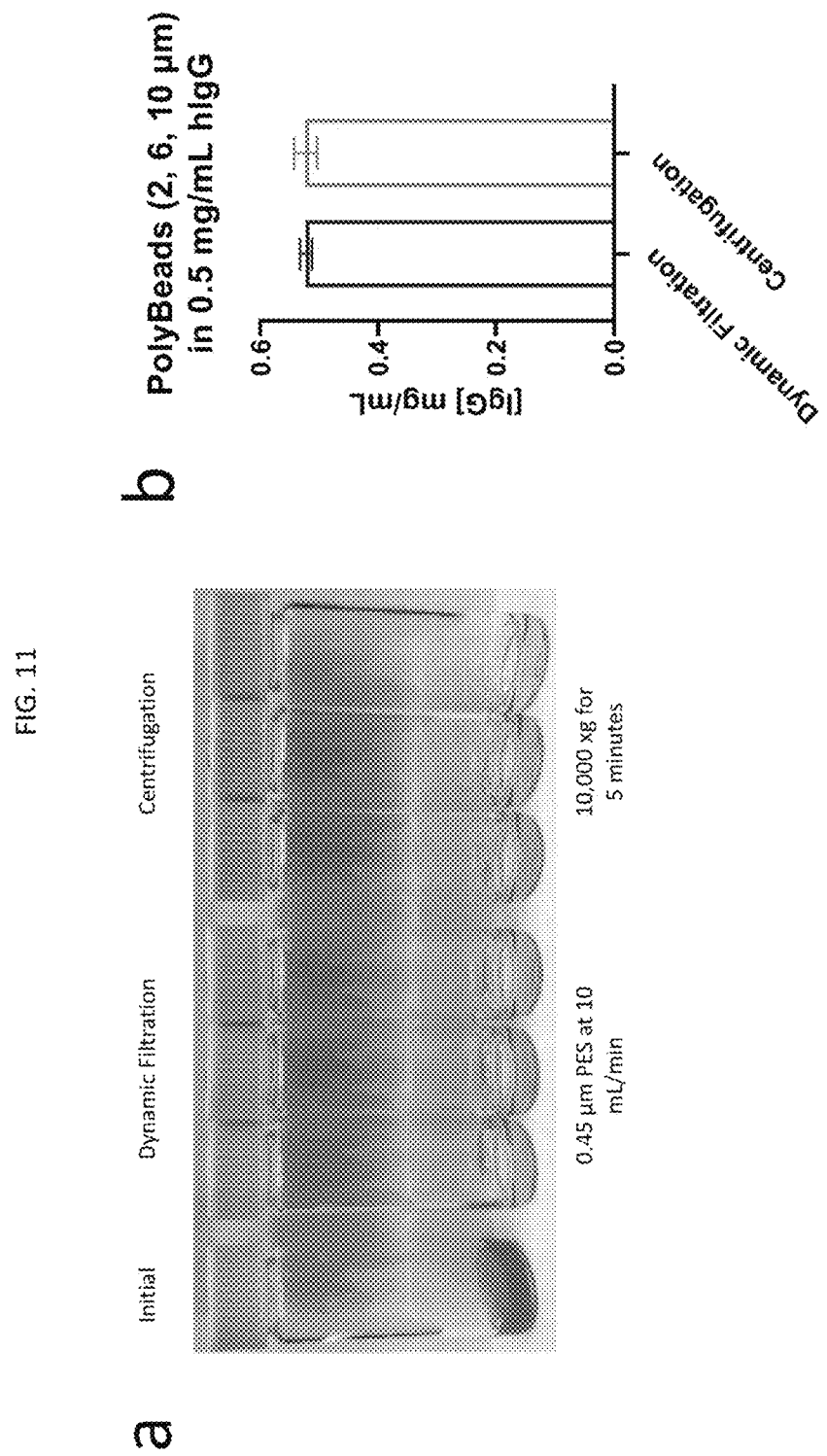
FIGS. 11A and 11D show the dynamic filtration of a heterogeneous mixture of PolyBeads suspended in a 0.5 mg/mL solution of human polyclonal IgG (hIgG) in 1×PBS at an input flow rate of 10 mL/min.
FIG. 11B is a graph showing the spectrophotometric comparison of the total protein concentration as determined by BCA assay of the filtrates obtained by dynamic filtration and the supernatant collected by centrifugation.
FIG. 11C depicts an image of a visual comparison (left-to-right) of the initial heterogeneous mixture of PolyBeads (0.5 µm, 0.75 µm, 1 µm, 2 µm, 3 µm, and 10 µm diameter at $7.3 \times 10^7$, $1.1 \times 10^8$, $1.1 \times 10^8$, $1.1 \times 10^8$, $3.4 \times 10^7$, and $1.0 \times 10^6$ particles/mL, respectively) suspended in a 0.5 mg/mL solution of hIgG in 1×PBS, the filtrate resulting from purification of the heterogeneous mixture with an exemplary dynamic filtration apparatus having a 0.45 µm PES filter membrane and a flow rate of 10 mL/min, and the supernatant collected from purification of the heterogeneous mixture by centrifugation (5 min at 10,000×g).
Figure 11:
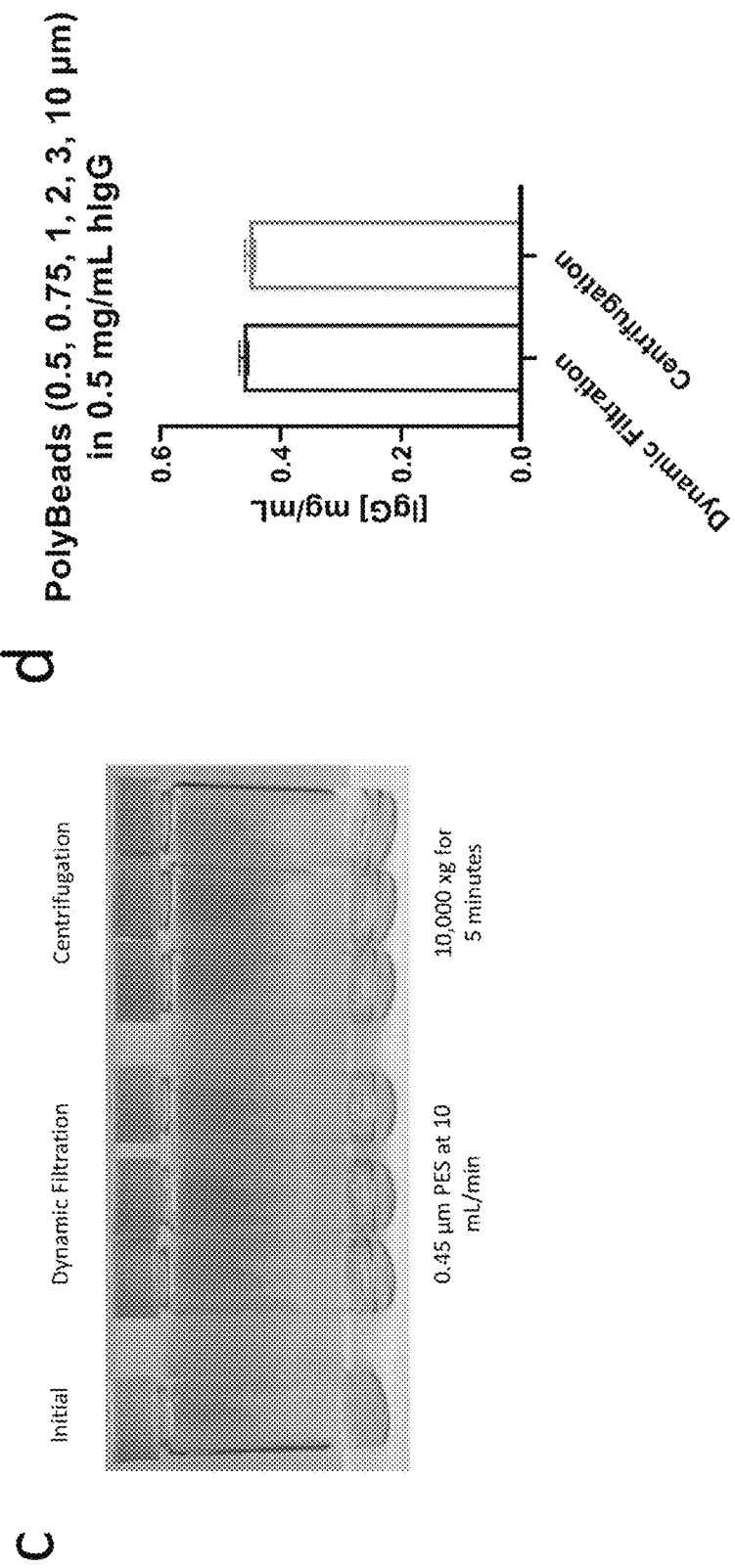

Example 4: Dynamic Filtration Module for Clarification of Polybeads from a Heterogeneous Mixture The exemplary dynamic filtration module described herein provided for continuous dynamic filtration that successfully purified a model target antibody, human polyclonal IgG (hIgG) from a heterogeneous mixture comprising Poly-Beads of different cell and cell debris mimicking sizes (0.5 µm, 0.75 µm, 1 µm, 2 µm, 3 µm, and 10 µm diameter at $7.3 \times 10^7$, $1.1 \times 10^8$, $1.1 \times 10^8$, $1.1 \times 10^8$, $3.4 \times 10^7$, and $1.0 \times 10^6$ particles/mL, respectively) suspended in a 0.5 g/L solution of human polyclonal IgG (hIgG) in 1×PBS at an input flow rate of 10 mL/min from a single slot die output head. Clarification of the PolyBeads resulted in a filtrate containing the purified hIgG. The protein recovery at a flow rate of 10 mL/min was comparable to a standard centrifugation process of 5 minutes at 10,000×g (FIGS. 11C and 11D).

The membrane support structure design and materials selection was important to enable continuous membrane transport at a velocity of 0.5 mm/sec while wetted and under sufficient negative pressure (gauge pressure of −0.9 bar), and thus the selection of materials that have a low static coefficient of friction when wetted for all membrane contacting surfaces (e.g. mechanically smooth PTFE) was of great importance (FIG. 8).

Figure 13:
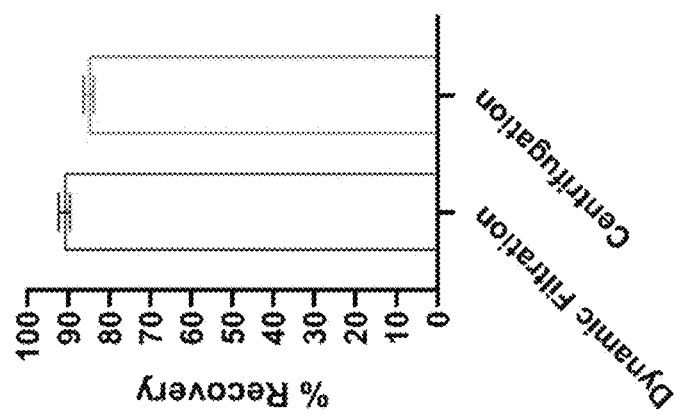
FIGS. 13A-13C show the comparison of cell clarification by dynamic filtration and centrifugation of an input heterogeneous mixture comprising a suspension cell culture in RPMI media spiked with hIgG to a final concentration of 1 g/L.

Example 5: Dynamic Filtration Module for Cell Clarification from a Heterogeneous Mixture The exemplary dynamic filtration module described herein provided for continuous dynamic filtration that successfully purified a model target antibody, human polyclonal IgG (hIgG) from a heterogeneous mixture comprising a suspension of murine myeloma cells ($2.0 \times 10^6$ cells/mL) in RPMI media spiked with hIgG to a final concentration a 1 g/L at an input flow rate of 2 mL/min from a single slot die output head. Clarification of the cells and cell debris resulted in a filtrate containing the purified hIgG. The protein recovery at a flow rate of 2 mL/min was comparable to a standard centrifugation process of 5 minutes at 10,000×g (FIGS. 13A-13C).

The membrane support structure design and materials selection was important to enable continuous membrane transport at a velocity of 0.5 mm/sec while wetted and under sufficient negative pressure (gauge pressure of −0.9 bar), and thus the selection of materials that have a low static coefficient of friction when wetted for all membrane contacting surfaces (e.g. mechanically smooth PTFE) was of great importance (FIG. 8).

Figure 12:
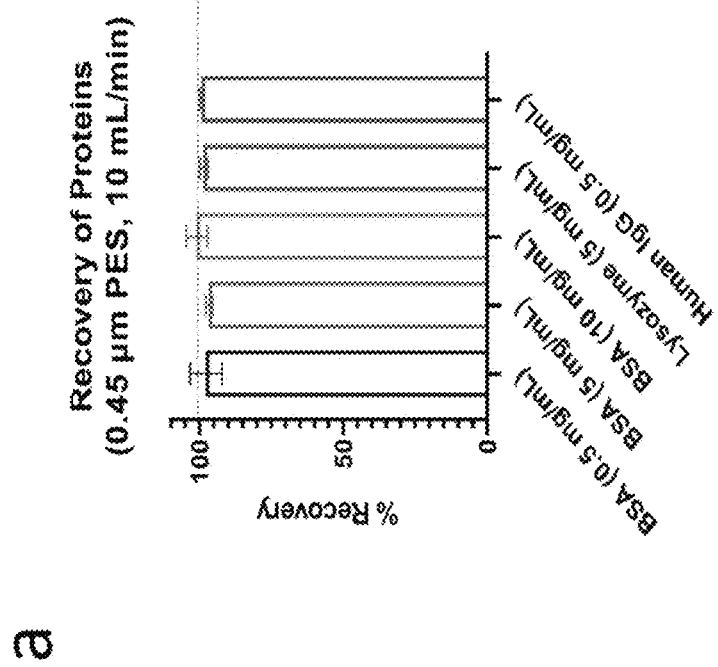

Example 6: Recovery of Proteins with Different Physicochemical Properties by a Dynamic Filtration Module Dynamic filtration via the exemplary dynamic filtration module equipped with a 0.45 µm PES filter membrane having a transport velocity of 0.5 mm/sec was performed with an input flow rate of 10 mL/min for solutions of different concentrations of BSA (0.5-10 g/L, MW of 66,000 Da, pI of 4.5-5), a solution of Lysozyme (5 g/L, MW of 14,000 Da, pI of 11), and a solution of hIgG (0.5 g/L, MW of 150,000, pI of 6-8) and a vacuum gauge pressure of −0.9 bar to evaluate protein recovery, as determined by spectrophotometric analysis of the resulting filtrates (n=3 for each solution) by BCA assay. The protein recovery was similar for all proteins and was observed to be >96% (FIG. 12A).

Example 7: Effect of Filter Membrane Material on Dynamic Filtration Module Performance Dynamic filtration via the exemplary dynamic filtration module equipped with different low protein binding filter membrane materials (PES, hydrophilic PVDF) and pore sizes (0.45 µm, 0.22 µm) having a transport velocity of 0.5 mm/sec was performed with an input flow rate of 10 mL/min for solutions of hIgG (0.5 g/L) and a vacuum gauge pressure of −0.9 bar to evaluate protein recovery, as determined by spectrophotometric analysis of the resulting filtrates (n=3 for each solution) by BCA assay. The protein recovery was similar for each filter membrane material and pore size and was observed to be >96% (FIG. 12B).

Example 8: Effect of Different Membrane Support Structure Geometries and Materials on Dynamic Filtration Module Performance Dynamic filtration via the exemplary dynamic filtration module equipped with mechanically smooth PTFE membrane support structures having different opening geometries (5 parallel slots, porous hydrophilic PE insert) and a 0.45 µm PES filter membrane having a transport velocity of 0.5 mm/sec was performed with an input flow rate of 10 mL/min for solutions of hIgG (0.5 g/L) and a vacuum gauge pressure of −0.9 bar to evaluate protein recovery, as determined by spectrophotometric analysis of the resulting filtrates (n=3 for each solution) by BCA assay. The protein recovery was similar for each membrane support structure and was observed to be >96% (FIG. 12C).

Example 9: Continuous, Long-Term Dynamic Filtration Module Performance

Continuous dynamic filtration via the exemplary dynamic filtration module equipped with mechanically smooth PTFE membrane support structure and a 0.45 µm PES filter membrane having a transport velocity of 0.5 mm/sec was performed with input flow rates of either 5 or 10 mL/min for solutions of Lysozyme (0.5 g/L) and a vacuum gauge pressure of −0.9 bar to evaluate longitudinal protein recovery over a 25 minute duration, as determined by spectrophotometric analysis of the resulting filtrates by BCA assay. The protein recovery was similar for each membrane support structure and was observed to be >96% (FIG. 12D).

Figure 20A:
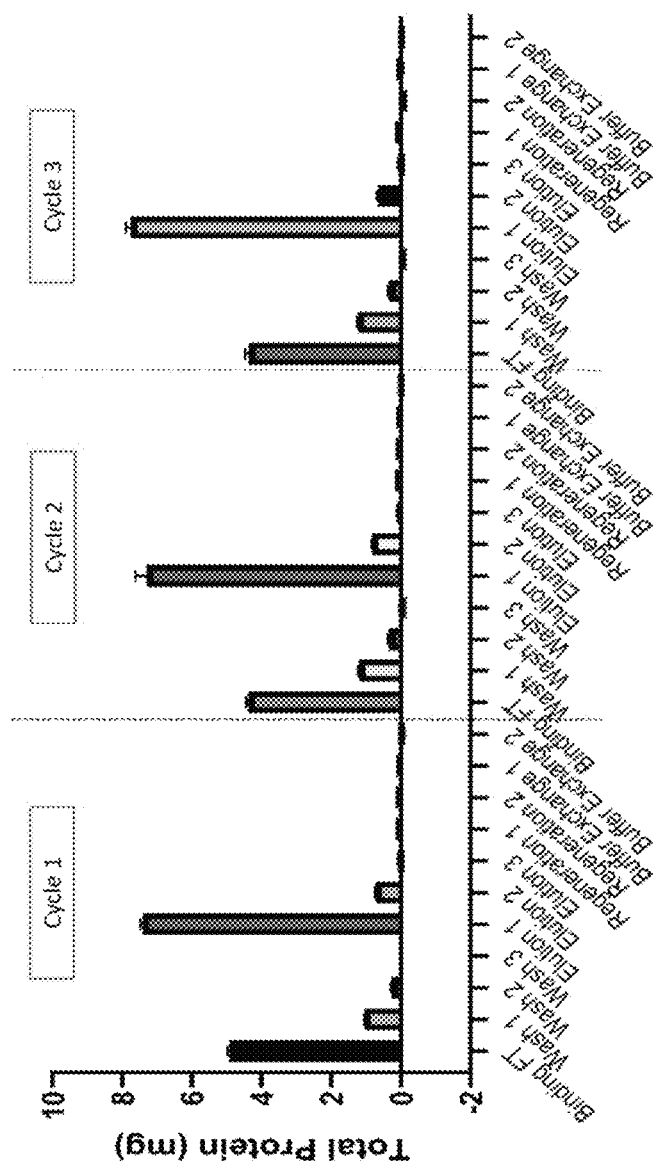
FIGS. 20A and 20B show the affinity-based, magnetic purification of a mixture of hIgG (target, 2 g/L input concentration) and Lysozyme (impurity, 1 g/L input concentration) performed with an affinity-based, magnetic purification apparatus charged with magnetic, Protein A-coated agarose beads.
Figure 20B:
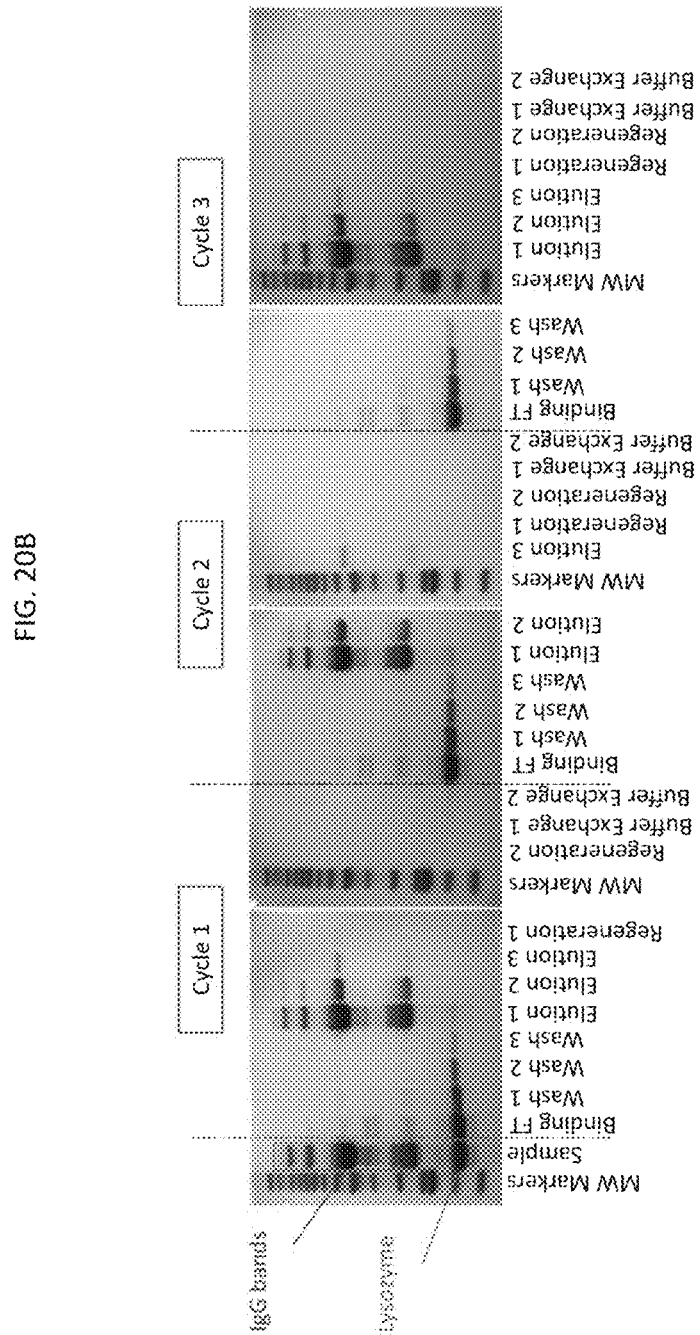

Example 10: Affinity-Based, Magnetic Purification of Polyclonal Human Igg from a Mixture The exemplary affinity-based, magnetic purification module described herein was utilized to purify hIgG from a mixture containing 2 g/L hIgG (affinity target) and 1 g/L Lysozyme (small impurity). Four milliliters of the mixture containing 8 mg hIgG and 4 mg Lysozyme in binding/wash buffer (0.025 M Tris, 0.15 M NaCl; pH 7) were added at 10 mL/min to a thin-walled vessel charged with 500 µL of settled, high affinity Protein A/G magnetic agarose (dynamic binding capacity of >40 mg hIgG/mL settled resin) and equilibrated for 30 minutes with gentle mixing to enable binding. Following the 30 minute binding equilibration, a permanent Nd magnet was manually placed within close proximity to the thin-walled vessel (e.g. mimicking a pick and place robotics system) to attract the magnet affinity beads to the vessel wall and allow for collection of the solution containing unbound hIgG and small impurities by aspiration. Following aspiration, the vessel was filled with 4 mL of binding/wash buffer (0.025 M Tris, 0.15 M NaCl; pH 7) at 10 mL/min and equilibrated for 5 minutes with gentle mixing to wash. Following the 5 minute wash, a permanent Nd magnet was manually placed within close proximity to the thin-walled vessel (e.g. mimicking a pick and place robotics system) to attract the magnet affinity beads to the vessel wall and allow for collection of the wash solution by aspiration. The wash step was repeated for a total 3 washes. Following aspiration of the wash fractions, the vessel was filled with 4 mL of low pH elution buffer (0.1 M glycine; pH 2) at 10 mL/min and equilibrated for 10 minutes with gentle mixing to elute. Following the 10 minute elution, a permanent Nd magnet was manually placed within close proximity to the thin-walled vessel (e.g. mimicking a pick and place robotics system) to attract the magnet affinity beads to the vessel wall and allow for collection of the eluate fraction by aspiration. The elution step was repeated for a total of 3 elutions. Following collection of the 3 eluate fractions, the vessel was filled with 4 mL of low pH elution buffer (0.1 M glycine; pH 2) at 10 mL/min and equilibrated for 5 minutes with gentle mixing to completely remove any residually bound hIgG to initiate regeneration of the magnetic affinity beads. Following the 5 minute residual elution, a permanent Nd magnet was manually placed within close proximity to the thin-walled vessel (e.g. mimicking a pick and place robotics system) to attract the magnet affinity beads to the vessel wall and allow for collection of the first regeneration solution by aspiration. Following collection of the first regeneration solution, the vessel was filled with 4 mL of regeneration buffer (0.25 M Tris; pH 8.5) at 10 mL/min and equilibrated for 5 minutes with gentle mixing to neutralize the pH of the magnetic affinity beads and remove any residual hIgG and small impurities to regenerate the magnetic affinity beads. Following the 5 minute regeneration, a permanent Nd magnet was manually placed within close proximity to the thin-walled vessel (e.g. mimicking a pick and place robotics system) to attract the magnet affinity beads to the vessel wall and allow for collection of the second regeneration solution by aspiration. Following collection of the second regeneration solution, the vessel was filled with 4 mL of a second regeneration buffer (0.025 M Tris, 0.15 M NaCl; pH 7) at 10 mL/min and equilibrated for 5 minutes with gentle mixing to buffer exchange the magnetic affinity beads and return the magnetic affinity beads to their initial condition. Following the 5 minute regeneration, a permanent Nd magnet was manually placed within close proximity to the thin-walled vessel (e.g. mimicking a pick and place robotics system) to attract the magnet affinity beads to the vessel wall and allow for collection of the buffer exchange solution by aspiration. The buffer exchange step was repeated for a total of 2 times to enable reuse of the magnetic affinity beads. The collected fractions for 3 consecutive process cycles and magnetic affinity bead recycling were analyzed spetrophotometrically by BCA and were observed to be robust and reproducible (FIG. 20A). The collected fractions for the 3 consecutive process cycles and magnetic affinity bead recycling were further characterized by SDS-PAGE to confirm the reproducibility and show the ability to purify the hIgG (FIG. 20B).

Example 11: Affinity-Based Purification of Polyclonal Human IGG from a Mixture

Figure 27A:
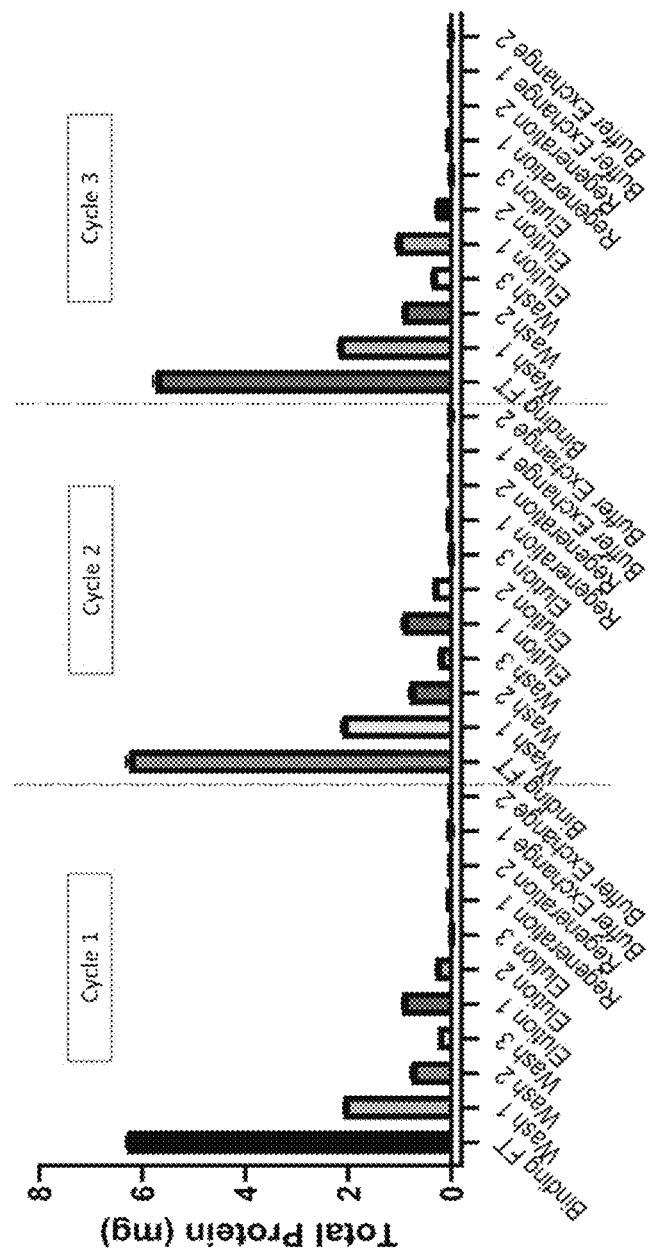
FIGS. 27A and 27B shows the affinity-based purification of a mixture of hIgG (target, 2 g/L input concentration) and Lysozyme (impurity, 1 g/L input concentration) performed with an affinity-based purification apparatus charged Protein A-coated agarose resin beads.
Figure 27B:
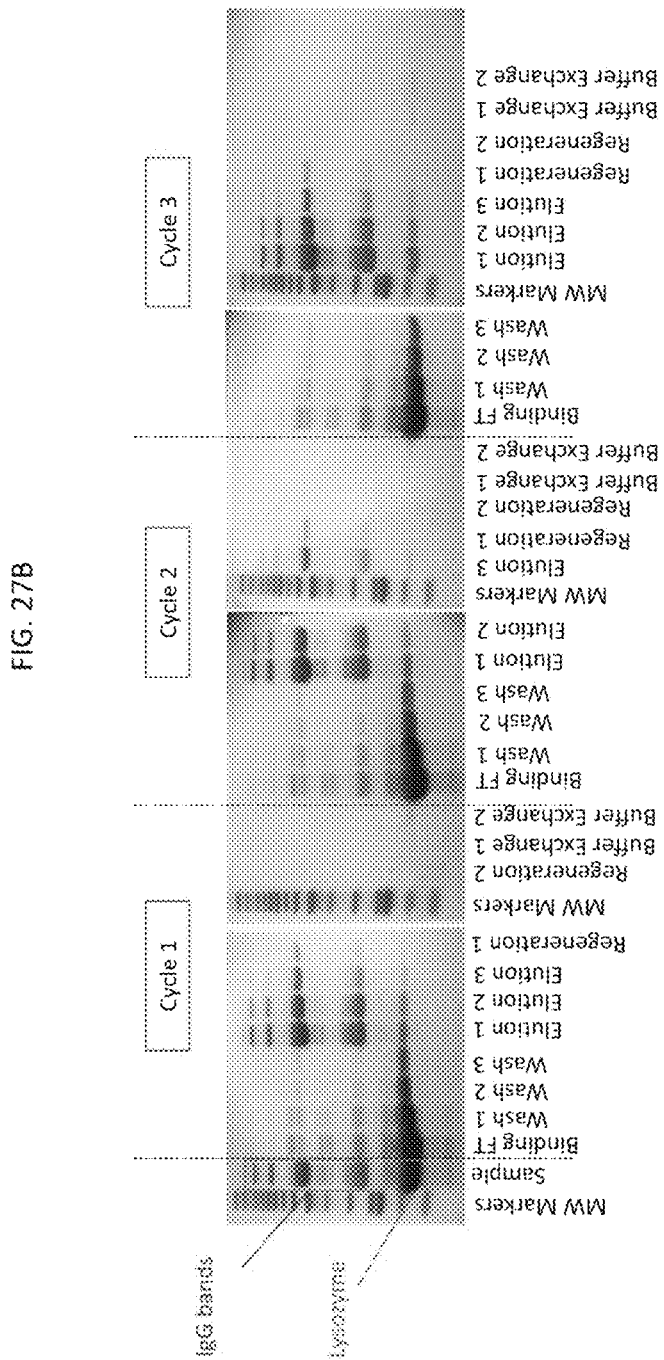

The exemplary affinity-based purification module described herein was utilized to purify hIgG from a mixture containing 2 g/L hIgG (affinity target) and 1 g/L Lysozyme (small impurity). Four milliliters of the mixture containing 8 mg hIgG and 4 mg Lysozyme in binding/wash buffer (0.025 M Tris, 0.15 M NaCl; pH 7) were added at 10 mL/min via with a lid system to a vessel containing a basement glass frit and charged with 500 μL of settled, high affinity Protein A agarose (90 μm, dynamic binding capacity of >35 mg hIgG/mL settled resin) and equilibrated for 30 minutes with gentle mixing to enable binding. Following the 30 minute binding equilibration, compressed air was introduced to the vessel at about 1 psi to allow for collection of the solution containing undbound hIgG and small impurities by pressure driven flow through. Following collection, the vessel was filled with 4 mL of binding/wash buffer (0.025 M Tris, 0.15 M NaCl; pH 7) at 10 mL/min and equilibrated for 5 minutes with gentle mixing to wash. Following the 5 minute wash, compressed air was introduced to the vessel at about 1 psi to allow for collection of the wash solution by pressure driven flow through. The wash step was repeated for a total 3 washes. Following collection of the 3 wash fractions, the vessel was filled with 4 mL of low pH elution buffer (0.1 M glycine; pH 2) at 10 mL/min and equilibrated for 10 minutes with gentle mixing to elute. Following the 10 minute elution, compressed air was introduced to the vessel at about 1 psi to allow for collection of the eluate fraction by pressure driven flow through. The elution step was repeated for a total of 3 elutions. Following collection of the 3 eluate fractions, the vessel was filled with 4 mL of low pH elution buffer (0.1 M glycine; pH 2) at 10 mL/min and equilibrated for 5 minutes with gentle mixing to completely remove any residually bound hIgG to initiate regeneration of the affinity resin beads. Following the 5 minute residual elution, compressed air was introduced to the vessel at about 1 psi to allow for collection of the first regeneration solution. Following collection of the first regeneration solution, the vessel was filled with 4 mL of regeneration buffer (0.25 M Tris; pH 8.5) at 10 mL/min and equilibrated for 5 minutes with gentle mixing to neutralize the pH of the affinity resin beads and remove any residual hIgG and small impurities to regenerate the affinity resin beads. Following the 5 minute regeneration, compressed air was introduced to the vessel at about 1 psi to allow for collection of the second regeneration solution. Following collection of the second regeneration solution, the vessel was filled with 4 mL of a second regeneration buffer (0.025 M Tris, 0.15 M NaCl; pH 7) at 10 mL/min and equilibrated for 5 minutes with gentle mixing to buffer exchange the affinity resin beads and return the affinity resin beads to their initial condition. Following the 5 minute regeneration, compressed air was introduced to the vessel at about 1 psi to allow for collection of the first regeneration solution. The buffer exchange step was repeated for a total of 2 times to enable reuse of the affinity resin beads. The collected fractions for 3 consecutive process cycles and magnetic affinity bead recycling were analyzed spetrophotometrically by BCA and were observed to be robust and reproducible (FIG. 27A). The collected fractions for the 3 consecutive process cycles and magnetic affinity bead recycling were further characterized by SDS-PAGE to confirm the reproducibility and show the ability to purify the hIgG (FIG. 27B).

Figure 40:
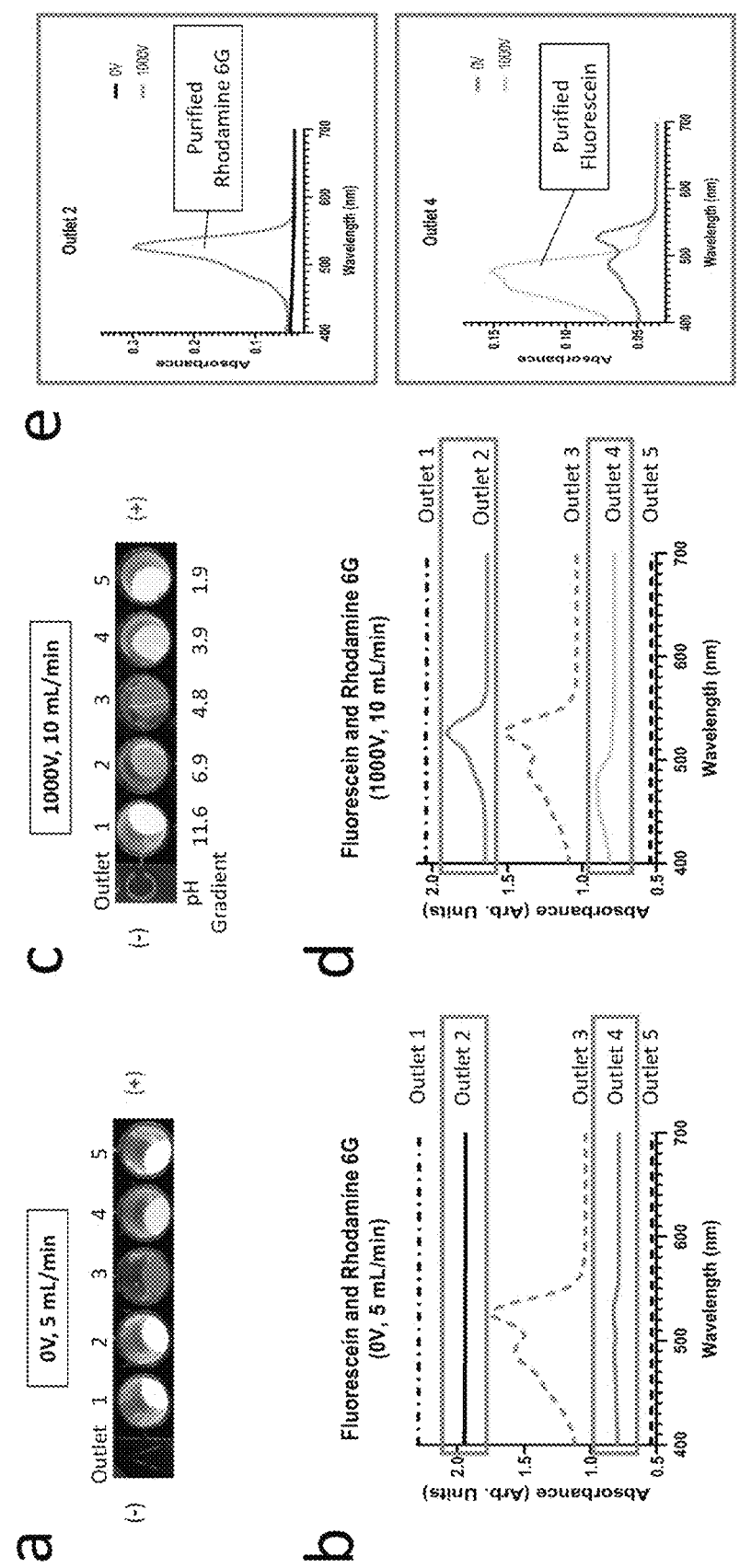
FIGS. 40A-40E show isoelectric point-based, fluidic purification of a mixture of Rhodamine 6G (0.25 mg/mL, net charge of +1) and Fluorescein (0.25 mg/mL, net charge of −1) with an isoelectric point-based purification apparatus with an anodic channel ($H_2SO_4$), a cathodic channel (NaOH), and a main separation channel having five inlets and five outlets flowing an ampholyte solution, wherein the mixture was introduced at the center of the apparatus' inlets (inlet 3).
Figure 41:
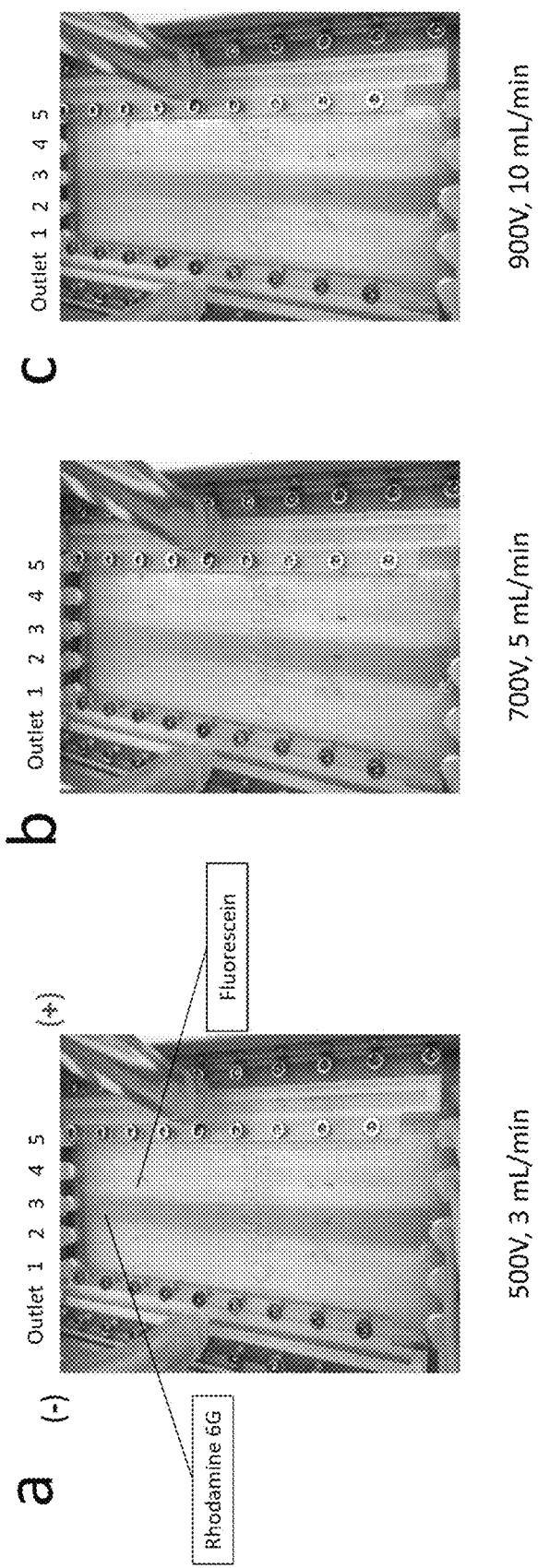
FIGS. 41A-41C show optical imaging of the purification of a mixture of Rhodamine 6G (0.25 mg/mL, net charge of +1) and Fluorescein (0.25 mg/mL, net charge of −1) under different operating conditions with an isoelectric point-based purification apparatus with an anodic channel ($H_2SO_4$), a cathodic channel (NaOH), and a main separation channel having five inlets and five outlets flowing an ampholyte solution, wherein the mixture was introduced at the center of the apparatus' inlets (inlet 3).

Example 12: Separation of Small-Molecules by High Flow Rate, Isoelectric Focusing Free-Flow Electrophoresis Using an Isoelectric Point-Based, Fluidic Purification Module A mixture of Rhodamine 6G (0.25 mg/mL) and Fluorescein (0.25 mg/mL) was introduced to the central inlet (inlet 3) of an exemplary free-flow electrophoresis apparatus comprising an anodic channel ($H_2SO_4$), a cathodic channel (NaOH), and a main separation channel having five inlets and five outlets flowing an ampholyte solution designed to achieve a stable, linear pH gradient between pH 2 and pH 12 under applied voltage to enable operation in an isoelectric focusing mode, a de-bubbling and de-gassing system to enable continuous, long-term operation, and an active cooling system (a thermal chuck with chilled circulating ethylene glycol/water) to remove Joule heat through the bottom plate and maintain a temperature between 4° C. and 37° C. When no voltage was applied, the mixture followed laminar flow and exited the apparatus at the central outlet (outlet 3) (FIGS. 40A and 40B). When 1000V is applied across the main separation channel having an ampholyte and sample input flow rate of 10 mL/min, a linear pH gradient was established and Rhodamine 6G and Fluorescein migrated to the cathode and anode, respectively, consistent with theoretical electrophoretic mobility predictions (FIGS. 40C and 40D). Spectrophotometric analysis of the fractions collected from outlet 2 and outlet 4 showed the presence of purified Rhodamine 6G and purified Fluorescein, respectively (FIG. 40E).

Figure 44:
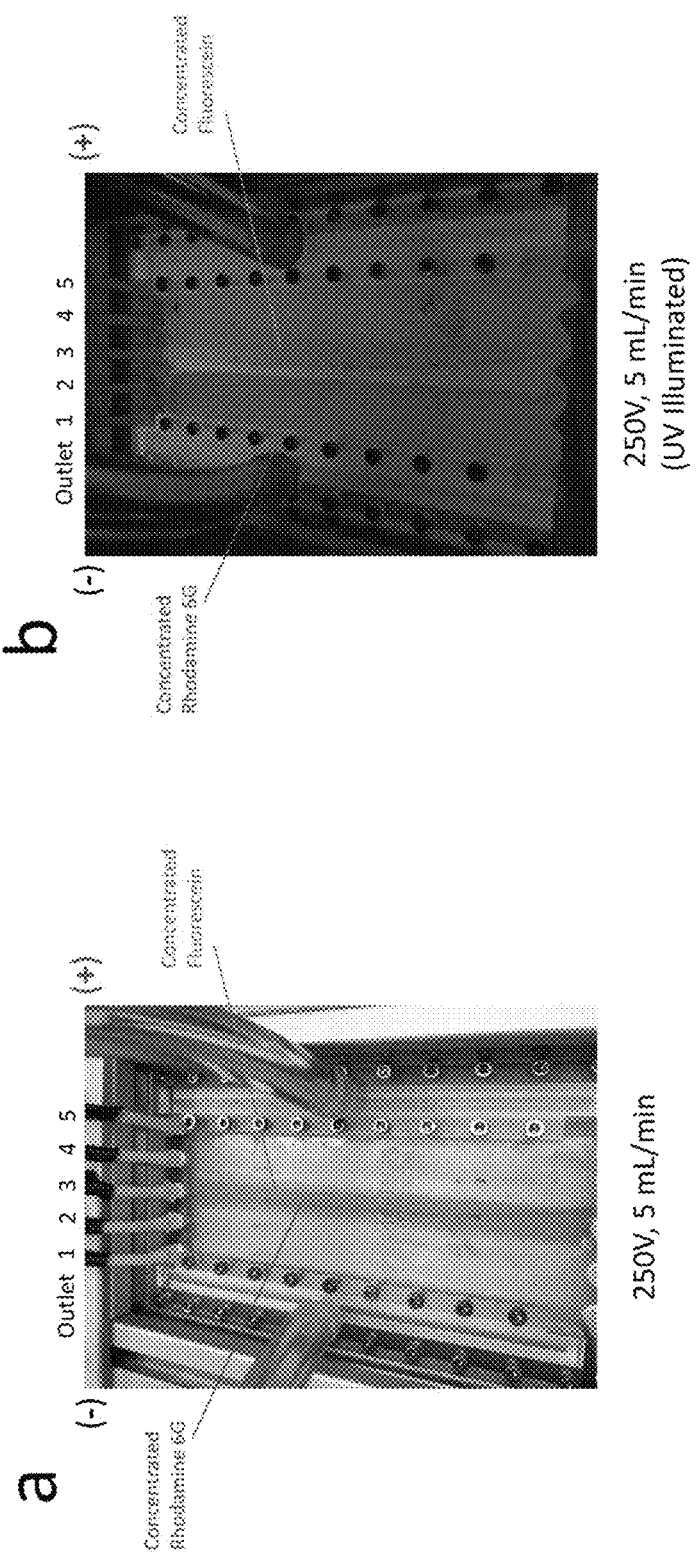
FIGS. 44A and 44B show optical imaging of the purification of a mixture of small-molecule dyes with an isoelectric point-based purification apparatus with an apparatus comprising anodic channel ($H_2SO_4$), a cathodic channel (NaOH), and a main separation channel having five inlets and five outlets flowing two ampholyte solutions separated by a spacer solution, wherein the mixture was introduced in the spacer solution at the center of the apparatus' inlets (inlet 3).

Example 13: Separation of Small-Molecules by High Flow Rate, Isotachophoresis Using an Isoelectric Point-Based, Fluidic Purification Module A mixture of Rhodamine 6G (0.25 mg/mL) and Fluorescein (0.25 mg/mL) was introduced to the central inlet (inlet 3) of an exemplary free-flow electrophoresis apparatus comprising an anodic channel ($H_2SO_4$), a cathodic channel (NaOH), and a main separation channel having five inlets and five outlets flowing a basic ampholyte solution (inlets 1 and 2), a spacer solution (inlet 3), and an acidic ampholyte solution (inlets 4 and 5) to enable operation in an isoelectric focusing mode, a de-bubbling and de-gassing system to enable continuous, long-term operation, and an active cooling system (a thermal chuck with chilled circulating ethylene glycol/water) to remove Joule heat through the bottom plate and maintain a temperature between 4° C. and 37° C. When no voltage was applied, the mixture followed laminar flow and exited the apparatus at the central outlet (outlet 3). When 250V was applied across the main separation channel having an ampholyte and sample input flow rate of 5 mL/min, Rhodamine 6G and Fluorescein migrated to the cathode and anode, respectively, forming highly focused, highly concentrated, and highly resolved bands (FIGS. 44A and 44B).

Figure 42:
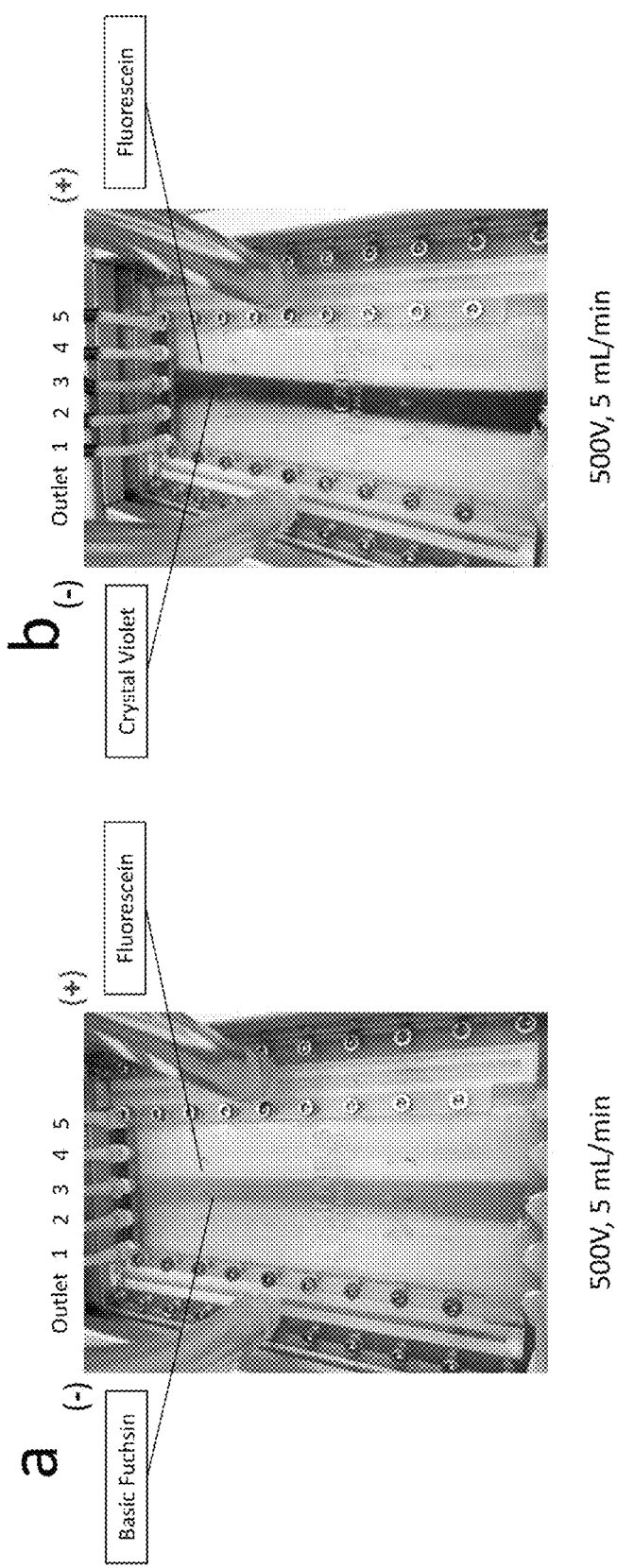
FIGS. 42A and 42B show optical imaging of the purification of a mixture of small-molecule dyes with an isoelectric point-based purification apparatus with an apparatus comprising anodic channel ($H_2SO_4$), a cathodic channel (NaOH), and a main separation channel having five inlets and five outlets flowing an ampholyte solution, wherein the mixture was introduced at the center of the apparatus' inlets (inlet 3).

Example 14: Separation of Basic and Acidic Small-Molecules by High Flow Rate, Isoelectric Focusing Free-Flow Electrophoresis Using an Isoelectric Point-Based, Fluidic Purification Module mixtures of Basic Fuchsin (0.05 mg/mL) and Fluorescein (0.25 mg/mL) or Crystal Violet (0.05 mg/mL) and Fluorescein (0.25 mg/mL) were introduced to the central inlet (inlet 3) of an exemplary free-flow electrophoresis apparatus comprising an anodic channel ($H_2SO_4$), a cathodic channel (NaOH), and a main separation channel having five inlets and five outlets flowing an ampholyte solution designed to achieve a stable, linear pH gradient between pH 2 and pH 12 under applied voltage to enable operation in an isoelectric focusing mode, a de-bubbling and de-gassing system to enable continuous, long-term operation, and an active cooling system (a thermal chuck with chilled circulating ethylene glycol/water) to remove Joule heat through the bottom plate and maintain a temperature between 4° C. and 37° C. When no voltage was applied, the mixtures followed laminar flow and exited the apparatus at the central outlet (outlet 3). When 500V was applied across the main separation channel having an ampholyte and sample input flow rate of 5 mL/min, a linear pH gradient was established and Basic Fuchsin and Fluorescein migrated to the cathode and anode, respectively, consistent with theoretical electrophoretic mobility predictions (FIG. 42A). Similarly, when 500V was applied across the main separation channel having an ampholyte and sample input flow rate of 5 mL/min, a linear pH gradient was established and Crystal Violet and Fluorescein migrated to the cathode and anode, respectively, consistent with theoretical electrophoretic mobility predictions (FIG. 42B).

Figure 43:
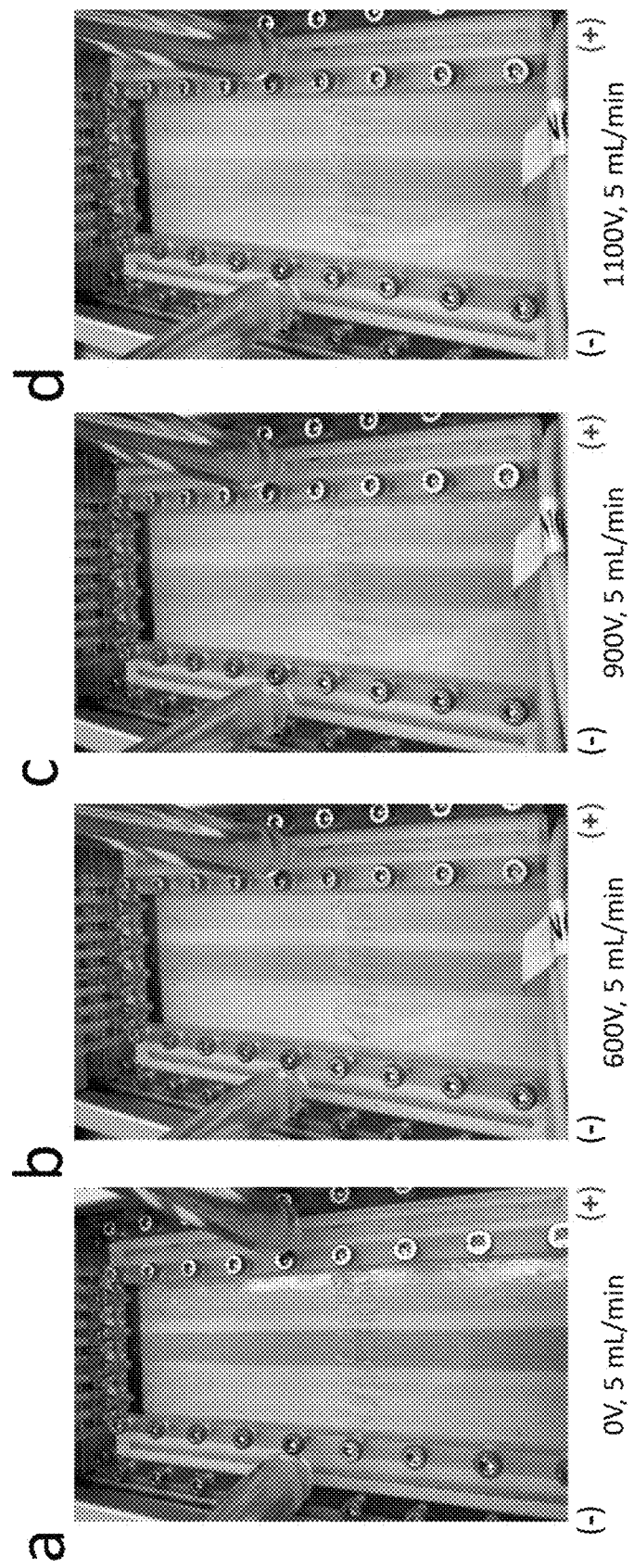
FIGS. 43A-43D show optical imaging of the purification of a mixture of Basic Fuchsin (0.005 mg/mL, net charge of +3) and Fluorescein (0.25 mg/mL, net charge of −1) with an isoelectric point-based purification apparatus operating in an isoelectric focusing free-flow electrophoresis mode across increasing applied voltages. The mixture was introduced into the central inlet (inlet 3) at a flow rate of 5 mL/min with an apparatus comprising an anodic channel, a cathodic channel, and a main separation channel having five inlets and ten outlets, wherein each channel was flowing the same ampholyte solution at 5 mL/min. When no voltage is applied, the mixture follows laminar flow and exits the apparatus at the central outlets (outlets 4 and 5) (FIG. 43A). When voltage is applied across the main separation channel having an ampholyte and sample input flow rate of 5 mL/min, a linear pH gradient is established and Basic Fuchsin and Fluorescein migrate to the cathode and anode, respectively, consistent with theoretical electrophoretic mobility predictions (FIGS. 43B-43D). As the applied voltage was increased from 600V (FIG. 43B), to 900V (FIG. 43C) to 1100V (FIG. 43D) to generate an increase in the E-field strength, the separation of the two molecules was observed to proportionally increase over the length of the main separation channel.

Example 15: Effect of Increasing E-Field on the Separation of Basic and Acidic Small-Molecules by High Flow Rate, Isoelectric Focusing Free-Flow Electrophoresis Using an Isoelectric Point-Based, Fluidic Purification Module A mixture of Basic Fuchsin (0.005 mg/mL) and Fluorescein (0.25 mg/mL) was introduced to the central inlet (inlet 3) of an exemplary free-flow electrophoresis apparatus comprising a main separation channel having five inlets and ten outlets flowing an ampholyte solution designed to achieve a stable, linear pH gradient between pH 2 and pH 12 under applied voltage to enable operation in an isoelectric focusing mode, an anodic and cathodic channel flowing the same ampholyte as the separation channel, a de-bubbling and de-gassing system to enable continuous, long-term operation, a liquid circuit breaker, and an active cooling system (a thermal chuck with chilled circulating ethylene glycol/water) to remove Joule heat through the bottom plate and maintain a temperature between 4° C. and 37° C. When no voltage was applied, the mixture followed laminar flow and exited the apparatus at the central outlets (outlets 4 and 5) (FIG. 43A). When voltage was applied across the main separation channel having an ampholyte and sample input flow rate of 5 mL/min, a linear pH gradient was established and Basic Fuchsin and Fluorescein migrated to the cathode and anode, respectively, consistent with theoretical electrophoretic mobility predictions (FIGS. 43B-43D). As the applied voltage was increased from 600V (FIG. 43B), to 900V (FIG. 43C) to 1100V (FIG. 43D) to generate an increase in the E-field strength, the separation of the two molecules was observed to proportionally increase over the length of the main separation channel.

Figure 45:
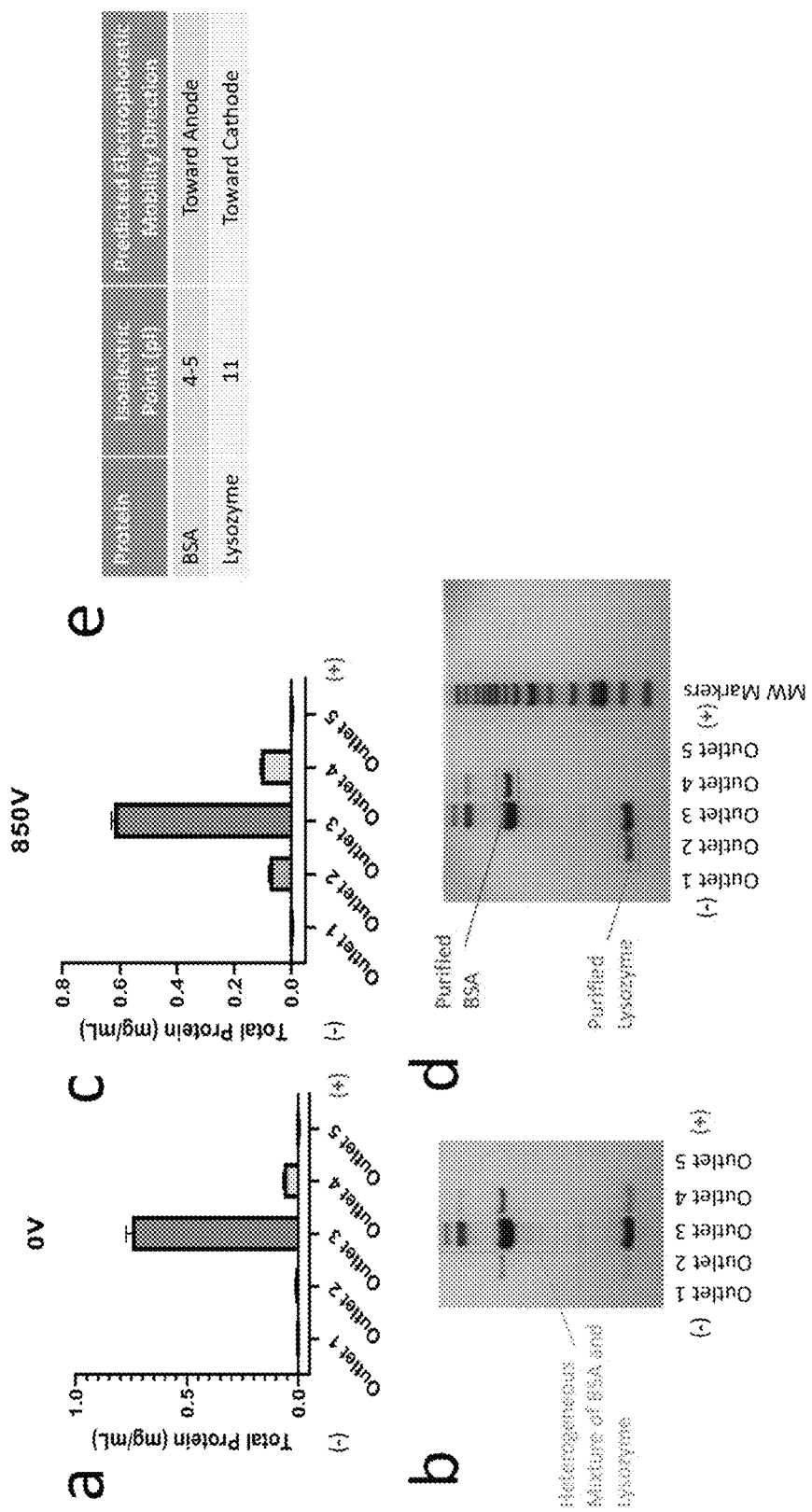
FIGS. 45A-45E show the purification of a mixture of BSA (0.5 mg/mL, pI of 4-5) and Lysozyme (0.25 mg/mL, pI of 11) with an isoelectric point-based purification apparatus with an apparatus comprising anodic channel ($H_2SO_4$), a cathodic channel (NaOH), and a main separation channel having five inlets and five outlets flowing an ampholyte solution, wherein the mixture was introduced at the center of the apparatus' inlets (inlet 3).

Example 16: Separation of Acidic and Basic Proteins by High Flow Rate, Isoelectric Focusing Free-Flow Electrophoresis Using an Isoelectric Point-Based, Fluidic Purification Module A mixture of BSA (0.5 mg/mL, pI of 4-5) and Lysozyme (0.25 mg/mL, pI of 11) was introduced to the central inlet (inlet 3) of an exemplary free-flow electrophoresis apparatus comprising an anodic channel ($H_2SO_4$), a cathodic channel (NaOH), and a main separation channel having five inlets and five outlets flowing an ampholyte solution designed to achieve a stable, linear pH gradient between pH 2 and pH 12 under applied voltage to enable operation in an isoelectric focusing mode, a de-bubbling and de-gassing system to enable continuous, long-term operation, and an active cooling system (a thermal chuck with chilled circulating ethylene glycol/water) to remove Joule heat through the bottom plate and maintain a temperature between 4° C. and 37° C. When no voltage was applied, the mixture followed laminar flow and exited the apparatus at the central outlet (outlet 3) (FIGS. 45A and 45B). When 850V was applied across the main separation channel having an ampholyte and sample input flow rate of 10 mL/min, a linear pH gradient was established and Lysozyme and BSA migrated to the cathode and anode (FIGS. 45C and 45D), respectively, consistent with theoretical electrophoretic mobility predictions (FIG. 45E).

Figure 46:
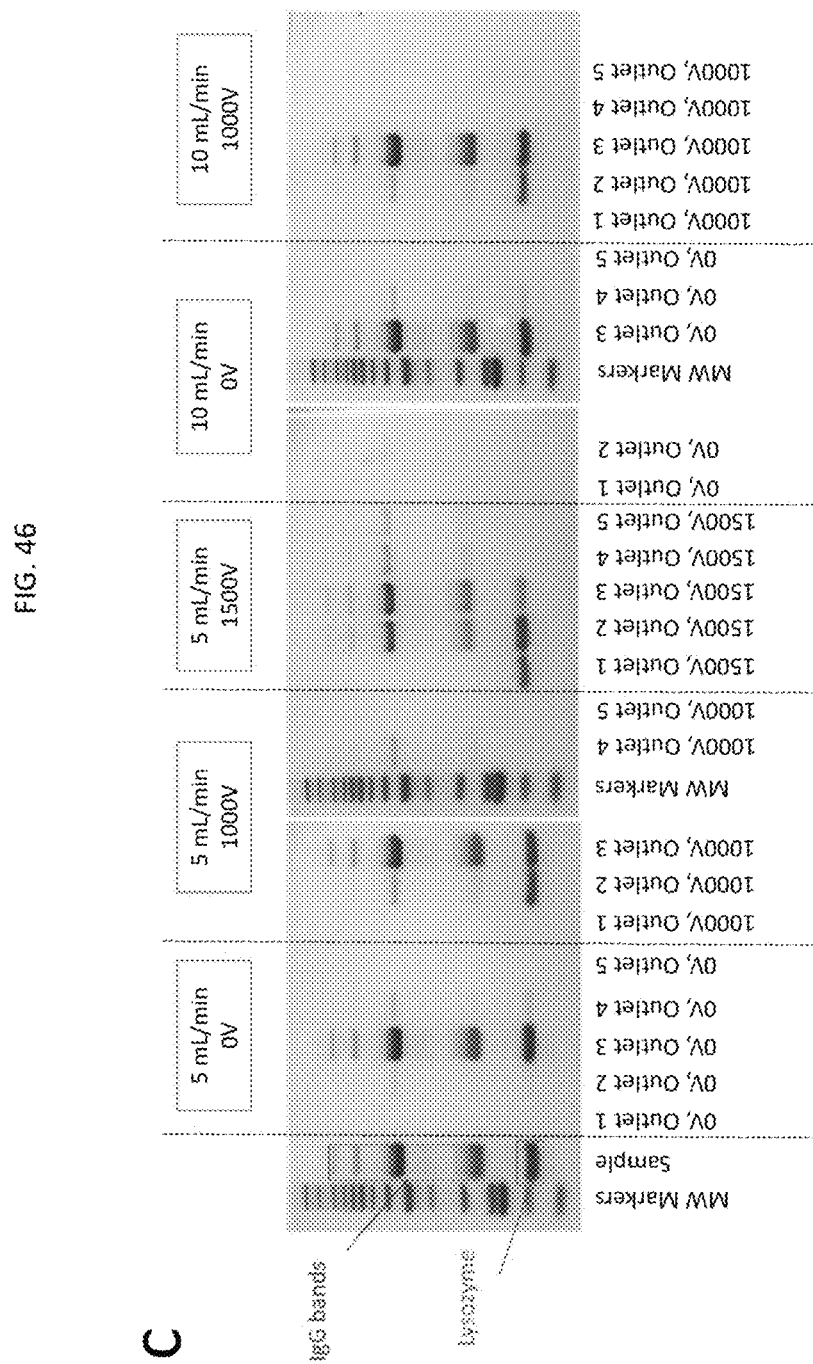
FIGS. 46A-46C show the purification of a mixture of hIgG (0.5 mg/mL, pI of 6-8) and Lysozyme (0.25 mg/mL, pI of 11) with an isoelectric point-based purification apparatus with an apparatus comprising anodic channel ($H_2SO_4$), a cathodic channel (NaOH), and a main separation channel having five inlets and five outlets flowing an ampholyte solution, wherein the mixture was introduced at the center of the apparatus' inlets (inlet 3).
Figure 47A:
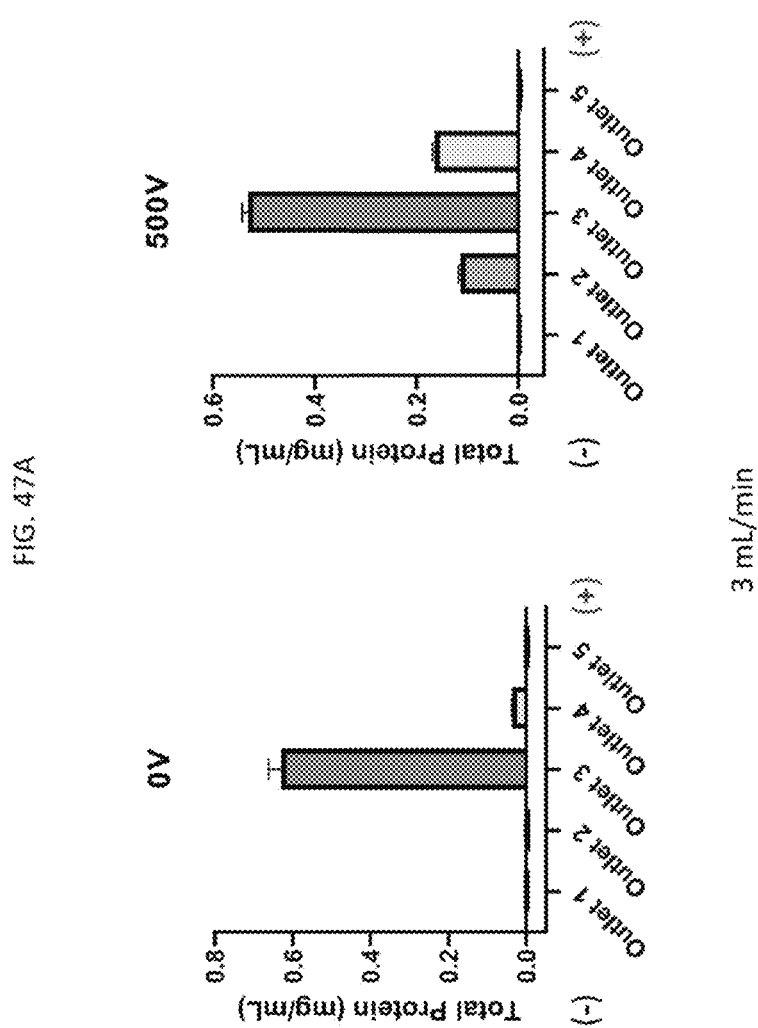
FIGS. 47A-47D show the purification of a mixture of BSA (0.5 mg/mL, pI of 4-5) and Lysozyme (0.25 mg/mL, pI of 11) with an isoelectric point-based purification apparatus with an apparatus comprising anodic channel ($H_2SO_4$), a cathodic channel (NaOH), and a main separation channel having five inlets and five outlets flowing an ampholyte solution, wherein the mixture was introduced at the center of the apparatus' inlets (inlet 3).
Figure 47B:
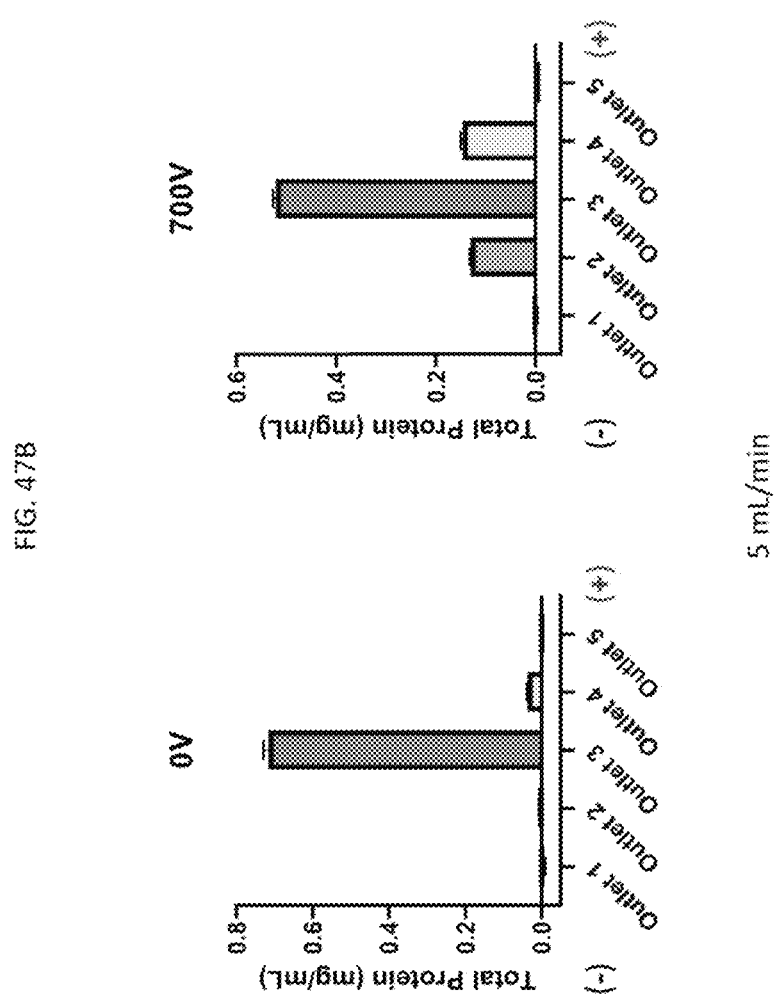
Figure 47C:
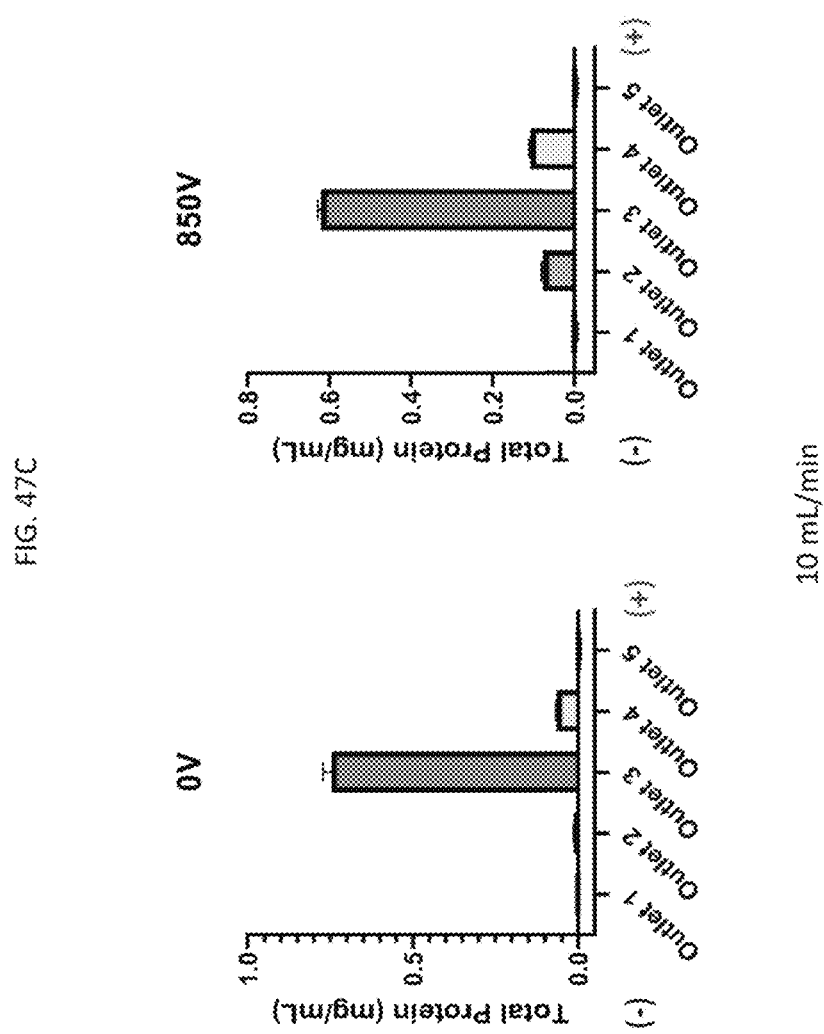
Figure 47D:
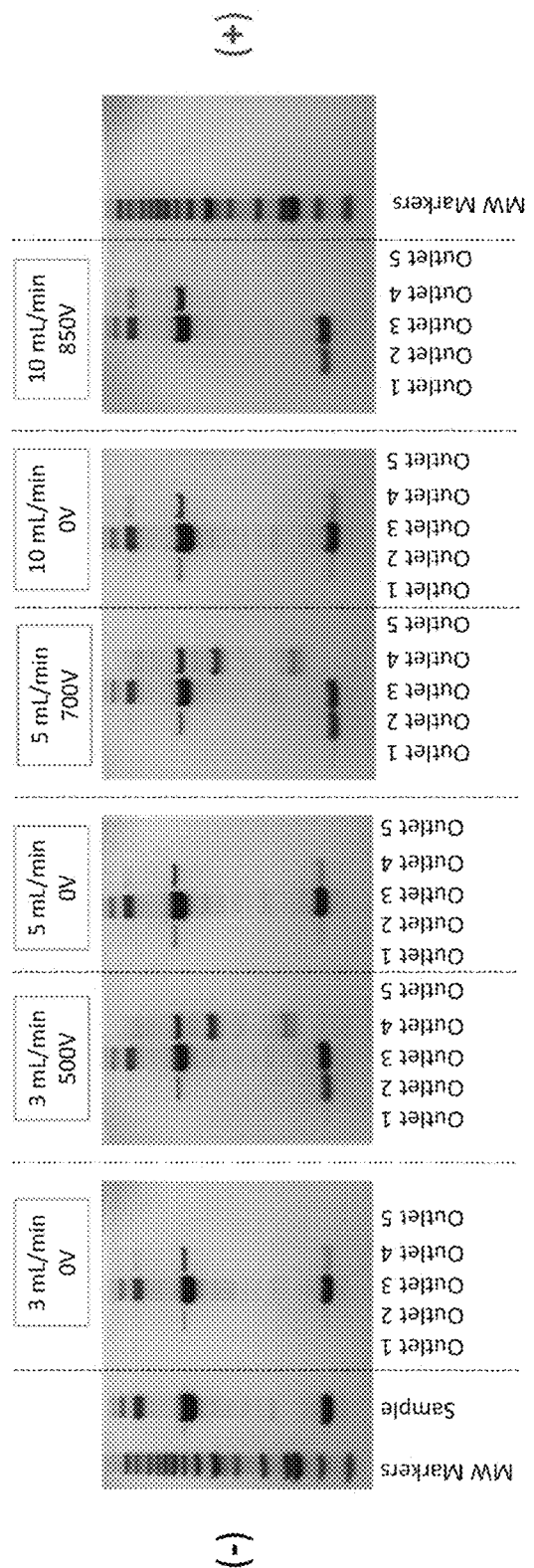

Example 17: Separation of Human Polyclonal Igg by High Flow Rate, Isoelectric Focusing Free-Flow Electrophoresis Using an Isoelectric Point-Based, Fluidic Purification Module A mixture of hIgG (0.5 mg/mL, pI of 6-8) and Lysozyme (0.25 mg/mL, pI of 11) was introduced to the central inlet (inlet 3) of an exemplary free-flow electrophoresis apparatus comprising an anodic channel ($H_2SO_4$), a cathodic channel (NaOH), and a main separation channel having five inlets and five outlets flowing an ampholyte solution designed to achieve a stable, linear pH gradient between pH 2 and pH 12 under applied voltage to enable operation in an isoelectric focusing mode, a de-bubbling and de-gassing system to enable continuous, long-term operation, and an active cooling system (a thermal chuck with chilled circulating ethylene glycol/water) to remove Joule heat through the bottom plate and maintain a temperature between 4° C. and 37° C. When no voltage was applied, the mixture followed laminar flow and exited the apparatus at the central outlet (outlet 3) (FIGS. 46A and 46C). When 1000V was applied across the main separation channel having an ampholyte and sample input flow rate of 5 mL/min, a linear pH gradient was established and the Lysozyme was observed to migrate to the cathode (FIGS. 46A and 46C), consistent with theoretical electrophoretic mobility predictions (FIG. 46B). Increasing the applied voltage to 1500V resulted in an increase in migration of the Lysozyme to the cathode. This increase in applied voltage also resulted in the migration of the hIgG to the cathode and anode (FIGS. 46A and 46C), consistent with theoretical electrophoretic mobility predictions for the range of pIs inherent to a polyclonal antibody (FIG. 46B).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All references, e.g., U.S. patents, U.S. patent application publications, PCT patent applications designating the U.S., published foreign patents and patent applications cited herein are incorporated herein by reference in their entireties. Genbank and NCBI submissions indicated by accession number cited herein are incorporated herein by reference. All other published references, documents, manuscripts, and scientific literature cited herein are incorporated herein by reference. In the case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for purifying a biological product, comprising:
    receiving, via an input line, a heterogeneous mixture containing the biological product;
    removing impurities from the heterogeneous mixture by filtration in a dynamic filtration module by feeding the biological product from at least one output head in fluid communication with the input line to the dynamic filtration module under negative pressure, thereby producing a filtrate comprising the biological product, the dynamic filtration module comprising a dynamic filtration apparatus having a filter membrane extending between a feed reel and a collection reel with at least one support member having a substantially smooth contact surface, a target region of the filter membrane that is configured to receive the heterogeneous mixture from at least one output head, and a membrane support member with a substantially smooth contact surface that is in communication with a vacuum collection system that is positioned between the feed reel and the collection reel;
    transferring the filtrate to a first module capable of separating the solution into two or more fractions wherein at least one fraction contains the biological product, the first module comprising an affinity-based purification apparatus, wherein the first module has at least one first inlet and at least one first outlet configured to permit fluid flow between the at least one first inlet and the at least one first outlet via a mechanical rotary system comprising a vessel carousel containing at least one discrete vessel comprising a suspension of beads;
    transferring the fraction containing the biological product from the at least one outlet of the first module to a second module having at least one inlet for receiving flow from the at least one first outlet of the first module, the second module comprises at least one free-flow electrophoresis apparatus, wherein the second module has at least one second inlet and at least one second outlet and is configured to permit continuous fluid flow between the second inlet and the second outlet; and
    recovering the biological product.

2. The process of claim 1, wherein the affinity-based purification apparatus further comprises a lid system and a collection vessel system in fluid communication with the at least one discrete vessel.

3. The process of claim 2, wherein the lid system comprises at least one lid having a gasket, at least two buffer inlets, a filling inlet, a gas inlet, and a venting valve.

4. The process of claim 2, wherein the lid system is capable of motion along the z-axis, the vessel carousel is capable of rotational motion in a plane transverse to the z-axis, and the collection vessel is capable of motion along the z-axis.

5. The process of claim 1, wherein the vessel carousel includes at least one position to bind the biological product, at least one position to wash to remove unbound products, at least one position to elute and collect the biological product, and at least one regeneration position to enable recycling of the beads.

6. The process of claim 1, wherein the surface of the beads is coupled to Protein A, Protein G, Protein L, an antigenic protein, a protein, a receptor, an antibody, or an aptamer configured to selectively bind said biological product.

7. The process of claim 1, wherein the initial concentration of the beads ranges from about 0.01% to about 25% by weight.

8. The process of claim 1, wherein the beads have a diameter ranging from about 0.2 μm to about 200 μm.

9. The process of claim 1, wherein the beads remain mobile during the process to maintain an increased surface area available for binding.

10. The process of claim 1, wherein the free-flow electrophoresis apparatus comprises electrode channels, including an anodic electrode channel and a cathodic electrode channel, having liquid contact with a main separation channel via a wall gap, the apparatus further having at least one electrode channel de-bubbler comprising at least one gas permeable and hydrophobic membrane configured to remove bubbles by a vacuum system creating a bubble-free main separation channel, and at least one liquid circuit breaker.

11. The process of claim 1, wherein the process maintains approximately a constant flow rate in the dynamic filtration module, the first module, and the second module, and wherein the flow rate ranges from about 0.1 mL/minute to about 50 mL/minute.

12. The process of claim 1, wherein the process for purifying a biological product is performed at a temperature in the range of about 4° C. to about 37° C.

13. The process of claim 1, further comprising at least two dynamic filtration modules, wherein each dynamic filtration module has a filter membrane comprising the same or different pore sizes.

14. The process of claim 1, further comprising at least two free-flow electrophoresis modules configured to operate in an isoelectric focusing mode, a zone electrophoresis mode, an isotachophoresis mode, or combinations thereof.

15. The process of claim 1, further comprising at least two dynamic filtration modules, at least two affinity-based purification modules, or at least two free-flow electrophoresis modules operated in parallel.

* * * * *